US008003779B2

(12) United States Patent
Kyrkanides

(10) Patent No.: US 8,003,779 B2
(45) Date of Patent: Aug. 23, 2011

(54) COMPOSITIONS AND METHODS FOR STUDYING AND TREATING INFLAMMATORY DISEASES AND DISORDERS

(75) Inventor: Stephanos Kyrkanides, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 11/795,789

(22) PCT Filed: Jan. 20, 2006

(86) PCT No.: PCT/US2006/002441
§ 371 (c)(1),
(2), (4) Date: Sep. 2, 2008

(87) PCT Pub. No.: WO2006/079068
PCT Pub. Date: Jul. 27, 2006

(65) Prior Publication Data
US 2009/0028825 A1    Jan. 29, 2009

Related U.S. Application Data

(60) Provisional application No. 60/646,099, filed on Jan. 20, 2005.

(51) Int. Cl.
*C07H 21/04* (2006.01)
*C07H 21/02* (2006.01)
*C12N 15/63* (2006.01)
*A61K 48/00* (2006.01)

(52) U.S. Cl. .................. 536/24.5; 536/23.1; 435/320.1; 514/44

(58) Field of Classification Search .................. None
See application file for complete search history.

(56) References Cited

U.S. PATENT DOCUMENTS

| | | | |
|---|---|---|---|
| 5,217,865 | A | 6/1993 | Myerowitz |
| 6,103,492 | A | 8/2000 | Yu |
| 6,258,556 | B1 | 7/2001 | Uhl et al. |
| 6,518,480 | B1 | 2/2003 | Conklin |
| 7,033,759 | B2 | 4/2006 | Kreek et al. |
| 2002/0068354 | A1 | 6/2002 | Johnston et al. |
| 2002/0147170 | A1 | 10/2002 | Kopin et al. |
| 2003/0003087 | A1 | 1/2003 | Eglitis et al. |
| 2004/0096912 | A1 | 5/2004 | Law et al. |
| 2004/0192630 | A1 | 9/2004 | Kyrkanides |
| 2004/0235017 | A1* | 11/2004 | Qin et al. ............. 435/6 |
| 2006/0009406 | A1 | 1/2006 | Kyrkanides |
| 2006/0025371 | A1* | 2/2006 | Trask et al. ............ 514/44 |
| 2007/0016968 | A1 | 1/2007 | Kyrkanides |

FOREIGN PATENT DOCUMENTS

| | | | |
|---|---|---|---|
| WO | WO 00/27422 | * 5/2000 | .......... 514/44 |
| WO | WO 01/75094 | 10/2001 | |
| WO | WO 02/44355 | 6/2002 | |
| WO | WO 02/059346 | 8/2002 | |
| WO | WO 02/101045 | 12/2002 | |
| WO | WO 03/025188 | 3/2003 | |
| WO | WO 03/092612 | 11/2003 | |
| WO | WO 2004/073646 | 9/2004 | |
| WO | WO 2005/080409 | 9/2005 | |
| WO | WO 2006/053343 | 5/2006 | |
| WO | WO 2006/079068 | 7/2006 | |

OTHER PUBLICATIONS

Saenz et al., FIV: from lentivirus to lentivector, 2004, The Journal of Gene Medicine, 6, pp. S95-S104.*
Abbott FV, Franklin KBJ, Conel B (1986). The stress of a novel environment reduces formalin pain: possible role of serotonin. Eur J Pharmacol 126:141-144.
Abdallah et al. Non-viral gene transfer: applications in developmental biology and gene therapy. *Biol Cell.* 1995 85(1):1-7.
Adamo et al. (2001) Connexin 43 expression in oral derived human osteoblasts after transforming growth factor-beta and $PGE_2$ exposure. J Oral Implantol 27:25-31.
Agarwal S, Long P, Gassner R, Piesco NP, Buckley MJ (2001). Cyclic tensile strain suppresses catabolic effects of interleukin-1beta in fibrochondrocytes from the temporomandibular joint. Arthr Rheum 44:608-17.
Ahmadzadeh N, Shingu M, Nobunaga M (1990). The effect of recombinant tumor necrosis factor-alpha on superoxide and metalloproteinase production by synovial cell and chondrocytes. Clin Exp Rheumatol 8:387-91.
Akima et al. A study on the microvasculature of the cerebellar cortex. The fundamental architecture and its senile change in the cerebellar hemisphere, Acta Neuropathol. 75 (1987) 69-76.
Akiyama, H., S. Barger, S. Barnum, B. Bradt, J. Bauer, G.M. Cole, N.R. Cooper, P. Eikelenboom, M. Emmerling, B.L. Fiebich, C.E. Finch, S. Frautschy, W.S. Griffin, H. Hampel, M. Hull, G. Landreth, L. Lue, R. Mrak, I.R. Mackenzie, P.L. McGeer, M.K. O'Banion, J. Pachter, G. Pasinetti, C. Plata-Salaman, J. Rogers, R. Rydel, Y. Shen, W. Streit, R. Strohmeyer, I. Tooyoma, F.L. Van Muiswinkel, R. Veerhuis, D. Walker, S. Webster, B. Wegrzyniak, G. Wenk and T. Wyss-Coray. Inflammation and Alzheimer's disease. Neurobiol Aging (2000) 21:383-421.
Akli et al. (1996) Restoration of hexosaminidase A activity in human Tay-Sachs fibroblasts via adenoviral vector mediated gene transfer. Gene Therapy 3:769-774. Alisky JM, Hughes SM, Sauter SL, Jolly D, Dubensky TW Jr, Staber PD, Chiorini JA, Davidson BL. Transduction of murine cerebellar neurons with recombinant FIV and AAV5 vectors. Neuroreport. Aug 21, 2000;11(12):2669-73.
Anderson GD, Hauser SD, McGarity KL, Bremer ME, Isakson PC and Gregory SA (1996). Selective inhibition of cyclooxygenase (COX)-2 reverses inflammation and expression of COX-2 and interleukin 6 in rat adjuvant arthritis. J Clin Invest 97:2672-79.
Andreev N, Urban L, Dray A. Opioids suppress spontaneous activity of polymodal nociceptors in rat paw skin induced by ultraviolet irradiation. Neuroscience. Feb. 1994;58(4):793-8.
Arend, W.P. The balance between IL-1 and IL-1Ra in disease. Cytokine & Growth Factor Rev. (2002) 13:323-340.
Arfi, et al. Bicistronic lentiviral vector corrects beta-hexosaminidase deficiency in transduced and cross-corrected human Sandhoff fibroblasts. Neurobiology of Disease. vol. 20, 2:583-593, 2005.
Asipu MA. et al., The specificity of the myelin basic protein gene promoter studied in transgenic mice. Biochemical & Biophysical Research Communications. 288(4):809-18, 2001.

(Continued)

*Primary Examiner* — Amy Bowman
(74) *Attorney, Agent, or Firm* — Ballard Spahr LLP

(57) ABSTRACT

Disclosed are compositions and methods that can be used in the treatment of diseases and disorders caused, exacerbated or otherwise affected by inflammation.

2 Claims, 13 Drawing Sheets

OTHER PUBLICATIONS

Figure 1:
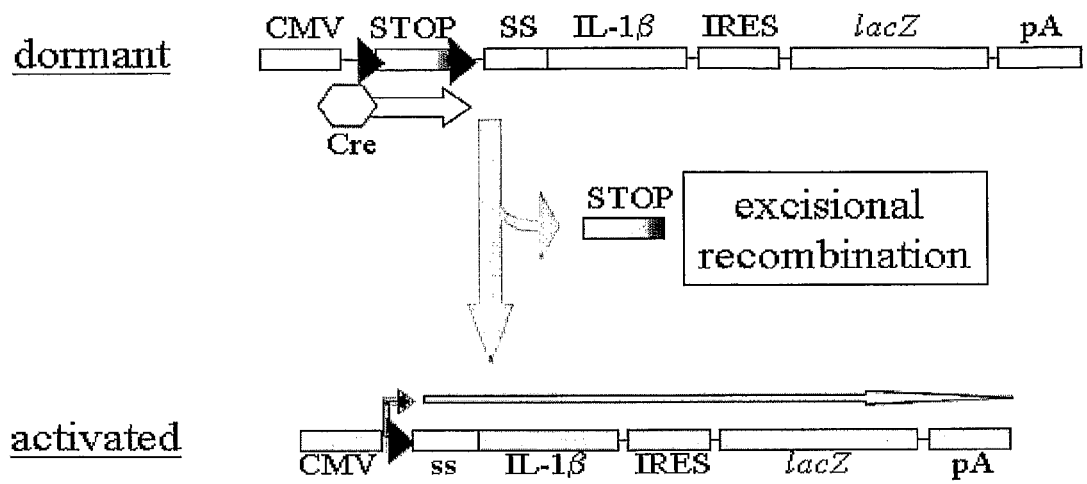

Balkhi KM, Tallents RH, Katzberg RW, Murphy W, Proskin H. Activity of anterior temporalis and masseter muscles during deliberate unilateral mastication. J Orofac Pain. 1993 Winter;7(1):89-97.

Barber A, Gottschlich R. Opioid agonists and antagonists:an evaluation of their peripheral actions in inflammation. Med Res Rev. Sep. 1992;12(5):525-62.

Barranger et al. Lessons learned from the development of enzyme therapy for Gaucher disease, J. Inherit. Metabol. Disord. 24 (2001) 89-96.

Bartho L, Stein C, Herz A. Involvement of capsaicin-sensitive neurones in hyperalgesia and enhanced opioid antinociception in inflammation. Naunyn Schmiedebergs Arch Pharmacol. Dec. 1990;342(6):666-70.

Bartlett and Samulski (1998) Fluorescent viral vectors: A new technique for the pharmacological analysis of gene therapy. Nat Medicine 4:635-637.

Bartlett et al. (2000) Infectious entry pathway of adeno-associated virus and adeno-associated virus vectors. J Virology 74:2777-2785.

Basu, A., J.K. Krady, M. O'Malley, S.D. Styren, S.T. DeKosky and S.W. Levinson. The type 1 interleukin-1 receptor is essential for the efficient activation of microglia and the induction of multiple proinflammatory mediators in response to brain injury. J. Neurosci. (2002) 22:6071-6082.

Baum BJ, Kok M, Tran SD, Yamano S. The impact of gene therapy on dentistry: a revisiting after six years. J Am Dent Assoc. Jan. 2002;133(1):35-44.

Beccari et al. (1992) Cloning and sequence analysis of a cDNA encoding the alpha-subunit of mouse beta-N-acetylhexosaminidase and comparison with the human enzyme. Biochem J 285(Pt 2):593-596.

Bellinger et al. (2001) Effects of interleukin-2 on the expression of corticotropin-releasing hormone in nerves and lymphoid cells in secondary lymphoid organs from the Fischer 344 rat. J Neuroimmunol 119:37-50.

Belsham.GJ, Sonenberg N. RNA-Protein Interactions in Regulation of Picornavirus RNA Translation. 1996. Microbiological Reviews. 60:499-511.

Ben-Shachar et al. (1988a) Picrotoxin, a γ-aminobutyric acid-receptor antagonist, retards craniofacial development in the weaning rat: I. Effect on mandibular bone growth. J Craniofac Genet Develop Biol 8:351-361.

Ben-Shachar et al. (1988b). Picrotoxin, a gamma-aminobutyric acid-receptor antagonist, retards craniofacial development in the weaning rat: II. Effect on mandibular condylar cartilage. J Craniof Genet Develop Biol 8:363-372.

Bernick S The vascular and nerve supply to the temporomandibular joint of the rat. Oral Surg Oral Med Oral Pathol. Apr. 1962;15:488-98.

Beutler E, Subunit Structure of Hexaminidase Isoenzymes. Advances in Genetics, Chp 9. 2001 44:93-100.

Biddulph et al. Inhibition of chondrogenesis by retinoic acid in limb mesenchymal cells in vitro: effects on PGE2 and cyclic AMP concentrations. Cell Differ Dev. Sep. 25, 1988(1):65-75.

Biddulph et al. Inhibition of prostaglandin synthesis reduces cyclic AMP levels and inhibits chondrogenesis in cultured chick limb mesenchyme. *Methods Cell Sci.* Mar. 22, 2000(1):9-16.

Birkenmeier et al. Increased life span and correction of metabolic defects in murine mucopolysaccharidosis type VII after syngeneic bone marrow transplantation. Blood 78 (1991) 3081-3092.

Björkdahl, O., P. Åkerblad, A. Gjörloff-Wingren, T. Leanderson and M. Dohlsten. Lymphoid hyperplasia in transgenic mice over-expressing a secreted form of the human interleukin-1β gene product. Immunology (1999) 96:128-137.

Blömer et al. Highly efficient and sustained gene transfer in adult neurons with a lentivirus vector, J. Virology 71 (1997) 6641-6649.

Bourgoin et al., Widespread distribution of beta-hexosaminidase activity in the brain of a Sandhoff mouse model after co-injection of adenoviral vector and mannitol. Gene Therapy, vol. 10, 21:1841-1849, 2003.

Bowers et al. (2000). Discordance between expression and genome transfer titering of HSV amplicon vectors: recommendation for standardized enumeration. Mol Ther 1:294-9.

Bradl, M., A. Flugel, The role of T cells in brain pathology, Curr. Topics Microbiol. Immunol. 265 (2002) 141-162.

Bragg, et al. Choroid plexus macrophages proliferate and release toxic factors in response to feline immunodeficiency virus, J. Neurovirol. 8 (2002) 225-239.

Brenner, M., W.C. Kisseberth, Y. Su, F. Besnard and A. Messing. GFAP promoter directs astrocyte-specific expresion in transgenic mice. J. Neurosci. (1994) 14:1030-1037.

Breyer RM, Bagdassarian CK, Myers SA and Breyer MD (2001). Prostanoid receptors: subtypes and signaling. Ann Rev Pharmacol Toxicol 41:661-90.

Brooks AI, Halterman MW, Federoff HJ (1999). Focal hippocampal gain of NGF function elicits specific septal cholinergic reorganization. Neuroreport. 10:337-44.

Brooks et al. (2002). Functional correction of established central nervous system deficits in an animal model of lysosomal storage disease with feline immunodeficiency virus-based vectors. Proc Natl Acad Sci USA 99:6216-6221.

Brooks et al. (1997). Nerve growth factor somatic mosaicism produced by herpes virus-directed expression of cre recombinase. Nat Biotech 15:57-62.

Brooks et al. Enzyme replacement treatment for Tay-Sachs disease brain cells in culture utilizing concanavalin A-mediated hexosaminidase a uptake: biochemical and morphological evidence of GM2 mobilization, Acta Neuropath. 50 (1980) 9-17.

Brooks, A.I., D.A. Cory-Siechta and H.J. Federoff. Gene-experience interaction alters the cholinergic septohippocampal pathway of mice. Proc. Natl. Acad. Sci. USA (2000) 97:13378-13383.

Brooks, A.I., M.W. Halterman, C.A. Chadwick, B.L. Davidson, M. Haak-Frendscho, C. Radel, C. Porter and H.J. Federoff. Reproducible and efficient murine CNS gene delivery using a microprocessor-controlled injector. J. Neurosci. Meth. (1998) 80:137-147.

Broton JG, Sessle BJ. Reflex excitation of masticatory muscles induced by algesic chemicals applied to the temporomandibular joint of the cat. Arch Oral Biol. 1988;33(10):741-7.

Brouxhon et al. (1998) Localization of corticotropin-releasing factor in primary and secondary lymphoid organs of the rat. Brain Behav lmmun 12:107-122.

Brugg, B., Y.L. Dubreuil, G. Huber, E.E. Wollman, N. Delhaye-Bouchard and J. Mariana. Inflammatory processes induce β-amyloid precursor protein changes in mouse brain. Proc. Natl. Acad. Sci. USA (1995) 92:3032-3035.

Bullough et al. Subchondral avascular necrosis: a common cause of arthritis. Jun. 1990 49(6):412-420.

Burcin, et al., A Regulatory System for Target Gene Expression. Frontiers in Bioscience. 3: p. 1-7, 1998.

Burns et al. (1993) Vesicular stomatitis virus G-glycoprotein pseudotyped retroviral vectors: Concentration to very high titer and efficient gene transfer into mammalian and nonmammalian cells. *Proc Natl Acad Scie USA* 90:8033-8037.

Burstein et al. (1987). Abnormalities of cellular immunity and natural killer cells in Gaucher's disease. J Clin Lab Immunol 23:149-151.

Byrd et al. (2000) Increased in vivo levels of neurotransmitters to trigeminal motoneurons: effects on craniofacial bone and TMJ. Anat Record 258:369-383.

Cairns BE, Hu JW, Arendt-Nielsen L, Sessle BJ, Svensson P. Sex-related differences in human pain and rat afferent discharge evoked by injection of glutamate into the masseter muscle. J Neurophysiol. Aug. 2001;86(2):782-91.

Cairns BE, Sessle BJ, Hu JW. Activation of peripheral $GABA_A$ receptors inhibits temporomandibular joint-evoked jaw muscle activity. J Neurophysiol. Apr. 1999;81(4):1966-9.

Cairns BE, Sessle BJ, Hu JW. Characteristics of glutamate-evoked temporomandibular joint afferent activity in the rat. J Neurophysiol. Jun. 2001;85(6):2446-54.

Cairns BE, Sessle BJ, Hu JW. Evidence that excitatory amino acid receptors within the temporomandibular joint region are involved in the reflex activation of the jaw muscles. J Neurosci. Oct 1, 1998;18(19):8056-64.

Campbell, I.L., C.R. Abraham, E. Masliah, P. Kemper, J.D. Inglis, M.B.A. Oldstone and L. Mucke. Neurologic disease induced in transgenic mice by cerebral overexpression of interleukin 6. Proc. Natl. Acad. Sci. USA (1993) 90:10061-10065.

Cannon PM, Anderson WF (2000) Retroviral vectors for gene therapy. In Gene Therapy: therapeutic mechanisms and strategies. NS. Templeton and DD Lasic, Editors. Marcel Dekker Inc, New York, pp. 1-16.

Capecchi et al. (1994) Targeted Gene Replacement. Scientific American. 270(3):34-41 (especially p. 38).

Capra NF. Localization and central projections of primary afferent neurons that innervate the temporomandibular joint in cats. Somatosens Res. 1987;4(3):201-13.

Carleson J, Alstergren P, Appelgren a, Appelgren B, Kopp S, Theodorsson E, et al. (1996). A model for the study of experimentally induced temporomandibular arthritis in rats: the effect of human recombinant interleukin-I alpha on neuropeptide like immunoreactivity. J Orofac Pain10:9-14.

Carneiro FA, Bianconi ML, Weissmuller G, Stauffer F, Da Poian AT. Membrane recognition by vesicular stomatitis virus involves enthalpy-driven protein-lipid interactions. J Virol. Apr. 2002;76(8):3756-64.

Chandrasekharan et al. COX-3, a cyclooxygenase-1 variant inhibited by acetaminophen and other analgesic/antipyretic drugs: cloning, structure, and expression. Proc Natl Acad Sci USA Oct. 15, 2002 99(21):13926-13931. Epub Sep. 19, 2002.

Chang JS, Gillman SC, Lewis AJ (1986). Interleukin 1 activates phospholipase A2 in rabbit chondrocytes: a possible signal for IL-1 action. J Immunol 136:1283-87.

Chang, J.W., P.D. Coleman and M.K. O'Banion. Prostaglandin G/H synthase-2 (cyclooxygenase-2) mRNA expression is decreased in Alzheimer's disease. Neurobiol. Aging (1996) 17:801-808.

Chavany C, Jendoubi M (1998) Biology and potential strategies for the treatment of $GM_2$ gangliosidoses. Mol Med Today 4:158-65.

Chen Y, Mestek A, Liu J, Hurley JA, Yu L. Molecular cloning and functional expression of a mu-opioid receptor from rat brain. Mol Pharmacol. Jul 1993;44(1):8-12.

Chepenik et al. Arachidonate metabolism during chondrogenesis in vitro. Calcif Tissue Int. Mar. 1984 36(2):175-181.

Choi HS, Lee HJ, Juan CY, Ju JS, Park JS, Ahn DK (2003). Central cyclooxygenase-2 participates in interleukin-β-induced hyperalgesia in the orofacial formalin test of freely moving rats. Neurosci Letters 352:187-90.

Cinato et al. (2001). Cre-mediated transgene activation in the developing and adult mouse brain. Genesis: the Journal of Genetics & Development. 31(3):118-25, 2001.

Clavelou P, Dallel R, Orliaguet T, Woda A. (1995). The orofacial formalin test in rats: effects of different formalin concentrations. Pain 62:295-301.

Cohen MM Jr. Kreiborg. S. The central nervous system in the Apert syndrome. Am J Med Genet 35:36-45. (1990).

Cohen-Tannoudji et al. Disruption of murine Hexa gene leads to enzymatic deficiency and to neuronal lysosomal storage, similar to that observed in Tay-Sachs disease. Mamm Genome. 6(12):844-9 (1995).

Conzelmann E, Sandhoff K (1983) Partial enzyme deficiencies: residual activities and the development of neurological disorders. Dev Neurosci 6:58-71.

Cotman, C.W., A.J. Tenner and B.J. Cummings. β-amyloid converts an acute phase injury response to chronic injury responses. Neurobiol. Aging (1996) 17:723-731.

Culiat et al. (1995). Deficiency of the beta 3 subunit of the type A gamma-aminobutyric acid receptor causes cleft palate in mice. Nature Genet 11:344-346.

Curran et al. Efficient transduction of pancreatic islets by feline immunodeficiency virus vectors, Transplantation 74 (2002) 299-306.

Daly et al. (1999) Neonatal gene transfer leads to widespread correction of pathology in a murine model of lysosomal storage disease. Proc Natl Acad Sci USA 96:2296-2300.

Daly et al. (1999) Neonatal intramuscular injection with recombinant adeno-associated virus results in prolonged beta-glucuronidase expression in situ and correction of liver pathology in mucopolysaccharidosis type VII mice. Hum Gene Ther 10:85-94.

Daly TM, Lorenz RG, Sands MS (2000). Abnormal immune function in vivo in a murine model of lysosomal storage disease. Pediatr Res 47:757-762.

Daly, et al. Prevention of systemic clinical disease in MPS VII mice following AAV-mediated neonatal gene transfer, Gene Ther. 8 (2001) 1291-1298.

de Bont LG, Boering G, Liem RS, Eulderink F, Westesson PL (1986). Osteoarthritis and internal derangement of the temporomandibular joint: a light microscopic study. J Oral & Maxillofac Surg 44:634-43.

de Crombrugghe et al. (2000) Transcriptional mechanisms of chondrocyte differentiation. Matrix Biol. 19:389-394.

Deng et al. (1998) Luciferase: a sensitive and quantitative probe for blood-brain barrier disruption. J Neurosci Methods 83:159-164.

Dijkgraaf LC, de Bont LG, Boering G, Liem RS (1995). The structure, biochemistry, and metabolism of osteoarthritic cartilage: a review of the literature. J Oral Maxillofac Surg 53:1182-92.

Dijkgraaf LC. Liem RS. de Bont LG (1997). Synovial membrane involvement in osteoarthritic temporomandibular joints: a light microscopic study. Oral Surg Oral Med Oral Pathol Oral Radio & Endodont 83:373-86.

Dijkgraaf LC. Spijkervet FK. de Bont LG (1999). Arthroscopic findings in osteoarthritic temporomandibular joints. J Oral & Maxillofac Surg 57:255-68.

Dinchuk et al. COX-3: in the wrong frame in mind. Mar. 3, 2003 86(1):121.

Dreessen D, Halata Z, Strasmann T. Sensory innervation of the temporomandibular joint in the mouse. Acta Anat (Basel). 1990;139(2):154-60.

Du, Y., R.C. Dodel, B.J. Eastwood, K.R. Bales, F. Gao, F. Lohmuller, U. Muller, A. Kurz, R. Zimmer, R.M. Evans, A. Hake, T. Gasser, W.H. Oertel, W.S. Griffin, S.M. Paul and M.R. Farlow. Association of an interleukin 1 alpha polymorphism with Alzheimer's disease. [see comments]. Neurology (2000) 55:480-483.

Dubuisson D, Dennis S. The formalin test: A quantitative study of the analgesic effects of morphine, meperidine, and brainstem stimulation in rats and cats. Pain 1977; 4:161-74.

Duvernoy, H., S. Delon, J.L. Vannson, The vascularization of the human cerebellar cortex, Brain Res. Bull. 11 (1983) 419-480.

Dziennis et al. The CD11b promoter directs high-level expression of reporter genes in macrophages in transgenic mice. Blood 85(2):319-29 (1995).

Eng, et al. A phase 1/2 clinical trial of enzyme replacement in fabry disease: pharmacokinetic, substrate clearance and safety studies, Am. J. Hum. Genet. 68 (2001) 711-722.

Evans CJ, Keith DE Jr, Morrison H, Magendzo K, Edwards RH. Cloning of a delta opioid receptor by functional expression. Science. Dec. 18, 1992;258(5090):1952-5.

Fernandes JC, Caron JP, Martel-Pelletier J, Javanovic D, Mineau F, Tardif G, Otterness IG, Pelletier JP (1997). Effects of tenidap on the progression of osteoarthritic lesions in a canine experimental model. Suppression of metalloprotease and interleukin-1 activity. Arthritis & Rheum 40:284-94.

Fields HL, Emson PC, Leigh BK, Gilbert RF, Iversen LI. Multiple opiate receptor sites on primary afferent fibres. Nature. Mar 27, 1980;284(5754):351-3.

Fink et al. Cell and gene therapy in the treatment of pain. Advanced Drug Delivery Reviews Aug. 2003. 55(8):1055-1064.

Fiorucci S, Meli R, Bucci M, Cirino G (2001) Dual inhibitors of cycloxygenase and 5-lipoxygenase. A new avenue in anti-inflammatory therapy? Biochem Pharmacol 62:1433-8.

Fitzgerald GA and Patrono C (2001). The coxibs, selective inhibitors of cyclooxygenase-2. N Engl J Med 345:433-42.

Forss-Petter et al. (1990). Transgenic mice expressing β-galactosidase in mature neurons under neuron-specific enolase promoter control. Neuron 5:187-197.

Fournet et al. (1986) Selective localization of calcium-binding protein in human brainstem, cerebellum and spinal cord. Brain Res 399:310-316.

Frautschy, S.A., F. Yang, M. Irrizarry, B. Hyman, T.C. Saido, K. Hsiao and G.M. Cole. Microglial response to amyloid plaques in APPsw transgenic mice. Am. J. Pathol. (1998) 152:307-317.

Friedlander, R.M., V. Gagliardini, N. Hara, K.B. Fink, W. Li, G. MacDonald, M.C. Fishman, A.H. Greenberg, M.A. Moskowitz and J. Yuan. Expression of a dominant negative mutant o interleukin- 1β converting enzyme in transgenic mice prevents neuronal cell death induced by trophic factor withdrawal and ischemic brain injury. J. Exp. Med. (1997) 185:933-940.
Frisella, et al. Intracranial injection of recombinant adeno-associated virus improves cognitive function in a murine model of mucopolysaccharidosis type VII, Mol. Ther. 3 (2001) 351-358.
Frommer J, Monroe CW. The morphology and distribution of nerve fibers and endings associated with the mandibular joint of the mouse. J Dent Res. Nov.-Dec. 1966;45(6):1762-6.
Furuta et al. Effect of 16,16-dimethyl prostaglandin E2 methyl ester on weanling rat skeleton: daily and systemic administration. Anat Rec. Jul. 1986 215(3):305-316.
Futaki N, Arai I, Hamasaka Y, Takahashi S, Higuchi S and Otomo S (1993). Selective inhibition of NS-398 on prostanoid production in inflamed tissue in rat carrageenan-air-pouch inflammation. J Pharmacol 45:753-55.
Gillman SC, Chang J, Zeigler PR, Uhl J, Mochan E (1988). Interleukin 1 activates phospholipase A2 in human synovial cells. Arthritis Rheum 31:126-30.
Gilroy DW, Colville-Nash PR, McMaster S, Sawatzky DA, Willoughby DA, Lawrence T (2003). Inducible cyclooxygenase-derived 15-deoxy(Delta)12-14PGJ2 brings about acute inflammatory resolution in rat pleurisy by inducing neutrophil and macrophage apoptosis. FASEB 17:2269-71.
Gilroy DW, Colville-Nash PR, Willis D, Chivers J, Paul-Clark MJ, Willoughby DA (1999). Inducible cyclooxygenase may have anti-inflammatory properties. Nat Med 5:698-701.
Gjörloff-Wingren, A., O. Björkdahl, T. Labuda, L. Björk, U. Andersson, U. Gullberg, G. Hedlund, H.-O. Sjögren, T. Kalland, B. Widegren and M. Dohlsten. Fusion of a signal sequence to the interleukin-1β gene directs the protein from cytoplasmic accumulation to extracellular release. Cell. Immunol. (1996) 169:226-237.
Goldberg, et al. CXCR3 expression in human central nervous system diseases, Neuropath. Appl. Neurobiol. 27 (2001) 127-138.
Goldgaber, D., H.H. Harris, T. Hla, T. Maciag, R.J. Donnelly, J.S. Jacobsen, M.P. Vitek and D.C. Gajdusek. Interleukin 1 regulates synthesis of amyloid β-protein precursor mRNA in human endothelial cells. Proc. Natl. Acad. Sci. USA (1989) 86:7606-7610.
Goldstein et al. (1986). In vitro studies of the blood-brain barrier using isolated brain capillaries and cultured endothelial cells. Ann NY Acad Sci 481:202-13.
Gravel et al. Biochemistry and genetics of Tay-Sachs disease. Can J Neurol Sci. 18(3 Suppl):419-23 (1991).
Gray, C.W. and A.J. Patel. Regulation of β-amyloid precursor protein isoform mRNAs by transforming growth factor-β1 and interleukin-1β in astroctyes. Mol. Brain Res. (1993) 19:251-256.
Greenwald RA, Moy WW (1997). Inhibition of collagen gelation by action of the superoxide radical. Arthritis Rheum 22:251-59.
Greenwood, et al. Lymphocyte adhesion and transendothelial migration in the central nervous system: the role of LFA-1, ICAM-1, VLA-4 and VCAM-1, Immunol. 86 (1995) 408-415.
Griffin, W.S., J.A. Nicoll, L.M. Grimaldi, J.G. Sheng and R.E. Mrak. The pervasiveness of interleukin-1 in alzheimer pathogenesis: a role for specific polymorphisms in disease risk. Exp Gerontol (2000) 35:481-487.
Griffin, W.S., J.G. Sheng, M.C. Royston, S.M. Gentleman, J.E. McKenzie, D.I. Graham, G.W. Roberts and R.E. Mrak. Glial-neuronal interactions in Alzheimer's disease: the potential role of a 'cytokine cycle' in disease progression. Brain Pathol. (1998) 8:65-72.
Griffin, W.S.T., J.G. Sheng, G.W. Roberts and R.E. Mrak. Interleukin-1 expression in different plaque types in Alzheimer's disease: significance in plaque evolution. J. Neuropath. Exp. Neurol. (1995) 54:276-281.
Griffin, W.S.T., L.C. Stanley, C. Ling, L. White, V. MacLeod, L.J. Perrot, C.L. White, III and C. Araoz. Brain interleukin 1 and S-100 immunoreactivity are elevated in Down syndrome and Alzheimer disease. Proc. Natl. Acad. Sci. USA (1989) 86:7611-7615.
Grilli, M., F. Goffi, M. Memo and P. Spano. Interleukin-1β and glutamate activate the NF-kappaB/Rel binding site form the regulatory region of the amyloid precursor protein gene in primary neuronal cultures. J. Biol. Chem. (1996) 271:15002-15007.
Grimaldi, L., V. Casadei, C. Ferri, F. Veglia, F. Licastro, G. Annoni, I. Biunno, G. De Bellis, S. Sorbi, C. Mariani, N. Canal, W. Griffin and M. Franceschi. Association of early-onset Alzheimer's disease with an interleukin-1 alpha gene polymorphism. Ann. Neurol. (2000) 47:361-365.
Gu et al. Upregulation of opiod-receptor expression potentialtes morphine antinocoception effect. Society for Neuroscience Abstracts 2001, 27(2):1607.
Guidotti et al. (1998) Retrovirus-mediated enzymatic correction of Tay-Sachs defect in transduced and non-transduced cells. Hum Mol Genet 7(5):831-838.
Guidotti et al. (1999) Adenoviral gene therapy of the Tay-Sachs disease in hexosaminidase A-deficient knock-out mice. Hum Mol Genet 8(5):831-838.
Gurtu et al. (1996). IRES bicistronic vectors for efficient creation of stable mammalian cell lines. Bioch Biophys Res Comm 229:295-298.
Halterman et al. Hypoxia-inducible factor-1alpha mediates hypoxia-induced delayed neuronal death that involves p53. Journal of Neuroscience. 19(16):6818-24, 1999.
Han R, Tsui S and Smith TJ (2002). Up-regulation of prostaglandin E2 synthesis by interleukin-1β in human orbital fibroblasts involves coordinate induction of prostaglandin H synthase-2 and glutathione-dependent prostaglandin E2 synthase expression. J Biol Chem 277:163555-64.
Hart RP, Shadiack AM, Jonakait GM (1991). Substance P. gene expression is regulated by interleukin-1 in cultured sympathetic ganglia. J Neurosci Res 29:282-291.
Hassan AH, Ableitner A, Stein C, Herz A. Inflammation of the rat paw enhances axonal transport of opioid receptors in the sciatic nerve and increases their density in the inflamed tissue. Neuroscience. Jul. 1993;55(1):185-95.
Havenga et al. (1998). Second gene expression in bicistronic constructs using short synthetic intercistrons and viral IRES sequences. Gene 222:319-327.
Hay et al. (2000) N- and E-cadherin mediate early human calvaria osteoblast differentiation promoted by bone morphogenetic protein-2. J Cell Physiol 183:117-128.
Helkimo E, Carlsson GE, Yehuda C (1975). Bite force in patients with functional disturbances of the masticatory system. J Oral Rehabil 2:397-406.
Helminen HJ, Kiraly K, Pelttari A, Tammi M, Vandenberg P, Pereira R, et al. (1993). An inbred line of transgenic mice expressing an internally deleted gene for type II procollagen (COL2A1). J Clin Invest 92:582-95.
Hickey WF (1991) Migration of hematogenous cells through the blood-brain barrier and the initiation of CNS inflammation. 1:97-105.
Hickey, et al. Bone marrow-derived elements in the central nervous system: an immunocytochemical and ultrastructural survey of rat chimeras, J. Neuropath. Exp. Neurol. 51 (1992) 246-256.
Hickey, W.F., B.L. Hsu, H. Kimura, T-lymphocyte entry into the central nervous system, J. Neurosci. Res. 28 (1991) 254-260.
Hickey, W.F., Basic principles of immunological surveillance of the normal central nervous system, GLIA 36 (2001) 118-124.
Hoffman WY and McCarthy JG (1994). The effects of facial nerve ablation on craniofacial skeletal development in neonatal rabbits. Plast Recostr Surg 93:1236-1240.
Hsiao, K., P. Chapman, S. Nilsen, C. Eckman, Y. Harigaya, S. Younkin, F. Yang and G. Cole. Correlative memory deficits, Aβ elevation and amyloid plaques in transgenic mice. Science (1996) 274:99-102.
Huang et al. (2001) Absence of monocyte chemoattractant protein 1 in mice leads to decreased local macrophage recruitment and antigen-specific T helper cell type 1 immune response in experimental autoimmune encephalomyelitis. J Exp Med 193:713-26.
Huang JQ, Trasler JM, Igdoura S, Michaud J, Hanel N. Gravel RA (1997) Apoptotic cell death in mouse models of $G_{M2}$ gangliosidosis and observations on human Tay-Sachs and Sandhoffs diseases. Hum Mol Genet 6:1879-85.
Huang, D., R. Pirskanen, P. Hjelmstrom and A.K. Lefvert. Polymorphisms in IL-1beta and IL-1 receptor antagonist genes are associated with myasthenia gravis. J. Neuroimmunol. (1998) 81:76-81.

Huard, et al. The route of administration is a major determinant of the transduction efficiency of rat tissues by adenoviral recombinants, Gene Ther. 2 (1995) 107-115.

Hutchins B, Patel H, Spears R (2002). Attenuation of pro-inflammatory neuropeptide levels produced by a cyclooxygenase-2 inhibitor in an animal model of chronic temporomandibular joint inflammation. J Orofac Pain 16:312-6.

Ichikawa H, Wakisaka S, Matsuo S, et al. (1989). Peptidergic innervation of the temporomandibular disk in the rat. Experientia 45:303-304.

Ionescu et al. (2001) PTHrP modulates chondrocyte differentiation through AP-1 and CREB signaling. J Biol Chem 276:11639-11647.

Israel HA, Diamond BE, Saed-Nejad F, Ratcliffe A (1997). Correlation between arthroscopic diagnosis of osteoarthritis and synovitis of the human temporomandibular joint and keratan sulfate levels in the synovial fluid. J Oral Maxillofacial Surg 55:210-7.

Israel HA, Saed-Nejad F, Ratcliffe A (1991). Early diagnosis of osteoarthrosis of the temporomandibular joint: correlation between arthroscopic diagnosis and keratan sulfate levels in the synovial fluid. J Oral Maxillofacial Surg 49:708-11.

Izikson et al. (2002) Targeting monocyte recruitment in CNS autoimmune disease. Clin Immunol 103:125-131.

Jakobsson PJ, Thorén S, Morgenstern R, Samuelsson B (1999). Identification of human prostaglandin E synthase: a microsomal, glutathione-dependent, inducible enzyme, constituting a potential novel drug target. Proc Natl Acad Sci USA 96:7220-25.

Jang et al. 1989. Initiation of protein synthesis by internal entry of ribosomes into the 5' nontranslated region of encephalomyocarditis virus RNA in vivo. J. of Virology, 63:1651-1660.

Jantzen PT, Connor KE, DiCarlo G,Wenk GL, Wallace JL, Rojiani AM, Coppola D, Morgan D, Gordon MN (2002). Microglial Activation and Beta-Amyloid Deposit Reduction Caused by a Nitric Oxide-Releasing Nonsteroidal Anti-Inflammatory Drug in Amyloid Precursor Protein Plus Presenilin-1 Transgenic Mice. J Neurosci 22:2246-54.

Jeyakumar et al. (2003). Central nervous system inflammation is a hallmark of pathogenesis in mouse models of GM1 and GM2 gangliosidosis. Brain 126:974-987.

Jiao Y, Ma X, Zhang Z (2001). Interleukin-1 increase nitric oxide synthesis through up-regulation of inducible nitric-oxide synthase by rabbit mandibular condylar cartilage cells in vitro. Chin J Stomatol 36:345-347.

Johansson A-S, Isacson G, Isberg A, et al. (1986) Distribution of substance P-like immunoreactive nerve fibers in temporomandibular joint soft tissues of monkey. Scand J Dent Res 94:225-232.

Jonakait GM, Schotland S (1990). Conditioned medium from activated splenocytes increases substance p in sympathetic ganglia. J Neurosci Res 26:24-30.

Jonakait GM, Schotland S, Hart RP (1991). Effects of lymphokines on substance P in injured ganglia of the peripheral nervous system. Ann NY Acad Sci 632:19-30.

Jonakait GM, Schotland S, Hart RP (1991). Interleukin-1 specifically increases substance P in injured sympathetic ganglia. Ann NY Acad Sci 594:222-30.

Joosten LA, Nelsen MM, Saxne T, van De Loo FA, Heinegard D, van Den Berg WB (1999). IL-1 alpha beta blockade prevents cartilage and bone destruction in murine type II collagen-induced arthritis, whereas TNF-alpha blockade only ameliorates joint inflammation. J Immunol; 163:5049-55.

Jovanovic DV, Fernandes JC, Martel-Pelletier J, Jolicoeur FC, Reboul P, Laufer S, Tries S, Pelletier JP (2001). In vivo dual inhibition of cyclooxygenase and lipoxygenase by ML-3000 reduces the progression of experimental osteoarthritis: suppression of collagenase 1 and interleukin-1beta synthesis. Arthr Rheumaton 44:2320-30.

Jow RW, Clark GT. Endurance and recovery from a sustained isometric contraction in human jaw-elevating muscles. Arch Oral Biol. 1989;34(11):857-62.

Kanaji et al. (2003) Improvement of skeletal lesions in mice with mucopolysaccharidosis type VII by neonatal adenoviral gene transfer. Mol Ther 8:718-725.

Kang Y, Stein CS, Heth JA, Sinn PL, Penisten AK, Staber PD, Ratliff KL, Shen H, Barker CK, Martins I, Sharkey CM, Sanders DA, McCray PB Jr, Davidson BL. In vivo gene transfer using a nonprimate lentiviral vector pseudotyped with Ross River Virus glycoproteins. J Virol. Sep. 2002;76(18):9378-88.

Kawai Y, Kubota, Okabe E (2000). Reactive oxygen species participation in experimentally induced arthritis of the temporomandibular joint in rats. J Dent Res 79:1489-95.

Kawakami M, Okabe E (1998). Superoxide anion radical-triggered Ca+2 release from cardiac sarcoplasmic reticulum through ryanodine receptor $Ca^{+2}$ channel. Mol Pharmacol 53:497-503.

Kehl LJ, Trempe TM, Hargreaves KM. A new animal model for assessing mechanisms and management of muscle hyperalgesia. Pain. Apr. 2000;85(3):333-43.

Kellendonk, C. et al., Regulation of Cre recombinase activity by the synthetic steroid RU 486. Nucleic Acids Research vol. 24: p. 1404-1411, 1996.

Kessler et al. The human tyrosine hydroxylase gene promoter. Brain Research. Molecular Brain Research. 112(1-2):8-23, 2003.

Kido MA, Kiyoshima T, Kondo T, Ayasaka N, Moroi R, Terada Y, Tanaka T. Distribution of substance P and calcitonin gene-related peptide-like immunoreactive nerve fibers in the rat temporomandibular joint. J Dent Res. Mar. 1993;72(3):592-8.

Kido MA, Kondo T, Ayasaka N, Terada Y, Tanaka T. The peripheral distribution of trigeminal nerve fibres in the rat temporomandibular joint studied by an anterograde axonal transport method with wheat germ agglutinin-horseradish peroxidase. Arch Oral Biol. 1991;36(5):397-400.

Kieffer BL, Befort K, Gaveriaux-Ruff C, Hirth CG. The delta-opioid receptor: isolation of a cDNA by expression cloning and pharmacological characterization. Proc Natl Acad Sci U S A. Dec. 15, 1992;89(24):12048-52.

Kieseier et al. (1997) the monocyte-macrophage system in affected in lysosomal storage disease: an immunoelectron microscopic study. Acta Neuropathol 94:359-362.

Kimmich, G.A., J. Roussie, M. Manglapus and J. Randles. Characterization of Na+-coupled glutamate/aspartate transport by a rat brain astrocyte line expressing GLAST and EAAC1. J. Membr. Biol. (2001) 182:17-30.

Kirtikara K, SG Morham, R Raghow, SJ Laulederkind, T Kanekura, S Goorhaand, LR Ballou (1998). Compensatory prostaglandin E2 biosynthesis in cyclooxygenase 1 or 2 null cells. J Exp Med 187:517-23.

Kis B, Snipes JA, Isse T, Nagy K, Busija DW. (2003) Putative cyclooxygenase-3 expression in rat brain cells. J Cereb Blood Flow Metab. 23:1287-92.

Kitanaka J, Hashimoto H, Gotoh M, Kondo K, Sakata K, Hirasawa Y, Sawada M, Suzumura A, Marunouchi T, Matsuda T and Baba A. (1996) Expression pattern of messenger RNAs for prostanoid receptors in glial cell cultures. Brain Res 707:282-87.

Kjaer I. (1990) Correlated appearance of ossification and nerve tissue in human fetal jaws. J Craniofac Genet Dev Biol. 10(3):329-336.

Kjaer I. (1998) Neuro-osteology. Crit Rev Oral Biol Med 9:224-244.

Klineberg I. Structure and function of temporomandibular joint innervation. Ann R Coll Surg Engl. Oct. 1971;49(4):268-88.

Koch et al. (1992) Enhanced production of monocyte chemoattractant protein-1 in rheumatoid arthritis. J Clin Invest 90:772-9.

Kolodny. Molecular Genetics of the Beta-Hexaminidase Isoenzymes: An Introduction. Advances in Genetics, Chp 10. 2001. 44:101-126.

Kordower et al. (1999) Lentiviral gene transfer to the nonhuman primate brain. Exp Neurol 160:1-16.

Korneluk et al. Isolation of cDNA clones coding for the alpha-subunit of human beta-hexosaminidase. Extensive homology between the alpha- and beta-subunits and studies on Tay-Sachs disease. *J Biol Chem.* Jun. 25, 1986;261(18):8407-8413.

Kornman, K.S., A. Crane, H.Y. Wang, F.S. di Giovine, M.G. Newman, F.W. Pirk, T.G. Wilson, Jr., F.L. Higginbottom and G.W. Duff. The interleukin-1 genotype as a severity factor in adult periodontal disease. J. Clin. Periodontol. (1997) 24:72-77.

Kosher et al. (1983) The effect of prostaglandins on in vitro limb cartilage differentiation. Exp Cell Res 145:145-153.

Krebsbach et al. Transgenic expression of COLL1A1-chloramphenicol acetyltransferase fusion genes in bone: differential utilization of promoter elements in vivo and in cultured cells. Molecular & Cellular Biology. 13(9):5168-74, 1993.

Kuboki T, Nakanishi T, Kanyama M, Sonoyama W, Fujisawa T, Kobayashi K, Ikeda T, Kubo T, Yamashita A, Takigawa M. Direct adenovirus-mediated gene delivery to the temporomandibular joint in guinea-pigs. Arch Oral Biol. Sep. 1999;44(9):701-9.

Kubota E, Kubota T, Matsumoto J, Shibata T, Murakami KI (1998). Synovial fluid cytokines and proteinases as markers of temporomandibular joint disease. J Oral Maxillofac Surg 56:192-98.

Kuchroo, et al., T cell response in experimental autoimmune encephalomyelitis (EAE): role of self and cross-reactive antigens in shaping, tuning and regulating the autopathogenic T cell repertoire, Ann. Rev. Immunol. 20 (2002) 101-123.

Kyrkanides et al. (1993) Development of the basilar part of the occipital bone in normal and pathological fetuses. J Craniofac Genet Develop Biol 13: 184-192.

Kyrkanides et al. (1995) Skeletal asymmetries of the nasomaxillary complex in non-cleft and post-surgical unilateral cleft lip and palate individuals. Cleft Palat Craniofac J 32:428-32.

Kyrkanides et al. (1996) Asymmetries of the upper lip and nose in non-cleft and post-surgical unilateral cleft lip and palate individuals. Cleft Palat Craniofac J 33:306-310.

Kyrkanides et al. (1999). TNF α and IL-1β mediate ICAM-1 induction via microglia-astrocyte interaction in CNS radiation injury. J Neuroimmunol 95:95-106.

Kyrkanides et al. (2000). Cranial base and facial skeleton asymmetries in individuals with unilateral cleft lip & palate. Cleft Palate-Craniofacial Journal 37:556-561.

Kyrkanides et al. (2001). Enhanced glial activation and expression of specific CNS inflammation-related molecules in aged versus young rats following cortical stab injury. J Neuroimmunol 119:269-77.

Kyrkanides et al. (2003) Systemic FIV vector administration: Transduction of CNS immune cells and Purkinje neurons. Mol Brain Res 119:1-9.

Kyrkanides et al. (2003) Transcriptional and post-translational regulation of Cre recombinase by RU486 as the basis for an enhanced inducible expression system. Molecular Therapy, 8:790-795.

Kyrkanides et al. (2005) beta-hexosaminidase lentiviral vectors: transfer into the CNS via systemic administration. Molecular Brain Research, Elsevier Science. 133(2):286-298.

Kyrkanides S, Kambylafkas P, Miller JH, Tallents RH (2004). Nonprimate lentiviral vector administration in the TMJ. J Dental Res 83:65-70.

Kyrkanides S, Moore AH, Olschowka JA, Daeschner JC, Williams JP, Hansen JT, Kerry O'Banion M. Cyclooxygenase-2 modulates brain inflammation-related gene expression in central nervous system radiation injury. Brain Res Mol Brain Res. Aug. 15, 2002;104(2):159-69.

Kyrkanides S, O'Banion MK, Subtelny JD (2000). Non-steroidal anti-inflammatory drugs in orthodontic tooth movement: Metalloproteinase activity and collagen synthesis by endothelial cells. Am J Orthod Dentofac Orthop 118:203-09.

Kyrkanides S, Tallents RH, Macher DJ, Olschowka JA, Stevens SY. Temporomandibular joint nociception: effects of capsaicin on substance P-like immunoreactivity in the rabbit brain stem. J Orofac Pain. 2002;16(3):229-36.

Lacorazza et al. (1996) Expression of human beta-hexosaminidase alpha-subunit gene (the gene defect of Tay-Sachs disease) in mouse brains upon engraftment of transduced progenitor cells. Nat Med. 2:424-429.

Lamotte C, Pert CB, Snyder SH. Opiate receptor binding in primate spinal cord: distribution and changes after dorsal root section. Brain Res. Aug. 13, 1976;112(2):407-12.

Lane NE (1997). Pain management in osteoarthritis: the role of COX-2 inhibitors. J Rheumatol 24 Suppl. 49:20-24.

Langenbach R, Morham SG, Tiano HF, Loftin CD, Ghanayem BI, Chulada PC, Mahler JF, Lee CA, Goulding EH, Kluckman KD, Kim HS, Smithies O (1995). Prostaglandin Synthase 1 Gene Disruption in Mice Reduces Arachidonic Acid-Induced Inflammation and Indomethacin-Induced Gastric Ulceration. Cell 83:483-92.

Lavigne P, Shi Q, Jolicoeur FC, Pelletier, Martel-Pelletier J, Fernandes JC (2002). Modulation of IL-1beta, IL-6, TNF-alpha and PGE(2) by pharmacological agents in explants of membranes from failed total hip replacement. Osteoarthritis & Cartilage 10:898-904.

Law PY, McGinn TM, Wick MF, Erikson LJ, Evans C, Loh HH. Analysis of delta-opioid receptor activities stably expressed in CHO cell lines: function of receptor density? J Pharmacol Exp Ther. Dec. 1994;271(3):1686-94.

Lee YC, Lai HL, Sun CN, Chien CL, Chern Y. Identification of nuclear factor 1 (NF1) as a transcriptional modulator of rat A(2A) adenosine receptor. Brain Res Mol Brain Res. 2003 111(1-2):61-73.

Lefebvre et al. (1997) SOX9 is a potent activator of the chondrocyte-specific enhancer of the pro alpha1(II) collagen gene. Mol Cell Biol 17:2336-2346.

Lehmann, J.M., J.M. Lenhard, B.B. Oliver, G.M. Ringold and S.A. Kleiwer (1997). Peroxisome proliferator-activated receptors alpha and gamma are activated by indomethacin and other nonsteroidal anti-inflammatory drugs. J Biol Chem 272:3406-10.

Levine JD, Taiwo YO, Hyperalgesic pain: a review. Anesth Prog. 1990 37 (2-3) 133-135.

Li JL, Ding YQ, Li YQ, Li JS, Nomura S, Kaneko T, Mizuno N. Immunocytochemical localization of mu-opioid receptor in primary afferent neurons containing substance P or calcitonin gene-related peptide. A light and electron microscope study in the rat. Brain Res. Jun. 1, 1998;794(2):347-52.

Li K, et al. (2002) A gene fusion method to screen for regulatory effects on gene expression: application to the LDL receptor. Human Molecular Genetics. 11(26):3257-3265.

Li TF, et al. (2004) PGE2 inhibits chondrocyte differentiation through PKA and PKC signaling. Exp Cell Res 300:159-169.

Li Y., L. Liu, S.W. Barger and W.S. Griffin. Interleukin-1 mediates pathological effects of microglia on tau phosphorylation and on synaptophysin synthesis in cortical neurons through a p38-MAPK pathway. J. Neurosci. (2003) 23:1605-1611.

Ling GS, MacLeod JM, Lee S, Lockhart SH, Pastemak GW. Separation of morphine analgesia from physical dependence. Science. Oct. 26, 1984;226(4673):462-4.

Ling GS, Spiegel K, Lockhart SH, Pasternak GW. Separation of opioid analgesia from respiratory depression: evidence for different receptor mechanisms. J Pharmacol Exp Ther. Jan. 1985;232(1):149-55.

Lipschutz et al. (2001). In utero delivery of adeno-associated viral vectors: Intraperitoneal gene transfer produces long-term expression. Mol Ther 3:284-92.

Lipsky PE and Isakson PC (1997). Outcome of specific COX-2 inhibition in rheumatoid arthritis. J Rheumatol 24:9-14.

Lipton, JA, Ship JA, Larach-Robinson D.—Estimated prevalence and distribution of reported orofacial pain the United States. Oct JADA 124 (10):115-21.

Liu et al. (1997) The mature osteoblasts phenotype is characterized by extensive plasticity. Exp Cell Res 232:97-105.

Liu et al. Transgenic mice expressing green fluorescent protein under the control of the melanocortin-4 receptor promoter. Journal of Neuroscience. 23(18):7143-54, 2003.

Liu F, Malayal L, Aubin JE (1997). The mature osteoblast phenotype is characterized by extensive plasticity. Exp Cell Res 232:97-105.

Liu Y et al. (1999) A genetic model of substrate deprivation therapy for a glycosphingolipid storage disorder. J Clin Invest 103:497-505.

Liu, C., Y. Bai, D. Ganea and R.P. Hart. Species-specific activity of rat recombinant interleukin-1 beta. J. Interferon Cytokine Res. (1995) 15:985-992.

Loddick, S.A. and N. J. Rothwell. Neuroprotective effects of human recombinant interleukin-1 receptor antagonist in focal cerebral ischaemia in the rat. J. Cereb. Blood Flow Metab. (1996) 16:932-940.

Lombardi et al. (1998) Microglial activation induced by factor(s) contained in sera from Alzheimer-related ApoE genotypes. J Neurosci Res 54:539-53.

Lu et al. Abnormalities in monocyte recruitment and cytokine expression in monocyte chemoattractant protein 1-deficient mice. J. Exp Med. 187(4):601-8 (1998).

Ludwig et al. (1994) Differential sorting of lysosomal enzymes in mannose 6-phosphate receptor-deficient fibroblasts. EMBO J. 13:3430-3437.

Lue, L.F., L. Brachova, W.H. Civin and J. Rogers. Inflammation, a beta deposition, and neurofibrillary tangle formation as correlates of Alzheimer's disease neurodegeneration. J. Neuropathol. Exp. Neurol. (1996) 55:1083-1088.

Lund JP, Donga R, Widmer CG, Stohler CS (1991). The pain adaptation model: A discussion of the relationship between chronic musculoskeletal pain and motor activity. Can J Physiol Pharmcol 69:683-694.

Macher DJ, Westesson PL, Brooks SL Hicks D and Tallents RH (1992). Temporomandibular joint surgically created disc displacement causes arthrosis in the rabbit. Oral Surg Oral Med Oral Pathol 73:645-49.

Mackenzie, I.R.A. and D.G. Munoz. Nonsteroidal anti-inflammatory drug use and Alzheimer-type pathology in aging. Neurology (1998) 50:986-990.

Maguire-Zeiss KA, Bowers WJ, Federoff HJ (2002). Somatic mosaic approaches and the aging brain. Neurobiol Aging 23:977-84.

Malmberg AB and Yaksh TL (1995). Cyclooxygenase inhibition and the spinal release of prostaglandin E2 and amino acids evoked by paw formalin injection: a microdialysis study in unanesthetized rats. J Neurosci 15:2768-76.

Mancini JA, Blood K, Guay J, Gordon R, Claveau D, Chan CC and Riendeau R (2001). Cloning, expression, and up-regulation of inducible rat prostaglandin e synthase during lipopolysaccharide-induced pyresis and adjuvant-induced arthritis. J Biol Chem 276:4469-75.

Mansour A, Fox CA, Thompson RC, Akil H, Watson SJ. mu-Opioid receptor mRNA expression in the rat CNS: comparison to mu-receptor binding. Brain Res. Apr. 18, 1994;643(1-2):245-65.

Martel-Pelletier J, Pelletier JP, Fahmi H (2003). Cyclooxygenase-2 and prostaglandins in articular tissues. Semin Arthritis Rheum 33:155-67.

Martin WR, Eades CG Demonstration of tolerance and physical dependence in the dog following a short-term infusion of morphine. J Pharmacol Exp Ther. Aug. 1961;133:262-70.

Martino et al. (2002) Absence of metabolic cross-correction in Tay-Sachs cells. J. Biol. Chem. 277:20177-20184.

Masaki M, Matsushita M and Wakitani K. Inhibitory effects of JTE-522, a novel prostaglandin H synthase-2 inhibitor, on adjuvant-induced arthritis and bone changes in rats. Inflamm Res 47:187-92.

Matsubara T, Ziff M (1986). Increased superoxide anion release from human endothelial cells in response to cytokines. J Immunol 137:3295-98.

Matthes HW, Maldonado R, Simonin F, Valverde O, Slowe S, Kitchen I, Befort K, Dierich A, Le Meur M, Dolle P, Tzavara E, Hanoune J, Rogues BP, Kieffer BL. Loss of morphine-induced analgesia, reward effect and withdrawal symptoms in mice lacking the mu-opioid-receptor gene. Nature. Oct. 31, 1996;383(6603):819-23.

McCord JM (1974). Free radicals and inflammation: protection of synovial fluid by superoxide dismutase. Science 185:529-31.

McCormack et al. (2001). Factors affecting long-term expression of a secreted transgene product after intravenous administration of a retroviral vector. Mol Ther 3:516-525.

McDowell, T.L., J.A. Symons, R. Ploski, O. Forre and G.W. Duff. A genetic association between juvenile rheumatoid arthritis and a novel interleukin-1 alpha polymorphism. Arthritis Rheum. (1995) 38:221-228.

Meng F, Taylor LP, Hoversten MT, Ueda Y, Ardati A, Reinscheid RK, Monsma FJ, Watson SJ, Civelli O, Akil H. Moving from the orphanin FQ receptor to an opioid receptor using four point mutations. J Biol Chem. Dec. 13, 1996;271(50):32016-20.

Milam SB, Magnuson VL, Steffensen B, Chen D, Klebe RJ (1991). II-1 bata and prostaglandins regulate integrin mRMA expression. J Cell Physiol 149:173-83.

Milam SB, Schmitz JP (1995). Molecular biology of temporomandibular joint disorders: proposed mechanisms of disease. J Oral Maxillofacial Surg 53:1448-54.

Minami M, Toya T, Katao Y, Maekawa K, Nakamura S, Onogi T, Kaneko S, Satoh M. Cloning and expression of a cDNA for the rat kappa-opioid receptor. FEBS Lett. Aug. 30, 1993;329(3):291-5.

Minami, M., K. Kuraishi, K. Yabuuchi, K. Yamazaki and M. Satoh. Induction of interleukin-1 mRNA in rat brain transient forebrain ischaemia. J. Neurochem. (1992) 58:390-392.

Minghetti L, Levi G (1998) Microglia as effector cells in brain damage and repair: focus on prostanoids and nitric oxide. Prog in Neurobiol 54:99-125.

Miyamoto et al. (2003) Simultaneous stimulation of EP2 and EP4 is essential to the effect of prostaglandin E2 in chondrocyte differentiation. Osteoarthritis Cartilage. 11(9):644-652.

Mizukawa H, Okabe E (1997). Inhibition by singlet molecular oxygen of the vascular reactivity in rabbit mesenteric artery. Br J Pharmacol 121:63-70.

Molin C. Vertical isometric muscle forces of the mandible. A comparative study of subjects with and without manifest mandibular pain dysfunction syndrome. Acta Odontol Scand. Oct. 1972;30(4):485-99.

Moller E, Sheikholeslam A, Lous I. Response of elevator activity during mastication to treatment of functional disorders. Scand J Dent Res. Feb. 1984;92(1):64-83.

Mollereau C, Parmentier M, Mailleux P, Butour JL, Moisand C, Chalon P, Caput D, Vassart G, Meunier JC. ORL1, a novel member of the opioid receptor family. Cloning, functional expression and localization. FEBS Lett. Mar. 14, 1994;341(1):33-8.

Moore AH, Olschowka JA, O'Banion MK (2004). Intraparenchymal administration of interleukin-1beta induces cyclooxygenase-2-mediated expression of membrane- and cytosolic-associated prostaglandin E synthases in mouse brain. J Neuroimmunol 148:32-40.

Moos V, Fickert S, Muller B, Weber U, Sieper J (1999). Immunohistological analysis of cytokine expression in human osteoarthritic and healthy cartilage. J Rheumatol 26:870-9.

Morham SG, Langenbach R, Loftin CD, Tiano HF, Vouloumanos N, Jennette JC, Mahler JF, Kluckman KD, Ledford A, Lee CA, Smithies O (1995). Prostaglandin Synthase 2 Gene Disruption Causes Severe Renal Pathology in the Mouse. Cell 83:473-82.

Mueller-Decker K, Hirschner W, Marks F, Fuerstenberger G (2002). The Effects of Cyclooxygenase Isozyme Inhibition on Incisional Wound Healing in Mouse Skin. J Invest Dermatol 119:1189-95.

Mullen et al. (1992) NeuN, a neuronal specific nuclear protein in vertebrates. Development 116:201-211.

Mullins et al. (1996) Perspectives Series: Molecular Medicine in Genetically Engineered Animals, Transgenesis in the rat and larger mammals. J Clin Invest. 97(7):1557-1560.

Munier-Lehmann et al. (1996) Re-expression of the mannose 6-phosphate receptors in receptor-deficient fibroblasts. Complementary function of the two mannose 6-phosphate receptors in lysosomal enzyme targeting. J Biol Chem 271:15166-15174.

Munier-Lehmann et al. (1996). Function of the two mannose 6-phosphate receptors in lysosomal enzyme transport. Biochem Soc Trans 24:133-136.

Murakami M, Naraba H, Tanioka T, Semmyo N, Nakatani Y, Kojima F, Ikeda T, Fueki M, Ueno A, Oh-ishi S and Kudo I (2000). Regulation of prostaglandin E2 biosynthesis by inducible membrane-associated prostaglandin E2 synthase that acts in concert with cyclooxygenase-2. J Biol Chem 275:32783-92.

Murphy, G.M., Jr., J.D. Claassen, J.J. DeVoss, N. Pascoe, J. Taylor, J.R. Tinklenberg and J.A. Yesavage. Rate of cognitive decline in AD is accelerated by the interleukin-1 alpha -889 *1 allele. Neurology (2001) 56:1595-1597.

Myerowitz et al. (2002) Molecular pathophysiology in Tay-Sachs and Sandhoff diseases as revealed by gene expression profiling. Hum Mol Genet 11:1343-1350.

Myerowitz et al. Human beta-hexosaminidase alpha chain: coding sequence and homology with the beta chain. *Proc Natl Acad Sci USA* Dec. 1985;82(23):7830-7834.

Myers SL, Flusser D, Brandt KD, Heck DA (1992). Prevalence of cartilage shards in synovium and their association with synovitis in patients with early and endstage osteoarthritis. J Rheumatol 19:1247-51.

Nakai H, Byers MG, Nowak NJ, Shows TB. Assignment of β-hexosaminidase A α-subunit to human chromosomal region 15q23→q24. Cytogenet Cell Gent. 1991; 56(3-4):164.

Nakamura et al. An immunohistochemical study of Purkinje cells in a case of hereditary cerebellar cortical atrophy, Acta Neuropathol. 97 (1999) 196-200.

Narumiya A and FitzGerald GA (2001). Genetic and pharmacological analysis of prostanoid receptor function. J Clin Invest 108:25-30.
Narumiya S, Sugimoto Y, Ushikuni F (1999). Prostanoid receptors: structures, properties and functions. Physiol. Rev. 79:1193-1226.
National Institutes of Health Grant No. K08 DE00471.
National Institutes of Health Grant No. R03 DE13860.
National Institutes of Health Grant No. R21 DE14700.
National Institutes of Health Grant No. R21 NS048522.
National Institutes of Health Grant No. RO1 NS048339.
National Institutes of Health Grant No. RO1 NS33553.
Neote et al. Characterization of the Human *HEXB* Gene encoding lysosomal beta-hexosamindase. Genomics 3. 1988. Accession No. A31250.
Nicoll, J., R. Mrak, D. Graham, J. Stewart, G. Wilcock, S. MacGowan, M. Esiri, L. Murray, D. Dewar, S. Love, T. Moss and W. Griffin. Association of interleukin-1 gene polymorphisms with Alzheimer's disease. Ann. Neurol. (2000) 47:365-368.
Niemann H. Transgenic farm animals get off the ground. Transgenic Animals in Agriculture, Conference Tahoe City, California, USA. Aug. 24-27, 1997. Transgenic Res. Jan. 1998 7(1):73-75.
Nolte et al. GFAP promoter-controlled EGFP-expressing transgenic mice: a tool to visualize astrocytes and astrogliosis in living brain tissue. GLIA. 33(1):72-86, 2001.
Nordenskiold UM, Grimby G. Grip force in patients with rheumatoid arthritis and fibromyalgia and in healthy subjects. A study with the Grippit instrument. Scand J Rheumatol. 1993;22(1):14-9.
Norflus et al. (1998) Bone marrow transplantation prolongs life span and ameliorates neurologic manifestations in Sandhoff disease mice. J Clin Invest 101:1881-1888.
Norflus et al. Promoters for the human beta-hexosaminidase genes, *HEXA* and *HEXB* . DNA Cell Biol. 15(2):89-97 (1996).
Norisue M, Todoki K, Okabe E (1997). Inhibition by hydroxyl radicals of calcitonin gene-related peptide-mediated neurogenic vasorelaxation in isolated canine lingual artery. J Pharmacol Exp Ther 280:492-500.
O'Keefe et al. (1992) Influence of prostaglandins on DNA and matrix synthesis in growth plate chondrocytes. J Bone Miner Res. 7(4):397-404.
O'Banion MK, Sadowski HB, Winn V, Young DA (1991). A serum- and glucocorticoid-regulated 4-kilobase mRNA encodes a cyclooxygenase-related protein. J Biol Chem 266:23261-7.
O'Banion MK, Winn VD, Young DA (1992). cDNA cloning and functional activity of a glucocorticoid-regulated inflammatory cyclooxygenase. Proc Natl Acad Sci U.S.A. 89:4888-92.
O'Banion, M.K., Cyclooxygenase-2: molecular biology, pharmacology, and neurobiology, Crit. Rev. Neurobiol. 13 (1999) 45-82.
O'Banion, M.K., J.C. Dusel, J.W. Chang, M.D. Kaplan and P.D. Coleman. Interleukin-1β induces prostaglandin G/H synthase-2 (cyclooxygenase-2) in primary murine astrocyte cultures. J. Neurochem. (1996) 66:2532-2540.
O'Byrne EM, Blancuzzi VJ, Wilson DE, et al. (1990). Increased intra-articular substance P and prostaglandin E2 following injection of interleukin-1 in rabbits. Int J Tissue React 12:11-4.
Ochi T, Ohkubo Y, Mutoh S (2003). Role of cyclooxygenase-2, but not cyclooxygenase-1, on type II collagen-induced arthritis in DBA/1J mice. Biochem Pharmacol 66:1055-60.
Oddo S, Caccamo A, Shepherd JD, Murphy MP, Golde TE, Kayed R, Metherate R, Mattson MP, Akbari Y, LaFerla FM. Triple-transgenic model of Alzheimer's disease with plaques and tangles: intracellular Abeta and synaptic dysfunction. Neuron. Jul. 31, 2003;39(3):409-21.
Ogura N, Tobe M, Sakamaki H, Kujiraoka H, Akiba M, Abiko Y, Nagura H (2002). Interleukin-1 beta induces interleukin-6 mRNA expression and protein production in synovial cells from human temporomandibular joint. J Oral Pathol Med 31:353-60.
Ohmi et al. (2003) Activated microglia in cortex of mouse models of mucopolysaccharidoses I and IIIB. Proc Natl Acad Sci USA 18:1902-1907.
Olschowka et al. Helper-free HSV-1 amplicons elicit a markedly less robust innat immune response in the CNS. Mol. Ther. 7(2):218-27 (2003.

Oya et al. (2000) Distribution of enzyme-bearing cells in GM2 gangliosidosis mice: regionally specific pattern of cellular infiltration following bone marrow transplantation. Acta Neuropathol 99:161-168.
Paddison, P. J., Caudy, A. A., Sachidanandam, R., and Hannon, G. J. (2004). Short hairpin activated gene silencing in mammalian cells. Methods Mol Biol 265, 85-100.
Paddison, P.J., A.A. Caudyand G.J. Hannon. Stable suppression of gene expression by RNAi in mammalian cells. Proc. Natl. Acad. Sci. USA (2002) 99:1443-1448.
Paesani DA, Tallents RH, Murphy WC and Proskin HM (1994). Evaluation of the reproducibility of rest activity of the anterior temporal and masseter muscles in asymptomatic and symptomatic temporomandibular subjects. J Orofacial Pain 8:402-06.
Pan YX, Xu J, Wan BL, Zuckerman A, Pasternak GW. Identification and differential regional expression of KOR-3/ORL-1 gene splice variants in mouse brain. FEBS Lett. Sep. 11, 1998;435(1):65-8.
Peel AL, Zolotukhin S, Schrimsher GW, Muzyczka N, Reier PJ. Efficient transduction of green fluorescent protein in spinal cord neurons using adeno-associated virus vectors containing cell type-specific promoters. Gene Ther. Jan. 1997;4(1):16-24.
Pennybacker, M., et al. Evidence for the Involvement of flu-355 in the catalytic Action of Human Beta-Hexosaminidase B*. The Journal of Biological Chemistry vol. 272, No. 12, Mar. 1997: p. 8002-8006.
Pennybacker, M., et al. Identification of Domains in Human Beta-Hexosaminidase That Determine Substrate Specificity*. The Journal of Bilogical Chemistry vol. 271, No. 29, Jul. 1996: p. 17377-17382.
Pfeifer A, Brandon EP, Kootstra Neeltje, Gage FH, Verma IM (2001). Delivery of the Cre recombinase by a self-deleting lentiviral vector: Efficient gene targeting in vivo. Proc Natl Acad Sci U.S.A. 98:11450-11455.
Phaneuf et al. (1996) Dramatically different phenotypes in mouse models of human Tay-Sachs and Sandhoff diseases. Hum Mol Genet 5:1-14.
Pociot, F., J. Molvig, L. Wogensen, H. Worsaae and J. Nerup. A TaqI polymorphism in the human interleukin-1 beta (IL-1 beta) gene correlates with IL-1 beta secretion in vitro. Eur. J. Clin. Invest. (1992) 22:396-402.
Poeschla, E.M., F. Wong-Staal and D.J. Looney. Efficient transduction of nondividing human cells by feline immunodeficiency virus lentiviral vectors. Nature Med. (1998) 4:354-357.
Pohl M, Braz J. Gene therapy of pain:emerging strategies and future directions. Eur J Pharmacol. Oct. 19, 2001;429(1-3):39-48.
Popovic et al. ID (2002) Inhibition of autoimmune encephalomyelitis by a tetracycline. Ann Neurol 51:215-23.
Porada et al. (1998) In utero gene therapy: transfer and long term expression of the bacterial *neo*[r] gene in sheep after direct injection of retroviral vectors into preimmune fetuses. Hum. Gene Ther. 9:1571-1585.
Portanova JP, Zhang Y, Anderson GD, Hauser SD, Masferrer JL, Seibert K, Gregory SA, Isakson PC. (1996) Selective neutralization of prostaglandin E2 blocks inflammation, hyperalgesia, and interleukin 6 production in vivo. J. Exp. Med 184:883-91.
Porzio et al. Mucosal delivery of anti-inflammatory IL-1Ra by sporulating recombinant bacteria. *BMC Biotechnol.* Oct. 30, 2004;4:27.
Priller et al. (2001a) Targeting gene-modified hematopoietic cells to the central nervous system: Use of green fluorescent protein uncovers microglial engraftment. Nat. Med. 7:1356-1361.
Priller et al. (2001b) Neogenesis of cerebellar Purkinje neurons from gene-marked bone marrow cells in vivo. J Cell Biol 155:733-738.
Priller, J., Grenzganger: adult bone marrow cells populate the brain. Histochem Cell Biol. 120(2):85-91 (2003).
Proia et al. (1984). Association of alpha- and beta-subunits during the biosynthesis of beta-hexosaminidase in cultured human fibroblasts. J Biol Chem 259:3350-3354.
Proia et al. (1988) Gene encoding the human beta-hexosaminidase beta chain: extensive holomogy of intron placement in the alpha- and beta-chain genes. Proc. Natl. Acad. Sci. 85:1883-1887.
Proia RL. (2001) Cloning the beta-hexosaminidase genes. Advances in Genetics, Chp 11. 44:127-135.

Purpura DP and Suzuki K (1976). Distortion of neuronal geometry and formation of aberrant synapses in neuronal storage disease. Brain Res 116:1-21.

Ransohoff et al. (1993) Astrocyte expression of mRNA encoding cytokines IP-10 and JE/MCP-1 in experimental autoimmune encephalomyelitis. FASEB 7:592-600.

Ratcliffe A, Billingham ME, Saed-Nejad F, Muir H, Hardingham TE (1992). Increased release of matrix components from articular cartilage in experimental canine osteoarthritis. J Ortho Res 10:350-8.

Ratcliffe A, Doherty M, Maini RN, Hardingham TE (1998). Increased concentrations of proteoglycan components in the synovial fluids of patients with acute but not chronic joint disease. Ann Rheum Dis 47:826-32.

Raynor K, Kong H, Mestek A, Bye LS, Tian M, Liu J, Yu L, Reisine T. Characterization of the cloned human mu opioid receptor. J Pharmacol Exp Ther. Jan. 1995;272(1):423-8.

Revell PA, Mayston V, Lalor P, Mapp P (1988). The synovial membrane in osteoarthritis: a histological study including the characterisation of the cellular infiltrate present in inflammatory osteoarthritis using monoclonal antibodies. Ann Rheum Dis 47:300-7.

Ricote M, Li AC, Willson TM, Kelly CJ and Glass CK (1998). The peroxisome proliferator-activated receptor-gamma is a negative regulator of macrophage activation. Nature 391:79-82.

Risau et al. (1986) Differentiatio-dependent expression of proteins in brain endothelium during development of the blood-brain barrier. Devel Biol 117:537-545.

Risau W, Wolburg H (1990) Development of blood-brain barrier. TINS 13:174-178.

Ritchlin CT, Haas-Smith SA, Li P, Hicks DG, Schwarz EM (2003). Mechanisms of TNF-alpha- and RANKL-mediated osteoclastogenesis and bone resorption in psoriatic arthritis. J Clin Investig 111:821-31.

Roberts CR, Roughley PJ, Mort JS (1989). Degradation of human proteoglycan aggregate induced by hydrogen peroxide. Protein fragmentation, amino acid modification and hyaluronic acid cleavage. Biochem J. 259:805-11.

Rogers, J., S. Webster, L.-F. Lue, L. Brachova, W.H. Civin, M. Emmerling, B. Shivers, D. Walker and P. McGeer. Inflammation and Alzheimer's disease pathogenesis. Neurobiol. Aging (1996) 17:681-686.

Rogers, J.T., L.M. Leiter, J. McPhee, C.M. Cahill, S. Zhan, H. Potter and L.N. Nilsson. Translation of the Alzheimer amyloid precursor protein mRNA is up-regulated by interleukin-1 through 5'-untranslated region sequences. J. Biol. Chem. (1999) 274:6421-6431.

Romfh JH, Capra NF, Gatipon GB. Trigeminal nerve and temporomandibular joint of the cat: a horseradish peroxidase study. Exp Neurol. Jul. 1979;65(1):99-106.

Rossi GC, Brown GP, Leventhal L, Yang K, Pasternak GW. Novel receptor mechanisms for heroin and morphine-6 beta-glucuronide analgesia. Neurosci Lett. Sep. 20, 1996;216(1):1-4.

Rothwell, N.J. and G.N. Luheshi. Interleukin 1 in the brain: biology, pathology and therapeutic target. Trends Neurosci. (2000) 23:618-625.

Rubinson, D. A., Dillon, C. P., Kwiatkowski, A. V., Sievers, C., Yang, L., Kopinja, J., Rooney, D. L., Ihrig, M. M., McManus, M. T., Gertler, F. B., et al. (2003). A lentivirus-based system to functionally silence genes in primary mammalian cells, stem cells and transgenic mice by RNA interference. Nat Genet 33, 401-406.

Russell NJ, Schaible HG, Schmidt RF. Opiates inhibit the discharges of fine afferent units from inflamed knee joint of the cat. Neurosci Lett. Apr. 23, 1987;76(1):107-12.

Sakuraba et al. (1997) Immunocytochemical detection of accumulated substrates in cultured fibroblasts from patients with the infantile and adult forms of Sandhoff disease. Clin Chim Acta 265:263-266.

Salvemini D, Misko TP, Masferrer JL (1993). Nitric oxide activates cycloxygenase enzymes. Proc Natl Acad Sci 90:7240-44.

Sands, et al. Enzyme replacement therapy for murine mucopolysaccharidosis type VII, J. Clin. Invest. 93 (1994) 2324-2331.

Sango et al. (1996) Mice lacking both subunits of lysosomal beta-hexosaminidase display gangliosidosis and mucopolysaccharidosis. Nature Genet 14:348-352.

Sango K et al. (1995) Mouse models of Tay-Sachs and Sandhoff diseases differ in neurologic phenotype and ganglioside metabolism. Nature Genet 11:170-176.

Schafer M, Imai Y, Uhl GR, Stein C. Inflammation enhances peripheral mu-opioid receptor-mediated analgesia, but not mu-opioid receptor transcription in dorsal root ganglia. Eur J Pharmacol. Jun. 12, 1995;279(2-3):165-9.

Schmued et al. (1997) Fluoro-Jade: a novel fluorochrome for the sensitive and reliable histochemical localization of neuronal degeneration. Brain Res 751:37-46.

Schroeder et al. (1995) Developmental regulation of the human antibody repertoire. Ann NY Acad Scie 764:242-260.

Schroeder JE, Fischbach PS, Zheng D, McCleskey EW. Activation of mu opioid receptors inhibits transient high- and low-threshold $Ca2+$ currents, but spares a sustained current. Neuron. Jan. 1991;6(1):13-20.

Schuller AG, King MA, Zhang J, Bolan E, Pan YX, Morgan DJ, Chang A, Czick ME, Unterwald EM, Pasternak GW, Pintar JE. Retention of heroin and morphine-6 beta-glucuronide analgesia in a new line of mice lacking exon 1 of Mor-1. Nat Neurosci. 1999 Feb;2(2):151-6.

Schwarz EM, Looney RJ, O'Keefe RJ (2000). Anti-TNF-alpha therapy as a clinical intervention for periprosthetic osteolysis. Arthritis Res 2:165-8.

Sciacca, F.L., C. Ferri, K. Vandenbroeck, F. Veglia, C. Gobbi, F. Martinelli, D. Franciotta, M. Zaffaroni, M. Marrosu, G. Martino, V. Martinelli, G. Comi, N. Canal and L.M. Grimaldi. Relevance of interleukin 1 receptor antagonist intron 2 polymorphism in Italian MS patients. Neurology (1999) 52:1896-1898.

Scott-Burden et al. (2002) Use of autologous auricular chondrocytes for lining artificial surfaces: A feasibility study. Ann Thorac Surg 73:1528-33.

Sessle BJ, Hu JW. sms of pain arising from articular tissues. Can J Physiol Pharmacol. May 1991;69(5):617-26.

Shaftel et al. (2003) COX-3: a splice variant of cyclooxygenase-1 in mouse neural tissue and cells. Brain Res Mol Brain Res. 119:213-215.

Sheng, J.G., R.E. Mrak and W.S. Griffin. Glial-neuronal interactions in Alzheimer disease: progressive association of IL-1alpha+ microglia and S100beta+ astrocytes with neurofibrillary tangle stages. J. Neuropathol. Exp. Neurol. (1997) 56:285-290.

Sheng, J.G., S.G. Zhu, R.A. Jones, W.S. Griffin and R.E. Mrak. Interleukin-1 promotes expression and phosphorylation of neurofilament and tau proteins in vivo. Exp. Neural. (2000) 163:388-391.

Shin S-j, Fermor B, Weinberg JB, Pisetsky DS, Guilak F (2003). Regulation of matrix turnover in meniscal explants: role of mechanical stress, interleukin-1, and nitric oxide. J Appl Physiol.; 95:308-13.

Sinsel et al. (1998) The effect of unilateral partial facial paralysis and muscle ablation on craniofacial growth and development: An experimental study in the rabbit. Plast Reconstr Surg 102:1894-1912.

Siqueira-Junior JM, Peters RR, Brum-Femandes AJ, Ribeiro-do-Valle RM (2003). Effects of valeryl salicylate, a COX-1 inhibitor, on models of acute inflammation in mice. Pharmacol Res 48:437-43.

Smith MD, Triantafillou S, Parker A, Youssef PP, Coleman M (1997). Synovial membrane inflammation and cytokine production in patients with early osteoarthritis. J Rheumatol 24:365-71.

Smith, WL, DeWitt DL, Garavito RM (2000). Cyclooxygenases: structural, cellular, and molecular biology. Annu Rev Biochem 69:145-82.

Srinivas S, Watanabe T, Lin C-S, Williams C, Tanabe Y, Jessell T, Costaniti F (2002). Cre reporter strains produced by targeted insertion of EYFP and ECFP into the ROSA26 locus. BMC Develop Biol 1:4-11.

Stalder, A.K., Carson, M.J., Pagenstecher, A., Asensio, V.C., Kincaid, C., Benedict, M., Powell, H.C., Masliah, E., Campbell, I.L. Late-onset chronic inflammatory encephalopathy in immune-competent and severe combined immune-deficient (SCID) mice with astrocyte-targeted expression of tumor necrosis factor. Am J Pathol, 1998 153(3):767-83.

Stegenga B, de Bont LG, Boering G (1989). Osteoarthrosis as the cause of craniomandibular pain and dysfunction: a unifying concept. J Oral Maxillofacial Surg 47:249-56.

Stegenga B, de Bont LG, Boering G, Van Willigen JD (1991). Tissue responses to degenerative changes in the temporomandibular joint: a review. J Oral Maxillofacial Surg 49:1079-88.

Stein C, Hassan AH, Przewlocki R, Gramsch C, Peter K, Herz A. Opioids from immunocytes interact with receptors on sensory nerves to inhibit nociception in inflammation. Proc Natl Acad Sci U S A. Aug. 1990;87(15):5935-9.

Stein C, Schafer M, Machelska H. Attacking pain at its source: new perspectives on opioids. Nat Med. Aug. 2003;9(8):1003-8.

Sternberg N, Hamilton D (1981). Bacteriophage P1 site-specific recombination. Recombination between loxP sites. J Mol Biol 150:467-86.

Stichtenoth DO, Thoren S, Bian H, Peters-Golden M, Jakobsson PJ and Crofford L (2001). Microsomal prostaglandin E synthase is regulated by proinflammatory cytokines in primary rheumatoid synovial cells. J. Immunol. (2001) 167:469-74.

Stohler CS (1999). Craniofacial pain and motor function: pathogenesis, clinical correlates, and implications. Crit Rev Oral Biol Med 10:504-18.

Stohler CS, Ashton-Miller JA, Carlson DS. The effects of pain from the mandibular joint and muscles on masticatory motor behaviour in man. Arch Oral Biol. 1988;33(3):175-82.

Stohler CS, Yamada Y, Ash MM (1985). Antagonistic muscle stiffness and associated reflex behavior in the pain-dysfunction state. Helv Odontol Acta vol. 29:13-20.

Sugimoto Y, Narumiya S and Ichikawa A (2000). Distribution and function of prostanoid receptors: studies from knockout mice. Prog Lipid Res 39:289-314.

Surnii H, Inoue H, Onoue J, Mod A, Oda T, Tsubokura T (1996). Superoxide dismutase activity in arthropathy: its role and measurement in the joints. Hiroshima J Med Sci 45:51-55.

Suzuki et al. (1988) The twitcher mouse: central nervous system pathology after bone marrow transplantation. Lab Investigator 58:302-309.

Suzuki et al. (1997) Mice deficient in all forms of lysosomal β-hexosaminidase show mucopolysaccharosis-like pathology. J Neuropath Exp Neurol 56:693-703.

Suzuki T, Segami N, Nisimura M, Nojima T (2002). Co-expression of interleukin-1beta and tumor necrosis factor alpha in synovial tissues and synovial fluids of temporomandibular joint with internal derangement: comparison with histological grading of synovial inflammation. J of Oral Pathology Med 31:549-57.

Swanborg, R.H., Experimental autoimmune encephalomyelititis in the rat: lessons in T-cell immunology and autoreactivity, Immunol. Rev. 184 (2001) 129-135.

Szpak et al. (2001) Neurones and microglia in central nervous system immune response to degenerative processes. Part 1: Alzheimer's disease and Lewy body variant of Alzheimer's disease. Quantitative study. Folia Neuropathol 39:181-92.

Takeda et al. Leptin regulates bone formation via the sympathetic nervous system. *Cell*. Nov. 1, 2002;111(3):305-317.

Tallents RH, Macher DJ Rivoli P, Scapino R, Puzas JE, Katzberg RW (1990). An animal model for disk displacement. J Craniomandib Disord Facial Oral Pain 4:233-40.

Tambeli CH, et al., J Dent Res 1997; 76:(Special Issue) abstr# 1263.

Tanaka A, Hase S, Miyazawa T, Ohno R, Takeuchi K (2002). Role of cyclooxygenase (COX)-1 and COX-2 inhibition in nonsteroidal anti-inflammatory drug-induced intestinal damage in rats: relation to various pathogenic events. J Pharmacol Exp Ther 303:1248-54.

Taniike M, et al. Neuropathology of mice with targeted disruption of *Hexa* gene, model of Tay-Sachs disease. Acta Neuropathol (Berl.) 89(4):296-304 (1995).

Tanioka T, Nakatani Y, Semmyo N, Murakami M and Kudo I (2000). Molecular identification of cytosolic prostaglandin E2 synthase that is functionally coupled with cylooxygenase-1 in immediate prostaglandin E2 biosynthesis. J Biol Chem 275:32775-82.

Tanzi, R.E. Alzheimer's disease risk and the interleukin-1 genes. Ann Neurol (2000) 47:283-285.

Tarantal et al. (2001) Rhesus monkey model for fetal gene transfer: studies with retroviral-based vector systems. Mol Ther 3:128-138.

Tawara T, Shingu M, Nobunaga M, Naono T (1991). Effects of recombinant human IL-Iβ on production of prostaglandin E2, leukotriene B4, NAG, and superoxide by human synovial cells and chondrocytes. Inflammation 15:145-57.

Tehranian, R., S. Andell-Jonsson, S.M. Beni, I. Yatsiv, E. Shohami, T.B. Bartfai, J. KLundkvist and K. Iverfeldt. Improved recovery and delayed cytokine induction after closed head injury in mice with central overexpression of the secreted isoform of the interleukin-1 receptor antagonist. J. Neurotrauma (2002) 19:939-951.

Teixeira et al. Retrovirus-mediated transfer and expression of β-hexosaminidase α-chain cDNA in human fibroblasts from $G_{M2}$-gangliosidosis B1 variant, Hum. Gene Ther. 12 (2001) 1771-1783.

Thilander B. Innervation of the Temporo-mandibular Disc in Man. Acta Odontol Scand. Feb. 1964;22:151-6.

Tian et al. Dystroglycan in the cerebellum is a laminin alpha 2-chain binding protein at the glial-vascular interface and is expressed in Purkinje cells, Eur. J. Neurosci. 8 (1997) 2739-2747.

Tiku ML, Liesch JB, Robertson FM (1990). Production of hydrogen peroxide by rabbit articular chondrocytes. Enhancement by cytokines. J Immunol 145:690-96.

Tilley SL, Coffman TM and Koller BH (2001). Mixed messages: modulation of inflammation and immune response by prostaglandins and thromboxanes. J Clin Invest 108:15-23.

Tiscornia, G., Singer, O., Ikawa, M., and Verma, I. M. (2003). A general method for gene knockdown in mice by using lentiviral vectors expressing small interfering RNA. Proc Natl Acad Sci U S A 100, 1844-1848.

Triggs-Raine et al. (1994) Characterization of the murine beta-hexosaminidase (HEXB) gene. Biochim Biophys Acta. 1227 (1-2):79-86.

Tuschl, T. RNA interference and small interfering RNAs. Chembiochem (2001) 2:239-245.

Ueno et al. (1985) The effects of prostaglandin E2 in rapidly growing rats: depressed longitudinal and radial growth and increased metaphyseal hard tissue mass. Bone 6:79-86.

Utsumi et al. (2002) Western blotting analysis of the beta-hexosaminidase alpha- and beta-subunits in cultured fibroblasts from cases of various forms of GM2 gangliosidosis. Acta Neurol Scand 105:427-30.

Vane JR, Bakhle YS, Bolling RM(1998). Cyclooxygenases 1 and 2. Annu. Rev. Pharmacol. Toxicol. 38:97-120.

Vignon et al. (1990) Histaminergic H1, serotoninergic, beta adrenergic and dopaminergic receptors in human osteoarthritic cartilage. Biochem Int. 20(2):251-255.

von Specht et al. (1979) Enzyme replacement therapy for Tay-Sachs disease. Neurol 29:848-854.

Wada et al. (2000) Microglial activation precedes acute neurodegeneration in Sandhoff disease and is suppressed by bone marrow transplatation. Proc. Natl. Acad. Sci. U.S.A. 97:10954-9.

Wada S, Okabe E (1997). Susceptibility of caffeine and INS(1,4,5)P3 induced contractions to oxidants in permeabilized vascular smooth muscle. Eur J Pharmacol 320:51-59.

Walkley et al. (1991). Neuroaxonal dystrophy in neuronal storage disorders: evidence for major GABAergic neuron involvement. J Neurol Sci 104:1-8.

Walkley et al. Bone marrow transplantation corrects the enzyme defect in neurons of the central nervous system in a lysosomal storage disease, Proc. Natl. Acad. Sci. U.S.A. 91 (1994) 2970-2974.

Walkley SU (1998) Cellular pathology of lysosomal storage disorders. Brain Path 8:175-193.

Walkley SU., Pathobiology of neuronal storage disease, Int Rev Neurobiol. 1988; 29:191-244.

Walkley, S.U., K. Dobrenis, Bone marrow transplantation for lysosomal diseases, Lancet 345 (1995) 1382-1383.

Wall RJ. (1996) Transgenic Livestock: Progress and Prospects for the Future. Theriogenology. 45:57-68.

Wang JB, Imai Y, Eppler CM, Gregor P, Spivak CE, Uhl GR. mu opiate receptor: cDNA cloning and expression. Proc Natl Acad Sci U S A. Nov. 1, 1993;90(21):10230-4.

Wang JB, Johnson PS, Imai Y, Persico AM, Ozenberger BA, Eppler CM, Uhl GR. cDNA cloning of an orphan opiate receptor gene family member and its splice variant. FEBS Lett. Jul. 4, 1994;348(1):75-9.

Webb GR, Westacott CI, Elson CJ. (1998) Osteoarthritic synovial fluid and synovium supernatants up-regulate tumor necrosis factor receptors on human articular chondrocytes. Osteoarthr & Cartil 6:167-76.

Weimann et al. (2003) Contribution of transplanted bone marrow cells to Purkinje neurons in human adult brain. Proc. Natl. Acad. Sci. U.S.A. 100:2088-2093.

Werz MA, MacDonald RL Opioid peptides selective for mu- and delta-opiate receptors reduce calcium-dependent action potential duration by increasing potassium conductance. Neurosci Lett. Dec. 2, 1983;42(2):173-8.

Westerman KA, Leboulch P. Reversible immortalization of mammalian cells mediated by retroviral transfer and site-specific recombination. Proc. Natl. Acad. Sci. USA 93:8971-8976, 1996.

Wildner, et al. Generation of a conditional neo$^r$-containing retroviral producer cell line: effects of neo$^r$ on retroviral titer and transgene expression. Gene Therapy. vol. 5, 5:684-691, 1998.

Wilhelmi G, Faust R (1976). Suitability of the C57 black mouse as an experimental animal for the study of skeletal changes due to ageing, with special reference to osteo-arthrosis and its response to tribenoside. Pharmacol 14:289-96.

Wingren AG, Bjorkdahl O, Labuda T, Bjork L, Andersson U, Gullberg U, Hedlund G, Sjogren HO, Kalland T, Widegren B, Dohlsten M (1996). Fusion of a signal sequence to the interleukin-1 beta gene directs the protein from cytoplasmic accumulation to extracellular release. Cell Immunol 169:226-37.

Wink CS, St Onge M, Zimny ML. Neural elements in the human temporomandibular articular disc. J Oral Maxillofac Surg. Apr. 1992;50(4):334-7.

Wolff et al. Direct gene transfer into mouse muscle in vivo. Science. Mar. 23, 1990 247(4949 Pt 1):1465-1468.

Wolff JA, Harding CO (2000) Principles of gene therapy for inborn errors of metabolism. In Gene Therapy: therapeutic mechanisms and strategies. NS. Templeton and DD Lasic, Editors. Marcel Dekker Inc, New York, pp. 507-533.

Wood et al. (1989) A rare Taql RFLP immediately 3' of the *HEXB* gene on chromosome 5. Nucleic Acid Research. 17:2368.

Woodruff T, Blake DR, Freeman J, Andrews FJ, Salt P, Lunec J (1986). Is chronic synovitis an example of reperfusion injury? Ann Rheum Dis 45:608-11.

Wu CL, Garry MG, Zollo RA, Yang J. Gene therapy for the management of pain: part II: molecular targets. Anesthesiology. Jul. 2001;95(1):216-40.

Xie GX, Meuser T, Pietruck C, Sharma M, Palmer PP. Presence of opioid receptor-like (ORL1) receptor mRNA splice variants in peripheral sensory and sympathetic neuronal ganglia. Life Sci. 1999;64(22):2029-37.

Xu et al. (2000) Enhanced expression of mu-opioid receptors in sensory neurons using adeno-associated viral vectors. Society for Neuroscience Abstracts, 26(1-2):1662, Abstract 608.7.

Xu et al. (2001) Adeno-associated virus mediated gene expression in dorsal root ganglia following remote vector delivery. Society for Neuroscience Abstracts 27(2):1607.

Xu et al. (2003) Adeno-associated viral transfer of opiod receptor gene to primary sensory neurons: a strategy to increase opioid antinociception. Proc. Natl. Acad. Sci. 100(10):6204-6209.

Xu et al. (2003) Efficiencies of transgene expression in nociceptive neurons through different routes of delivery of adeno-associated viral vectors. Human Gene Therapy. 14(9):897-906.

Yaksh TL, Dirig DM, Conway CM, Svensson C, Luo ZD, Isakson PC (2001). The acute antihyperalgesic action of nonsteroidal, anti-inflammatory drugs and release of spinal prostaglandin E2 is mediated by the inhibition of constitutive spinal cyclooxygenase-2 (COX-2) but not COX-1. J Neurosci 21:5847-53.

Yaksh TL, Jessell TM, Gamse R, Mudge AW, Leeman SE. Intrathecal morphine inhibits substance P release from mammalian spinal cord in vivo. Nature. Jul. 10, 1980;286(5769):155-7.

Yaksh TL. Substance P release from knee joint afferent terminals: modulation by opioids. Brain Res. Aug. 23, 1988;458(2):319-24.

Yamamoto Y, Yin MJ, Lin KM and Gaynor RB (1999). Sulindac inhibits activation of the NF-$\kappa$B pathway. J Biol Chem. 274:27307-314.

Yamanaka et al. (1994) Targeted disruption of the *Hexa* gene results in mice with biochemical and pathologic features of Tay-Sachs disease. Proc Natl Acad Sci USA. 91(21):9975-9979.

Yamasaki, Y., N. Matsuura, H. Shozuhara, H. Onodera, Y. Itoyama and K. Kogure. Interleukin-1 as a pathogenetic mediator of ischemic brain damage in rats. Stroke (1995) 26:676-681.

Yang, D., F. Buchholz, Z. Huang, A. Goga, C.-Y. Chen, F.M. Brodskyand J.M. Bishop. Short RNA duplexes produced by hydrolysis with *Escherichia coli* RNase III mediate effective RNA interference in mammalian cells. Proceedings of the National Academy of Sciences (2002) 99:9942-994.

Yang, Y., W.W. Quitschke and G.J. Brewer. Upregulation of amyloid precursor protein gene promoter in rat primary hippocampal neurons by phorbol ester, IL-1, and retinoic acid, but not by reactive oxygen species. Mol. Brain Res. (1998) 60:40-49.

Yaworsky et al. Transgenic analyses reveal developmentally regulated neuron- and muscle-specific elements in the murine neurofilament light chain gene promoter. Journal of Biological Chemistry. 272(40):25112-20, 1997.

Yermakova, A.V., J. Rollins, L.M. Callahan, J. Rogers and M.K. O'Banion. Cyclooxygenase-1 in human Alzheimer's and control brain: quantitative analysis of expression by microglia and CA3 hippocampal neurons. J. Neuropathol. Exp. Neurol. (1999) 58:1135-1146.

Yin MJ, Yamamoto Y and Gaynor RB (1998). The anti-inflammatory agents aspirin and salicylate inhibit the activity of IkB kinase-$\beta$. Nature 396:77-80.

Yoshida H, Fukumura Y, Fujita S, Nishida M, Iizuka T (2002). The expression of cyclooxygenase-2 in human temporomandibular joint samples: an immunohistochemical study. J Oral Rehab 29:1146-52.

Yoshino K, Kawagishi S, Amano N. Morphological characteristics of primary sensory and postsynaptic sympathetic neurones supplying the temporomandibular joint in the cat. Arch Oral Biol. Sep. 1998;43(9):679-86.

Yrjanheikki et al. (1998) Tetracyclines inhibit microglial activation and are neuroprotective in global brain ischemia. Proc Natl Acad Sci USA 95:15769-74.

Yrjanheikki et al. (1999) A tetracycline derivative, minocycline, reduces inflammation and protects against focal cerebral ischemia with a wide therapeutic window. Proc Natl Acad Sci USA 96:13496-500.

Zhang et al. (2001) A highly efficient and consistent method for harvesting large volumes of high-titre lentiviral vectors. Gene Therapy. 8:1745-1751.

Zhang J, S Goorha, R Raghowand, Lr Ballou (2002). The tissue-specific, compensatory expression of cyclooxygenase-1 and -2 in transgenic mice. Prostagland Other Lipid Mediat 67:121-35.

Zheng et al. Treatment of the mouse model of mucopolysaccharidosis I with retrovirally transduced bone marrow. Mol Genet Metab. Aug. 2003 79(4):233-244.

Zhou et al. (1998) Temperature-sensitive neuromuscular transmission in Kv1.1 null mice: Role of potassium channels under the myelin sheath in young nerves. J. Neurosci 18:7200-15.

Zhou et al. Frontotemporal dementia: neuropil spheroids and presynaptic terminal degeneration, Ann. Neurol. 44 (1998) 99-109.

Zhu J, Musco ML, Grace MJ (1999). Three-color flow cytometry analysis of tricistronic expression of eBFP, eGFP, and eYFP using EMCV-IRES linkages. Cytometry 37:51-9.

Zhu X, Conklin D, Eisenach JC (2003). Cyclooxygenase-1 in the spinal cord plays an important role in postoperative pain. Pain 104:15-23.

Lai et al., Gene Transfer Into the Central Nervous System in Vivo Using a Recombinanat Lentivirus Vector. Journal of Neuroscience Research, vol. 67, No. 3, pp. 363-371, 2002.

Kyrkanides et al., Amelioration of Pain and Histopathologic Joint Abnormalities in the Col1-IL-1 beta (XAT) Mouse Model of Arthritis by Intraarticular Induction of mu-Opiad Receptor into the Temporomandibular Joint. Arthritis & Rheumatism vol. 56, No. 6, pp. 2038-2048, 2007.

Akaneya, Yukio et al. (2005) J. Neurophysiology 93: 594-602.

Morris, K.V. et al. (2004) Science 305: 1289-1292.

Yang, S. et al. (2002) Inflammation Research 51: 342-350.

PCT/US2006/002441 International Search Report mailed on May 9, 2008.
PCT/US2006/002441 Written Opinion mailed on May 9, 2008.
PCT/US2006/002441 International Preliminary Report on Patentability and Written Opinion mailed on Mar. 10, 2009.
EP 06719341 European Supplemental Search Report and Search Opinon mailed on Mar. 23, 2010.
Supplementary European Search Report issued Dec. 19, 2007 for Application Serial No. 04712863.2 (EP Publication No. 1599231), which claims priority to PCT/US2004/004914 filed on Feb. 19, 2004 (Applicant—University of Rochester; Inventor—Stephanos Kyrkanides et al.).
Reply to Communication filed on Sep. 29, 2010 for Application Serial No. 05851904.2 (EP1814385), which claims priority to PCT/US2005/042058 filed on Nov. 14, 2005 (Applicant—University of Rochester; Inventor—Stephanos Kyrkanides et al.).
Communication pursuant to Article 94(3) issued Mar. 19, 2010 for Application Serial No. 05851904.2 (EP1814385), which claims priority to PCT/US2005/042058 filed on Nov. 14, 2005 (Applicant—University of Rochester; Inventor—Stephanos Kyrkanides et al.).
Reply to Communication filed on Apr. 3, 2009 for Application Serial No. 05851904.2 (EP1814385), which claims priority to PCT/US2005/042058 filed on Nov. 14, 2005 (Applicant—University of Rochester; Inventor—Stephanos Kyrkanides et al.).
Communication pursuant to Article 94(3) issued Sep. 24, 2008 for Application Serial No. 05851904.2 (EP1814385), which claims priority to PCT/US2005/042058 filed on Nov. 14, 2005 (Applicant—University of Rochester; Inventor—Stephanos Kyrkanides et al.).
Reply to Communication filed on Jul. 14, 2008 for Application Serial No. 05851904.2 (EP1814385), which claims priority to PCT/US2005/042058 filed on Nov. 14, 2005 (Applicant—University of Rochester; Inventor—Stephanos Kyrkanides et al.).
Communication pursuant to Rule 70(2) EPC issued May 13, 2008 for Application Serial No. 05851904.2 (EP1814385), which claims priority to PCT/US2005/042058 filed on Nov. 14, 2005 (Applicant—University of Rochester; Inventor—Stephanos Kyrkanides et al.).
Supplementary European Search Report issued Apr. 24, 2008 for Application Serial No. 05851904.2 (EP1814385), which claims priority to PCT/US2005/042058 filed on Nov. 14, 2005 (Applicant—University of Rochester; Inventor—Stephanos Kyrkanides et al.).
Reply to Communication filed on Jul. 26, 2007 for Application Serial No. 05851904.2 (EP1814385), which claims priority to PCT/US2005/042058 filed on Nov. 14, 2005 (Applicant—University of Rochester; Inventor—Stephanos Kyrkanides et al.).
Communication pursuant to Rule 94(3) EPC issued on Jul. 20, 2010 for Application Serial No. 06719341.7 (EP1883427), which claims priority to PCT/US2006/002441 filed on Jan. 20, 2006 (Applicant—University of Rochester; Inventor—Stephanos Kyrkanides).
Reply to Communication filed on Jun. 18, 2010 for Application Serial No. 06719341.7 (EP1883427), which claims priority to PCT/US2006/002441 filed on Jan. 20, 2006 (Applicant—University of Rochester; Inventor—Stephanos Kyrkanides).
Communication pursuant to Rule 70(2) EPC issued on Apr. 9, 2010 with Supplementary European Search Report issued on Mar. 23, 2010 for Application Serial No. 06719341.7 (EP1883427), which claims priority to PCT/US2006/002441 filed on Jan. 20, 2006 (Applicant—University of Rochester; Inventor—Stephanos Kyrkanides).
Response to Communication filed Jun. 23, 2009 for Application Serial No. 06719341.7 (EP1883427), which claims priority to PCT/US2006/002441 filed on Jan. 20, 2006 (Applicant—University of Rochester; Inventor—Stephanos Kyrkanides).
Replacement Claims filed on Mar. 31, 2008 for Application Serial No. 06719341.7 (EP1883427), which claims priority to PCT/US2006/002441 filed on Jan. 20, 2006 (Applicant—University of Rochester; Inventor—Stephanos Kyrkanides).
Reply to Communication filed on Nov. 30, 2007 for Application Serial No. 06719341.7 (EP1883427), which claims priority to PCT/US2006/002441 filed on Jan. 20, 2006 (Applicant—University of Rochester; Inventor—Stephanos Kyrkanides).
Noting of Loss of Rights pursuant to Rule 69(1) EPC issued on Oct. 2, 2007 for Application Serial No. 06719341.7 (EP1883427), which claims priority to PCT/US2006/002441 filed on Jan. 20, 2006 (Applicant—University of Rochester; Inventor—Stephanos Kyrkanides).

Preliminary Amendment filed Jan. 14, 2009 for U.S. Appl. No. 12/373,838, which was filed on Dec. 7, 2009 (Inventor—Stephanos Kyrkanides).
Notice of Acceptance issued May 27, 2010 for Australian Application Serial No. 2004213019, which claims priority to PCT/US2004/004914 filed Feb. 19, 2004 (Applicant—University of Rochester; Inventor—Stephanos Kyrkanides et al.).
Examiner's Report issued May 10, 2010 for Australian Application Serial No. 2004213019, which claims priority to PCT/US2004/004914 filed Feb. 19, 2004 (Applicant—University of Rochester; Inventor—Stephanos Kyrkanides et al.).
Response to Examiner's Report filed May 4, 2010 for Australian Application Serial No. 2004213019, which claims priority to PCT/US2004/004914 filed Feb. 19, 2004 (Applicant—University of Rochester; Inventor—Stephanos Kyrkanides et al.).
Examiner's Report issued Sep. 1, 2008 for Australian Application Serial No. 2004213019, which claims priority to PCT/US2004/004914 filed Feb. 19, 2004 (Applicant—University of Rochester; Inventor—Stephanos Kyrkanides et al.).
Request for Examination filed Aug. 29, 2007 for Australian Application Serial No. 2004213019, which claims priority to PCT/US2004/004914 filed Feb. 19, 2004 (Applicant—University of Rochester; Inventor—Stephanos Kyrkanides et al.).
Direction to Request Examination issued Mar. 14, 2007 for Australian Application Serial No. 2004213019, which claims priority to PCT/US2004/004914 filed Feb. 19, 2004 (Applicant—University of Rochester; Inventor—Stephanos Kyrkanides et al.).
Request for Examination filed Jan. 19, 2009 for Japanese Application Serial No. 2007-552370, which claims priority to PCT/US2006/002441 filed Jan. 20, 2006 (Applicant—University of Rochester; Inventor—Stephanos Kyrkanides).
Letters Patent issued Aug. 14, 2008 for New Zealand Application Serial No. 536899, which claims priority to PCT/US2003/013672 filed May 2, 2003 (Applicant—University of Rochester; Inventor—Stephanos Kyrkanides).
Notice of Acceptance of Completed Specification issued Apr. 1, 2008 for New Zealand Application Serial No. 536899, which claims priority to PCT/US2003/013672 filed May 2, 2003 (Applicant—University of Rochester; Inventor—Stephanos Kyrkanides).
Notice of Acceptance issued Jul. 28, 2008 for Australian Application Serial No. 2003234337, which claims priority to PCT/US2003/013672 filed May 2, 2003 (Applicant—University of Rochester; Inventor—Stephanos Kyrkanides).
Response to Examiner's Report filed Jul. 23, 2008 for Australian Application Serial No. 2003234337, which claims priority to PCT/US2003/013672 filed May 2, 2003 (Applicant—University of Rochester; Inventor—Stephanos Kyrkanides).
Response pursuant to Section 45(3) filed Dec. 7, 2006 for Australian Application Serial No. 2003234337, which claims priority to PCT/US2003/013672 filed May 2, 2003 (Applicant—University of Rochester; Inventor—Stephanos Kyrkanides).
Acknowledgement of Request for Examination issued Feb. 25, 2010 for Canadian Application No. 2557595, which claims priority to PCT/US2005/004885 filed on Feb. 16, 2005 (Applicant—University of Rochester; Inventor—Stephanos Kyrkanides).
Voluntary Amendment filed May 21, 2008 for Canadian Application No. 2557595, which claims priority to PCT/US2005/004885 filed on Feb. 16, 2005 (Applicant—University of Rochester; Inventor—Stephanos Kyrkanides).
Examiner's Report issued Oct. 19, 2009 for Australian Application No. 2005214363, which claims priority to PCT/ US2005/004885 filed on Feb. 16, 2005 (Applicant—University of Rochester; Inventor—Stephanos Kyrkanides).
Direction to Request Examination issued Apr. 8, 2008 for Australian Application No. 2005214363, which claims priority to PCT/US2005/004885 filed on Feb. 16, 2005 (Applicant—University of Rochester; Inventor—Stephanos Kyrkanides).
International Preliminary Report on Patentability with Written Opinion issued Jan. 20, 2009 for PCT/US2007/073609 filed Jul. 16, 2007 and published as WO 2008/011381 on Jan. 24, 2008 (Applicant—University of Rochester; Inventor—Stephanos Kyrkandies).

International Search Report issued Jul. 11, 2008 for PCT/US2007/073609 filed Jul. 16, 2007 and published as WO 2008/011381 on Jan. 24, 2008 (Applicant—University of Rochester; Inventor—Stephanos Kyrkanides).

International Preliminary Report on Patentability with Written Opinion issued on Mar. 10, 2009 for PCT/US2006/002441 filed Jan. 20, 2006 and published as WO 2006/079068 on Jul. 27, 2006 (Applicant—University of Rochester; Inventor—Stephanos Kyrkanides).

International Search Report issued May 9, 2008 for PCT/US2006/002441 filed Jan. 20, 2006 and published as WO 2006/079068 on Jul. 27, 2006 (Applicant—University of Rochester; Inventor—Stephanos Kyrkanides).

Notice of Abandonment issued Apr. 19, 2010 for Canadian Patent Application No. 2,555,996, which claims priority to PCT/US2004/004914 filed on Feb. 19, 2003 (Applicant—University of Rochester; Inventor—Stephanos Kyrkanides et al.).

Reminder—Request for Examination issued Oct. 21, 2008 for Canadian Patent Application No. 2,555,996, which claims priority to PCT/US2004/004914 filed on Feb. 19, 2003 (Applicant—University of Rochester; Inventor—Stephanos Kyrkanides et al.).

Voluntary Amendment and Submission of Sequence Listing filed Feb. 19, 2004 for Canadian Patent Application No. 2,555,996, which claims priority to PCT/US2004/004914 filed on Feb. 19, 2003 (Applicant—University of Rochester; Inventor—Stephanos Kyrkanides et al.).

Banerjee P, Boyers MJ, Berry-Kravis E, Dawson G. (1994) Preferential beta-hexosaminidase (Hex) A (alpha beta) formation in the absence of beta-Hex B (beta beta) due to heterozygous point mutations present in beta-Hex beta-chain alleles of a motor neuron disease patient. J Biol Chem. 269(7): 4819-4826.

Brown CA, Mahuran DJ. (1993) beta-Hexosaminidase isozymes from cells cotransfected with alpha and beta cDNA constructs: analysis of the alpha-subunit missense mutation associated with the adult form of Tay-Sachs disease. Am J Hum Genet. 53(2): 497-495.

Chen SR, Pan HL. (2006) Loss of TRPV1-expressing sensory neurons reduces spinal mu opioid receptors but paradoxically potentiates opioid analgesia. J Neurophysiol. 95(5): 3086-3096.

Cowan PJ, Shinkel TA, Fisicaro N, Godwin JW, Bernabéu C, Almendro N, Rius C, Lonie AJ, Nottle MB, Wigley PL, Paizis K, Pearse MJ, d'Apice A. (2003) Targeting gene expression to endothelium in transgenic animals: a comparison of the human ICAM-2, PECAM-1 and endoglin promoters. Xenotransplantation. 10(3): 223-231.

Elvenes J, Andjelkov N, Figenschau Y, Seternes T, Bjorkoy G, Johansen O. (2003) Expression of functional mu-opioid receptors in human osteoarthritic cartilage and chondrocytes. Biochem Biophys Res Commun. 311(1): 202-207.

Ghivizzani SC, Kang R, Georgescu HI, Lechman ER, Jaffurs D, Engle JM, Watkins SC, Tindal MH, Suchanek MK, McKenzie LR, Evans CH, Robbins PD. (1997) Constitutive intra-articular expression of human IL-1 beta following gene transfer to rabbit synovium produces all major pathologies of human rheumatoid arthritis. J Immunol. 159(7): 3604-3612.

Giri R, Selvaraj S, Miller CA, Hofman F, Yan SD, Stern D, Zlokovic BV, Kalra VK. (2002) Effect of endothelial cell polarity on beta-amyloid-induced migration of monocytes across normal and AD endothelium. Am J Physiol Cell Physiol. 283(3): C895-C904.

Goswami MT, Desai KV, Kondaiah P. (2003) Comparative functional analysis of rat TGF-beta1 and *Xenopus laevis* TGF-beta5 promoters suggest differential regulations. J Mol Evol. 57(1): 44-51.

Gu Y, Xu Y, Li GW, Huang LY. (2005) Remote nerve injection of mu opioid receptor adeno-associated viral vector increases antinociception of intrathecal morphine. J Pain. 6(7): 447-454.

Hammer RE, Maika SD, Richardson JA, Tang JP, Taurog J. (1990) Spontaneous inflammatory disease in transgenic rats expressing HLA-B27 and human beta 2m: an animal model of HLA-B27-associated human disorders. Cell. 63(5): 1099-1112.

Notice of Abandonment issued Dec. 27, 2010 for U.S. Appl. No. 10/781,142, which was filed on Feb. 18, 2004 (Inventor—Stephanos Kyrkanides).

Non-Final Office Action issued May 10, 2010 for U.S. Appl. No. 10/781,142, which was filed on Feb. 18, 2004 (Inventor—Stephanos Kyrkanides).

Amendment and Response to Office Action filed Jan. 8, 2010 for U.S. Appl. No. 10/781,142, which was filed on Feb. 18, 2004 (Inventor—Stephanos Kyrkanides).

Final Office Action issued Jul. 8, 2009 for U.S. Appl. No. 10/781,142, which was filed on Feb. 18, 2004 (Inventor—Stephanos Kyrkanides).

Response to Notice of Non-Compliant Amendment filed Feb. 9, 2009 for U.S. Appl. No. 10/781,142, which was filed on Feb. 18, 2004 (Inventor—Stephanos Kyrkanides).

Notice of Non-Compliant Amendment issued Jan. 8, 2009 for U.S. Appl. No. 10/781,142, which was filed on Feb. 18, 2004 (Inventor—Stephanos Kyrkanides).

Amendment and Response under 37 C.F.R. 1.111 filed Sep. 26, 2008 for U.S. Appl. No. 10/781,142, which was filed on Feb. 18, 2004 (Inventor—Stephanos Kyrkanides).

Non-Final Office Action issued Mar. 26, 2008 for U.S. Appl. No. 10/781,142, which was filed on Feb. 18, 2004 (Inventor—Stephanos Kyrkanides).

Declaration under 37 C.F.R. 1.132 filed Mar. 21, 2008 for U.S. Appl. No. 10/781,142, which was filed on Feb. 18, 2004 (Inventor—Stephanos Kyrkanides).

Response to Final Office Action filed Dec. 20, 2007 for U.S. Appl. No. 10/781,142, which was filed on Feb. 18, 2004 (Inventor—Stephanos Kyrkanides).

Amendment and Response to Office Action filed on Oct. 11, 2010 for U.S. Appl. No. 11/506,184, which was filed on Aug. 16, 2006 (Inventor—Stephanos Kyrkanides).

Final Office Action issued on Jun. 11, 2010 for U.S. Appl. No. 11/506,184, which was filed on Aug. 16, 2006 (Inventor—Stephanos Kyrkanides).

Amendment and Response to Non-Final Office Action filed on Mar. 3, 2010 for U.S. Appl. No. 11/506,184, which was filed on Aug. 16, 2006 (Inventor—Stephanos Kyrkanides).

Non-Final Office Action issued on Sep. 3, 2009 for U.S. Appl. No. 11/506,184, which was filed on Aug. 16, 2006 (Inventor—Stephanos Kyrkanides).

Response to Restriction Requirement filed on Jun. 10, 2009 for U.S. Appl. No. 11/506,184, which was filed on Aug. 16, 2006 (Inventor—Stephanos Kyrkanides).

Restriction Requirement issued on Dec. 10, 2008 for U.S. Appl. No. 11/506,184, which was filed on Aug. 16, 2006 (Inventor—Stephanos Kyrkanides).

Notice of Abandonment issued Jun. 23, 2009 for U.S. Appl. No. 10/978,927, which was filed on Nov. 1, 2004 (Inventor—Stephanos Kyrkanides et al.).

Notice of Appeal filed Oct. 14, 2008 for U.S. Appl. No. 10/978,927, which was filed on Nov. 1, 2004 (Inventor—Stephanos Kyrkanides et al.).

Advisory Action issued Oct. 8, 2008 for U.S. Appl. No. 10/978,927, which was filed on Nov. 1, 2004 (Inventor—Stephanos Kyrkanides et al.).

Response to Office Action filed Sep. 18, 2008 for U.S. Appl. No. 10/978,927, which was filed on Nov. 1, 2004 (Inventor—Stephanos Kyrkanides et al.).

Final Office Action issued Apr. 11, 2008 for U.S. Appl. No. 10/978,927, which was filed on Nov. 1, 2004 (Inventor—Stephanos Kyrkanides et al.).

Final Office Action issued Dec. 14, 2010 for U.S. Appl. No. 10/546,179, which was filed on Aug. 8, 2006 (Inventor—Stephanos Kyrkanides et al.).

Amendment and Response to Office Action filed Oct. 12, 2010 for U.S. Appl. No. 10/546,179, which was filed on Aug. 8, 2006 (Inventor—Stephanos Kyrkanides et al.).

Non-Final Office Action issued Jun. 11, 2010 for U.S. Appl. No. 10/546,179, which was filed on Aug. 8, 2006 (Inventor—Stephanos Kyrkanides et al.).

Amendment and Response to Office Action filed Mar. 8, 2010 for U.S. Appl. No. 10/546,179, which was filed on Aug. 8, 2006 (Inventor—Stephanos Kyrkanides et al.).

Non-Final Office Action issued Oct. 7, 2009 for U.S. Appl. No. 10/546,179, which was filed on Aug. 8, 2006 (Inventor—Stephanos Kyrkanides et al.).

Response to Restriction Requirement filed Jul. 29, 2009 for U.S. Appl. No. 10/546,179, which was filed on Aug. 8, 2006 (Inventor—Stephanos Kyrkanides et al.).
Restriction Requirement issued Apr. 3, 2009 for U.S. Appl. No. 10/546,179, which was filed on Aug. 8, 2006 (Inventor—Stephanos Kyrkanides et al.).
Final Office Action issued Dec. 10, 2010 for U.S. Appl. No. 11/667,392, which was filed on Mar. 4, 2008 (Inventor—Stephanos Kyrkanides et al.).
Amendment and Response to Office Action filed Oct. 1, 2010 for U.S. Appl. No. 11/667,392, which was filed on Mar. 4, 2008 (Inventor—Stephanos Kyrkanides et al.).
Declaration under 37 C.F.R. 1.111 filed Oct. 1, 2010 for U.S. Appl. No. 11/667,392, which was filed on Mar. 4, 2008 (Inventor—Stephanos Kyrkanides et al.).
Non-Final Office Action issued Apr. 2, 2010 for U.S. Appl. No. 11/667,392, which was filed on Mar. 4, 2008 (Inventor—Stephanos Kyrkanides et al.).
Response to Restriction Requirement filed Feb. 19, 2010 for U.S. Appl. No. 11/667,392, which was filed on Mar. 4, 2008 (Inventor—Stephanos Kyrkanides et al.).
Restriction Requirement issued Oct. 19, 2009 for U.S. Appl. No. 11/667,392, which was filed on Mar. 4, 2008 (Inventor—Stephanos Kyrkanides et al.).
Noting of Loss of Rights pursuant to Rule 112(1) EPC issued Jan. 25, 2010 for EP Application Serial No. 05723138.3 (EP Publication No. 1718659), which claims priority to PCT/US2005/004885 filed on Feb. 16, 2005 (Applicant—University of Rochester; Inventor—Stephanos Kyrkanides).
Communication pursuant to Article 94(3) EPC issued Apr. 7, 2009 for EP Application Serial No. 05723138.3 (EP Publication No. 1718659), which claims priority to PCT/US2005/004885 filed on Feb. 16, 2005 (Applicant—University of Rochester; Inventor—Stephanos Kyrkanides).
Proceeding pursuant to Rule 70(2) EPC issued Dec. 1, 2008 for EP Application Serial No. 05723138.3 (EP Publication No. 1718659), which claims priority to PCT/US2005/004885 filed on Feb. 16, 2005 (Applicant—University of Rochester; Inventor—Stephanos Kyrkanides).
Supplementary European Search Report issued Nov. 12, 2008 for EP Application Serial No. 05723138.3 (EP Publication No. 1718659), which claims priority to PCT/US2005/004885 filed on Feb. 16, 2005 (Applicant—University of Rochester; Inventor—Stephanos Kyrkanides).
Communication regarding Expiry of Time Limit for Notice of Opposition issued Aug. 25, 2010 for EP Application Serial No. 03728653.1 (EP Publication No. 1501465), which claims priority to PCT/US2003/013672 filed on May 2, 2003 (Applicant—University of Rochester; Inventor—Stephanos Kyrkanides).
Decision to Grant a European Patent pursuant to Article 97(1) EPC issued Sep. 24, 2009 for EP Application Serial No. 03728653.1 (EP Publication No. 1501465), which claims priority to PCT/US2003/013672 filed on May 2, 2003 (Applicant—University of Rochester; Inventor—Stephanos Kyrkanides).
Decision on the Request for Further Processing under Rule 135(3) issued Jul. 21, 2009 for EP Application Serial No. 03728653.1 (EP Publication No. 1501465), which claims priority to PCT/US2003/013672 filed on May 2, 2003 (Applicant—University of Rochester; Inventor—Stephanos Kyrkanides).
Request for Further Processing filed Jul. 7, 2009 for EP Application Serial No. 03728653.1 (EP Publication No. 1501465), which claims priority to PCT/US2003/013672 filed on May 2, 2003 (Applicant—University of Rochester; Inventor—Stephanos Kyrkanides).
Communication under Rule 71(3) issued Nov. 20, 2008 for EP Application Serial No. 03728653.1 (EP Publication No. 1501465), which claims priority to PCT/US2003/013672 filed on May 2, 2003 (Applicant—University of Rochester; Inventor—Stephanos Kyrkanides).
Reply to Communication filed Jun. 3, 2008 for EP Application Serial No. 03728653.1 (EP Publication No. 1501465), which claims priority to PCT/US2003/013672 filed on May 2, 2003 (Applicant—University of Rochester; Inventor—Stephanos Kyrkanides).
Invitation pursuant to Article 94(3) and Rule 71(1) EPC issued Mar. 28, 2008 for EP Application Serial No. 03728653.1 (EP Publication No. 1501465), which claims priority to PCT/US2003/013672 filed on May 2, 2003 (Applicant—University of Rochester; Inventor—Stephanos Kyrkanides).
Reply to Communication file Feb. 6, 2008 for EP Application Serial No. 03728653.1 (EP Publication No. 1501465), which claims priority to PCT/US2003/013672 filed on May 2, 2003 (Applicant—University of Rochester; Inventor—Stephanos Kyrkanides).
Noting of Loss of Rights pursuant to Rule 112(1) EPC issued Jan. 22, 2009 for Application Serial No. 04712863.2 (EP Publication No. 1599231), which claims priority to PCT/US2004/004914 filed on Feb. 19, 2004 (Applicant—University of Rochester; Inventor—Stephanos Kyrkanides et al.).
Communication pursuant to Article 94(3) EPC issued Jun. 6, 2008 for Application Serial No. 04712863.2 (EP Publication No. 1599231), which claims priority to PCT/US2004/004914 filed on Feb. 19, 2004 (Applicant—University of Rochester; Inventor—Stephanos Kyrkanides et al.).
Response to EPO Form 1224 filed Mar. 12, 2008 for Application Serial No. 04712863.2 (EP Publication No. 1599231), which claims priority to PCT/US2004/004914 filed on Feb. 19, 2004 (Applicant—University of Rochester; Inventor—Stephanos Kyrkanides et al.).
Proceeding pursuant to Rule 70(2) EPC issued Jan. 7, 2008 for Application Serial No. 04712863.2 (EP Publication No. 1599231), which claims priority to PCT/US2004/004914 filed on Feb. 19, 2004 (Applicant—University of Rochester; Inventor—Stephanos Kyrkanides et al.).
Heikinheimo O, Kekkonen R. (1993) Dose-response relationships of RU 486. Ann Med. 25(1): 71-76.
Hennecke M, Kwissa M, Metzger K, Oumard A, Kröger A, Schirmbeck R, Reimann J, Hauser H. (2001) Composition and arrangement of genes define the strength of IRES-driven translation in bicistronic mRNAs. Nucleic Acids Res. 29 (16): 3327-3334.
Hennighausen L, Fleckenstein B. (1986) Nuclear factor 1 interacts with five DNA elements in the promoter region of the human cytomegalovirus major immediate early gene. EMBO J. 5(6): 1367-1371.
Hobbs SM. Artificial DNA. Bicistronic eukaryotic expression vector pSVIRES-N. Locus AJ000156. Available at http://www.ncbi.nlm.nih.gov/nuccore/2329859.
Iwakura Y. (2002) Roles of IL-1 in the development of rheumatoid arthritis: consideration from mouse models. Cytokine Growth Factor Rev. 13(4-5): 341-355.
Jin HK, Schuchman EH. (2003) Ex vivo gene therapy using bone marrow-derived cells: combined effects of intracerebral and intravenous transplantation in a mouse model of Niemann-Pick disease. Mol Ther. 8(6): 876-885.
Kim DG, Kang HM, Jang SK, Shin HS. (1992) Construction of a bifunctional mRNA in the mouse by using the internal ribosomal entry site of the encephalomyocarditis virus. Mol Cell Biol. 12(8): 3636-3643.
Kistner A, Gossen M, Zimmermann F, Jerecic J, Ullmer C, Lübbert H, Bujard H. (1996) Doxycycline-mediated quantitative and tissue-specific control of gene expression in transgenic mice. Proc Natl Acad Sci U S A. 93(20): 10933-10938.
Klimatcheva E, Rosenblatt JD, Planelles V. (1999) Lentiviral vectors and gene therapy. Front Biosci. 4: D481-D496.
Kost TA, Theodorakis N, Hughes S. (1983) The nucleotide sequence of the chick cytoplasmic beta-actin gene. Nucleic Acids Res. 11(23): 8287-8301.
Invitrogen, ViraPower™ HiPerform™ T-Rex™, Gateway® Expression System, Gateway®-adapted lentiviral systems for regulated, high-level expression in dividing and non-dividing mammalian cells, Catalog No. A11141.
Lai YC, Shaftel SS, Miller JN, Tallents RH, Chang Y, Pinkert CA, Olschowka JA, Dickerson IM, Puzas JE, O'Banion MK, Kyrkanides S. (2006) Intraarticular induction of interleukin-1beta expression in the adult mouse, with resultant temporomandibular joint pathologic changes, dysfunction, and pain. Arthritis Rheum. 54(4): 1184-1197.
Laporte J, Malet I, Andrieu T, Thibault V, Toulme JJ, Wychowski C, Pawlotsky JM, Huraux JM, Agut H, Cahour A. (2000) Comparative analysis of translation efficiencies of hepatitis C virus 5' untranslated regions among intraindividual quasispecies present in chronic infection: opposite behaviors depending on cell type. J Virol. 74(22): 10827-10833.

Lichtler A, Stover ML, Angilly J, Kream B, Rowe DW. (1989) Isolation and characterization of the rat alpha 1(I) collagen promoter. Regulation by 1,25-dihydroxyvitamin D. J Biol Chem. 264(6): 3072-3077.

Lim WH, Toothman J, Miller JH, Tallents RH, Brouxhon SM, Olschowka ME, Kyrkanides S. (2009) IL-1beta inhibits TGFbeta in the temporomandibular joint. J Dent Res. 88(6): 557-562.

Makar TK, Wilt S, Dong Z, Fishman P, Mouradian MM, Dhib-Jalbut S. (2002) IFN-beta gene transfer into the central nervous system using bone marrow cells as a delivery system. J Interferon Cytokine Res. 22(7): 783-791.

Mizuguchi H, Xu Z, Ishii-Watabe A, Uchida E, Hayakawa. (2000) IRES-dependent second gene expression is significantly lower than cap-dependent first gene expression in a bicistronic vector. Mol Ther. 1(4): 376-382.

Nakano K, Migita M, Mochizuki H, Shimada T. (2001) Differentiation of transplanted bone marrow cells in the adult mouse brain. Transplantation. 71(12): 1735-1740.

Nicolau C, Le Pape A, Soriano P, Fargette F, Juhel MF. (1983) in vivo expression of rat insulin after intravenous administration of the liposome-entrapped gene for rat insulin I. Proc Natl Acad Sci U S A. 80(4): 1068-1072.

Niwa H, Yamamura K, Miyazaki J. (1991) Efficient selection for high-expression transfectants with a novel eukaryotic vector. Gene. 108(2): 193-199.

Rickard DJ, Kazhdan I, Leboy PS. (1995) Importance of 1,25-dihydroxyvitamin D3 and the nonadherent cells of marrow for osteoblast differentiation from rat marrow stromal cells. Bone. 16(6): 671-678.

Rossi FM, Guicherit OM, Spicher A, Kringstein AM, Fatyol K, Blakely BT, Blau HM. (1998) Tetracycline-regulatable factors with distinct dimerization domains allow reversible growth inhibition by p16. Nat Genet. 20(4): 389-393.

Sauer B. (1998) Inducible gene targeting in mice using the Cre/lox system. Methods. 14(4):381-392.

Sawada M, Imai F, Suzuki H, Hayakawa M, Kanno T, Nagatsu T. (1998) Brain-specific gene expression by immortalized microglial cell-mediated gene transfer in the mammalian brain. Febs Lett. 433(1-2): 37-40.

Schuette CG, Doering T, Kolter T, Sandhoff K. (1999) The glycosphingolipidoses—from disease to basic principles of metabolism. Biol Chem. 380(7-8): 759-766.

Shaftel SS, Kyrkanides S, Olschowka JA, Miller JN, Johnson RE, O'Banion MK. (2007) Sustained hippocampal IL-1 beta overexpression mediates chronic neuroinflammation and ameliorates Alzheimer plaque pathology. J Clin Invest. 117(6): 1595-1604.

Sigma Product Information Sheet for 4-Methylumbellifery1-7-(6-sulfo-2-acetamido-2-deoxy-(3-D-glucopyranoside) sodium salt.

Somia N, Verma IM.(2000) Gene therapy: trials and tribulations. Nat Rev Genet. 1(2): 91-99.

Terada N, Hamazaki T, Oka M, Hoki M, Mastalerz DM, Nakano Y, Meyer EM, Morel L, Petersen BE, Scott EW. (2002) Bone marrow cells adopt the phenotype of other cells by spontaneous cell fusion. Nature. 416(6880): 542-545.

Wang Y, O'Malley BW Jr, Tsai SY, O'Malley BW. (1994) A regulatory system for use in gene transfer. Proc Natl Acad Sci U S A. 91(17): 8180-8184.

Zhang X, Bao L, Guan JS. (2006) Role of delivery and trafficking of delta-opioid peptide receptors in opioid analgesia and tolerance. Trends Pharmacol Sci. 27(6): 324-329.

Response to Communication pursuant to Article 94(3) filed on Mar. 30, 2011 for Application Serial No. 06719341.7 (EP1883427), which claims priority to PCT/US2006/002441 filed on Jan. 20, 2006 (Applicant—University of Rochester; Inventor—Stephanos Kyrkanides).

Preliminary Amendment filed Sep. 9, 2008 for U.S. Appl. No. 12/282,251, which claims priority to PCT/IB2007/004351 filed on Mar. 9, 2007 (Inventors: Kyrkanides et al.).

* cited by examiner

COMPOSITIONS AND METHODS FOR STUDYING AND TREATING INFLAMMATORY DISEASES AND DISORDERS

I. CROSS-REFERENCE TO RELATED APPLICATIONS

This application claims benefit of U.S. Provisional Application No. 60/646,099 filed Jan. 20, 2005, which is hereby incorporated herein by reference in its entirety.

II. BACKGROUND

There are a number of diseases and disorders related to inflammation, as well as a number of pathways and molecules related to inflammation. Disclosed are methods of treating inflammatory disease using compositions and methods identified herein.

III. SUMMARY

In accordance with the purposes of this invention, as embodied and broadly described herein, this invention, in one aspect, relates to vector constructs that can be used to inhibit inflammation and treat subjects with inflammatory disease.

Disclosed are methods and compositions related to polypeptides, nucleic acids, vectors, cells, transgenic animals for the study and treatment of inflammatory diseases and disorders, and methods of making and using thereof.

IV. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 shows IL-1$\beta^{XAT}$—an excisionally activated transgene. IL-1$\beta^{XAT}$ is a bicistronic gene comprized of the cytomegalovirus promoter (CMV), followed by a "floxed" transcriptional termination cassette (▶STOP▶), the human IL-1 RA peptide secretion signal (ss) fused to the mature human IL-1β ORF (ssIL-1β), the reporter lacZ gene and the bovine growth hormone poly A mRNA tail (pA). An internal ribosomal entry signal facilitates translation and expression of the second ORF, lacZ, at approximately 45% of the first ORF.

Figure 2:
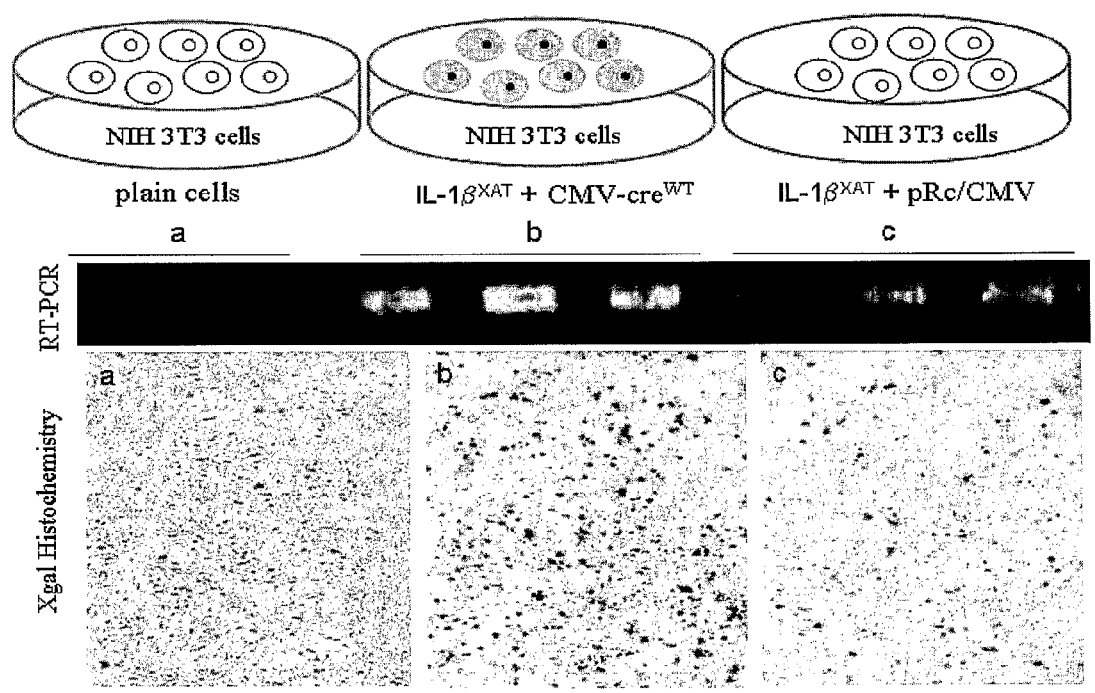

FIG. 2 shows Cre-mediated activation of the inducible IL-1$\beta^{XAT}$ transgene. The IL-1$\beta^{XAT}$ gene was transfected into the murine fibroblast NIH 3T3 cell line. Transient expression of Cre recombinase following co-transfection of the expression vector pRc/CMV-CreWT resulted in IL-1$\beta^{XAT}$ activation and higher levels of IL-1β mRNA detected by RT-PCR, as well as lacZ expression assessed by X-gal histochemistry (10×). Control conditions included (a) plain NIH 3T3 cells, as well as (b) cells co-transfected with IL-1$\beta^{XAT}$ and (c) the pRc/CMV-backbone vector, which displayed background levels of IL-1β and lacZ expression presumably due to minimal spontaneous read-through from the strong CMV promoter.

Figure 3:
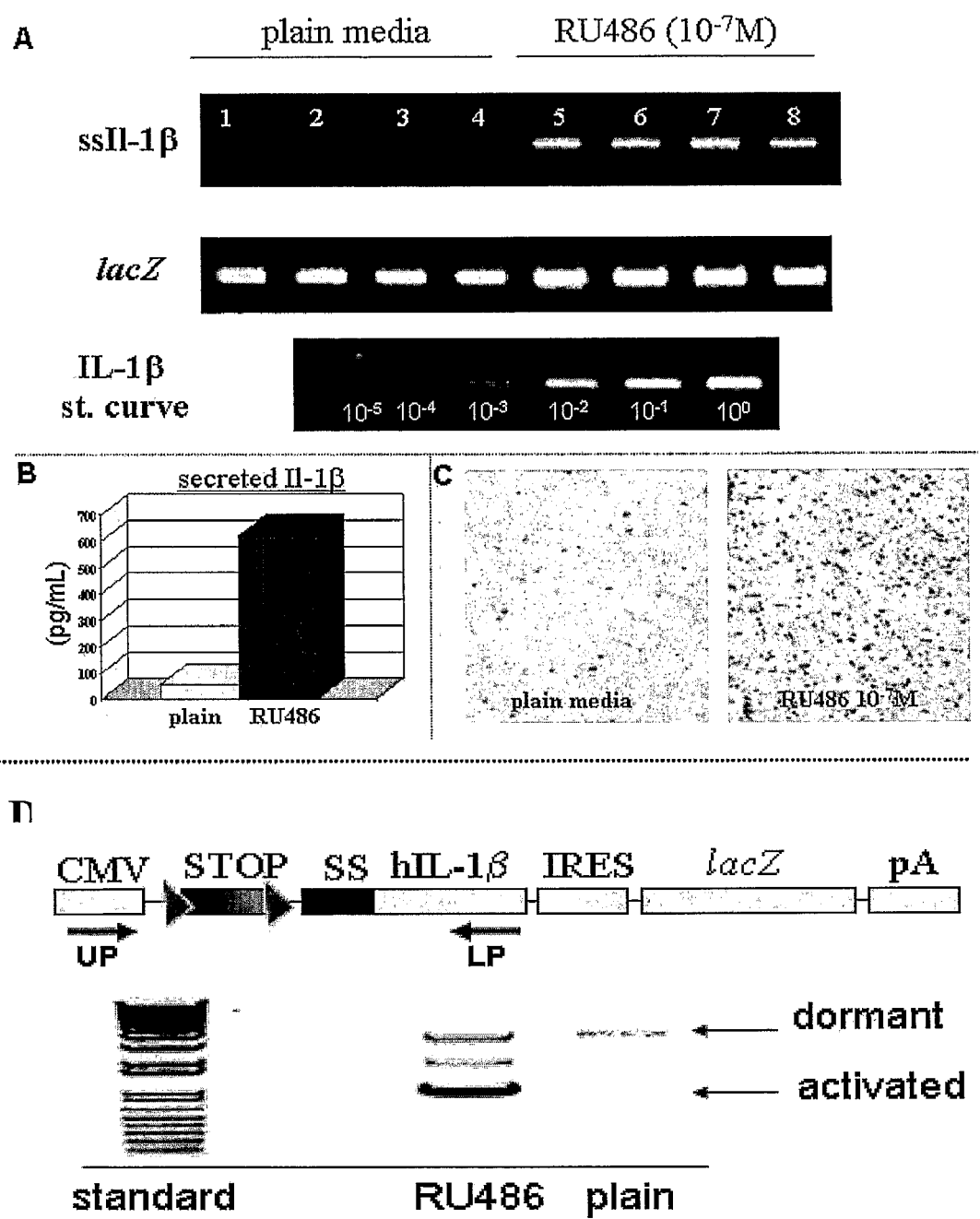

FIG. 3 shows CrePr induces loxP-directed IL-1$\beta^{XAT}$ excisional recombination and gene activation. The IL-1$\beta^{XAT}$ gene was transiently transfected into 293HGLVP/CrePr cells and the expression of IL-1β and lacZ were evaluated following RU486 (10-7 M) administration. (A) Activation of Cre recombinase by RU486 resulted in up-regulation of both IL-1β and lacZ mRNA as assessed by RT-PCR. For demonstration purposes, an IL-1β standard curve (1 μg-10-5 μg) is included in this panel. (B) Concomitantly, significantly higher levels of secreted IL-1β protein were found in the supernatant media of RU486-treated cells as assessed by ELISA for human IL-1β. (C) The expression of the reporter gene β-galactosidase was also confirmed by Xgal histochemistry: naïve cells present only minimal levels of background staining, whereas addition of RU486 in the culture media resulted in significant increase in the number of X-gal positive cells. (D) IL-1$\beta^{XAT}$ excisional DNA recombination was confirmed by PCR of genomic DNA extracts from cells treated with plain growth media as well as media containing RU486 (10-7M) using a primer set (UP & LP) that flanked the ▶STOP▶ sequence. PCR amplification of cells under plain media yielded a full-length product (~3 Kb), indicative of a dormant IL-1$\beta^{XAT}$ state. In contrast, RU486-treated cells yielded a PCR product of 1 Kb in size, indicative of DNA recombination and excision of the ▶STOP▶ cassette.

Figure 4:
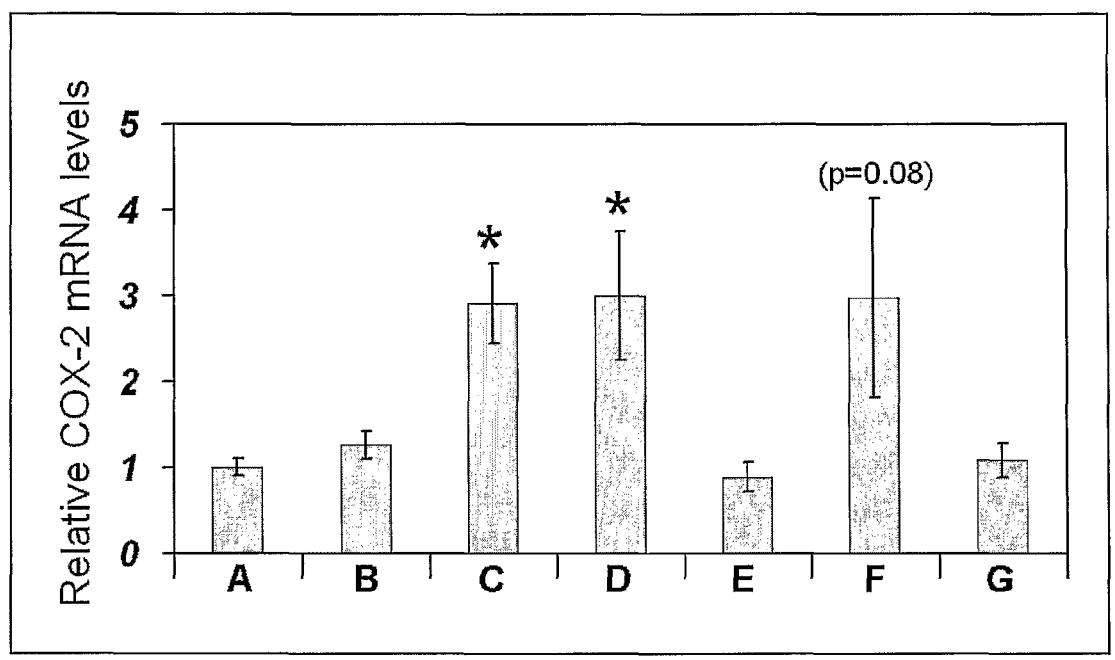

FIG. 4 shows IL-1$\beta^{XAT}$ activation results in expression of biologically potent IL-1β cytokine. The biological potency of the transgene-derived IL-1β cytokine was evaluated in vitro as follows. Murine fibroblasts were treated with conditioned media collected from cultured NIH 3T3 cells that had been previously transfected with Cre-induced IL-1$\beta^{XAT}$ as described in FIG. 2 above (co-transfection with the pRc/CMV-creWT vector). COX-2 transcript levels were measured as previously described in the target cells (murine fibroblasts) and was employed as a measure of IL-1β biological potency. Conditioned media were incubated with the neutralizing antibodies for 2 hours at 37° C. prior to addition to target cells. (A) Conditioned medium collected form naïve NIH 3T3 cells (containing <3.9 pg/mL IL-1β as determined by ELISA) were placed on murine fibroblasts, which in turn showed low levels of murine COX-2 mRNA. Moreover, (B) conditioned medium from NIH 3T3 cells transfected with IL-1$\beta^{XAT}$+pRc/CMV-backbone vector (contained <3.9 pg/mL hIL-1β) also showed low levels of murine COX-2 mRNA. In contrast, (C) conditioned medium from IL-1$\beta^{XAT}$+pRc/CMV-CreWT transfected NIH 3T3 cells (1 ng/mL hIL-1β) significantly induced COX-2 mRNA in the target cells; (D) pre-incubation of the conditioned medium with a control rabbit IgG antibody (5 μg/mL IgG1 isotype) had minimal effects on COX-2 regulation. However, (E) pre-incubation of the conditioned medium with a rabbit anti-hIL-1β (5 μg/mL IgG1) antibody attenuated the COX-2 induction. (F) Positive control: additional of human recombinant IL-1β (1 ng/mL+5 μg IgG1 isotype). (G) human recombinant IL-1β pre-incubated with 5 μg/mL neutralizing antibody. Results are shown as fold induction of COX-2 mRNA relative to group A. In conclusion, this experiment demonstrated that activation of the IL-1$\beta^{XAT}$ gene results in production of biologically potent IL-1β and subsequently up-regulation of the inducible COX-2. (N=3). *p<0.05; S.E.M.

Figure 5:
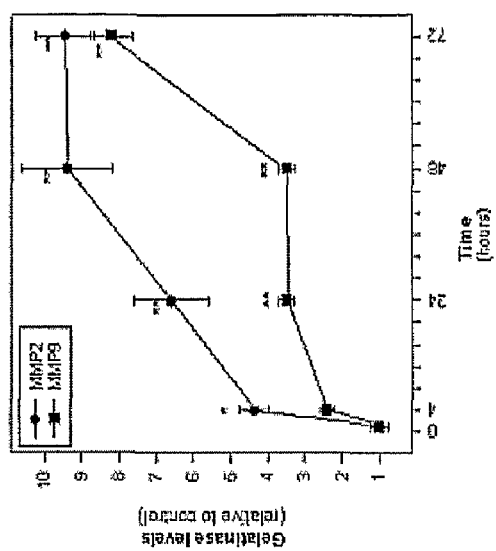
Figure 5:
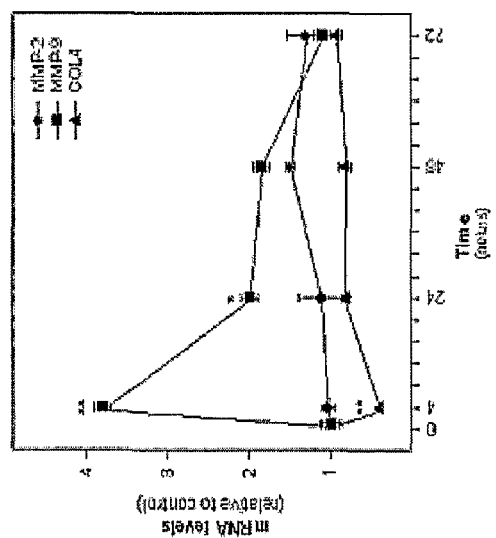
Figure 5:
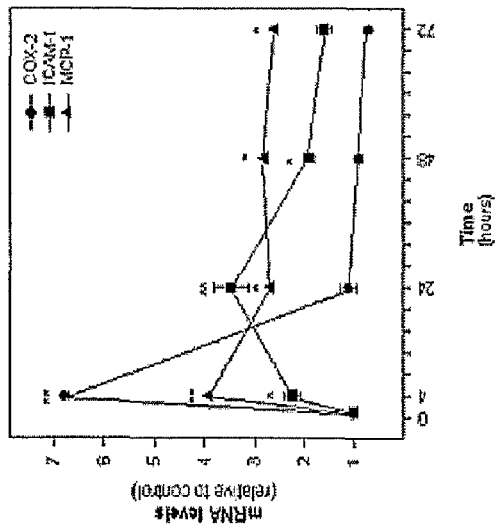

FIG. 5 shows IL-1β induces inflammation-related genes. The effects of IL-1β were evaluated in vitro utilizing primary rat endothelial cell cultures as a representative rodent cell type. In this experiment, murine IL-1β (10 ng/mL) was administered to cultured primary cells, and subsequently examined for the regulation of several inflammation-related genes at the transcript level over the course of 72 hours. These molecules include (A) the inducible isoform of cyclooxygenase (COX-2), intercellular adhesion molecule-1 (ICAM-1) and monocyte chemoattractant protein-1 (MCP-1), as well as (B) the collagenase-A (MMP-2) and -B (MMP-9). Panel (C) depicts enzyme activity levels of MMP-2 and MMP-9 as evaluated by zymography.

Figure 6:
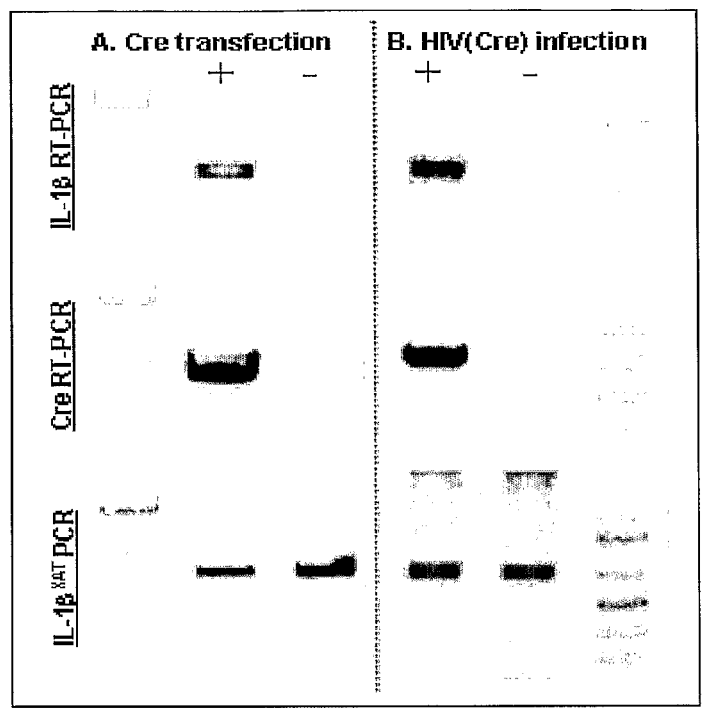

FIG. 6 shows Cre-mediated activation of the COLL1-IL1$\beta^{XAT}$ gene. The 3.6 Kb promoter of the A1 chain of procollagen I gene, which has been shown to target gene expression in bone and cartilage, drove the expression of the IL-1$\beta_{XAT}$ gene in NIH 3T3 stable cell line following trasfection with the pRc/CMV-CreWT vector and infection with the HIV(Cre) virus. Panel (A) depicts transfection (+) of such a stable cell line with pRc/CMV-CreWT, leading to expression of human IL-1β expression concomitantly with Cre recombinase as detected by RT-PCR. In contrast, untreated cells (−) were characterized by the absence of IL-1β and Cre recombinase. Panel (B) depicts similar IL-1β and Cre expression as assessed by RT-PCR following infection of the COLL1-IL1$\beta^{XAT}$ cell line with the HIV(Cre) virus. The presence of IL-1$\beta^{XAT}$ in the cells was confirmed by PCR as shown.

Figure 7:
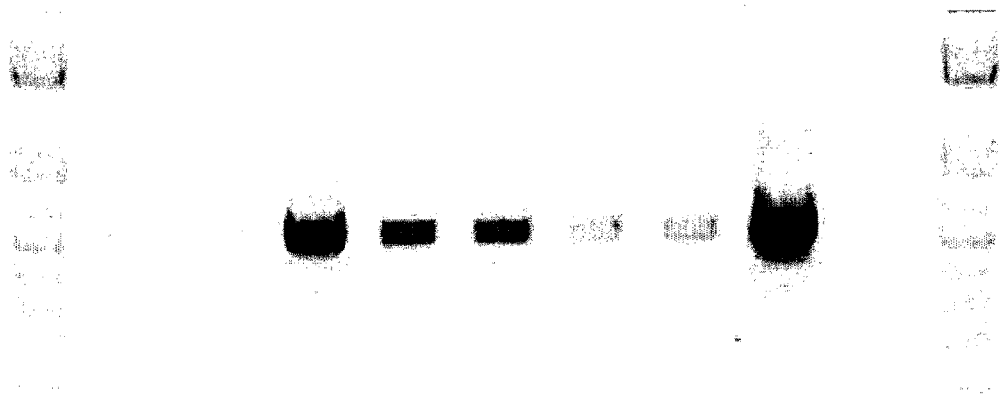

FIG. 7 shows COLL1A1-IL-1$\beta^{XAT}$ transgenic mice. Two series of micro-injections yielded 3 strong candidate transgenic COLL1A1-IL-1$\beta^{XAT}$ mouse lines: #4, #11 and #12. This figure depicts PCR amplification of the transgene using a set of primers that also amplify the endogenous murine IL-1β gene at low levels. Transgene transmission was examined in the offspring of #4, 11 and 12 transgenic founders. F2 mice were bilaterally injected with FIV(cre) into the knee joint and are being monitored weekly for changes in locomotive behavior and mass. c=control; 4, 11, 12, 13, 14=Transgenic mouse lines; +=PCR positive control; −−=PCR primers control.

Figure 8:
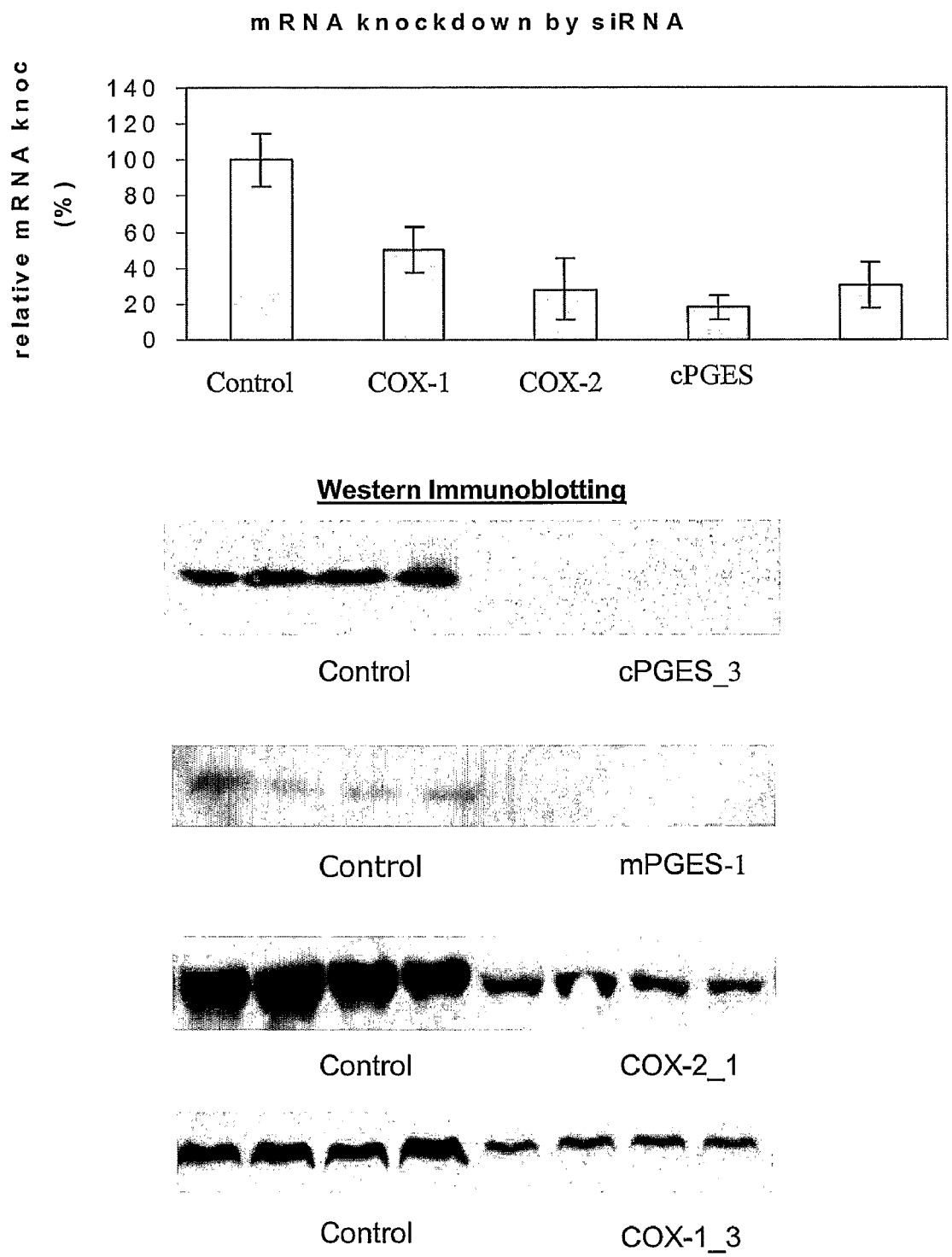

FIG. 8 shows mRNA knockdown by siRNA. siRNA knockdown of mRNA's encoding genes of the Prostaglandin E2 inflammatory pathway. NIH3T3's were transfected under standard condition with 100-200 nM chemically synthesized siRNA species and total RNA was collected 60 hrs later. mRNA knockdown was determined using QRT-PCR. Western immunoblotting was used to demonstrate siRNA knockdown of cPGES, mPGES, COX-2, and COX-1 protein. NIH3T3 cells were transfected with 200 nM of chemically synthesized siRNA complementary to the cPGES, mPGES, COX-2, and COX-1, and total protein collected 60 hrs later. Samples were probed with an anti-mouse cPGES, mPGES, COX-2, and COX-1 antibody, respectively.

Figure 9:
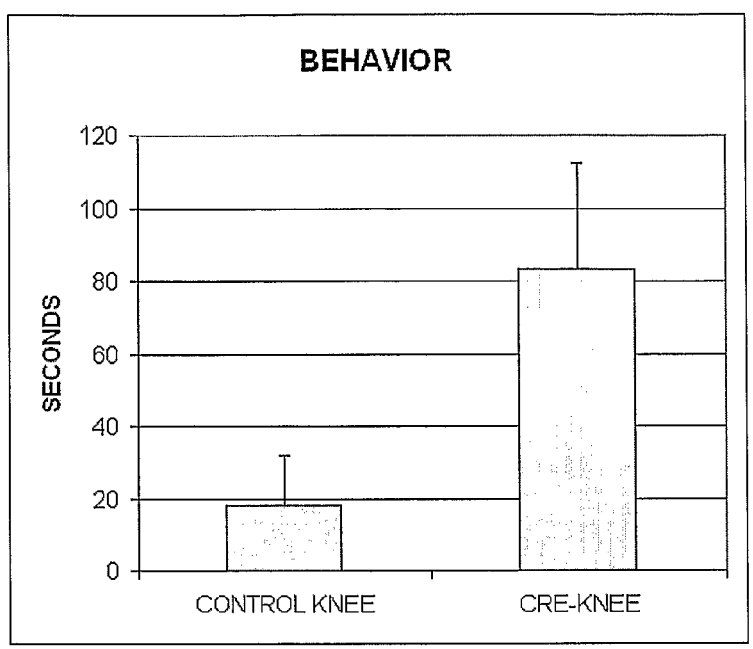

FIG. 9 shows behavioral changes in Col1-IL1$\beta^{XAT}$ mice after injection of FIV(Cre) in the knees. A group of Col1$\beta^{XAT}$ transgenic mice (N=3) received a single intra-articular injection of $10^6$ infectious particles of FIV(Cre) in the right and left knees at 2 months of age. In addition, a second group of mice (N=3) received saline injection and served as controls. During a session, each mouse was videotaped for 1 hour. The tape was then transferred digitally to a computer and analyzed in 20 periods of 3 minutes each. The duration of each mouse displaying grooming and licking was recorded and summed as seconds. The analysis of the behaviors was made by an investigator who was blind to the animal group assignment. Statistical analysis was performed by t-Test. Error bars=SEM. *=P<0.05.

Figure 10:
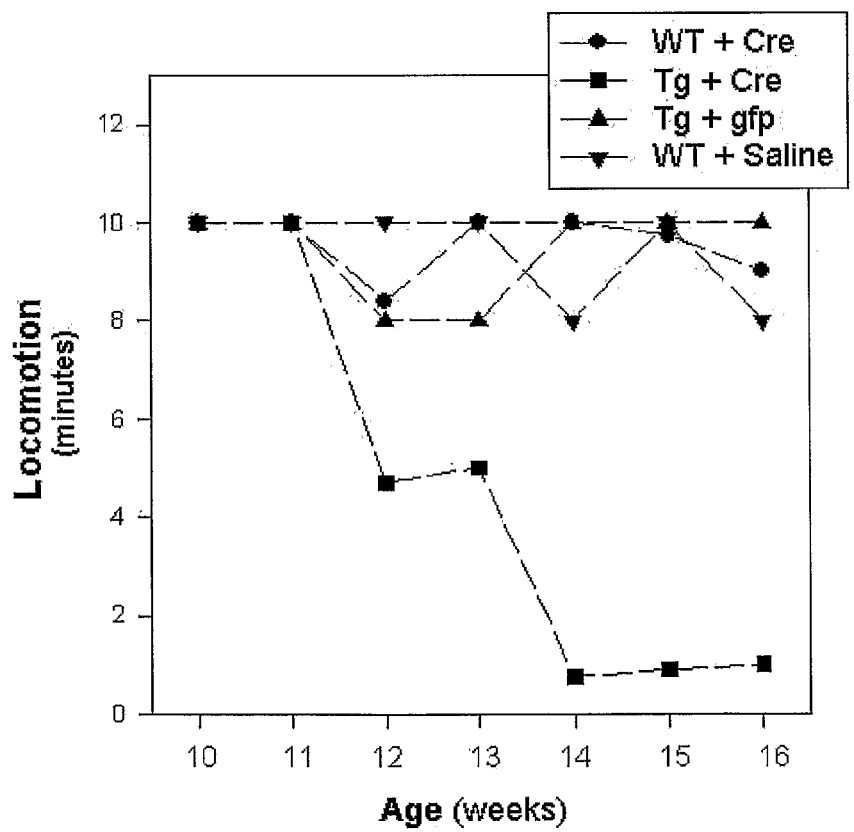

FIG. 10 shows locomotive deterioration in Col1-IL1$\beta^{XAT}$ mice after injection of FIV(Cre) in the knees. Four groups of mice (N=3) were evaluated in terms of locomotive behavior by the rotorod appliance (Columbus Instruments, Columbus Ohio) and the lapse time until the mice well off the rotating cylinder (20 rpm) was recorded. The mice were evaluated over a period of 8 weeks following the intra-articular injections (8 wks-16 wks of age).

Figure 11:
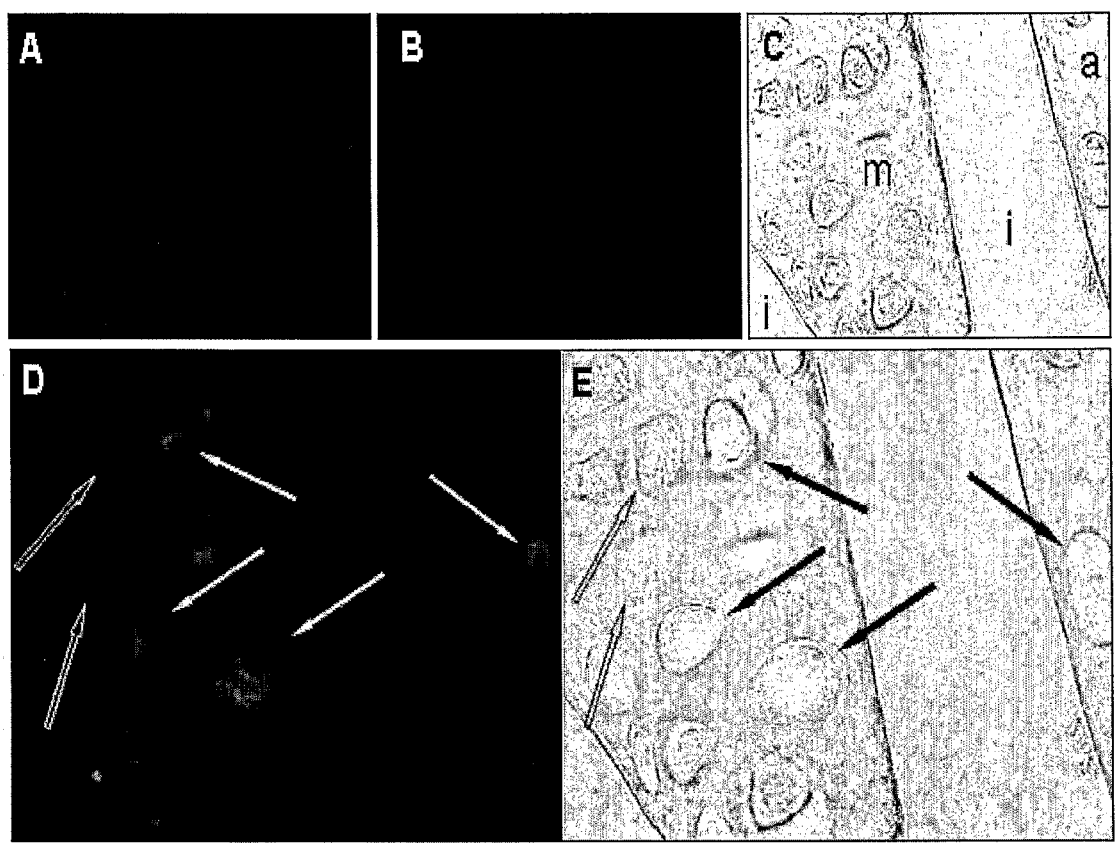

FIG. 11 shows FIV(Cre) injection in the knee of Col1-IL1$\beta^{XAT}$ mice resulted in transgene induction. Immunocytochemical detection of the reporter gene β-galactosidase was employed to confirm the activation of the Col1-IL1$\beta^{XAT}$ transgene by FIV(Cre) in this mouse model using antibodies raised against β-galactosidase and Cre recombinase. (A) FICT-conjugated immu-nodetection of β-galactosidase, (B) Texas Red-conjugated immunodetection of Cre recombinase, and (C) B/W image of the same microscopic field. (D) Overlap of panels A+B, and (E) overlap of panels A+B+C demonstrating co-expression of β-galactosidase and Cre recombinase in vivo (solid arrows). All images were captured at a magnification of 20×. "m"=meniscus; "a"=articular surface; "I"=intra-articular space.

Figure 12:
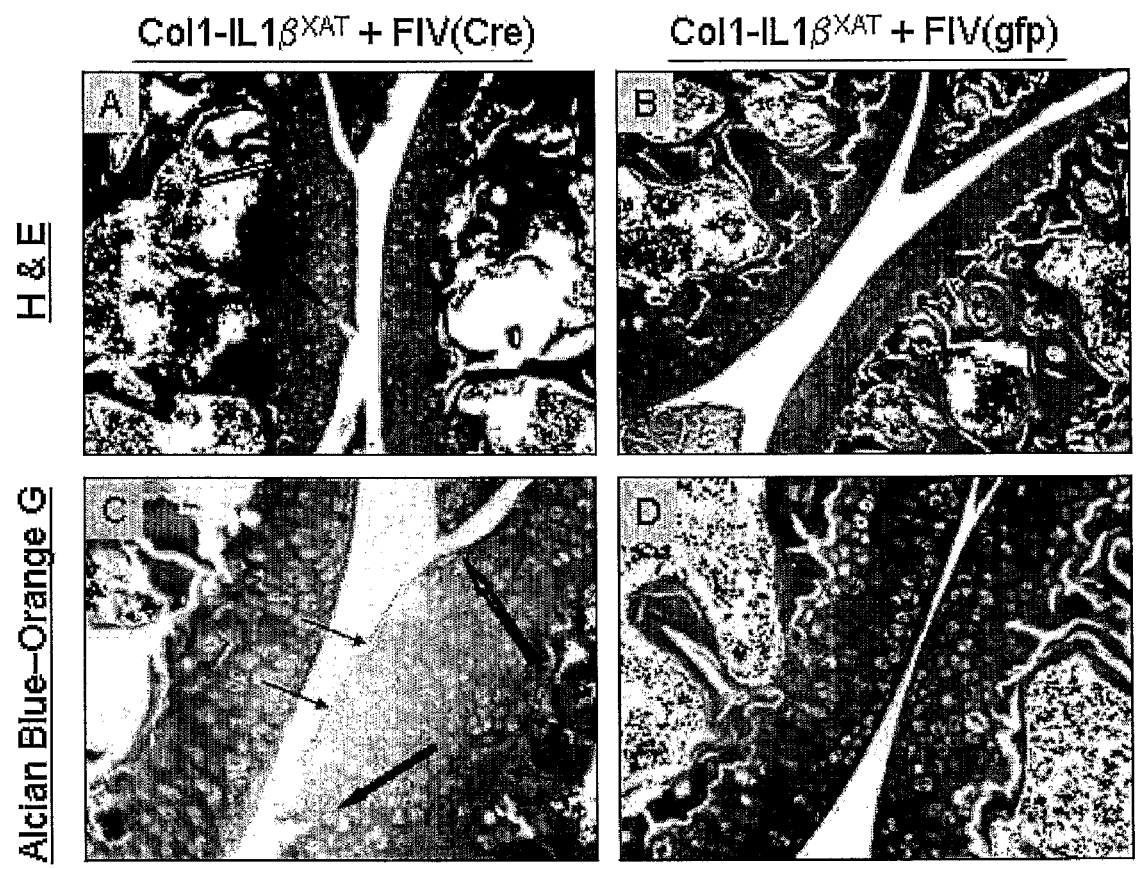

FIG. 12 shows arthritic changes in the knee joint of Col1-IL1$\beta^{XAT}$ mice following injection of FIV(Cre). (A) H&E staining of a knee section harvested from a 4 month old Col1-IL1$\beta^{XAT}$ transgenic mouse injected with FIV(Cre) revealed the formation of fibrillations (solid arrow) and of an articular lip (open arrow). In contrast, (B) a transgenic mouse that received the control vector FIV(GFP) did not develop such anatomic aberrations. (C) Alcian blue/orange semi-quantitative evaluation showed a decrease in cartilage and bone density in the Col1-IL1$\beta^{XAT}$+FIV(Cre) knees compared to (D) controls. Moreover, increased cloning along with thickening of the articular surfaces was observed in the experimental animals (indicated by small arrows).

Figure 13:
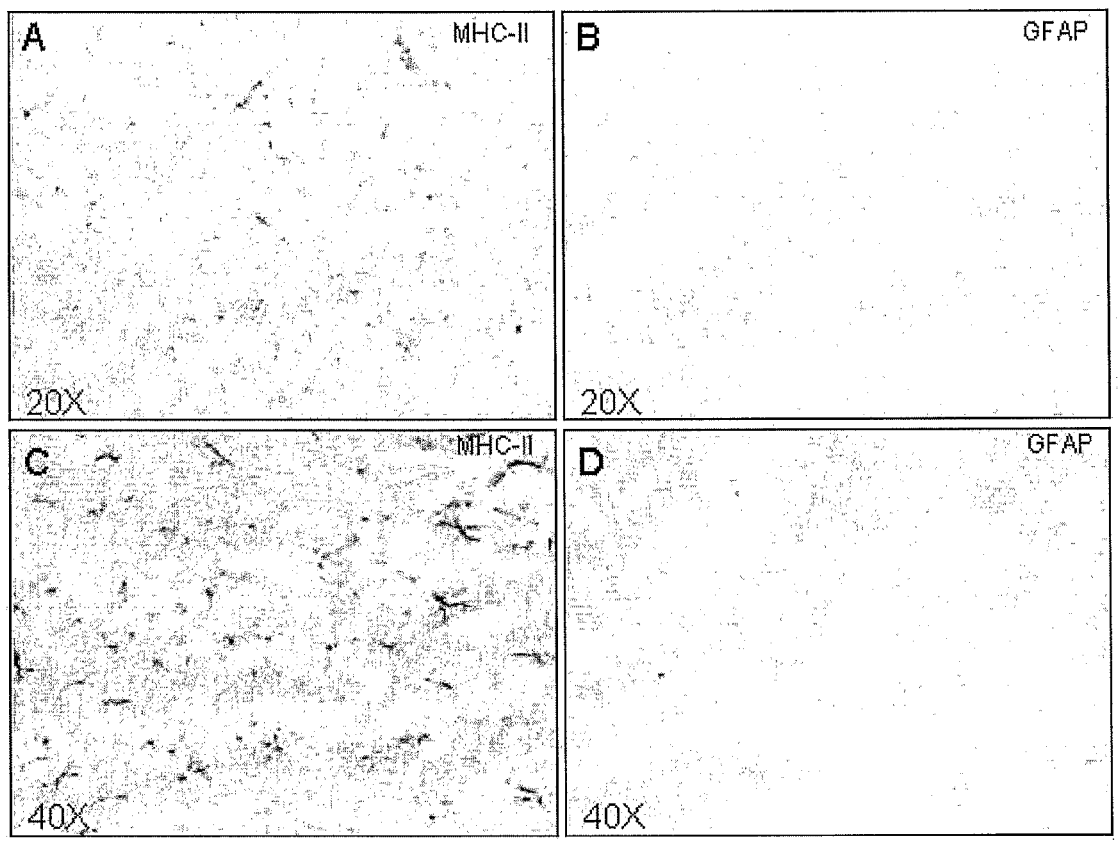

FIG. 13 shows brain inflammation in Col1-1$\beta^{XAT}$ mice following injection of FIV(Cre) in the knee and TMJ. Eight weeks after FIV(Cre) injection in the knee and TMJ of Col1-IL1$\beta^{XAT}$ mice the brain was evaluated for activation of microglia and astrocytes by immunocytochemistry. (A) Using a monoclonal antibody raised against the MHC-class II antigen, the presence of activated microglia was detected in the brain. In contrast, control animals did not display any MHC-II positive cells. (C) Larger magnification of panel A. (B) There was lack of astrocyte activation in the brains of these animals as assessed by glial fibrillary acidic protein (GFAP). (D) Larger magnification of panel B.

Figure 14:
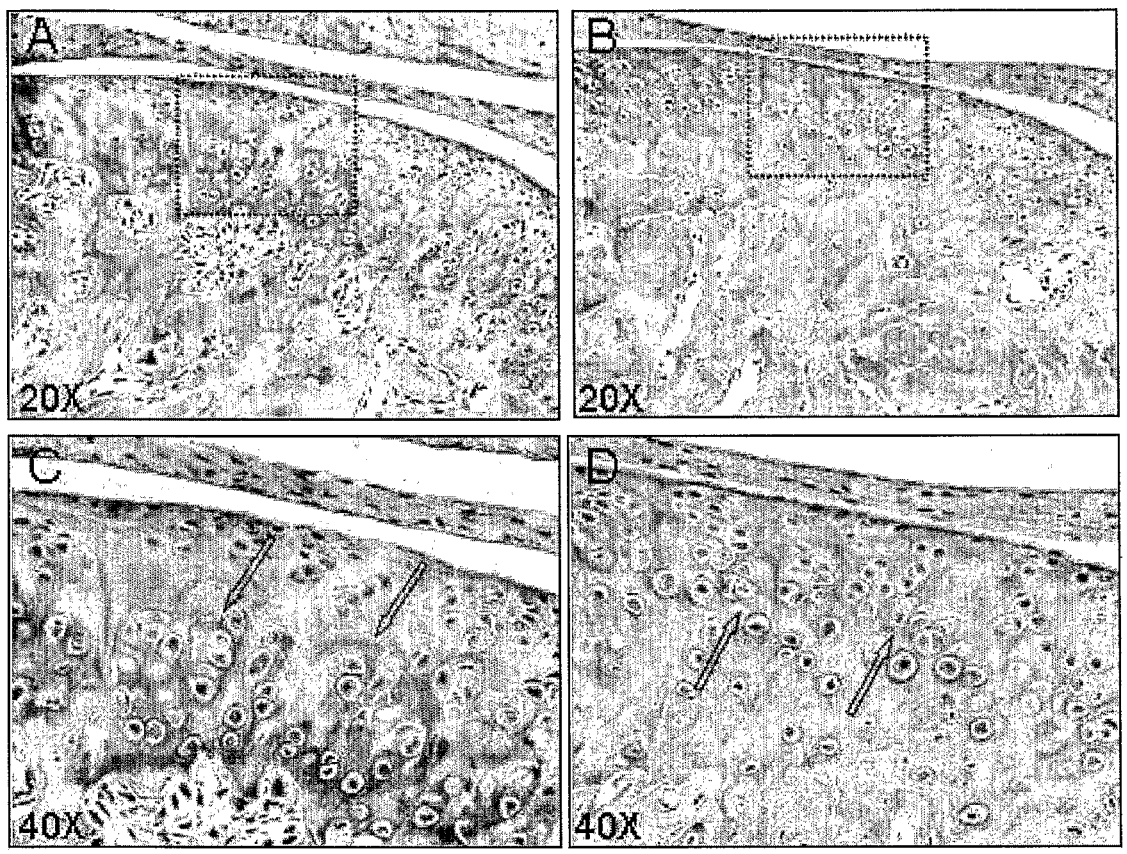

FIG. 14 shows arthritis-like changes in the TMJ of Col1-IL1$\beta^{XAT}$ mice after intra-articular injection of FIV(Cre). Eight weeks after FIV(Cre) injection in the TMJ of Col1-IL1$\beta^{XAT}$ mice anatomic aberrations of the joint were evaluated by semi-quantitative Alcian blue-orange G histochemistry. (A) TMJ section from an inactive Col1-IL1$\beta^{XAT}$ mouse depicting the condylar head as well as the meniscus. In comparison, (B) a TMJ section harvested from a Col1-IL1$\beta^{XAT}$ mouse injected with FIV(Cre) in the TMJ. (C) Larger magnification of the identified area of panel A. (D) Larger magnification of the identified area of panel B.

Figure 15:
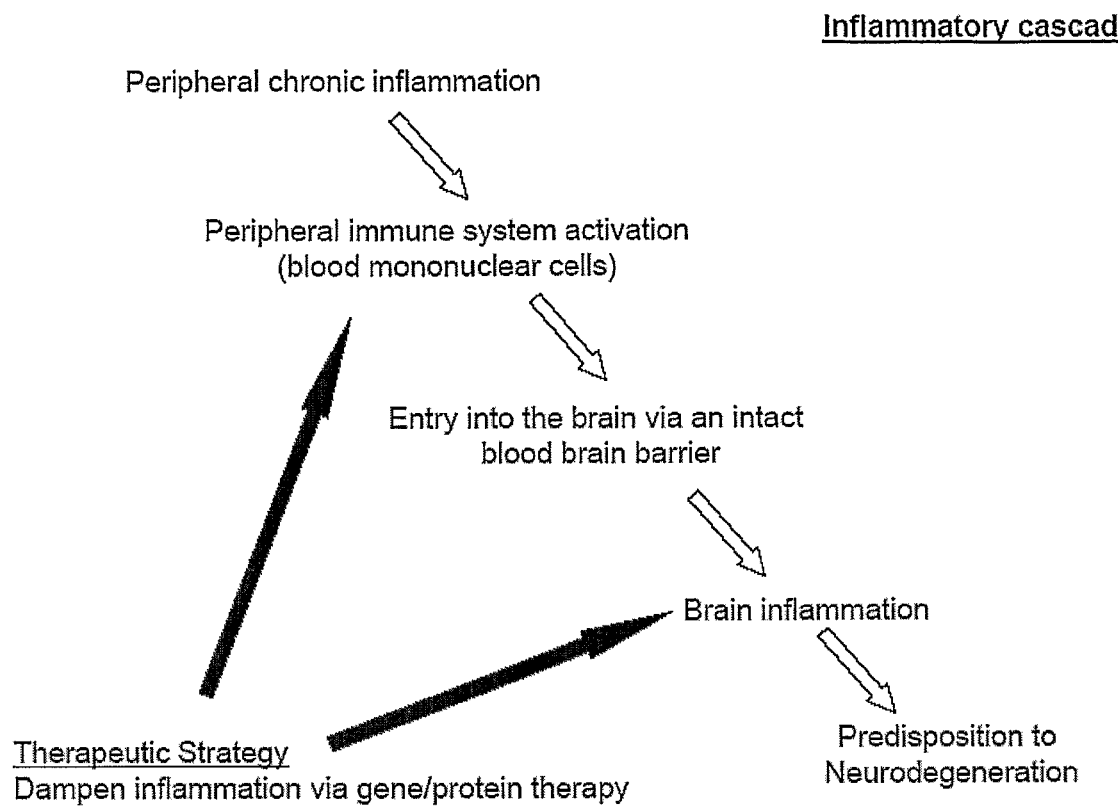

FIG. 15 shows the inflammatory cascade and strategic targets in the cascade for gene and protein therapies. FIG. 13, shows inhibition of IL-1β's biologic activity by a neutralizing antibody. (A) Conditioned medium collected form naïve NIH 3T3 cells were placed on murine fibroblasts, which in turn showed low levels of murine COX-2 mRNA. (B) Conditioned medium from NIH 3T3 cells transfected with IL-1$\beta^{XAT}$+pRc/CMV-backbone vector also showed low levels of murine COX-2 mRNA. In contrast, (C) conditioned medium from IL-1$\beta^{XAT}$+pRc/CMV-CreWT transfected NIH 3T3 cells significantly induced COX-2 mRNA in the target cells; (D) preincubation of the conditioned medium with a control rabbit IgG antibody (5 ng/mL IgG1 isotype) had minimal effects on COX-2 regulation. However, (E) pre-incubation of the conditioned medium with a rabbit anti-IL1β (5 ng/mL IgG1) antibody attenuated the COX-2 induction. (F) Positive control: addition of human recombinant IL-1β (1 ng/mL+5 ng IgG1 isotype). (G) human recombinant IL-1β pre-incubated with 5 ng/mL neutralizing antibody. Results are shown as fold induction of COX-2 mRNA relative to group A.

Figure 16:
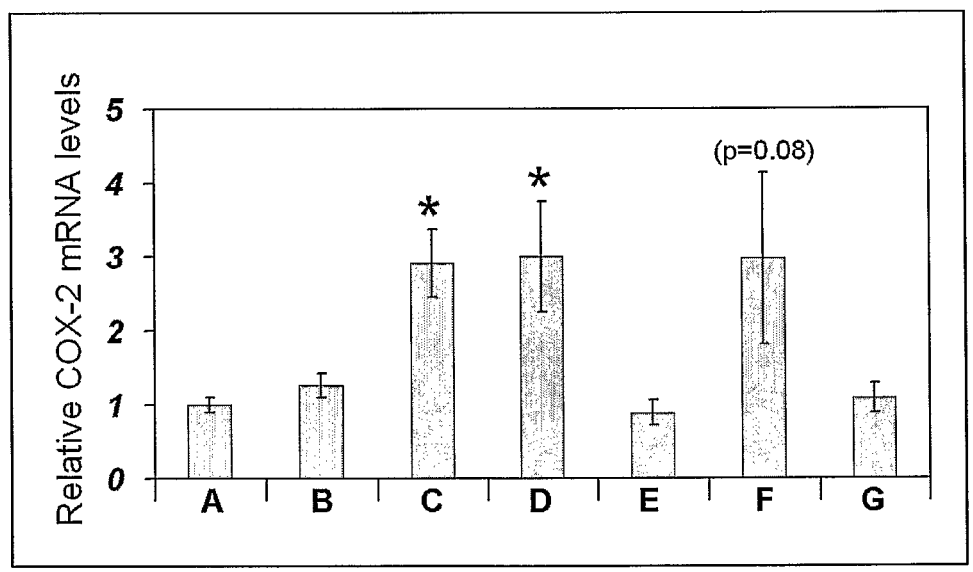

FIG. 16 shows inhibition of IL-1β's biologic activity by a neutralizing antibody. (A) Conditioned medium collected form naïve NIH 3T3 cells were placed on murine fibroblasts, which in turn showed low levels of murine COX-2 mRNA.

(B) Conditioned medium from NIH 3T3 cells transfected with IL-1β$^{XAT}$+pRc/CMV-backbone vector also showed low levels of murine COX-2 mRNA. In contrast, (C) conditioned medium from IL-1β$^{XAT}$+pRc/CMV-CreWT transfected NIH 3T3 cells significantly induced COX-2 mRNA in the target cells; (D) preincubation of the conditioned medium with a control rabbit IgG antibody (5 ng/mL IgG1 isotype) had minimal effects on COX-2 regulation. However, (E) preincubation of the conditioned medium with a rabbit anti-IL1β (5 ng/mL IgG1) antibody attenuated the COX-2 induction. (F) Positive control: addition of human recombinant IL-1β (1 ng/mL+5 ng IgG1 isotype). (G) human recombinant IL-1β pre-incubated with 5 ng/mL neutralizing antibody. Results are shown as fold induction of COX-2 mRNA relative to group A.

Figure 17:
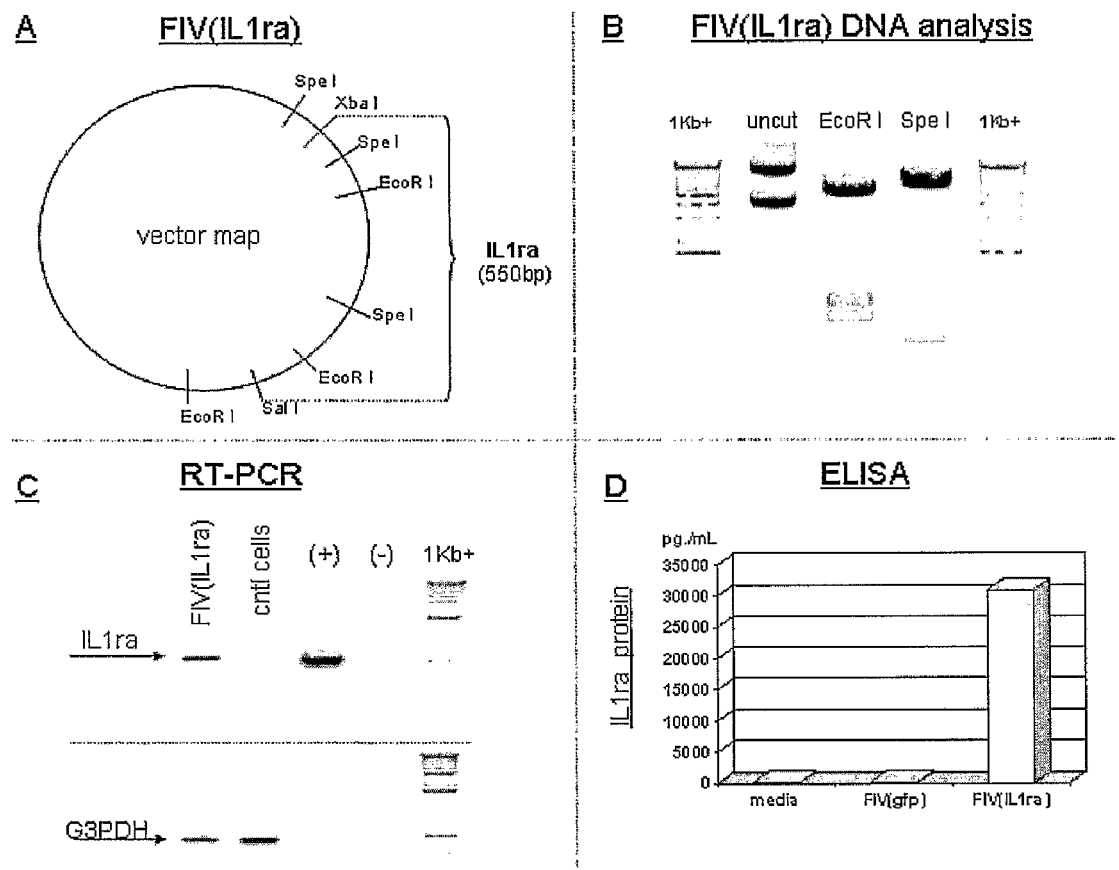

FIG. 17 shows FIV(IL1ra) successfully transduces cells with a gene expressing IL-1ra receptor antagonist. FIV (IL1ra) was constructed as depicted in panel A and confirmed by restriction enzyme analysis depicted in panel B. FIV (IL1ra) was then tested in vitro; IL1ra expression was evaluated in murine NIH 3T3 cells infected with this virus at the mRNA and protein levels. (C) RT-PCR analysis of infected cells demonstrated the expression of IL1ra mRNA. In contrast, naïve cells did not display any IL1ra expression. The housekeeping gene G3PDH was also employed. (D) IL1ra protein level in the media of injected cells was assessed by ELISA. Infection of cells by FIV(IL1ra) resulted in therapeutic IL1ra levels (>30 µg/mL). In contrast, FIV(gfp) and naïve cells did not express IL1ra.

V. DETAILED DESCRIPTION

The disclosed method and compositions can be understood more readily by reference to the following detailed description of particular embodiments and the Example included therein and to the Figures and their previous and following description.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such can, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation.

"Probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Compositions and Methods

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular vector is disclosed and discussed and a number of vector components including the promoters are discussed, each and every combination and permutation of promoters and other vector components and the modifications that are possible unless specifically indicated to the contrary Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

1. Inflammatory Disease

Provided herein are compositions, including polypeptides, nucleic acids, vectors, and cells, that can be used in the study and treatment of inflammatory diseases and disorders. Inflammation is a localized protective reaction of tissue to irritation, injury, or infection, characterized by pain, redness, swelling, and sometimes loss of function. As used herein, "inflammatory disorder" or "inflammatory disease" refers to any condition, disease or disorder wherein inflammation is involved, such as the sustained or chronic inflammation that occurs when tissues are injured by viruses, bacteria, trauma, chemicals, heat, cold or any other harmful stimulus. Irritation or discomfort can result from inflammation in a mammal due to, for example, skin inflammation, eye inflammation, gut inflammation or the like. Further, it is generally believed that chronic inflammation can increase the risk to develop other disease or ailment, such as osteoarthritis, autoimmune disease, cancer or the like.

In one aspect, the provided compositions and methods relate to the study and treatment of arthritis. Arthritis as a disease can include many different disorders and symptoms and can affect many parts of the body. Arthritis typically causes pain, loss of movement and sometimes swelling. Arthritis is actually a term used for a set of more than 100 current medical conditions. Arthritis is most commonly associated with older individuals, but can start as early as infancy. Some forms affect people in their young-adult years. A common aspect among arthritic conditions is that they affect the musculoskeletal system and specifically the joints—where two or more bones meet. Arthritis-related joint problems can include pain, stiffness, inflammation and damage to joint cartilage (the tough, smooth tissue that covers the ends of the bones, enabling them to glide against one another) and surrounding structures. Such damage can lead to joint weakness, instability and visible deformities depending on the location of joint involvement. Many of the arthritic conditions are systemic, in that they affect the whole body. In these diseases, arthritis can cause damage to virtually any bodily organ or system, including the heart, lungs, kidneys, blood vessels and skin.

Some different types of arthritis are Osteoarthritis, Rheumatoid arthritis, Gout, Ankylosing spondylitis, Juvenile arthritis, Systemic lupus erythematosus (lupus), Scleroderma, and Fibromyalgia. Osteoarthritis is a degenerative joint disease in which the cartilage that covers the ends of bones in the joint deteriorates, causing pain and loss of movement as bone begins to rub against bone. It is the most prevalent form of arthritis. Rheumatoid arthritis is an autoimmune disease in which the joint lining becomes inflamed as part of the body's immune system activity. Rheumatoid arthritis is one of the most serious and disabling types, affecting mostly women. Gout affects mostly men. It is usually the result of a defect in body chemistry. This painful condition most often attacks small joints, especially the big toe. Fortunately, gout almost always can be completely controlled with medication and changes in diet. Ankylosing spondylitis is a type of arthritis that affects the spine. As a result of inflammation, the bones of the spine grow together. Juvenile arthritis is a general term for all types of arthritis that occur in children. Children can develop juvenile rheumatoid arthritis or childhood forms of lupus, ankylosing spondylitis or other types of arthritis. Systemic lupus erythematosus (lupus) is a disorder that can inflame and damage joints and other connective tissues throughout the body. Scleroderma is a disease of the body's connective tissue that causes a thickening and hardening of the skin. Fibromyalgia is a disorder in which widespread pain affects the muscles and attachments to the bone. It affects mostly women.

In another aspect, the provided compositions and methods relate to the study and treatment of neuroinflammation. Neuroinflammation, characterized by activated microglia and astrocytes and local expression of a wide range of inflammatory mediators, is a fundamental reaction to brain injury, whether by trauma, stroke, infection, or neurodegeneration. This local tissue response is surely part of a repair and restorative process. Yet, like many inflammatory conditions in peripheral diseases, neuroinflammation can contribute to the pathophysiology of CNS disorders. For example, in Alzheimer's disease (AD), glial-driven inflammatory responses to Aβ deposition are thought to promote neurodegeneration, as evidenced by the extent of neuroinflammation in AD, increased risk for AD with certain polymorphisms of proinflammatory cytokine genes, and reduction in disease risk for individuals taking nonsteroidal anti-inflammatory drugs (NSAIDs).

Considered herein is the use of the provided compositions and methods relate to the study and treatment of any inflammatory disease. Thus, the provided compositions and methods relate to the study and treatment of inflammatory bowel disease. The provided compositions and methods relate to the study and treatment of chronic dermatological disorders.

A particular advantage of the provided compositions and methods is the herein described ability to deliver inflammatory mediators, and the disclosed modulators thereof, to the brain by means of peripheral administration. For example, FIV vectors are disclosed herein that can deliver the herein disclosed nucleic acids to target sites within the subject. The disclosed FIV constructs can be delivered systemically by injection into the circulation or locally by injection into the target site, such that either method of administration can result in the delivery of the nucleic acid to cells in the brain, such as, for example, microglia or astrocytes. The use of FIV vectors to deliver nucleic acids or transgenes to the brain following systemic administration is described in Patent Cooperation Treaty Application No. PCT/US03/13672 and U.S. Provisional Patent Application No. 10/781,142, which are herein incorporated by reference in their entirety as they related to this teaching. Thus, neural inflammatory disorders, as disclosed herein, can be treated through delivery of an inflammatory mediator, as discussed herein, via, for example, injection in the joint of the subject. In addition, inflammatory conditions related to bone and/or joints can be treated by injection into the joint or through system injection or IP injection as discussed herein.

2. Inflammatory mediator

Inflammatory diseases such as arthritis and neuroinflammation can be treated in part by inhibiting the expression or activity of an inflammatory mediator. An inflammatory mediator, as used herein, refers to a protein that modulates inflammation and includes, for example, cytokines (e.g., IL-1β) prostaglandins (e.g., prostaglandin $E_2$ ($PGE_2$)), prostaglandin synthases (e.g., COX-1, COX-2, cPGES, and mPGES), and modulators thereof.

a) Interleukin-1

An example of an inflammatory mediator is interleukin-1 (IL-1). IL-1 is a potent immunomodulating cytokine that exists as two principal isoforms, IL-1α and IL-1β. These two molecules show significant divergence in sequence and have somewhat different roles with IL-1α generally thought to be involved in direct cell:cell communication, whereas IL-1β is secreted. Nevertheless, these two molecules act through the same membrane-associated receptor known as IL-1 receptor type 1 (IL-1R1) to promote a proinflammatory signaling cascade that includes the activation of NFκB and MAP kinases [Rothwell, N. J. and G. N. Luheshi. Trends Neurosci. (2000) 23:618-625].

At least two molecules have been identified that antagonize the effects of IL-1. IL-1 receptor antagonist (IL-1ra) competes for receptor binding, and IL-1 receptor type 2 (IL-1R2), which lacks an intracellular domain, is thought to serve as a decoy receptor [Rothwell, N. J. and G. N. Luheshi. Trends Neurosci. (2000) 23:618-625]. Expression of each of these molecules is regulated. The contribution of IL-1 to an inflammatory response therefore depends on the relative balance of expression between these family members [Arend, W. P. Cytokine & Growth Factor Rev. (2002) 13:323-340]. In one example, the mature form of IL-1β is attached to the secretion signal from IL-1ra, which is the same sequence as the secretion signal sequence of IL-1β.

Lavage and explant studies from normal and osteoarthritic cartilage support the contention that cytokines are up regulated in disease states. Specifically, Moos et al. [Moos V, et al. (1999) J Rheumatol 26:870-9] have demonstrated that cartilage from knee or hip joints in 10 patients with osteoarthritis (OA) compared to controls demonstrated cytokines, including IL-1β that are up regulated in OA cartilage. Shin et al. [Shin S-j, et al. (2003) J Appl Physiol.; 95:308-13] examined the influence of mechanical stress on matrix turnover in the meniscus in the presence of IL-1β to determine the role of nitric oxide (NO) in these processes. Stimulation of proteoglycan release in response to compression was dependent on NOS2 regardless of the presence of IL-1. These finding suggest that IL-1 can modulate the effects of mechanical stress on extracellular matrix turnover through a pathway that is dependent on NO. Joosten et al. [Joosten L A, et al (1999) J Immunol; 163:5049-55] have demonstrated that blocking of IL-1 is a cartilage and bone protective therapy in destructive arthritis, whereas the TNF-alpha antagonist has little effect on tissue destruction. Webb et al. [Webb G R, et al. (1998) Osteoarthr & Cartil 6167-76] demonstrated that OA synovium supernatants contained higher concentrations of interleukin-1 beta (IL-1 beta) and interleukin-6 (IL-6) than normal synovial supernatants and neutralizing antibodies to these cytokines either partially or totally abrogated the ability of the OA supernatants to increase chondrocyte p55 TNF-R expression. These results suggest that IL-1 and IL-6 produced by OA synovium contribute to the progression of the disease by rendering chondrocytes more susceptible to stimulation by catabolic cytokines. Smith et al. [Smith M D, et al. (1997) J Rheumatol 24:365-71] examined the production of IL-1α, IL-1β and TNFα in synovial membranes from patients with OA, irrespective of the degree of articular cartilage damage. They suggest that chronic inflammatory changes with production of proinflammatory cytokines are a feature of synovial membranes from patients with early OA, with the most severe changes seen in patients at the time of joint replacement surgery. This low grade synovitis results in the production of cytokines that can contribute to the pathogenesis of OA.

Although both isoforms of IL-1 are made in brain, most work has focused on the role of IL-1β. Principally produced by microglia, IL-1β is rapidly induced following CNS injury. IL-1β affects many cellular targets, including astrocytes, neurons, and endothelial cells. In these cells, IL-1 up-regulates cytokines and chemokines, induces the expression of cell surface adhesion molecules and matrix metalloproteases, and stimulates cell proliferation [St Pierre, B. A., et al. Effects of cytokines on CNS cells: glia, in: (Ed.) Ransohoff, R. M., E. N. Beveniste, Cytokines and the CNS, CRC Press, Boca Raton, (1996) pp. 151-168]. Moreover, it has been demonstrated that IL-1β induces COX-2 in brain astrocytes, leading to production of the proinflammatory prostaglandin $PGE_2$ [O'Banion, M. K., et al. Neurochem. (1996) 66:2532-2540]. Taken together, the myriad effects of IL-1 on multiple brain cell types suggest a critical role for IL-1 family members in coordinating brain neuroinflammatory responses.

The profound influence of IL-1 on neuroinflammation and its ubiquitous expression in conditions ranging from frank brain trauma to neurodegenerative disease suggests that it might contribute to CNS injury [Rothwell, N. J. and G. N. Luheshi. Trends Neurosci. (2000) 23:618-625]. This appears to be the case. For example, IL-1β is induced in experimental models of stroke [Minami, M., K. et al. J. Neurochem. (1992) 58:390-392] and infusion of IL-1β exacerbates damage whereas treatment with IL-1ra or IL-1 blocking antibodies significantly attenuates tissue injury [Loddick, S. A. and N. J. Rothwell. J. Cereb. Blood Flow Metab. (1996) 16:932-940 and Yamasaki, Y., N. Matsuura, H. Shozuhara, H. Onodera, Y. Itoyama and K. Kogure. Stroke (1995) 26:676-681]. Similarly, ischemic injury is significantly attenuated in interleukin-1 converting enzyme deficient mice [Friedlander, R. M., et al. J. Exp. Med. (1997) 185:933-940]. As another example, GFAP directed expression of a human IL-1ra transgene attenuates edema, cytokine production and neurological deficits in a murine model of closed head injury [Tehranian, R., S. et al. J. Neurotrauma (2002) 19:939-951]. Finally, studies of penetrating brain injury in mice lacking the type 1 IL-1 receptor showed dramatic attenuation in microglial activation, leukocyte infiltration, and astrocyte activation [Basu, A., et al. J. Neurosci. (2002) 22:6071-6082]. Expression of numerous inflammatory mediators, including vascular cell adhesion molecule-1, several cytokines, and COX-2 was also greatly reduced in the IL-1R1 knockout mice, indicating that the IL-1 signaling pathway is essential for glial activation and the neuroinflammatory response. However, short-term infusion and viral delivery systems do not provide chronic stimuli and the genetic knockout systems are complicated by potential compensatory changes during development.

b) cyclooxygenase COX

Another example of an inflammatory mediator is the enzyme cyclooxygenase (COX). Cyclooxygenase is the principal target of non-steroidal anti-inflammatory drugs (NSAIDs), which are a mainstay of treatment for many inflammatory conditions. Cyclooxygenase catalyzes the first step in the conversion of arachidonic acid to prostanoids, a group of potent lipid mediators acting in diverse physiological processes.

Cyclooxygenase is known to exist in two isoforms: COX-1, which in many tissues appears to be constitutively expressed and responsible for homeostatic production of prostanoids, and COX-2, which is often referred to as the "inducible" isoform since its expression is rapidly modulated in response to diverse stimuli such as growth factors, cytokines, and hormones [O'Banion M K, et al. (1991). J Biol Chem 266: 23261-7; O'Banion M K, et al. (1992). Proc Natl Acad Sci U.S.A. 89:4888-92]. The distinction between these two COX isoforms, the roles they play, and the actions of prostanoids have been previously reviewed [Vane J R, et al. (1998). Annu. Rev. Pharmocol. Toxicol. 38:97-120; Smith, W L, et al. (2000). Annu Rev Biochem 69:145-82].

Interest in selectively inhibiting production of $PGE_2$, the principle inflammatory prostanoid, has been heightened by recognition of at least two $PGE_2$ synthase isoforms that are reportedly coupled to distinct COX isoforms. More specifically, a membrane-associated isoform (mPGES) is functionally coupled to COX-2, whereas a cytosolic enzyme (cPGES) appears to be linked to a COX-1-dependent production of $PGE_2$ (Tanioka et al. 2000; Murakami et al., 2000). Although cellular localization can play some role, functional coupling is largely a factor of expression patterns: as with COX-2, mPGES is dramatically upregulated by proinflammatory stimuli, whereas cPGES is constitutively expressed in cell systems examined to date (Jackobson et al., 1999; Stichtenoth et al., 2001; Han et al., 2002). In addition, COX-2 and mPGES are coordinately upregulated in a rat model of adjuvant arthritis (Mancini et al., 2001).

3. Inhibition

Provided herein are compositions that act to modulate an activity of an inflammatory mediator. "Activity," as used herein, refers to any function or process of a composition disclosed herein and includes, for example, transcription, translation, post-translational modification, translocation, homophilic or heterophilic binding, secretion, endocytosis, or degradation. Disclosed therefore are compositions that inhibit one or more activities of an inflammatory mediator provided herein. These compositions are referred to herein as inflammatory mediator inhibitors. Inhibition or a form of inhibition, such as inhibit or inhibiting, as used herein means to restrain or limit. Reduce or a form of reduce, such as reducing or reduces, as used herein, means to diminish, for example in size or amount. It is understood that wherever one of inhibit or reduce is used, unless explicitly indicated otherwise, the other can also be used. For example, if something is referred to as "inhibited," it is also considered referred to as "reduced."

a) Knockdown of Gene Expression

The activity of an inflammatory mediator can be modulated at the gene expression level. The disclosed inflammatory mediator inhibitor can be a gene expression inhibitor. Methods of targeting gene expression are generally based on the sequence of the gene to be targeted. Disclosed are any such methods that can be applied to the targeted knockdown of an inflammatory mediator. By "knockdown" is meant a decrease in detectable mRNA expression. Nucleic acids are generally used to knockdown gene expression and generally comprise a sequence capable of hybridizing to the target sequence, such as mRNA. Examples of such functional nucleic acids include antisense molecules, ribozymes, triplex forming nucleic acids, external guide sequences (EGS), and small interfering RNAs (siRNA).

Antisense molecules are designed to interact with a target nucleic acid molecules through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($k_d$) less than or equal to $10^{-6}$, $10^{-8}$, $10^{10}$, or $10^{-12}$. A representative sample of methods and techniques which aid in the design and use of antisense molecules can be found in the following non-limiting list of U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437. However, the effect of iRNA or siRNA or their use is not limited to any type of mechanism.

Disclosed herein are any antisense molecules designed as described above based on the sequences for the herein disclosed inflammatory mediators. Examples of antisense sequences are disclosed herein for IL-1α (SEQ ID NO:70), IL-1β (SEQ ID NO:71), COX-1 (SEQ ID NO:72), COX-2 (SEQ ID NO:73), cPGES (SEQ ID NO:74), and mPGES (SEQ ID NO:75).

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, (for example, but not limited to the following U.S. Pat. Nos. 5,334,711, 5,436,330, 5,616, 466, 5,633,133, 5,646,020, 5,652,094, 5,712,384, 5,770,715, 5,856,463, 5,861,288, 5,891,683, 5,891,684, 5,985,621, 5,989,908, 5,998,193, 5,998,203, WO 9858058 by Ludwig and Sproat, WO 9858057 by Ludwig and Sproat, and WO 9718312 by Ludwig and Sproat) hairpin ribozymes (for example, but not limited to the following U.S. Pat. Nos. 5,631,115, 5,646,031, 5,683,902, 5,712,384, 5,856,188, 5,866,701, 5,869,339, and 6,022,962), and tetrahymena ribozymes (for example, but not limited to the following U.S. Pat. Nos. 5,595,873 and 5,652,107). There are also a number of ribozymes that are not found in natural systems, but which have been engineered to catalyze specific reactions de novo (for example, but not limited to the following U.S. Pat. Nos. 5,580,967, 5,688,670, 5,807,718, and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in the following non-limiting list of U.S. Pat. Nos. 5,646,042, 5,693,535, 5,731,295, 5,811,300, 5,837,855, 5,869,253, 5,877,021, 5,877,022, 5,972,699, 5,972,704, 5,989,906, and 6,017,756.

Disclosed herein are any ribozymes designed as described above based on the sequences for the herein disclosed inflammatory mediators. Hammerhead ribozymes can cleave RNA substrates at for example, a 5'-GUC-3' sequence, cleaving the mRNA immediately 3' to the GUC site. Engineered hammerhead ribozymes, which cleave at a different sequence are known and disclosed, for example, in the patents disclosed herein, and are incorporated by reference. A hammerhead ribozyme is typically composed of three parts. The first part is a region which will hybridize to the sequence 5' of the GUC recognition site, and can be called a first hybridzation arm. A second part consists of a core catalytic domain of the hammerhead ribozyme, and typically has the sequence 3'CAAAGCAGGAGUGCCUGAGUAGUC5' (SEQ ID NO:82). Variations on this sequence are known and are herein disclosed and incorporated by reference, for example, in the patents disclosed herein. A third part consists of sequence capable of hybridizing to the sequence immediately 3' to the GUC cleavage site, and can be called a second hybridization arm. The hybridization arms can be any length allowing binding to the substrate, such as, from 3-40 nucleotides long, 5-30 nucleotides long, 8-20, nucleotides long and 10-15 nucleotides long, as well as any length up to 50 nucleotides. As an example, hammerhead ribozymes can be designed by identifying a nucleic acid triplet GUC within the mRNA target sequence, and then identifying the appropriate hybridizing arms as discussed herein to the catalytic core as discussed herein. Examples of hammerhead ribozyme sequences are disclosed herein for IL-1α (SEQ ID NO:76), IL-1β (SEQ ID NO:77), COX-1 (SEQ ID NO:78), COX-2 (SEQ ID NO:79), cPGES (SEQ ID NO:81), and mPGES (SEQ ID NO:80), but it is understood that others are also disclosed as discussed herein. Furthermore, using assays as discussed herein, one can test a given ribozyme (or any functional nucleic acid, such as an siRNA or antisense) for its level of activity, both in vitro and in vivo.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a $k_d$ less than $10^{-6}$, $10^{-8}$, $10^{-10}$, or $10^{-12}$. Representative examples of how to make and use triplex forming molecules to bind a variety of different target molecules can be found in the following non-limiting list of U.S. Pat. Nos. 5,176,996, 5,645,985, 5,650,316, 5,683,874, 5,693,773, 5,834,185, 5,869,246, 5,874,566, and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (WO 92/03566 by Yale, and Forster and Altman, Science 238:407-409 (1990)). Similarly, eukaryotic EGS/RNAse P-directed cleavage of RNA can be utilized to cleave desired targets within eukarotic cells. (Yuan et al., Proc. Natl. Acad. Sci. USA 89:8006-8010 (1992); WO 93/22434 by Yale; WO 95/24489 by Yale; Yuan and Altman, EMBO J 14:159-168 (1995), and Carrara et al., Proc. Natl. Acad. Sci. (USA) 92:2627-2631 (1995)). Representative examples of how to make and use EGS molecules to facilitate cleavage of a variety of different target molecules are found in the following non-limiting list of U.S. Pat. Nos. 5,168,053, 5,624,824, 5,683,873, 5,728,521, 5,869,248, and 5,877,162.

Gene expression can also be effectively silenced in a highly specific manner through RNA interference (RNAi). This silencing was originally observed with the addition of double stranded RNA (dsRNA) (Fire, A., et al. (1998) Nature, 391, 806 811) (Napoli, C., et al. (1990) Plant Cell 2, 279 289) (Hannon, G. J. (2002) Nature, 418, 244 251). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, S. M., et al. (2001) Genes Dev., 15:188-200) (Bernstein, E., et al. (2001) Nature, 409, 363 366) (Hammond, S. M., et al. (2000) Nature, 404:293-296). In an ATP dependent step, the siRNAs become integrated into a multi-subunit protein complex, commonly known as the RNAi induced silencing complex (RISC), which guides the siRNAs to the target RNA sequence (Nykanen, A., et al. (2001) Cell, 107:309 321). At some point the siRNA duplex unwinds, and it appears that the antisense strand remains bound to RISC and directs degradation of the complementary mRNA sequence by a combination of endo and exonucleases (Martinez, J., et al. (2002) Cell, 110:563-574). However, the effect of iRNA or siRNA or their use is not limited to anytype of mechanism.

Short Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs. Sequence specific gene silencing can be achieved in mammalian cells using synthetic, short double-stranded RNAs that mimic the siRNAs produced by the enzyme dicer (Elbashir, S. M., et al. (2001) Nature, 411:494 498) (Ui-Tei, K., et al. (2000) FEBS Lett 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER siRNA Construction Kit. Disclosed herein are any siRNA designed as described above based on the sequences for the herein disclosed inflammatory mediators. Examples of siRNA include: COX-1 (SEQ ID NOs:47-52), COX-2 (SEQ ID NOs:53-58), cPGES (SEQ ID NOs:41-46), and mPGES (SEQ ID NO:59).

The production of siRNA from a vector is more commonly done through the transcription of a shRNA. Kits for the production of vectors comprising shRNA are available, such as for example Ingenex's GeneSuppressor Construction Kits and Invitrogen's BLOCK-iT inducible RNAi plasmid and lentivirus vectors. Disclosed herein are any shRNA designed as described above based on the sequences for the herein disclosed inflammatory mediators. Examples of shRNA primer sequences are disclosed for COX-1 (SEQ ID NOs:64-65), COX-2 (SEQ ID NOs:66-67), cPGES (SEQ ID NOs:60-61), and mPGES (SEQ ID NO:62-63).

b) Inhibition of Binding

Another activity of an inflammatory mediator that can be targeted is homophilic and heterophilic binding to other molecules, such as, for example, receptors. Thus, the inflammatory mediator inhibitor can be a ligand binding inhibitor. Methods for inhibiting the binding of a protein to its receptor can, for example, be based on the use of molecules that compete for the binding site of either the ligand or the receptor.

Thus, a ligand binding inhibitor can be, for example, a polypeptide that competes for the binding of a receptor without activating the receptor. Likewise, a ligand binding inhibitor can be a decoy receptor that competes for the binding of ligand. Such a decoy receptor can be a soluble receptor (e.g., lacking transmembrane domain) or it can be a mutant receptor expressed in a cell but lacking the ability to transduce a signal (e.g., lacking cytoplasmic tail). Antibodies specific for either a ligand or a receptor can also be used to inhibit binding. The ligand binding inhibitor can also be naturally produced by a subject. Alternatively, the inhibitory molecule can be designed based on targeted mutations of either the receptor or the ligand.

Thus, as an illustrative example, the ligand binding inhibitor can be IL-1 receptor antagonist (IL-1ra). The ligand binding inhibitor can also be a polypeptide comprising a fragment of IL-1ra, wherein the fragment is capable of binding IL-1R1. ligand binding inhibitor can further be IL-1R2, which is a soluble form of the receptor that can compete for IL-1 binding. The ligand binding inhibitor can further be a polypeptide comprising a fragment of IL-1R1. The IL-1R1 fragment can lack the cytoplasmic tail, which includes the Toll/interleukin-1 (IL-1) receptor (TIR) domain (amino acids 384-528 of SEQ ID NO:8). The fragment of IL-1R1 can lack the amino acids corresponding to the transmembrane domain.

4. Antibodies

Antibodies specific for inflammatory mediators or their receptors can be used herein. For example, disclosed for use in the provided compositions and methods are neutralizing antibodies specific for IL-1β or IL-1 receptor, or nucleic acids encoding said antibodies.

(1) Antibodies Generally

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with inflammatory mediators or their receptors such that inflammatory mediators is inhibited from interacting with its receptor. The antibodies can be tested for their desired activity using the in vitro assays described herein, or by analogous methods, after which their in vivo therapeutic and/or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., Proc. Natl. Acad. Sci. USA, 81:6851-6855 (1984)).

The disclosed monoclonal antibodies can be made using any procedure which produces mono clonal antibodies. For example, disclosed monoclonal antibodies can be prepared using hybridoma methods, such as those described by Kohler and Milstein, Nature, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro, e.g., using the HIV Env-CD4-co-receptor complexes described herein.

The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

(2) Human Antibodies

The disclosed human antibodies can be prepared using any technique. Examples of techniques for human monoclonal antibody production include those described by Cole et al. (*Monoclonal Antibodies and Cancer Therapy*, Alan R. Liss, p. 77, 1985) and by Boerner et al. (J. Immunol., 147(1):86-95, 1991). Human antibodies (and fragments thereof) can also be produced using phage display libraries (Hoogenboom et al., J. Mol. Biol., 227:381, 1991; Marks et al., J. Mol. Biol., 222: 581, 1991).

The disclosed human antibodies can also be obtained from transgenic animals. For example, transgenic, mutant mice that are capable of producing a full repertoire of human antibodies, in response to immunization, have been described (see, e.g., Jakobovits et al., Proc. Natl. Acad. Sci. USA, 90:2551-255 (1993); Jakobovits et al., Nature, 362:255-258 (1993); Bruggermann et al., Year in Immunol., 7:33 (1993)). Specifically, the homozygous deletion of the antibody heavy chain joining region (J(H)) gene in these chimeric and germline mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

(3) Humanized Antibodies

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., Nature, 321:522-525 (1986), Reichmann et al., Nature, 332:323-327 (1988), and Presta, Curr. Opin. Struct. Biol., 2:593-596 (1992)).

Methods for humanizing non-human antibodies are well known in the art. For example, humanized antibodies can be generated according to the methods of Winter and co-workers (Jones et al., Nature, 321:522-525 (1986), Riechmann et al., Nature, 332:323-327 (1988), Verhoeyen et al., *Science,* 239: 1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

(4) Administration of Antibodies

Administration of the antibodies can be done as disclosed herein. Nucleic acid approaches for antibody delivery also exist. The broadly neutralizing anti xxx antibodies and antibody fragments can also be administered to patients or subjects as a nucleic acid preparation (e.g., DNA or RNA) that encodes the antibody or antibody fragment, such that the patient's or subject's own cells take up the nucleic acid and produce and secrete the encoded antibody or antibody fragment. The delivery of the nucleic acid can be by any means, as disclosed herein, for example.

C. Compositions

Disclosed herein are constructs capable of inhibiting an activity of an inflammatory mediator. In one aspect, the constructs are vectors comprising a nucleic acid, wherein the nucleic acid encodes for the inhibitor. The nucleic acids of the constructs can be based on the sequence of an inflammatory mediator.

1. Inflammatory Mediators—Sequences

The disclosed constructs can comprise a nucleic acid based on the sequence of IL-1 alpha. The nucleic acid sequence can be based on the sequence of human IL-1 alpha. An example of a nucleic acid encoding human IL-1 alpha is SEQ ID NO:1, Accession No. NM_000575.

The disclosed constructs can comprise a nucleic acid based on the sequence of IL-1 beta. The nucleic acid sequence can based on the sequence of human IL-1 beta. An example of a nucleic acid encoding human IL-1 beta is SEQ ID NO:2, Accession No. NM_000576.

The disclosed constructs can comprise a nucleic acid based on the sequence of IL-1ra. The nucleic acid sequence can based on the sequence of human IL-1ra. An example of a nucleic acid encoding human IL-1ra is SEQ ID NO:5, Accession No. NM_173842.

The disclosed constructs can comprise a nucleic acid based on the sequence of IL-1R1. The nucleic acid sequence can based on the sequence of human IL-1RA. An example of a nucleic acid encoding human IL-1R1 is SEQ ID NO:8, Accession No. NM_000877.

The disclosed constructs can comprise a nucleic acid based on the sequence of IL-1R2. The nucleic acid sequence can based on the sequence of human IL-1R2. An example of a nucleic acid encoding human IL-1R2 is SEQ ID NO:9, Accession No. NM_173343.

The disclosed constructs can comprise a nucleic acid based on the sequence of COX-1. The nucleic acid sequence can based on the sequence of human COX-1. An example of a nucleic acid encoding human COX-1 is SEQ ID NO:10, Accession No. M59979.

The disclosed constructs can comprise a nucleic acid based on the sequence of COX-2. The nucleic acid sequence can based on the sequence of human COX-2. An example of a nucleic acid encoding human COX-2 (SEQ ID NO:11, Accession No. NM_000963.

The disclosed constructs can comprise a nucleic acid based on the sequence of mPGES. The nucleic acid sequence can based on the sequence of human mPGES. An example of a nucleic acid encoding human mPGES is SEQ ID NO:12, Accession No. NM_004878.

The disclosed constructs can comprise a nucleic acid based on the sequence of cPGES. The nucleic acid sequence can based on the sequence of human cPGES/p23. An example of a nucleic acid encoding human cPGES/p23 is SEQ ID NO:13, Accession No. L24804.

Disclosed herein is a functional nucleic acid wherein the nucleic acid can inhibit the expression of a mediator of inflammation. Also disclosed herein is a construct comprising a nucleic acid encoding the functional nucleic acid operably linked to an expression control sequence. The functional nucleic acid can comprise an siRNA. The siRNA can be derived from the nucleic acid sequence for COX-1 (SEQ ID NO:10). Thus, the siRNA can have the nucleic acid sequence SEQ ID NO:47, 48, 49, 50, 51, or 52. The siRNA can be derived from the nucleic acid sequence for COX-2 (SEQ ID NO:11). Thus, the siRNA can have the nucleic acid sequence SEQ ID NO:53, 54, 555, 56, 57, or 58. The siRNA can be derived from the nucleic acid sequence for mPGES (SEQ ID NO:12). Thus, the siRNA can have the nucleic acid sequence SEQ ID NO:59. The siRNA can be derived from the nucleic acid sequence for cPGES (SEQ ID NO:13). Thus, the siRNA can have the nucleic acid sequence SEQ ID NO:41, 42, 43, 44, 45, or 46.

Disclosed herein is a construct comprising a nucleic acid encoding a polypeptide operably linked to an expression control sequence, wherein the polypeptide can inhibit the binding of IL-1 to IL-1R1. The polypeptide can comprise IL-1ra. The polypeptide can have the amino acid sequence SEQ ID NO:38. The polypeptide can comprise a fragment of IL-1ra. The polypeptide can have at least 70%, 75%, 80%, 85%, 90%, 95% identity to the amino acid sequence SEQ ID NO:38. The nucleic acid can comprise the sequence SEQ ID NO:5. The nucleic acid encode a polypeptide that with at least 70%, 75%, 80%, 85%, 90%, 95% identity to the nucleic acid sequence SEQ ID NO:5. Also disclosed are nucleic acids that can hybridize under stringent conditions, or other conditions, as described herein, with the nucleic acid sequence SEQ ID NO:5.

The polypeptide can comprise a fragment of IL-1R1, wherein the fragment is capable of binding IL-1 and wherein the fragment has a reduced ability to activate a signal cascase. It is understood that one skilled in the art can readily determine the ability of a polypeptide to bind IL-1 or activate a signal cascase using standard biochemical and molecular genetics techniques and reagents. As an example, the fragment can be a truncation lacking the transmembrane domain. Wherein the transmembrane domain has not been identified, it is understood that one skilled in the art can estimate the approximate location of this domain based on the amino acid sequence using, for example, hydrophobicity plots. As another example, the fragment can lack part of the cytoplasmic tail, which includes the Toll/interleukin-1 (IL-1) receptor (TIR) domain (amino acids 384-528 of SEQ ID NO:8). The polypeptide can have the amino acid sequence SEQ ID NO:39. The polypeptide can have at least 70%, 75%, 80%, 85%, 90%, 95% identity to the amino acid sequence SEQ ID NO:39. The nucleic acid can comprise the sequence SEQ ID NO:8. The nucleic acid encode a polypeptide that with at least 70%, 75%, 80%, 85%, 90%, 95% identity to the nucleic acid sequence SEQ ID NO:8. Also disclosed are nucleic acids that can hybridize under stringent conditions, or other conditions, as described herein, with the nucleic acid sequence SEQ ID NO:8.

The polypeptide can comprise IL-1R2. The polypeptide can have the amino acid sequence SEQ ID NO:40. The polypeptide can comprise a fragment of IL-1R2, wherein the fragment is capable of binding IL-1 and wherein the fragment has a reduced ability to activate a signal cascase. The polypeptide can have at least 70%, 75%, 80%, 85%, 90%, 95% identity to the amino acid sequence SEQ ID NO:40. The nucleic acid can comprise the sequence SEQ ID NO:9. The nucleic acid encode a polypeptide that with at least 70%, 75%, 80%, 85%, 90%, 95% identity to the nucleic acid sequence SEQ ID NO:9. Also disclosed are nucleic acids that can hybridize under stringent conditions, or other conditions, as described herein, with the nucleic acid sequence SEQ ID NO:9.

The herein disclosed polypeptides can further comprise a secretion signal. The secretion signal can be the IL-1ra secretion signal sequence, which is the same sequence as the secretion signal sequence of IL-1β. Thus, the secretion signal can comprise the polypeptide sequence SEQ ID NO:14. The secretion signal can be encoded by nucleic acid sequence SEQ ID NO:68.

The disclosed constructs can be integrated into a vector delivery system. Thus, disclosed are vectors comprising the nucleic acids provided herein. The expression control sequence is generally a promoter. The promoter can be any promoter, such as those discussed herein.

Targeted and global delivery of the constructs provided herein is also disclosed. Disclosed is a pseudotyped feline immunodeficiency virus (FIV) for global transgene delivery. Stable expression of the therapeutic gene aids prolonged restoration of the genetic anomaly enhancing treatment efficacy and contributing to long-term therapeutic outcomes. One of the backbone FIV systems disclosed herein is set forth in Poeschla E M, et al., Nature Medicine 4: 354-357. (1998). For example, disclosed herein is stable expression of the reporter gene lacZ for over 3 months in mice following perinatal systemic FIV(lacZ) administration.

A model system for the study of these constructs is the IL-1β exisionally activated transgenic (XAT) mouse (IL-1β$^{XAT}$) and variations thereof. Variations include the use of tissue specific promoters such as in for example the COLL1A1-IL-1β$^{XAT}$ mouse. This mouse model is the subject of U.S. Patent Application No. 60/627,604, which is herein incorporated by reference in its entirety for teachings related to the disclosed mouse models. This mouse model allows for the induction of localized inflammation based on the delivery of a Cre recombinase expression vector such as FIV(Cre) to the target site. For example, the delivery of FIV(Cre) to the joints of the COLL1A1-IL-1β$^{XAT}$ mouse can induce inflammation to model arthritis. This mouse model can thus be used to, for example, test or optimize the effects of the provided constructs on arthritis. Also disclosed herein is the ability of FIV vectors to deliver any of the herein provided nucleic acids or transgenes to the brain of a subject following injection of the vector into either the circulation or joints. Thus, the IL-1β$^{XAT}$ and variations thereof can be used as a model of neuroinflammation following delivery of FIV(Cre) into the circulation or joints.

2. Nucleic Acids

There are a variety of molecules disclosed herein that are nucleic acid based, including for example the nucleic acids that encode, for example, IL-1ra as well as any other proteins disclosed herein, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

a) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989, 86, 6553-6556), A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

b) Sequences

There are a variety of sequences related to, for example, IL-1ra as well as any other protein disclosed herein that are disclosed on Genbank, and these sequences and others are herein incorporated by reference in their entireties as well as for individual subsequences contained therein.

A variety of sequences are provided herein and these and others can be found in Genbank, at www.pubmed.gov. Those of skill in the art understand how to resolve sequence discrepancies and differences and to adjust the compositions and methods relating to a particular sequence to other related sequences. Primers and/or probes can be designed for any sequence given the information disclosed herein and known in the art.

c) Primers and Probes

Disclosed are compositions including primers and probes, which are capable of interacting with the genes disclosed herein. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the nucleic acid or region of the nucleic acid or they hybridize with the complement of the nucleic acid or complement of a region of the nucleic acid.

3. Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis., or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment. It is understood that any of the methods typically can be used and that in certain instances the results of these various methods can differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

4. Hybridization/Selective Hybridization

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization can involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154:367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions can provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

5. Delivery of the Compositions to Cells

The herein disclosed nucleic acids can be delivered to cells or cells in a subject. There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

a) Nucleic Acid Based Delivery Systems

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids, such as, for example, the IL-1ra, COX-1 siRNA, COX-2 siRNA, cPGES siRNA, or mPGES siRNA constructs into the cell without degradation and include a promoter yielding expression of the disclosed sequences in the cells into which it is delivered. In some embodiments the vectors for the IL-1ra, COX-1 siRNA, COX-2 siRNA, cPGES siRNA, or mPGES siRNA constructs are derived from a virus, retrovirus, or lentivirus. Viral vectors can be, for example, Adenovirus, Adeno-associated virus, Herpes virus, Vaccinia virus, Polio virus, AIDS virus, neuronal trophic virus, Sindbis and other RNA viruses, including these viruses with the HIV backbone, and lentiviruses. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene, such as, the disclosed IL-1ra, COX-1 siRNA, COX-2 siRNA, cPGES siRNA, or mPGES siRNA constructs or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector, which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

(1) Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer. In Microbiology-1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

(2) Adenoviral Vectors

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virons are generated in a cell line such as the human 293 cell line. In another preferred embodiment both the E1 and E3 genes are removed from the adenovirus genome.

(3) Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The vectors of the present invention thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and can contain upstream elements and response elements.

(4) Lentiviral Vectors

The vectors can be lentiviral vectors, including but not limited to, SIV vectors, HIV vectors or a hybrid construct of these vectors, including viruses with the HIV backbone.

These vectors also include first, second and third generation lentiviruses. Third generation lentiviruses have lentiviral packaging genes split into at least 3 independent plasmids or constructs. Also vectors can be any viral family that share the properties of these viruses which make them suitable for use as vectors. Lentiviral vectors are a special type of retroviral vector which are typically characterized by having a long incubation period for infection. Furthermore, lentiviral vectors can infect non-dividing cells. Lentiviral vectors are based on the nucleic acid backbone of a virus from the lentiviral family of viruses. Typically, a lentiviral vector contains the 5' and 3' LTR regions of a lentivirus, such as SIV and HIV. Lentiviral vectors also typically contain the Rev Responsive Element (RRE) of a lentivirus, such as SIV and HIV.

(a) Feline Immunodeficiency Viral Vectors

One type of vector that the disclosed constructs can be delivered in is the VSV-G pseudotyped Feline Immunodeficiency Virus system developed by Poeschla et al (1998). This lentivirus has been shown to efficiently infect dividing, growth arrested as well as post-mitotic cells. Furthermore, due to its lentiviral properties, it allows for incorporation of the transgene into the host's genome, leading to stable gene expression. This is a 3-vector system, whereby each confers distinct instructions: the FIV vector carries the transgene of interest and lentiviral apparatus with mutated packaging and envelope genes. A vesicular stomatitis virus G-glycoprotein vector (VSV-G; Burns et al., 1993) contributes to the formation of the viral envelope in trans. The third vector confers packaging instructions in trans (Poeschla et al., 1998). FIV production is accomplished in vitro following co-transfection of the aforementioned vectors into 293-T cells. The FIV-rich supernatant is then collected, filtered and can be used directly or following concentration by centrifugation. Titers routinely range between $10^4$-$10^7$ bfu/ml.

(5) Packaging Vectors

As discussed above, retroviral vectors are based on retroviruses which contain a number of different sequence elements that control things as diverse as integration of the virus, replication of the integrated virus, replication of un-integrated virus, cellular invasion, and packaging of the virus into infectious particles. While the vectors in theory could contain all of their necessary elements, as well as an exogenous gene element (if the exogenous gene element is small enough) typically many of the necessary elements are removed. Since all of the packaging and replication components have been removed from the typical retroviral, including lentiviral, vectors which will be used within a subject, the vectors need to be packaged into the initial infectious particle through the use of packaging vectors and packaging cell lines. Typically retroviral vectors have been engineered so that the myriad functions of the retrovirus are separated onto at least two vectors, a packaging vector and a delivery vector. This type of system then requires the presence of all of the vectors providing all of the elements in the same cell before an infectious particle can be produced. The packaging vector typically carries the structural and replication genes derived from the retrovirus, and the delivery vector is the vector that carries the exogenous gene element that is preferably expressed in the target cell. These types of systems can split the packaging functions of the packaging vector into multiple vectors, e.g., third-generation lentivirus systems. Dull, T. et al., "A Third-generation lentivirus vector with a conditional packaging system" J. Virol 72(11):8463-71 (1998)

Retroviruses typically contain an envelope protein (env). The Env protein is in essence the protein which surrounds the nucleic acid cargo. Furthermore cellular infection specificity is based on the particular Env protein associated with a typical retrovirus. In typical packaging vector/delivery vector systems, the Env protein is expressed from a separate vector than for example the protease (pro) or integrase (in) proteins.

(6) Packaging Cell Lines

The vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals. One type of packaging cell line is a 293 cell line.

(7) Large Payload Viral Vectors

Molecular genetic experiments with large human herpesviruses have provided a means whereby large heterologous DNA fragments can be cloned, propagated and established in cells permissive for infection with herpesviruses (Sun et al., Nature genetics 8: 33-41, 1994; Cotter and Robertson, Curr Opin Mol Ther 5: 633-644, 1999). These large DNA viruses (herpes simplex virus (HSV) and Epstein-Barr virus (EBV), have the potential to deliver fragments of human heterologous DNA >150 kb to specific cells. EBV recombinants can maintain large pieces of DNA in the infected B-cells as episomal DNA. Individual clones carried human genomic inserts up to 330 kb appeared genetically stable The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA >220 kb and to infect cells that can stably maintain DNA as episomes.

Other useful systems include, for example, replicating and host-restricted non-replicating vaccinia virus vectors.

b) Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, in addition to the disclosed nucleic acids or vectors, the compositions can comprise, for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Felgner et al. *Proc. Natl. Acad. Sci. USA* 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129: 57-80, (1992); and Roffler, et al., Biochem. Pharmacol, 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

Nucleic acids that are delivered to cells which are to be integrated into the host cell genome, typically contain integration sequences. These sequences are often viral related sequences, particularly when viral based systems are used. These viral intergration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

c) In Vivo/Ex Vivo

As described above, the compositions can be administered in a pharmaceutically acceptable carrier and can be delivered to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

6. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

a) Viral Promoters and Enhancers

Preferred promoters controlling transcription from vectors in mammalian host cells can be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., Nature, 273: 113 (1978)). The immediate early promoter of the human cytomegalovirus is conveniently obtained as a HindIII E restriction fragment (Greenway, P. J. et al., Gene 18: 355-360 (1982)). Of course, promoters from the host cell or related species also are useful herein.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell Bio. 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, α-fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promoter and/or enhancer can be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTF.

Expression vectors used in eukaryotic host cells (yeast, fungi, insect, plant, animal, human or nucleated cells) can also contain sequences necessary for the termination of transcription which could affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

In certain embodiments the promoters are constitutive promoters. This can be any promoter that causes transcription regulation in the absence of the addition of other factors. Examples of this type of promoter are the CMV promoter and the beta actin promoter, as well as others discussed herein. In certain embodiments the promoter can consist of fusions of one or more different types of promoters. For example, the regulatory regions of the CMV promoter and the beta actin promoter are well known and understood, examples, of which are disclosed herein. Parts of these promoters can be fused together to, for example, produce a CMV-beta actin fusion promoter, such as the one shown in SEQ ID NO:18. It is understood that this type of promoter has a CMV component and a beta actin component. These components can function independently as promoters, and thus, are themselves considered beta actin promoters and CMV promoters. A promoter can be any portion of a known promoter that causes promoter activity. It is well understood that many promoters, including the CMV and Beta Actin promoters have functional domains which are understood and that these can be used as a beta actin promoter or CMV promoter. Furthermore, these domains can be determined. For example, SEQ ID NO:s 15-33 display a number of CMV promoters, beta actin promoters, and fusion promoters. These promoters can be compared, and for example, functional regions delineated, as described herein. Furthermore, each of these sequences can function independently or together in any combination to provide a promoter region for the disclosed nucleic acids.

The promoters can also be non-constitutive promoters, such as cell specific promoters. These are promoters that are turned on at specific time in development or stage or a particular type of cell, such as a cardiac cell, or neural cell, or a bone cell. Some examples of cell specific promoters are, the neural enolase specific promoter (NSE), the procollagen promoters COL1A1 (SEQ ID NO:35) and COL2A1 (SEQ ID NO:36), the CD11b promoter (PBMC-microglia/macrophage/monocyte specific) (SEQ ID NO:69), and the glial specific glial fibrillary acetic protein (GFAP) promoter (SEQ ID NO:34).

It is understood that the recombinant systems can be expressed in a tissue-specific manner. It is understood that tissue specific expression can occur due to the presence of a tissue-specific promoter. Typically, proteins under control of a tissue-specific promoter are transcribed when the promoter becomes active by virtue of being present in the tissue for which it is specific. Therefore, all cells can encode for a particular gene without global expression. As such, labeled proteins can be shown to be present in certain tissues without expression in other nearby tissues that could complicate results or expression of proteins in tissues where expression is detrimental to the host. Disclosed are methods wherein the cre recombinase is under the control of the EIIA promoter, a promoter specific for breast tissue, such as the WAP promoter, a promoter specific for ovarian tissue, such as the ACTB promoter, or a promoter specific for bone tissue, such as osteocalcin. Any tissues specific promoter can be used. Promoters specific for prostate, testis, and neural are also disclosed. Examples of some tissue-specific promoters include but are not limited to MUC1, EIIA, ACTB, WAP, bHLH-EC2, HOXA-1, Alpha-fetoprotein (AFP), opsin, CR1/2, Fc-γ-Receptor 1 (Fc-γ-R1), MMTVD-LTR, the human insulin promote, Pdha-2. For example, use of the AFP promoter creates specificity for the liver. Another example, HOXA-1 is a neuronal tissue specific promoter, and as such, proteins expressed under the control of HOXA-1 are only expressed in neuronal tissue. Sequences for these and other tissue-specific promoters are known in the art and can be found, for example, in Genbank, at www.pubmed.gov.

b) Markers

The viral vectors can include nucleic acid sequence encoding a marker product. This marker product is used to determine if the gene has been delivered to the cell and once delivered is being expressed. Preferred marker genes are the *E. Coli* lacZ gene, which encodes β-galactosidase, and green fluorescent protein.

In some embodiments the marker can be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

c) Post Transcriptional Regulatory Elements

The disclosed vectors can also contain post-transcriptional regulatory elements. Post-transcriptional regulatory elements can enhance mRNA stability or enhance translation of the transcribed mRNA. An exemplary post-transcriptional regulatory sequence is the WPRE sequence isolated from the woodchuck hepatitis virus. [Zufferey R, et al., J Virol; 73:2886-92 (1999)]. Post-transcriptional regulatory elements can be positioned both 3' and 5' to the exogenous gene, but it is preferred that they are positioned 3' to the exogenous gene.

d) Transduction Efficiency Elements

Transduction efficiency elements are sequences that enhance the packaging and transduction of the vector. These elements typically contain polypurine sequences. An example of a transduction efficiency element is the ppt-cts sequence that contains the central polypurine tract (ppt) and central terminal site (cts) from the HIV-1 pSG3 molecular clone (SEQ ID NO:1 bp 4327 to 4483 of HIV-1 pSG3 clone).

e) 3' Untranslated Regions

Expression vectors used in eukaryotic host cells (yeast, fungi, insect, plant, animal, human or nucleated cells) may also contain sequences necessary for the termination of transcription which could affect mRNA expression. These 3' untranslated regions are transcribed as polyadenylated segments in the untranslated portion of the mRNA encoding the exogenous gene. The 3' untranslated regions also include transcription termination sites. The transcription unit also can contain a polyadenylation region. One benefit of this region is that it increases the likelihood that the transcribed unit will be processed and transported like mRNA. The identification and use of polyadenylation signals in expression constructs is well established. Homologous polyadenylation signals can be used in the transgene constructs. In an embodiment of the transcription unit, the polyadenylation region is derived from the SV40 early polyadenylation signal and consists of about 400 bases. Transcribed units can contain other standard sequences alone or in combination with the above sequences improve expression from, or stability of, the construct.

7. Peptides a) Protein Variants

Disclosed herein are constructs comprising nucleic acids that encode polypeptides. As discussed herein, there can be numerous variants of each of these polypeptides, such as IL-1ra, that are herein contemplated. In addition, to the known functional proteins that are disclosed, such as IL-1ra, there are also derivatives of these proteins which also function in the disclosed methods and compositions. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof can be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviations | |
|---|---|---|
| Alanine | Ala | A |
| allosoleucine | AIle | |
| Arginine | Arg | R |
| asparagine | Asn | N |
| aspartic acid | Asp | D |
| Cysteine | Cys | C |
| glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| phenylalanine | Phe | F |
| proline | Pro | P |
| pyroglutamic acid | pGlu | |
| Serine | Ser | S |
| Threonine | Thr | T |
| Tyrosine | Tyr | Y |
| Tryptophan | Trp | W |
| Valine | Val | V |

TABLE 2

Amino Acid Substitutions
Original Residue Exemplary Conservative Substitutions, others are known in the art.

| | |
|---|---|
| Ala | Ser |
| Arg | Lys; Gln |
| Asn | Gln; His |
| Asp | Glu |
| Cys | Ser |
| Gln | Asn, Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NO:5 sets forth a particular sequence of IL-1ra and SEQ ID NO:9 sets forth a particular sequence of a IL-1R2 protein. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. MoL. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. It is also understood that while no amino acid sequence indicates what particular DNA sequence encodes that protein within an organism, where particular variants of a disclosed protein are disclosed herein, the known nucleic acid sequence that encodes that protein in the particular organism from which that protein arises is also known and herein disclosed and described.

It is understood that there are numerous amino acid and peptide analogs which can be incorporated into the disclosed compositions. For example, there are numerous D amino acids or amino acids which have a different functional substituent then the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $—CH_2NH—$, $—CH_2S—$, $—CH_2—CH_2—$, $—CH=CH—$ (cis and trans), $—COCH_2—$, $—CH(OH)CH_2—$, and $—CHH_2SO—$ (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) ($—CH_2NH—$, $CH_2CH_2—$); Spatola et al. Life Sci 38:1243-1249 (1986) ($—CH\ H_2—S$); Hann J. Chem. Soc Perkin Trans. 1307-314 (1982) ($—CH—CH—$, cis and trans); Almquist et al. J. Med. Chem. 23:1392-1398 (1980) ($—COCH_2—$); Jennings-White et al. Tetrahedron Lett 23:2533 (1982) ($—COCH_2—$); Szelke et al. European Appln, EP 45665 CA (1982): 97:39405 (1982) ($—CH(OH)CH_2—$); Holladay et al. Tetrahedron. Lett 24:4401-4404 (1983) ($—C(OH)CH_2—$); and Hruby Life Sci 31:189-199 (1982) ($—CH_2—S—$); each of which is incorporated herein by reference. A particularly preferred non-peptide linkage is $—CH_2NH—$. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

8. Pharmaceutical Carriers/Delivery of Pharmaceutical Products

The compositions disclosed herein can also be administered in vivo in a pharmaceutically acceptable carrier. By "pharmaceutically acceptable" is meant a material that is not biologically or otherwise undesirable, i.e., the material can be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions can be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials can be in solution, suspension (for example, incorporated into microparticles, liposomes, or cells). These can be targeted to a particular cell type via antibodies, receptors, or receptor ligands. The following references are examples of the use of this technology to target specific proteins to tumor tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129: 57-80, (1992); and Roffler, et al., Biochem. Pharmacol, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The pharmaceutical composition can be administered in a number of ways depending on whether local or systemic treatment is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like could be necessary or desirable.

Compositions for oral administration include powders or granules, suspensions or solutions in water or non-aqueous media, capsules, sachets, or tablets. Thickeners, flavorings, diluents, emulsifiers, dispersing aids or binders could be desirable.

Some of the compositions can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions can be determined empirically, and making such determinations is within the skill in the art. The dosage ranges for the administration of the compositions are those large enough to produce the desired effect in which the symptoms of disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

Following administration of a disclosed composition, such as a vector, for treating, inhibiting, or preventing inflammation, the efficacy of the therapeutic vector can be assessed in various ways well known to the skilled practitioner. For instance, one of ordinary skill in the art will understand that a composition, such as a vector, disclosed herein is efficacious in treating or inhibiting inflammation in a subject by observing that the composition reduces inflammation.

9. Animals

Provided herein are transgenic animals comprising germline transmission of any of the vectors or nucleic acids provided herein. In one aspect, the transgenic animal provided herein is an excision activated transgenic (XAT) animal. The disclosed transgenic animals can have temporally and spatially regulated transgene expression (Brooks, A I, et al. 1991. Nature Biotech 15:57-62; Brooks, A I, et al. 1999. Neuroreport 10:337-344; Brooks, A I., et al. 2000. Proc Natl Acad Sci USA 97:13378-13383) of an inflammation element. It is understood that where the transgenic animal comprises a nucleic acid comprising a recombination site, as disclosed herein, delivery of a recombinase, such as Cre recombinase to cells within the provided transgenic animal will result in the expression of the inflammatory modulator, e.g., IL-1, IL-1ra, COX-2, within those cells.

By a "transgene" is meant a nucleic acid sequence that is inserted by artifice into a cell and becomes a part of the genome of that cell and its progeny. Such a transgene an be (but is not necessarily) partly or entirely heterologous (e.g., derived from a different species) to the cell. The term "transgene" broadly refers to any nucleic acid that is introduced into an animal's genome, including but not limited to genes or DNA having sequences which are perhaps not normally present in the genome, genes which are present, but not normally transcribed and translated ("expressed") in a given genome, or any other gene or DNA which one desires to introduce into the genome. This can include genes which are normally be present in the nontransgenic genome but which one desires to have altered in expression, or which one desires to introduce in an altered or variant form. A transgene can include one or more transcriptional regulatory sequences and any other nucleic acid, such as introns, that can be necessary for optimal expression of a selected nucleic acid. A transgene can be as few as a couple of nucleotides long, but is preferably at least about 50, 100, 150, 200, 250, 300, 350, 400, or 500 nucleotides long or even longer and can be, e.g., an entire genome. A transgene can be coding or non-coding sequences, or a combination thereof. A transgene usually comprises a regulatory element that is capable of driving the expression of one or more transgenes under appropriate conditions. By "transgenic animal" is meant an animal comprising a transgene as described above. Transgenic animals are made by techniques that are well known in the art. The disclosed nucleic acids, in whole or in part, in any combination, can be transgenes as disclosed herein.

Disclosed are animals produced by the process of transfecting a cell within the animal with any of the nucleic acid molecules disclosed herein. Disclosed are animals produced by the process of transfecting a cell within the animal any of the nucleic acid molecules disclosed herein, wherein the animal is a mammal. Also disclosed are animals produced by the process of transfecting a cell within the animal any of the nucleic acid molecules disclosed herein, wherein the mammal is mouse, rat, rabbit, cow, sheep, pig, or primate.

The disclosed transgenic animals can be any non-human animal, preferably a non-human mammal (e.g. mouse, rat, rabbit, squirrel, hamster, rabbits, guinea pigs, pigs, micropigs, prairie dogs, baboons, squirrel monkeys and chimpanzees, etc), bird or an amphibian, in which one or more cells contain heterologous nucleic acid introduced by way of human intervention, such as by transgenic techniques well known in the art. The nucleic acid is introduced into the cell, directly or indirectly, by introduction into a precursor of the cell, such as by microinjection or by infection with a recombinant virus. The disclosed transgenic animals can also include the progeny of animals which had been directly manipulated or which were the original animal to receive one or more of the disclosed nucleic acids. This molecule can be integrated within a chromosome, or it can be extrachromosomally replicating DNA. For techniques related to the production of transgenic animals, see, inter alia, Hogan et al (1986) Manipulating the Mouse Embryo—A Laboratory Manual Cold Spring Harbor Laboratory, Cold Spring Harbor, N.Y., 1986).

Animals suitable for transgenic experiments can be obtained from standard commercial sources such as Charles River (Wilmington, Mass.), Taconic (Germantown, N.Y.), and Harlan Sprague Dawley (Indianapolis, Ind.). For example, if the transgenic animal is a mouse, many mouse strains are suitable, but C57BL/6 female mice can be used for embryo retrieval and transfer. C57BL/6 males can be used for mating and vasectomized C57BL/6 studs can be used to stimulate pseudopregnancy. Vasectomized mice and rats can be obtained from the supplier. Transgenic animals can be made by any known procedure, including microinjection methods, and embryonic stem cells methods. The procedures for manipulation of the rodent embryo and for microinjection of DNA are described in detail in Hogan et al., Manipulating the Mouse Embryo (Cold Spring Harbor Laboratory, Cold Spring Harbor, N.Y., 1986), the teachings of which are generally known and are incorporated herein.

Transgenic animals can be identified by analyzing their DNA. For this purpose, for example, when the transgenic animal is an animal with a tail, such as rodent, tail samples (1 to 2 cm) can be removed from three week old animals. DNA from these or other samples can then be prepared and analyzed, for example, by Southern blot, PCR, or slot blot to detect transgenic founder (F (0)) animals and their progeny (F (1) and F (2)). The present invention further provides transgenic non-human animals that are progeny of crosses between a transgenic animal of the invention and a second animal. Transgenic animals can be bred with other transgenic animals, where the two transgenic animals were generated using different transgenes, to test the effect of one gene product on another gene product or to test the combined effects of two gene products.

The provided compositions can be evaluated using a mouse model of arthritis. As prolonged expression of IL-1β in the joint can lead to the development of arthrosis similar to that seen in arthritis patients, disclosed is a mouse model of arthritis based on prolonged, low level intra-articular transgenic expression of IL-1β. The role of IL-1β, TNFα and other inflammatory mediators, such as prostanoids, are well recognized in the pathogenesis of arthritis. The two most commonly forms of arthritis are osteoarthritis (OA), which affects about 80%-90% of all adults over the age of 65, and rheumatoid arthritis (RA), which affects approximately 1% of the general U.S. population. Although distinct differences exist between OA and RA, both appear to develop secondary to a pro-inflammatory cascade. Previous animal models have proven valuable in studying arthritis and testing novel therapies, including the model of methylated bovine serum albumin/IL-1β, intra-articular administration of IL-1β, constitutive intra-articular expression of IL-1β following ex vivo transfer of genetically engineered synoviocytes, as well as the TNFα transgenic mouse model. The aforementioned IL-1β models are based on the direct administration of a deleterious agent, whereas the TNFα transgenic mouse is based on the prolonged expression of TNFα in vivo and has thus far yielded valuable insight on the role of TNFα in the development of arthritis. However, as with the majority of transgenic mice, TNFα transgenesis is susceptible to uncontrolled and uncharacterized developmental compensatory changes.

The provided mouse model is based on a method (somatic mosaic analysis) utilizing a germline transmitted recombinational substrate containing a dormant transcription unit and somatic gene transfer of a viral vector that expresses Cre recombinase that "activates" the gene of interest. IL-1β excisionally activated transgenic (IL-1β$^{XAT}$) mice, and variations thereof, have been generated using this method. The provided mouse model is the subject of U.S. Patent Application No. 60/627,604, which is herein incorporated by reference in its entirety. This mouse model allows for the induction of localized inflammation based on the delivery of a Cre recombinase expression vector such as FIV(Cre) to the target site. Variations include the use of cell or tissue specific promoters such as in for example the COL1A1-IL-1β$^{XAT}$ mouse. For example, the delivery of FIV(Cre) to, for example, the joints of the COLL1A1-IL-1β$^{XAT}$ mouse can induce inflammation to model arthritis. This mouse model can thus be used to, for example, test or optimize the effects of the provided constructs on arthritis. As another example, delivery of FIV(Cre) to the circulation or joint of the COLL1A1-IL-1β$^{XAT}$ mouse can induce inflammation in the brain to model, for example, Alzheimer's disease.

IL-1β$^{XAT}$ regulation is controlled in a temporal (time) and spatial (location) fashion by the Cre/loxP molecular genetic method utilizing (1) a germline transmitted recombinational substrate (e.g. COLL1-IL1β$^{XAT}$) containing a dormant transcription unit and (2) somatic gene transfer of a viral vector that expresses Cre recombinase which "activates" the gene of interest. Thus, these mice can be used herein to induce IL-1β constitutive expression in the joints (e.g., knee) of mice. As an example, localized transgene activation, i.e., IL-1β, can be accomplished in IL-1β$^{XAT}$ mice by the intracapsular injection of FIV(Cre), a lentivirus capable of transducing soft and hard tissues of joints, to the area of interest, and subsequent recombinational excision of the ►STOP► cassette leading to gene transcription. Recombination-mediated gene "activation" permanently alters the genetic constitution of infected cells thus allowing chronic IL-1β synthesis. The COLL1A1 promoter can further be used to target gene expression to chondrocytes, osteocytes and fibroblasts, making this transgenic mouse available for the study of arthritis in any joint of interest. This promoter has been shown to target gene expression in bone and cartilage and was cloned in the IL-1β$^{XAT}$ gene in place of the CMV promoter (FIG. 1): (COLL1A1-IL1β$^{XAT}$) COLL1A1=>►STOP►ssIL1β-IRES-lacZ COLL2 is another suitable promoter. This transgene has been constructed and tested in a murine NIH 3T3 stable cell line following expression of Cre recombinase by the transient transfection of the pRc/CMV-CreWT expression vector or after infection by the lentiviral vector FIV(Cre).

The somatic gene transfer of the recombinase, such as Cre can be performed using any type of vector system producing the recombinase. However, in certain embodiments, the vector system is a self inactivating vector system, wherein the promoter, for example, of the recombinase is flanked by recombination sites so that upon production of the recombinase, the recombinase will down regulate its own production. The delivery vectors for the recombinase can be CRE mediated.

For example, activation of the dormant COLL1-IL1β$^{XAT}$ can be mediated by the transfer of Cre recombinase to the area of interest (e.g. knee) via a self-inactivating Cre feline immunodeficiency virus FIV(Cre). The effects of this FIV vector system have been previously examined using the reporter gene lacZ (β-galactosidase) in mice that received intra-articular injections of a viral solution [Kyrkanides S, et al. (2004). J Dental Res 83: 65-70], wherein transduction of soft (articular disc) and hard (cartilage) TMJ tissues was demonstrated. The FIV(Cre) vector has been constructed by cloning a loxP-flanked ("floxed") nlsCre cassette in the place of the lacZ gene; the nuclear localization signal (nls) was fused to the cre open reading frame by PCR and subsequently cloned into the TOPO 2.1 vector (Invitrogen) per manufacturer's instructions employing a custom-made floxed cloning cassette. The reason for developing a self-inactivating cre gene is based on a recent paper [Pfeifer A and Brandon E P, Kootstra Neeltje, Gage F H, Verma I M (2001). Proc Natl Acad Sci U.S.A. 98: 11450-5], whereby the authors reported cytotoxicity due to prolonged expression of Cre recombinase mediated by infection using a lentiviral vector. In the provided construct, upon production of adequate levels of Cre recombinase to produce excisional activation of COLL1-IL1$\beta^{XAT}$ following successful transduction of target cells with FIV(Cre), Cre is anticipated to de-activate the cre gene by loxP-directed self excisional recombination.

10. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include primers to perform the amplification reactions discussed in certain embodiments of the methods, as well as the buffers and enzymes required to use the primers as intended.

D. Methods of Making the Compositions

The compositions disclosed herein and the compositions necessary to perform the disclosed methods can be made using any method known to those of skill in the art for that particular reagent or compound unless otherwise specifically noted.

1. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., *Molecular Cloning: A Laboratory Manual,* 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356 (1984), (phosphotriester and phosphite-triester methods), and Narang et al., *Methods Enzymol.,* 65:610-620 (1980), (phosphotriester method). Protein nucleic acid molecules can be made using known methods such as those described by Nielsen et al., *Bioconjug. Chem.* 5:3-7 (1994).

2. Peptide Synthesis

One method of producing the disclosed proteins, such as SEQ ID NO:5, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides can be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

3. Processes for Making the Compositions

Disclosed are processes for making the compositions as well as making the intermediates leading to the compositions. There are a variety of methods that can be used for making these compositions, such as synthetic chemical methods and standard molecular biology methods. It is understood that the methods of making these and the other disclosed compositions are specifically disclosed.

Disclosed are nucleic acid molecules produced by the process comprising linking in an operative way a promoter element and a nucleic acid element disclosed herein. The nucleic acid element can, for example, encode a ligand binding inhibitor. Thus, disclosed are nucleic acid molecules produced by the process comprising linking in an operative way a promoter element and an IL-1ra element. Also disclosed is a nucleic acid molecule produced by the process comprising linking in an operative way a promoter element and an IL-1R2 element. Also disclosed is a nucleic acid molecules produced by the process comprising linking in an operative way a promoter element and an IL-1R1 fragment element. Also disclosed is a nucleic acid molecules produced by the process comprising linking in an operative way a promoter element and an IL-1 fragment element.

Also disclosed are nucleic acid molecules produced by the process comprising linking in an operative way a promoter element and a nucleic acid element wherein the nucleic acid encodes a gene expression inhibitor disclosed herein. As an example, disclosed are nucleic acid molecules produced by the process comprising linking in an operative way a promoter element and a COX-1 siRNA element. Also disclosed are nucleic acid molecules produced by the process comprising linking in an operative way a promoter element and a COX-2 siRNA element. Also disclosed are nucleic acid molecules produced by the process comprising linking in an operative way a promoter element and a mPGES siRNA element. Also disclosed are nucleic acid molecules produced by the process comprising linking in an operative way a promoter element and cPGES siRNA element.

Further disclosed are cells produced by the process of transforming the cell with any of the disclosed nucleic acids. Disclosed are cells produced by the process of transforming the cell with any of the non-naturally occurring disclosed nucleic acids.

Disclosed are any of the peptides produced by the process of expressing any of the disclosed nucleic acids. Disclosed are any of the non-naturally occurring disclosed peptides produced by the process of expressing any of the disclosed nucleic acids. Disclosed are any of the disclosed peptides produced by the process of expressing any of the non-naturally disclosed nucleic acids.

Disclosed are animals produced by the process of transfecting a cell within the animal with any of the nucleic acid molecules disclosed herein. Disclosed are animals produced by the process of transfecting a cell within the animal any of the nucleic acid molecules disclosed herein, wherein the animal is a mammal. Also disclosed are animals produced by the process of transfecting a cell within the animal any of the nucleic acid molecules disclosed herein, wherein the mammal is mouse, rat, rabbit, cow, sheep, pig, or primate. Also disclosed are mammals wherein mammal is a murine, ungulate, or non-human primate.

Also disclose are animals produced by the process of adding to the animal any of the cells disclosed herein.

E. Methods of Using the Compositions

1. Methods of Using the Compositions as Research Tools

The disclosed compositions can be used in a variety of ways as research tools. For example, the disclosed compositions, such as SEQ ID NOs:5 can be used to study the interactions between IL-1 and IL-1R1, by for example acting as inhibitors of binding.

2. Therapeutic Uses

Effective dosages and schedules for administering the compositions can be determined empirically, and making such determinations is within the skill in the art. The dosage ranges for the administration of the compositions are those large enough to produce the desired effect in which the symptoms of the disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products.

Following administration of a disclosed composition, such as the disclosed constructs, for treating, inhibiting, or preventing inflammation, the efficacy of the therapeutic construct can be assessed in various ways well known to the skilled practitioner. For instance, one of ordinary skill in the art will understand that a composition, such as the disclosed constructs, disclosed herein is efficacious in treating inflammation or inhibiting or reducing the effects of inflammation in a subject by observing that the composition reduces the onset of the conditions associated with these diseases. Furthermore, the amount of protein or transcript produced from the constructs can be analyzed using any diagnostic method. For example, it can be measured using polymerase chain reaction assays to detect the presence of construct nucleic acid or antibody assays to detect the presence of protein produced from the construct in a sample (e.g., but not limited to, blood or other cells, such as neural cells) from a subject or patient.

F. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Construction of an Inducible Interleukin-1β Transgene-IL-1β$^{XAT}$

The human IL-1 cDNA was cloned from human U937 cells (ATCC, Manassas Va.) by polymerase chain reaction (PCR) as follows: Total mRNA was extracted employing the TRIzol® reagent (Invitrogen, Carlsbad Calif.) per manufacturer's instructions. PCR primers were designed for the amplification of the portion of the cDNA that corresponds to the mature, secreted IL-1β protein. The peptide secretion signal (ss) of the human IL-1 receptor antagonist gene (IL1-RA) was incorporated into the upper PCR primer, upstream to the IL-1β open reading frame (ORF), to ensure proper compartmentalization and secretion of the transgenic IL-1β peptide. This PCR-synthesized ss-IL1β fusion construct was cloned directly into the TOPO 2.1 vector (Invitrogen) per manufacturer's instructions. Subsequently, the cell autonomous and gratuitous β-galactosidase reporter gene (lacZ) was inserted down-stream to the IL-1β ORF, followed by the bovine growth hormone poly A tail (pA) sequence: ssIL-1β-IRES-lacZ bicistronic gene (FIG. 1). Translation of the second ORF, lacZ, is facilitated by an internal ribosomal entry sequence (IRES). During the initial stages of experimentation, expression of the bicistronic ssIL-1β-IRES-lacZ transgene was ubiquitously driven by the cytomegalovirus promoter (CMV), the transcription of which was inhibited by a loxP-flanked (floxed) transcriptional termination cassette STOPfl/fl. Transcriptional activation and transgene expression can be turned-on by loxP-directed DNA recombination mediate by the bacteriophage P1 Cre recombinase (Cre/loxP system).

a) Cre-Mediated Activation of the Inducible IL-1β$^{XAT}$ Transgene

The function of IL-1β$^{XAT}$ was tested in vitro by two different experimental strategies. First, IL-1β$^{XAT}$ regulation by Cre recombinase was evaluated in NIH 3T3 murine fibroblasts (ATCC) in vitro. The IL-1β$^{XAT}$ gene was transiently co-expressed with the wild type cre gene (cloned into the expression vector pRc/CMV-CreWT; Invitrogen) following transient transfection using the LIPOFECTAMINE 2000 reagent (Invitrogen) per manufacturer's instructions. As anticipated, transient expression of Cre recombinase resulted in loxP-directed DNA recombination of IL-1β$^{XAT}$ and excision of the "floxed" transcriptional termination signal ►STOP►, ultimately leading to gene activation. Control conditions included co-transfection of IL-1β$^{XAT}$ with the expression vector pRc/CMV- (lacking any gene), as well as naïve NIH 3T3 cells. IL-1β expression was assessed at the mRNA level by reverse transcriptase PCR (RT-PCR), and lacZ expression was evaluated by X-gal histochemistry. In brief, no IL-1β transcript was detected in naïve NIH 3T3 cells; in contrast, IL-1β$^{XAT}$+Cre co-transfection resulted in induction of ssIL-1β and lacZ gene expression (FIG. 2). In addition, IL-1β$^{XAT}$ function was evaluated in the inducible Cre recombinase cell line, 293HGLVP/CrePr, a stable cell line recently developed for testing the regulation of excisionally-activated genes utilizing the Cre/loxP technology and described in U.S. patent application Ser. No. 10/978,927, herein incorporated by reference). This cell line comprises an inducible, loxP-directed DNA recombination system by placing Cre recombinase under dual transcriptional and post-translational control (Kyrkanides et al., 2003, herein incorporated by reference). In brief, the system is comprised of two components: (1) The chimeric transcriptional activator GLVP and (2) the CrePr fusion protein, which consists of the bacterial Cre recombinase and the mutated progesterone receptor hPR891 gene, driven by a custom GAL45/TATA minimal promoter. The mutated hPR891 receptor is highly sensitive to the synthetic progesterone compound mifepristone (RU486). Binding of RU486 to hPR891 results in activation of GLVP and subsequent synthesis of CrePr, the activity of which is also turned-on by RU486 at the post-translational level. RU486 administration to 293HGLVP/CrePr cells following IL-1β$^{XAT}$ transfection resulted in DNA excisional recombination and subsequent expression of human IL-1β and the bacterial β-galactosidase reporter gene (lacZ). Please refer to FIG. 3 for summary of the experiment.

b) IL-1β$^{XAT}$ Activation Produces a Biologically Potent IL-1β Cytokine

The ability of murine cells to synthesize and secrete biologically active IL-1β cytokine was tested in vitro as follows. In an experiment similar to that described in FIG. 2, murine NIH 3T3 fibroblasts were transfected with the IL-1β$^{XAT}$ gene. Concomitantly, Cre recombinase was transiently expressed in these cells (co-transfection of the pRc/CMV-CreWT vector), and the conditioned supernatant media were collected at 72 hours. The presence of human IL-1β was confirmed by ELISA. The conditioned media were then placed on naïve murine fibroblasts, and levels of the inducible cyclooxygenase COX-2 were evaluated as a measure of cytokine potency by quantitative RT-PCR in total mRNA extracts using protocols previously described [Moore, A H, et al. Journal of Neuroimmunology. 148(1-2):32-40, 2004]. Control experimental conditions included conditioned media derived from cells co-transfected with the pRc/CMV-backbone vector (lacking the cre gene) along with the IL-1β$^{XAT}$ gene, as well as naïve cells. In brief, murine fibroblasts treated with conditioned medium collected from Cre-activated IL-1β$^{XAT}$ cells resulted in significant COX-2 induction compared to cells exposed to media derived from pRc/CMV-treated or naïve cells. Please see FIG. 4 for a summary of the experiment.

c) IL-1β Induces Down-Stream Inflammation-Related Genes

IL-1β is a multi-potent pro-inflammatory cytokine, the expression of which is rapidly upregulated following trauma and/or inflammation. Moreover, a plethora of inflammation-related genes are in turn induced by IL-1β, leading to exacerbation of the inflammatory response. IL-1β regulates downstream inflammatory genes, including the inducible isoform of cyclooxygenase (COX-2) and the intercellular adhesion molecule-1 (ICAM-1), the monocyte chemoattractant protein-1 (MCP-1), as well as collagenases A (MMP-2) and B (MMP-9). ICAM-1 and MCP-1 are molecules associated with the recruitment of circulating immune cells at the site of injury (i.e. neutrophils and monocytes, respectively), whereas MMP-2 and MMP-9 are collagenases associated with tissue destruction during arthritis and injury. Primary rat endothelial cells were employed as a representative rodent model to investigate the effects of IL-1β on the regulation of ICAM-1, MCP-1, MMP-2 and MMP-9 at the transcriptional level (mRNA) as well as the enzyme activity level (zymography). FIG. 5 summarizes the regulation of these genes over time. IL-1β upregulated the synthesis of COX-2, MCP-1, ICAM-1 and the inducible collagenase B (MMP-9). mRNA levels of the constitutive collagenase B (MMP-2) were not altered by IL-1β, but interestingly MMP-2 enzyme activity also increased with time, presumably due to post-translational activation from other MMPs.

d) The COLL1A1 Promoter Drives IL-1β$^{XAT}$ Expression to Collagen I Producing Cells Prolonged expression of IL-1β in the joint can lead to the development of arthrosis similar to that seen in arthritis patients. This can be demonstrated using temporally and spatially controlled expression of IL-1β in mice, which can be accomplished by targeting IL-1β$^{XAT}$ transgene expression to chondrocytes, osteocytes and fibroblasts by the 3.6 Kb promoter of the A1 chain of pro-collagen 1 gene. This promoter has been shown to target gene expression in bone and cartilage and was cloned in the IL-1β$^{XAT}$ gene in place of the CMV promoter (FIG. 1): (COLL1A1-IL1β$^{XAT}$) COLL1A1=> ►STOP►ssIL1β-IRES-lacZ The collagen 1 promoter was chosen based on the prediction that FIV(Cre) would primarily infect cells located superficially within the joint capsule, including the meniscus, cartilage, and perhaps bone (Kyrkanides et al., 2004). COLL2 is another suitable promoter. This transgene has been constructed and tested in a murine NIH 3T3 stable cell line following expression of Cre recombinase by the transient transfection of the pRc/CMV-CreWT expression vector or after infection by the lentiviral vector FIV(Cre). Expression of Cre recombinase led to transgene activation and IL-1β expression. Please refer to FIG. 6 for summary of the experiment.

e) Transgene Activation in Joints of Col1-IL1β$^{XAT}$ Mice

In order to evaluate the effect of transgene activation in the joints of Col1-IL1β$^{XAT}$ mice, two sets of Col1A1-IL1β$^{XAT}$ mice received intra-articular FIV(Cre) injections (a total of $10^6$ infectious particles) in the right and left knee, as well as the left and right temporomandibular joint (TMJ). The mice were monitored over a period of 8 weeks for changes in grooming behavior and locomotion. The mice were subsequently sacrificed and their knees and TMJs were histologically analyzed.

Behavioral changes were assessed as previously described (Dubuisson, D. and Dennis, S. Pain 1977; 4: 161-74; Abbott F V, et al. Eur J Pharmacol 1986; 126:126-41), which are herein incorporated by reference for teachings related to these methods. In brief, a group of Col1-IL1β$^{XAT}$ transgenic mice (N=3) received a single intra-articular injection of $10^6$ infectious particles of FIV(Cre) in the right and left knees at 2 months of age. In addition, a second group of mice (N=3) received saline injection and served as controls. During a session, each mouse was videotaped for 1 hour. The tape was then transferred digitally to a computer and analyzed in 20 periods of 3 minutes each. The duration of each mouse displaying grooming and licking was recorded and summed as seconds by an investigator who was blind to the animal group assignment. Injection of FIV(Cre) into the knee of Col1-IL1β$^{XAT}$ transgenic mice resulted in a four-fold increase in the duration of grooming as compared to saline-injected controls (FIG. 9, P<0.05).

Four groups of mice (N=3) were evaluated in terms of locomotive behavior by the rotorod appliance (Columbus Instruments, Columbus Ohio) and the lapse time until the mice fell off the rotating cylinder (20 rpm) was recorded. The mice were evaluated over a period of 8 weeks following the intra-articular injections (8 wks-16 wks of age). As seen in FIG. 10, it was demonstrated that FIV(Cre)-injected Col1-IL1β$^{XAT}$ transgenic mice developed significant locomotive deterioration (Tg+Cre) compared to transgenic mice injected with the control FIV(gfp) vector (TG+gfp), as well as the other control animals groups (WT-Cre & WT-saline).

Immunocytochemical detection of the reporter gene β-galactosidase was employed to confirm the activation of the Col1-IL1β$^{XAT}$ transgene by FIV(Cre) in this mouse model using antibodies raised against β-galactosidase and Cre recombinase. Shown in FIG. 11 is FITC-conjugated immunodetection of β-galactosidase (FIG. 11A), Texas Red-conjugated immunodetection of Cre recombinase (FIG. 11B), B/W image of the same microscopic field (FIG. 11C), overlap of panels A+B (FIG. 11D), and overlap of panels A+B+C (FIG. 11E). Demonstrated is the co-expression of β-galactosidase and Cre recombinase in vivo (FIG. 11, solid arrows). Note that there are more red cells than green cells (FIG. 11, open arrows) indicating that not all infected cells express the transgene Col1A1→IL1β-IRES-lacZ in the same capacity.

H&E staining of a knee section harvested from a 4 month old Col1-IL1β$^{XAT}$ transgenic mouse injected with FIV(Cre) revealed the formation of fibrillations (FIG. 12A, solid arrow) and of an articular lip (FIG. 12B, open arrow). In contrast, a transgenic mouse that received the control vector FIV(GFP) did not develop such anatomic aberrations (FIG. 12B). Alcian blue/orange semi-quantitative evaluation showed a decrease in cartilage (FIG. 12C, less blue stain) and bone (FIG. 12D, less red stain) density in the Col1-IL1β$^{XAT}$+FIV(Cre) knees compared to controls (FIG. 12E). Moreover, increased cloning along with thickening of the articular surfaces was observed in the experimental animals (FIG. 12C, indicated by small arrows). These observations indicate the presence of arthritis in the knee following transgene induction by Cre recombinase.

Eight weeks after FIV(Cre) injection in the knee and TMJ of Col1-IL1β$^{XAT}$ mice, the brain was evaluated for activation of microglia and astrocytes by immunocytochemistry. Using a monoclonal antibody raised against the MHC-class II antigen, the presence of activated microglia was detected in the brain (FIGS. 13A,C). In contrast, control animals did not display any MHC-II positive cells. Interestingly, there was lack of astrocyte activation in the brains of these animals as assessed by glial fibrillary acidic protein (GFAP) (FIGS. 13B, D). In general, control animals (inactive transgenic mice) displayed no signs of brain inflammation by MHC-II or GFAP immunocytochemistry.

Eight weeks after FIV(Cre) injection in the TMJ of Col1-IL1β$^{XAT}$ mice anatomic aberrations of the joint were evaluated by semi-quantitative Alcian blue-orange G histochemistry. Shown in FIGS. 14A and C are a TMJ section from an inactive Col1-IL1β$^{XAT}$ mouse depicting the condylar head as well as the meniscus. In comparison, FIGS. 14B and C depict a TMJ section harvested from a Col1-IL1β$^{XAT}$ mouse injected with FIV(Cre) in the TMJ. An apparent reorganization of the TMJ cell layers was observed following FIV(Cre) injection, whereby a loss of the most superficial cell layer was noted accompanied by disorganization of the proliferative layer of chondrocytes (FIG. 14, open arrows). In addition, a decrease in cartilage content was observed in the condylar head of FIV(Cre)-treated Col1-IL1β$^{XAT}$ mice as evaluated semi-quantitatively by Alcian blue-orange G histochemistry (FIG. 14).

2. Example 2

Development of Arthritis in the Adult Mouse: the IL-1β Somatic Mosaic Model a) Development of the IL-1B Somatic Mosaic Mouse Prolonged, low-level intra-articular expression of IL-1β in the adult mouse can result in the development of arthritis. This can be demonstrated using the somatic mosaic analysis method for the induction of long-term expression of IL-1β, due to a permanent change in the genetic constitution of infected cells, at a particular location and during a specific developmental stage. The somatic mosaic analysis model offers significant advantages compared to traditional transgenic mice, because it avoids compensatory adaptations often encountered in transgenic mice during development and allows regional activation of a gene (Brooks et al., 1997, 1999). The collagen I promoter was chosen based to drive transgene expression based on the prediction that FIV(Cre) would primarily infect cells located superficially within the joint capsule, including the meniscus, cartilage, and perhaps cancellous osteocytes. COLL2 is another choice of suitable promoter.

COLL1-IL1β$^{XAT}$ was microinjected in fertilized C57BL/6 oocytes and subsequently implanted into pseudo-pregnant mothers. One set of micro-injection has already been performed that yielded 8 pups, of which 3 were identified as positive founders by PCR of genomic DNA extracted from tail snips employing primers specifically designed against the IL1β$^{XAT}$ transgene. The 3 founders have been bred with C57B1/6 wild type stock mice for analysis of germ-line transmission of a functional transgene (Ngo et al., 2002; Pinkert 2003). In fact, at least two founders have successfully given transgenic pups at the time of grant submission, which were being raised to maturity for further breeding.

b) Characterize the activation of COLL1-IL1β$^{XAT}$ In Vivo

COLL1-IL1β$^{XAT}$ function can be evaluated in transgenic lines after FIV(Cre) injection into the knee joint capsule (approximately 10$^7$ infectious particles in 50 μl volume) in 3 month old mice and activation of the dormant COLL1-IL1β$^{XAT}$. The ability of FIV(Cre) to activate the dormant COLL1-IL1β$^{XAT}$ gene has been previously described in U.S. Patent Application No. 60/627,604, herein incorporated by reference for this teaching. COLL1-IL1β$^{XAT}$ activation can be evaluated as follows. First, lacZ expression can be readily assessed in decalcified histology sections by X-gal histochemistry and immunocytochemistry as previously described (Kyrkanides et al., 2001, 2004). ssIL-1β and lacZ transcript levels can be assessed by semi-quantitative RT-PCR in total mRNA knee extracts from experimental FIV (Cre) intra-articular injection and control FIV(lacZ) intra-articular injection mice. Localization of ssIL-1β and β-galactosidase can be achieved on histology sections by immunocytochemistry using antibodies raised specifically against bacterial β-galactosidase and human IL-1β; the identity of transduced cells can be confirmed by double immunofluorescence employing antibodies raised against the following antigens. Osteocytes/osteblasts can be confirmed by the expression alkaline phosphatase, osteocalcin, type I collagen. Chondrocytes can be confirmed by detection of collagen II (Scott-Burden et al., 2002). Histologically, ssIL-1β mRNA localization can be performed by in situ hybridization (ISH); the identity of transduced cells can be confirmed by coupling ISH with immunocytochemistry (ICC), employing aforementioned antibodies. The levels of secreted human IL-1β in joint synovial fluid can be analyzed by ELISA as described in Example 1 (Catalog #DLB50; R&D Systems Inc, Minneapolis Minn.). 3-5 mouse lines can be analyzed for transgene function at the mRNA, protein and histology levels following gene activation. For this purpose, transgenic mice can be injected intra-articularly with FIV(Cre), FIV(lacZ) or saline at 2 months of age and subsequently analyzed 4 weeks later. Two mouse lines would result, one expressing "high" and another with "moderate" levels of IL-1β that can be further analyzed.

c) Investigate the Long-Term Effects of IL-1B Expression in the Knee

The effects of IL-1β expression in the knee can be studied in young adult (3 month old) COLL1-IL1β$^{XAT}$ transgenic mice over time (4-8-12-16 weeks) after intra-articular injection of FIV(Cre), FIV(lacZ) or saline. Intra-articular transfer of Cre recombinase to the knee of COLL1-IL1β$^{XAT}$ transgenic mice can result in sustained expression of human IL-1β by infected cells. In contrast, FIV(lacZ)-injected mice would lack detectable human IL1β expression. Saline-treated mice can also serve as controls. After intra-articular injections, the animals can be returned to their cages. Subsequently, the effects of FIV(Cre), FIV(lacZ) and saline intra-articular injection can be analyzed in the two COLL1-IL1β$^{XAT}$ transgenic mouse lines identified above: one characterized by the highest expression of IL-1β among the mouse lines analyzed (as determined by ELIZA in knee homogenates) following FIV(Cre) intra-articular injection ("high"), and a second mouse line with median expression of IL-1β ("moderate"). The effects of IL-1β expression can be evaluated over time (4-8-12-16 weeks).

d) Clinical—Behavioral Evaluation

Arthralgia and joint dysfunction (knee pain) can be measured by (1) Locomotive performance, as evaluated on a rotating cylinder (rotorod appliance, Columbus Instruments, Columbus Ohio) and (2) Muscle strength, as evaluated by the inverted mesh method. In brief, this method evaluates neuromuscular condition by assessing grip strength. A clear plastic cylinder (20 cm×20 cm×30 cm) that was covered on the one end by a wire mesh has been constructed. The mesh wire bars were 1 mm in diameter and 1 cm apart. A rectangular area of the screen was taped so that the animals were confined in the center of the mesh. After the mice were placed on the screen, the cylinder was turned up-side-down over bedding: the lapse time until their fall from the mesh was recorded in seconds. If a mouse fell in less than 10 s in the first try, this animal was given a second chance. These methods have been adopted from clinical experience and aim at replicating behavioral and somatic events seen in human patients with arthralgia. The total lapse time until the mouse falls off the mesh can thus be recorded.

e) Peripheral Evaluation

Since IL-1β is a multipotent cytokine known to induce a number of inflammation-related genes, the expression of cytokines (TNFα, IL-6, murine IL-1β), adhesion molecules (ICAM-1, VCAM-1), chemokines (MCP-1), and collagenases (MMP-3, MMP-9) can be evaluated at the mRNA and protein level. In addition, the levels of the inducible COX-2, COX-1, mPGES and cPGES can be measured at the mRNA and protein levels as previously described (REF), as well as production of prostaglandin PGE$_2$. Moreover, joint morphology can be assessed in H&E-stained histology sections as follows. Degenerative changes in the articular cartilage can be evaluated and graded in sagittal sections examined under light microscope, and scored into five categories: grade 0, no apparent changes; grade 1, superficial fibrillation of articular cartilage; grade 2, defects limited to uncalcified cartilage; grade 3, defects extending into calcified cartilage; and grade 4, exposure of subchondral bone at the articular surface. Each joint can be graded according to the highest score observed within the serial sections. The presence of inflammatory cells, including neutrophils, monocytes/macrophages and lymphocytes in the joint can be investigated at the histology level by immunocytochemistry and double immuno-fluorescence in experimental and control mice sacrificed 4-8-12-16 weeks after treatment. In brief, neutrophils can be detected by a rat anti-murine neutrophil antibody (MCA771 GA; Serotec, Raleigh, N.C.); monocytes & macrophages can be stained with a rat anti-mouse CD11b antibody (MC A74; Serotec Inc); activated cells can be immunolocalized by a rat anti-major histocompatibility complex class-II antibody (MHC-II; Bachem, Torrance, Calif.; clone ER-TR3). Lymphocytes can be detected by a monoclonal antibody raised against CD3 (MCA 1477; Serotec) and CD4 (Serotec) Quantification of the number of cells can be described both in terms of number of positive cells per field, as well as staining profile. Endothelial cells can be detected by antibodies raised against PECAM-1 (CD31) (Kyrkanides et al. 2003).

Since the introduction of FIV proteins can elicit an immunologic response in mice treated with FIV vectors, the host's immunologic response can be characterized following FIV intra-articular injection. The presence (titers) of antibodies against viral and transgenic proteins can be quantitatively assessed in blood serum at the different experimental time points. To this end, IgG and IgM titers for the FIV p24 antigen as well as human IL-1β can be assessed by customized ELISA method. In brief, ELISA plates can be coated with 5 μg of human IL-1β (Sigma; St. Louis Mo.) or p24 recombinant proteins (IDEXX Laboratories Inc.; Westbrook Me.). After incubation with the test sera, the plates can be incubated with alkaline phosphatase-conjugated goat anti-mouse IgG and IgM (Southern Biotechnology Associates, Inc; Birmingham Ala.). Antibody titers can be established as the serum dilution that reached absorbance levels (at 405 nm) of saline injected mice assuming linear extrapolation (Kang et al., 2002).

f) Central Nervous System Evaluation

A number of small neuropeptides, such as substance P(SP) and calcitonin-gene related peptide (CGRP), have been implicated in the transmission of pain from the periphery to the central nervous system (CNS). Sustained expression of IL-1β in the mouse knee could elicit, in addition to a peripheral inflammatory response, changes in the expression of neurotransmitters in the CNS. Therefore, the expression of SP and CGRP can be evaluated in the spinal cord of experimental and control mice adapting methods previously described (Kyrkanides et al. 2002a, 2002b). Particular emphasis can be given to the region of the spinal cord where nociceptive afferents from the knee synapse at the dorsal horn of the spinal cord.

g) Results and Alternatives

Intra-articular injection of FIV(Cre) can result in expression of IL-1β: FIV-mediated Cre recombinase expression in the joint can permanently alter the genetic constitution of infected cells in the knee and result in intra-articular expression of IL-1β. Previous work with FIV demonstrated successful infection of soft and hard articular tissues by the virus following intra-articular injection (Kyrkanides S., et al. Journal of Dental Research. 83(1):65-70, 2004, herein incorporated by reference for this teaching). FIV(Cre) injections can also be repeated to COLL1-IL1β$^{XAT}$ transgenic mice, allowing the animals to survive for 26 weeks, at which time they could be sacrificed and analyzed as previously described. The COLL1-IL1β gene can also be cloned into the FIV backbone vector using established molecular biology methods to develop FIV(COLL1-IL1β), a virus capable of transducing cells with a COLL1A1-driven ssIL-IL1β. Moreover, a stronger promoter, such as the chicken β-actin/CMV fusion promoter (Daly et al., 1999) can be employed to drive ssIL-1β in the knee following intra-articular injection of the new FIV (COLL1-IL1β) vector. This is a viable alternative to the somatic mosaic model. To this end, expression of the reporter gene β-galactosidase has been observed for up to 5 weeks in the knee (Kyrkanides et al., 2004), and up to 3 months in the liver and brain in vivo. The advantage of the somatic mosaic model is that FIV(Cre) injection will result in a permanent alteration of the cell genome and lead to a chronic low-level inflammation similar to that observe in human patients.

3. Example 3

Small Inhibitory siRNA-Based Treatment for the Management of Arthritis

IL-1β is an inducer of cyclooxygenase-2 (COX-2), a key rate-limiting enzyme in the production of prostanoids during inflammation. COX-2 is of particular therapeutic interest since it is the target of commercially available over-the-counter and prescription drugs often utilized in cases of arthralgia. Small inhibitory RNA (siRNA) constructs have been developed that are capable of attenuating COX-2, as well as other members of the cyclooxygenase-prostaglandin pathway, including mPGES and cPGES. These siRNA constructs can be expressed from a feline immuno-deficiency viral platform, for example, FIV(siRNA), and can be used for gene therapy for the treatment of arthritis. Therefore, FIV (siRNA) transfer vectors can be generated for COX-2, the constitutive isoform COX-1, as well as cPGES and mPGES. To this end, joint pathology and behavior can be investigated in IL-1β$^{XAT}$ mice treated with FIV(siRNA) at various time points after induction of arthritis, and compared to mice treated with pharmacologic selective inhibitors for COX-2 and COX-1, as well as a mixed inhibitor (i.e. ibuprofen).

a) Anti-Inflammatory Regimen in COLL1Pr-IL1β$^{XAT}$ Transgenic Mice

It has been established that IL-1β drives the expression of COX-2 to form prostaglandin E$_2$ (PGE$_2$), a principal mediator of inflammation in a number of tissues, including joints. COX-2, as well as the constitutively expressed COX-1, an be temporally (time course) and spatially (sites of expression) characterized at the molecular level, and can be correlated with PGE$_2$ levels and other inflammatory mediators related to arthritis, as well as neurotransmitter expression and behavioral measures in the IL-1β$^{XAT}$ transgenic mice. Transgenic mice of the founder line identified in Example 2 can be treated with FIV(siRNA) for COX-1, COX-2, mPGES and cPGES. In addition, other groups of mice can be given a pharamocologic inhibitor for COX-2 (NS-398) as well as the NSAID ibuprofen in the chow. In brief, knee inflammation can be induced in 8 weeks old COLL1-IL1β$^{XAT}$ transgenic mice by intra-articular injection of FIV(Cre). In keeping with the clinical use of anti-inflammatory regimes, anti-inflammatory treatment can be initiated at a time when the FIV(Cre)-injected mice begin to demonstrate knee joint pathology and dysfunction (based on the data derived from Example 2). Alternatively, anti-inflammatory treatment can begin at a set time before or after the FIV(Cre) injection. The mice can be sacrificed at various time points following initiation of anti-inflammatory treatment (4-8-12-16 weeks). Consequently, the effects of therapy can be characterized on knee arthritis (anatomic, histologic, molecular changes) and dysfunction (behavioral changes), as well as on central nervous system changes.

b) FIV(siRNA) Development and Administration

A pseudotyped lentivirus can be used to drive expression of small inhibitory RNA (siRNA) species mouse joints where interleukin-1 driven inflammation has been initiated. These snort double stranded RNAs with sizes of 19-21 base pairs can efficiently mediate gene silencing in mammalian cells by guiding sequence-specific degradation of target mRNA sequences both in vitro and in vivo (Hannon, 2002)., FIV based vectors that contain an RNA polymerase III promoter, which drives expression of single stranded RNA can be used to deliver inhibitory RNA species in vivo. These RNA species contain stem-loop structures that form short hairpin RNAs (shRNA) after intracellular processing (System Biosciences; Paddison et al., 2004). Approaches such as these have been used in a wide variety of in vivo systems (Tiscornia et al., 2003; Rubinson et al., 2003) including localized silencing of specific gene expression in brain (Hommel et al., 2003). siRNAs are disclosed herein that effectively mediate gene silencing of a number of key molecules involved in the production of the lipid mediate Prostaglandin E$_2$. This includes, for example, COX-1 and -2, and the cytosolic and type-1 membrane associated prostaglandin E2 synthases (PGES). Sequences coding for shRNA's can be sub-cloned into FIV cloning vectors containing green fluorescent protein (GFP) reporter genes. After successful testing of siRNA activity upon transfection of cells in culture, VSV-G pseudotyped viral particles can be packaged by simultaneous expression of the lentiviral expression/cloning vector and packaging vectors in 293T cells. These viral particles can be infection competent but replication incompetent and can be tested and tittered in vitro before being injected into inflamed joints.

c) Pharmacologic Anti-Inflammatory Regimen

A COX-2 selective inhibitor (NS-398; Kyrkanides et al., 2002), a COX-1 inhibitor SC-560 (64 ppm in chow) or a mixed inhibitor (ibuprofen at 375 ppm in chow) can be administered to mice via chow. This route of administration simplifies long-term treatment (weeks-months) and the oral doses required for specifically inhibiting these enzymes in vivo have been previously determined (Jantzen et al., 2002; Mueller-Decker et al., 2002).

d) Results & Alternatives

Anti-inflammatory therapy can attenuate nociception. However, NSAIDs could influence inflammation by COX-independent mechanisms. For example, some NSAIDs are ligands for peroxisome proliferator-activated receptor PPAR-γ and could exert anti-inflammatory effects by this mechanism. In addition, several NSAIDS have been shown to downregulate pro-inflammatory NF-κB activity by inhibiting IκB kinase. Another point of potential importance is that drugs targeting COX isoforms could lead to concomitant upregulation of the parallel 5-lipoxygenase pathway. Recent studies on the effectiveness of dual inhibitors of cyclooxygenase and 5-lipoxygenase (ML3000) suggest that simultaneous inhibition may be required to obtain adequate levels of anti-inflammatory action. In fact, such drugs are currently in Phase III clinical trials in Europe. Such avenues can also be used herein.

Interestingly, COX-1 and COX-2, in addition to their roles in peripheral inflammation, both appear to be involved to some degree in the central processing of pain at the level of the central nervous system. Overall, behavioral and pathological benefits are expected from NS-398 administration and COX-2 knockout mice. In some model systems COX-1 has been found to influence inflammation and pain. Thus, results with the COX-1 selective inhibitor and COX-1 knockout mice could also show benefits. Recently, in addition to COX-1 and COX-2, at least two new $PGE_2$ synthase isoforms have been added to the family of enzymes that result in the production of prostaglandins: the membrane-associated mPGES, which is functionally coupled to COX-2, and the cytosolic cPGES that appears to be linked to COX-1 dependent $PGE_2$ production. Although cellular localization may play some role, functional coupling is largely a factor of expression patterns: as with COX-2, mPGES is dramatically upregulated by proinflammatory stimuli, whereas cPGES is constitutively expressed in cell systems examined to date. In addition, COX-2 and mPGES are coordinately upregulated in a rat model of adjuvant arthritis. Therefore, mPGES could play a role in IL-1β-induced arthritis. Thus, the regulation of mPGES is also considered herein. This can be readily accomplished by employing established and routinely used methods. In fact, recent data suggests that COX-2 regulates mPGES at the transcriptional level, at least in an IL-1β induced brain inflammation model (Moore et al. 2004).

It is important to point out that the doses chosen have been previously shown to inhibit COX activity in long-term mouse experiments without evidence of serious toxicity. However, animals fed NSAID chow (and controls) can be weighed each week to assess possible toxic effects of drug treatment.

G. References

Abbott F V, Franklin K B J, Conel B (1986). The stress of a novel environment reduces formalin pain: possible role of serotonin. Eur J Pharmacol 126: 126-41.

Abramowitz M and Stegun I A (1964). Handbook of Mathematical Functions, Applied Mathematics Series, vol. 55 (Washington: National Bureau of Standards; reprinted 1968 by Dover Publications, New York).

Adamo C T, Mailhot J M, Smith A K, Borke J L (2001) Connexin 43 expression in oral derived human osteoblasts after transforming growth factor-beta and PGE2 exposure. J Oral Implantol 27: 25-31

Agarwal S, Long P, Gassner R, Piesco N P, Buckley M J (2001). Cyclic tensile strain suppresses catabolic effects of interleukin-1beta in fibrochondrocytes from the temporomandibular joint. Arthr Rheum 44:608-17.

Ahmadzadeh N, Shingu M, Nobunaga M (1990). The effect of recombinant tumor necrosis factor-alpha on superoxide and metalloproteinase production by synovial cell and chondrocytes. Clin Exp Rheumatol 8:387-91.

Anderson G D, Hauser S D, McGarity K L, Bremer M E, Isakson P C and Gregory S A (1996). Selective inhibition of cyclooxygenase (COX)-2 reverses inflammation and expression of COX-2 and interleukin 6 in rat adjuvant arthritis. J Clin Invest 97:2672-79.

Balkhi K M, Tallents R H, Hutta J, Murphy W, Proskin H (1993). Electromyographic Evaluation of the Bellinger D L, Felten D L, Lorton D. Brouxhon S M (2001). Effects of interleukin-2 on the expression of corticotropin-releasing hormone in nerves and lymphoid cells in secondary lymphoid organs from the Fischer 344 rat. J Neuroimmunol 119:37-50.

Breyer R M, Bagdassarian C K, Myers S A and Breyer M D (2001). Prostanoid receptors: subtypies and signaling. Ann Rev Pharmacol Toxicol 41:661-90.

Brooks A I, Halterman M W, Federoff H J (1999). Focal hippocampal gain of NGF function elicits specific septal cholinergic reorganization. Neuroreport. 10:337-44.

Brooks A I, Muhkerjee B, Panahian N, Cory-Slechta D, Federoff H J (1997). Nerve growth factor somatic mosaicism produced by herpes virus-directed expression of cre recombinase. Nat Biotech 15(1):57-62

Brummelkamp, T. R., R. Bemardsand R. Agami. A system for stable expression of short interfering RNAs in mammalian cells. Science (2002) 296:550-553.

Bullough P G, DiCarlo E F (1990). Subchondral avascular necrosis: a common cause of arthritis. Ann Rheum Dis 49:412-20

Burkhardt H, Schwingel M, Menninger H, Macartney H W, Tschesche H (1986). Oxygen radicals as effectors of cartilage destruction. Direct degradative effect on matrix components and indirect action via activation of latent collagenase from polymorphonuclear leukocytes. Arthritis Rheum 29:379-87.

Calvelou P, Dallel R, Orliaguet T, Woda A (1995). The orofacial formalin test in rats: effects of different formalin concentrations. Pain 62:295-301.

Carleson J, Alstergren P, Appelgren A, Appelgren B, Kopp S, Theodorsson E, et al. (1996). A model for the study of experimentally induced temporomandibular arthritis in rats: the effect of human recombinant interleukin-I alpha on neuropeptide like immunoreactivity. J Orofac Pain 10:9-14.

Chandrasekharan N V, Dai H, Roos K L, Evanson N K, Tomsik J, Elton T S, Simmons D L (2002). COX-3, a cyclooxygenase-1 variant inhibited by acetaminophen and other analgesic/antipyretic drugs: cloning, structure, and expression. Proc Natl Acad Sci USA. 99:13926-31.

Chang J S, Gillman S C, Lewis A J (1986). Interleukin 1 activates phospholipase A2 in rabbit chondrocytes: a possible signal for IL-1 action. J Immunol 136:1283-87.

Choi H S, Lee H J, Juan C Y, Ju J S, Park J S, Ahn D K (2003). Central cyclooxygenase-2 participates in interleukin-β-induced hyperalgesia in the orofacial formalin test of freely moving rats. Neurosci Letters 352: 187-90.

Crombie I K, Croft P R, Linton S J, LeResche L, Von Korff M (eds). Epidemiology of Pain: A report of the Task Force on epidemiology of the International Association for the Study of Pain. Seattle: IASP, 1999.

Daly T M, Vogler C, Levy B, Haskins M E, Sands M S (1999) Neonatal gene transfer leads to widespread correction of pathology in a murine model of lysosomal disease. Proc Natl Acad Sci USA 96: 2296-3000.

de Bont L G, Boering G, Liem R S, Eulderink F, Westesson P L (1986). Osteoartliritis and internal derangement of the temporomandibular joint: a light microscopic study. J Oral & Maxillofac Surg 44:634-43.

Dubuisson D, Dennis S. The formalin test: A quantitative study of the analgesic effects of morphine, meperidine, and brainstem stimulation in rats and cats. Pain 1977; 4: 161-74.

Dijkgraaf L C, de Bont L G, Boering G, Liem R S (1995). The structure, biochemistry, and metabolism of osteoarthritic cartilage: a review of the literature. J Oral Maxillofac Surg 53:1182-92.

Dijkgraaf L C. Liem R S. de Bont L G (1997). Synovial membrane involvement in osteoarthritic temporomandibular joints: a light microscopic study. Oral Surg Oral Med Oral Pathol Oral Radiol & Endodont 83:373-86.

Dijkgraaf L C. Spijkervet F K. de Bont L G (1999). Arthroscopic findings in osteoarthritic temporomandibular joints. J Oral & Maxillofac Surg 57:255-68.

Dinchuk J E, Liu R Q, Trzaskos J M (2003) COX-3: in the wrong frame in mind. Immunol Lett. 86:121.

Elbashir, S. M., J. Harborth, W. Lendeckel, A. Yalcin, K. Weberand T. Tuschl. Duplexes of 21-nucleotide RNAs mediate RNA interference in cultured mammalian cells. Nature (2001) 411:494-498.

Fernandes J C, Caron J P, Martel-Pelletier J, Javanovic D, Mineau F, Tardif G, Otterness I G, Pelletier J P (1997). Effects of tenidap on the progression of osteoarthritic lesions in a canine experimental model. Suppression of metalloprotease and interleukin-1 activity. Arthritis & Rheum 40:284-94.

Fiorucci S, Meli R, Bucci M, Cirino G (2001) Dual inhibitors of cycloxygenase and 5-lipoxygenase. A new avenue in anti-inflammatory therapy? Biochem Pharmacol 62: 1433-8.

Fitzgerald G A and Patrono C (2001). The coxibs, selective inhibitors of cyclooxygenase-2. N Engl J Med 345:433-42.

Futaki N, Arai I, Hamasaka Y, Takahashi S, Higuchi S and Otomo S (1993). Selective inhibition of NS-398 on prostanoid production in inflamed tissue in rat carrageenan-air-pouch inflammation. J Pharmacol 45:753-55.

Gillman S C, Chang J, Zeigler P R, Uhl J, Mochan E (1988). Interleukin 1 activates phospholipase A2 in human synovial cells. Arthritis Rheum 31:126-30.

Gilroy D W, Colville-Nash P R, McMaster S. Sawatzky D A, Willoughby D A, Lawrence T (2003). Inducible cyclooxygenase-derived 15-deoxy(Delta)12-14PGJ2 brings about acute inflammatory resolution in rat pleurisy by inducing neutrophil and macrophage apoptosis. FASEB 17:2269-71.

Gilroy D W, Colville-Nash P R, Willis D, Chivers J, Paul-Clark M J, Willoughby D A (1999). Inducible cyclooxygenase may have anti-inflammatory properties. Nat Med 5:698-701.

Greenwald R A, Moy W W (1997). Inhibition of collagen gelation by action of the superoxide radical. Arthritis Rheum 22:251-59.

Han R, Tsui S and Smith T J (2002). Up-regulation of prostaglandin E2 synthesis by interleukin-1β in human orbital fibroblasts involves coordinate induction of prostaglandin H synthase-2 and glutathione-dependent prostaglandin E2 synthase expression. J Biol Chem 277:163555-64.

Hannon, G. J. (2002). RNA interference. Nature 418, 244-251

Havenga M J, Vogels R, Braakman E, Kroos N, Valerio D, Hagenbeek A, van Es H H (1998). Second gene expression in bicistronic constructs using short synthetic intercistrons and viral IRES sequences. Gene. 222:319-27.

Helminen H J, Kiraly K, Pelttari A, Tammi M, Vandenberg P, Pereira R, et al. (1993). An inbred line of transgenic mice expressing an internally deleted gene for type II procollagen (COL2A1). J Clin Invest 92:582-95.

Hommel, J. D., Sears, R. M., Georgescu, D., Simmons, D. L., and DiLeone, R. J. (2003). Local gene knockdown in the brain using viral-mediated RNA interference. Nat Med 9, 1539-1544.

Hutchins B, Patel H, Spears R (2002). Attenuation of proinflammatory neuropeptide levels produced by a cyclooxygenase-2 inhibitor in an animal model of chronic temporomandibular joint inflammation. J Orofac Pain 16:312-6.

Irwin, M. H., W. D. Pogozelski, and C A Pinkert (2002). PCR optimization for detection of transgene integration, p. 475-484. In C. A. Pinkert (ed.), Transgenic animal technology: a laboratory handbook. 2nd ed. Academic Press, Inc., San Diego.

Jakobsson P J, Thoren S, Morgenstern R, Samuelsson B (1999). Identification of human prostaglandin E synthase: a microsomal, glutathione-dependent, inducible enzyme, constituting a potential novel drug target. Proc Natl Acad Sci USA 96:7220-25.

Jantzen P T, Connor K E, DiCarlo G, Wenk G L, Wallace J L, Rojiani A M, Coppola Di, Morgan D, Gordon M N (2002). Microglial Activation and β-Amyloid Deposit Reduction Caused by a Nitric Oxide-Releasing Nonsteroidal Anti-Inflammatory Drug in Amyloid Precursor Protein Plus Presenilin-1 Transgenic Mice. J Neurosci 22:2246-54.

Jiao Y, Ma X, Zhang Z (2001). Interleukin-1 increase nitric oxide synthesis through up-regulation of inducible nitric-oxide synthase by rabbit mandibular condylar cartilage cells in vitro. Chin J Stomatol 36:345-7.

Johansson A-S, Isacson G, Isberg A, et al. (1986) Distribution of substance P-like immunoreactive nerve fibers in temporomandibular joint soft tissues of monkey. Scand J Dent Res 94:225-30.

Jonakait G M, Schotland S (1990). Conditioned medium from activated splenocytes increases substance P in sympathetic ganglia. J Neurosci Res 26:24-30.

Jonakait G M, Schotland S, Hart R P (1991). Effects of lymphokines on substance P in injured ganglia of the peripheral nervous system. Ann NY Acad Sci 632:19-30.

Jonakait G M, Schotland S, Hart R P (1991). Interleukin-1 specifically increases substance P in injured sympathetic ganglia. Ann NY Acad Sci 594:222-30.

Joosten L A, Helsen M M, Saxne T, van De Loo F A, Heinegard D, van Den Berg W B (1999). IL-1 alpha beta blockade prevents cartilage and bone destruction in murine type II collagen-induced arthritis, whereas TNF-alpha blockade only ameliorates joint inflammation. J Immunol; 163:5049-55.

Jovanovic D V, Fernandes J C, Martel-Pelletier J. Jolicoeur F C, Reboul P, Laufer S, Tries S, Pelletier J P (2001). In vivo dual inhibition of cyclooxygenase and lipoxygenase by ML-3000 reduces the progression of experimental osteoarthritis: suppression of collagenase 1 and interleukin-1beta synthesis. Arthr Rheumaton 44:2320-30.

Jow R W and Clark G T (1989). Endurance and recovery from a sustained isometric contraction of human jaw elevating muscles. Arch Oral Biol 34: 857-62.

Kang Y, Stein C S, Heth J A, Sinn P L, Penisten A K, Staber P D, Ratliff K L, Shen H, Barker C K, Martins I, Sharkey C M, Sanders D A, McCray P B Jr., Davidson BL (2002). In vivo gene transfer using a nonprimate lentiviral vector pseudotyped with ross river virus glycoproteins. J Virol 76 9378-88.

Kawai Y, Kubota, Okabe E (2000). Reactive oxygen species participation in experimentally induced arthritis of the temporomandibular joint in rats. J Dent Res 79:1489-95.

Kawakami M, Okabe E (1998). Superoxide anion radical-triggered Ca+2 release from cardiac sarcoplasmic reticulum through ryanodine receptor $Ca^{+2}$ channel. Mol Pharmacol 53:497-503.

Kehl L J, Trempea T M and Hargreaves K M (2000). A new animal model for assessing mechanisms and management of muscle hyperalgesia. Pain 85:333-43.

Kirtikara K, S G Morham, R Raghow, S J Laulederkind, T Kanekura, S Goorhaand, L R Ballou (1998). Compensatory prostaglandin E2 biosynthesis in cyclooxygenase 1 or 2 null cells. J Exp Med 187:517-23.

Kis B, Snipes J A, Isse T, Nagy K, Busija D W. (2003) Putative cyclooxygenase-3 expression in rat brain cells. J Cereb Blood Flow Metab. 23: 1287-92.

Kitanaka J, Hashimoto H, Gotoh M, Kondo K, Sakata K, Hirasawa Y. Sawada M, Suzumura A, Marunouchi T, Matsuda T and Baba A. (1996) Expression pattern of messenger RNAs for prostanoid receptors in glial cell cultures. Brain Res 707:282-87.

Krebsbach P H, Harrison J R, Lichtler A C, Woody C O, Rowe D W, Kream B E (1993). Transgenic expression of COL1A1-chloramphenicol acetyltransferase fusion genes in bone: differential utilization of promoter elements in vivo and in cultured cells. Mol Cell Biol 13: 5168-74.

Kubota E, Kubota T, Matsumoto J, Shibata T, Murakami K 1 (1998). Synovial fluid cytokines and proteinases as markers of temporomandibular joint disease. J Oral Maxillofac Surg 56:192-98.

Kyrkanides S, Kambylafkas P, Miller J H, Tallents R H (2004). Non-primate lentiviral vector administration in the TMJ. J Dental Res 83: 65-70.

Kyrkanides S, Miller J H, Bowers W A, Federoff H J (2003). Transcriptional and post-translational regulation of Cre recombinase by RU486 as the basis for an enhanced inducible expression system. Mol Ther 8: 790-95.

Kyrkanides S, Miller J H, Federoff H J (2003). Systemic FIV vector administration: Transduction of CNS immune cells and Purkinje neurons. Mol Brain Res 119: 1-9.

Kyrkanides S, Moore A H, Olschowka J A, Williams J P, Hansen J T, O'Banion MK (2002). COX-2 modulates inflammation related genes in CNS radiation injury. Mol Brain Res 104: 159-69.

Kyrkanides S, O'Banion M K, Subtelny J D (2000). Nonsteroidal anti-inflammatory drugs in orthodontic tooth movement: Metalloproteinase activity and collagen synthesis by endothelial cells. Am J Orthod Dentofac Orthop 118: 203-09.

Kyrkanides S, Olschowka J A, Whitley P, O'Banion MK (2001). Enhanced glial activation and expression of specific CNS inflammation-related molecules in aged versus young rats following cortical stab injury. J Neuroimmunol 119: 269-77.

Kyrkanides S, Olschowka J A, Williams J P, Hansen J T, O'Banion MK (1999). TNFα & IL-1β mediate ICAM-1 induction via microglia-astrocyte interaction in CNS radiation injury. J Neuroimmunol 95:95-106.

Kyrkanides S, Tallents R H, Macher D J, Olschowka J A, Stevens S Y (2002). Temporomandibular joint nociception: effects of capsaicin on substance P-like immunoreactivity in the rabbit brain stem. J Orofac Pain 16:229-35.

Lane N E (1997). Pain management in osteoarthritis: the role of COX-2 inhibitors. J Rheumatol 24 Suppl. 49:20-24.

Langenbach R, Morham S G, Tiano H F, Loftin C D, Ghanayem B I, Chulada P C, Mahler J F, Lee C A, Goulding E H, Kluckman K D, Kim H S, Smithies 0 (1995). Prostaglandin Synthase 1 Gene Disruption in Mice Reduces Arachidonic Acid-Induced Inflammation and Indomethacin-Induced Gastric Ulceration. Cell 83:483-92.

Lavigne P, Shi Q, Jolicoeur F C, Pelletier, Martel-Pelletier J, Fernandes J C (2002). Modulation of IL-1beta, IL-6, TNF-alpha and PGE(2) by pharmacological agents in explants of membranes from failed total hip replacement. Osteoarthritis & Cartilage 10:898-904.

Lehmann, J. M., J. M. Lenhard, B. B. Oliver, G. M. Ringold and S. A. Kleiwer (1997). Peroxisome proliferator-activated receptors alpha and gamma are activated by indomethacin and other non-steroidal anti-inflammatory drugs. J Biol Chem 272:3406-10.

Lipsky P E and Isakson P C (1997). Outcome of specific COX-2 inhibition in rheumatoid arthritis. J Rheumatol 24:9-14.

Lipton J A, Ship J A, Larach-Luchini S, Merskey H (1993). Estimated prevalence and distribution of reported orofacial pain in the United States. JADA 124:115-21.

Liu F, Malaval L, Aubin J E (1997). The mature osteoblasts phenotype is characterized by extensive plasticity. Exp Cell Res 232: 97-105.

Macher D J, Westesson P L, Brooks S L Hicks D and Tallents R H (1992). Temporomandibular joint surgically created disc displacement causes arthrosis in the rabbit. Oral Surg Oral Med Oral Pathol 73:645-49.

Maguire-Zeiss K A, Bowers W J, Federoff H J (2002). Somatic mosaic approaches and the aging brain. Neurobiol Aging 23:977-84.

Malmberg A B and Yaksh T L (1995). Cyclooxygenase inhibition and the spinal release of prostaglandin E2 and amino acids evoked by paw formalin injection: a microdialysis study in unanesthetized rats. J Neurosci 15:2768-76.

Mancini J A, Blood K, Guay J, Gordon R, Claveau D, Chan C C and Riendeau R (2001). Cloning, expression, and up-regulation of inducible rat prostaglandin e synthase during lipopolysaccharide-induced pyresis and adjuvant-induced arthritis. J Biol Chem 276:4469-75.

Martel-Pelletier J, Pelletier J P, Fahmi H (2003). Cyclooxygenase-2 and prostaglandins in articular tissues. Semin Arthritis Rheum 33:155-67.

Masaki M, Matsushita M and Wakitani K. Inhibitory effects of JTE-522, a novel prostaglandin H synthase-2 inhibitor, on adjuvant-induced arthritis and bone changes in rats. Inflamm Res 47:187-92.

Matsubara T, Ziff M (1986). Increased superoxide anion release from human endothelial cells in response to cytokines. J Immunol 137:3295-98.

McCord J M (1974). Free radicals and inflammation: protection of synovial fluid by superoxide dismutase. Science 185:529-31.

Mizukawa H, Okabe E (1997). Inhibition by singlet molecular oxygen of the vascular reactivity in rabbit mesenteric artery. Br J Pharmacol 121:63-70.

Molin C (1972). Vertical isometric muscle forces of the mandible. A comparative study of subjects with and without manifest mandibular pain dysfunction syndrome. Acta Odontol Scand 30:485-99.

Moore A H, Olschowka J A, O'Banion MK (2004). Intraparenchymal administration of interleukin-1beta induces cyclooxygenase-2-mediated expression of membrane- and cytosolic-associated prostaglandin E synthases in mouse brain. J Neuroimmunol 148: 32-40.

Moos V, Fickert S, Muller B, Weber U, Sieper J (1999). Immunohistological analysis of cytokine expression in human osteoarthritic and healthy cartilage. J Rheumatol 26:870-9.

Morham S G, Langenbach R, Loftin C D, Tiano H F, Vouloumanos N, Jennette J C, Mahler J F, Kluckman K D, Ledford A, Lee C A, Smithies 0 (1995). Prostaglandin Synthase 2 Gene Disruption Causes Severe Renal Pathology in the Mouse. Cell 83:472-82.

Mueller-Decker K, Hirschner W, Marks F, Fuerstenberger G (2002). The Effects of Cyclooxygenase Isozyme Inhibition on Incisional Wound Healing in Mouse Skin. J Invest Dermatol 119: 1189-95.

Murakami M, Naraba H, Tanioka T, Semmyo N, Nakatani Y, Kojima F, Ikeda T, Fueki M, Ueno A, Oh-ishi S and Kudo I (2000). Regulation of prostaglandin E2 biosynthesis by inducible membrane-associated prostaglandin E2 synthase that acts in concert with cyclooxygenase-2. J Biol Chem 275:32783-92.

Murray R and Spiegel S (1988). Theory and Problems of Statistics, 2nd ed. Schaum's Outline Series, McGraw-Hill Publishing, New York, Chapter 5, p 110-21.

Myers S L, Flusser D, Brandt K D, Heck D A (1992). Prevalence of cartilage shards in synovium and their association with synovitis in patients with early and endstage osteoarthritis. J Rheumatol 19:1247-51.

Nagy A, Gertsenstein M, Vintersten K, and Behringer R. (2003) Manipulating the Mouse Embryo: A Laboratory Manual. 3rd ed., Cold Spring Harbor Laboratory Press, Cold Spring Harbor, N.Y.

Narumiya A and FitzGerald G A (2001). Genetic and pharmacological analysis of prostanoid receptor function. J Clin Invest 108:25-30.

Narumiya S, Sugimoto Y, Ushikuni F (1999). Prostanoid receptors: structures, properties and functions. Physiol. Rev. 79:1193-1226.

Ngo L, Jay G (2002). Analysis of transgene expression, p. 486-513. In CA Pinkert (ed.), Transgenic animal technology: a laboratory handbook. 2nd ed. Academic Press, Inc., San Diego.

Norisue M, Todoki K, Okabe E (1997). Inhibition by hydroxyl radicals of calcitonin gene-related peptide-mediated neurogenic vasorelaxation in isolated canine lingual artery. J Pharmacol Exp Ther 280:492-500.

Norsdenskiold U M and Grimby G (1993). Grip force in patients with rheumatoid arthritis and fibromyalgia and in healthy subjects: a study with the Grippit instrument. Scand J Rheumatol 22: 14-9.

O'Banion M K (1999). Cyclooxygenase-2: molecular biology, pharmacology, and neurobiology. Crit Rev Neurobiol 13: 45-82.

O'Banion M K, Sadowski H B, Winn V, Young D A (1991). A serum- and glucocorticoid-regulated 4-kilobase mRNA encodes a cyclooxygenase-related protein. J Biol Chem 266: 23261-7.

O'Banion M K, Winn V D, Young D A (1992). cDNA cloning and functional activity of a glucocorticoid-regulated inflammatory cyclooxygenase. Proc Natl Acad Sci U.S.A. 89:4888-92.

O'Byrne E M, Blancuzzi V J, Wilson D E, et al. (1990). Increased intra-articular substance P and prostaglandin E2 following injection of interleukin-1 in rabbits. Int J Tissue React 12:11-4.

Ochi T, Ohkubo Y, Mutoh S (2003). Role of cyclooxygenase-2, but not cyclooxygenase-1, on type II collagen-induced arthritis in DBA/1J mice. Biochem Pharmacol 66:1055-60.

Ogura N, Tobe M, Sakamaki H, Kujiraoka H, Akiba M, Abiko Y, Nagura H (2002). Interleukin-1 beta induces interleukin-6 mRNA expression and protein production in synovial cells from human temporomandibular joint. J Oral Pathol Med 31:353-60.

Overbeek P A (2002). DNA microinjection and transgenic animal production, p. 72-112. In C. A. Pinkert (Ed.), Transgenic animal technology: a laboratory handbook. 2nd ed. Academic Press, Inc., San Diego.

Paddison, P. J., Caudy, A. A., Sachidanandam, R., and Hannon, G. J. (2004). Short hairpin activated gene silencing in mammalian cells. Methods Mol Biol 265, 85-100.

Paddison, P. J., A. A. Caudy and G. J. Hannon. Stable suppression of gene expression by RNAi in mammalian cells. Proc. Natl. Acad. Sci. USA (2002) 99:1443-1448.

Pfeifer A, Brandon E P, Kootstra Neeltje, Gage F H, Verma I M (2001). Delivery of the Cre recombinase by a self-deleting lentiviral vector: Efficient gene targeting in vivo. Proc Natl Acad Sci U.S.A. 98: 11450-5.

Pinkert C. A. (2002) Transgenic Animal Technology: A Laboratory Handbook 2nd ed., Academic Press, San Diego.

Pinkert C A (2003). Transgenic animal technology: Alternatives in genotyping and phenotyping. Comp Med 53:116-29.

Polites H G, Pinkert C A (2002). DNA microinjection and transgenic animal production, p. 15-70. In C. A. Pinkert (ed.), Transgenic animal technology: a laboratory handbook. 2nd ed. Academic Press, Inc., San Diego.

Portanova J P, Zhang Y, Anderson G D, Hauser S D, Masferrer J L, Seibert K, Gregory S A, Isakson P C. (1996) Selective neutralization of prostaglandin E2 blocks inflammation, hyperalgesia, and interleukin 6 production in vivo. J. Exp. Med 184:883-91.

Ratcliffe A, Billingham M E, Saed-Nejad F, Muir H, Hardingham T E (1992). Increased release of matrix components from articular cartilage in experimental canine osteoarthritis. J Ortho Res 10:350-8.

Revell P A, Mayston V, Lalor P, Mapp P (1988). The synovial membrane in osteoarthritis: a histological study including the characterisation of the cellular infiltrate present in inflammatory osteoarthritis using monoclonal antibodies. Ann Rheum Dis 47:300-7.

Ricote M, Li A C, Willson T M, Kelly C J and Glass C K (1998). The peroxisome proliferator-activated receptor-☐ is a negative regulator of macrophage activation. Nature 391:79-82.

Ritchlin C T, Haas-Smith S A, Li P, Hicks D G, Schwarz E M (2003). Mechanisms of TNF☐ and RANKL-mediated osteoclastogenesis and bone resorption in psoriatic arthritis. J Clin Investig 111:821-31.

Roberts C R, Roughley P J, Mort J S (1989). Degradation of human proteoglycan aggregate induced by hydrogen peroxide. Protein fragmentation, amino acid modification and hyaluronic acid cleavage. Biochem J 259:805-11.

Rubinson, D. A., Dillon, C. P., Kwiatkowski, A. V., Sievers, C., Yang, L., Kopinja, J., Rooney, D. L., Ihrig, M. M., McManus, M. T., Gertler, F. B., et al. (2003). A lentivirus-based system to functionally silence genes in primary mammalian cells, stem cells and transgenic mice by RNA interference. Nat Genet 33, 401-406.

Salvemini D, Misko T P, Masferrer J L (1993). Nitric oxide activates cycloxygenase enzymes. Proc Natl Acad Sci 90:7240-44.

Schwarz E M, Looney R J, O'Keefe R J (2000). Anti-TNF-alpha therapy as a clinical intervention for periprosthetic osteolysis. Arthr Res 2:165-8.

Scott-Burden T, Bosley J P, Rosenstrauch D, Henderson K D, Clubb F J, Eichstaedt H C, Eya K, Gregoric I, Myers T J, Radovancevic B, Frazier O H (2002). Use of autologous auricular chondrocytes for lining artificial surfaces: A feasibility study. Ann Thorac Surg 73: 1528-33.

Sessle B J, Hu J W (1991). Mechanisms of pain arising from articular tissues. Can J Physiol Pharmacol 69: 617 626.

Shaftel S S, Olschowka J A, Hurley S D, Moore A H, O'Banion MK (2003). COX-3: a splice variant of cyclooxygenase-1 in mouse neural tissue and cells. Brain Res Mol Brain Res. 119: 213-5.

Shin S-j, Fermor B, Weinberg J B, Pisetsky D S, Guilak F (2003). Regulation of matrix turnover in meniscal explants: role of mechanical stress, interleukin-1, and nitric oxide. J Appl Physiol.; 95:308-13.

Siqueira-Junior J M, Peters R R, Brum-Fernandes A J, Ribeiro-do-Valle R M (2003). Effects of valeryl salicylate, a COX-1 inhibitor, on models of acute inflammation in mice. Pharmacol Res 48:437-43.

Smith M D, Triantafillou S, Parker A, Youssef P P, Coleman M (1997). Synovial membrane inflammation and cytokine production in patients with early osteoarthritis. J Rheumatol 24:365-71.

Smith, W L, DeWitt D L, Garavito R M (2000). Cyclooxygenases: structural, cellular, and molecular biology. Annu Rev Biochem 69:145-82.

Srinivas S, Watanabe T, Lin C-S, Williams C, Tanabe Y, Jessell T, Costaniti F (2002). Cre reporter strains produced by targeted insertion of EYFP and ECFP into the ROSA26 locus. BMC Develop Biol 1:4-11.

Stegenga B, de Bont L G, Boering G (1989). Osteoarthrosis as the cause of craniomandibular pain and dysfunction: a unifying concept. J Oral Maxillofacial Surg 47:249-56.

Stegenga B, de Bont L G, Boering G, Van Willigen J D (1991). Tissue responses to degenerative changes in the temporomandibular joint: a review. J Oral Maxillofacial Surg 49:1079-88.

Sternberg N, Hamilton D (1981). Bacteriophage P1 site-specific recombination. Recombination between loxP sites. J Mol Biol 150: 467-86.

Stichtenoth D O, Thoren S, Bian H, Peters-Golden M, Jakobsson P J and Crofford L (2001). Microsomal prostaglandin E synthase is regulated by proinflammatory cytokines in primary rheumatoid synovial cells. J. Immunol. (2001) 167:469-74.

Sugimoto Y, Narumiya S and Ichikawa A (2000). Distribution and function of prostanoid receptors: studies from knock-out mice. Prog Lipid Res 39:289-314.

Surnii H, Inoue H, Onoue J, Mori A, Oda T, Tsubokura T (1996). Superoxide dismutase activity in arthropathy: its role and measurement in the joints. Hiroshima J Med Sci 45:51-55.

Suzuki T, Segami N, Nisimura M, Nojima T (2002). Co-expression of interleukin-1beta and tumor necrosis factor alpha in synovial tissues and synovial fluids of temporomandibular joint with internal derangement: comparison with histological grading of synovial inflammation. J of Oral Pathology Med 31:549-57.

Tallents R H, Macher D J, Rivoli P, Scapino R, Puzas J E, Katzberg R W (1990). An animal model for meniscus displacement in the rabbit. J Craniomandib Disord Facial Oral Pain 4:233-40.

Tanaka A, Hase S, Miyazawa T, Ohno R, Takeuchi K (2002). Role of cyclooxygenase (COX)-1 and COX-2 inhibition in nonsteroidal anti-inflammatory drug-induced intestinal damage in rats: relation to various pathogenic events. J Pharmacol Exp Ther 303: 1248-54.

Tanioka T, Nakatani Y, Semmyo N, Murakami M and Kudo I (2000). Molecular identification of cytosolic prostaglandin E2 synthase that is functionally coupled with cylooxygenase-1 in immediate prostaglandin E2 biosynthesis. J Biol Chem 275:32775-82.

Tawara T, Shingu M, Nobunaga M, Naono T (1991). Effects of recombinant human IL-1β on production of prostaglandin E2, leukotriene B4, NAG, and superoxide by human synovial cells and chondrocytes. Inflammation 15:145-57.

Tiku M L, Liesch J B, Robertson F M (1990). Production of hydrogen peroxide by rabbit articular chondrocytes. Enhancement by cytokines. J Immunol 145:690-96.

Tilley S L, Coffman T M and Koller B H (2001). Mixed messages: modulation of inflammation and immune response by prostaglandins and thromboxanes. J Clin Invest 108:15-23

Tinkle B T, Jay G (2002). Analysis of transgene integration, p. 459-474. In C A Pinkert (ed.), Transgenic animal technology: a laboratory handbook. 2nd ed. Academic Press, Inc., San Diego.

Tiscornia, G., Singer, O., Ikawa, M., and Verma, I. M. (2003). A general method for gene knockdown in mice by using lentiviral vectors expressing small interfering RNA. Proc Natl Acad Sci USA 100, 1844-1848.

Tuschl, T. RNA interference and small interfering RNAs. Chembiochem (2001) 2:239-245.

Vane J R, Bakhle Y S, Botting R M (1998). Cyclooxygenases 1 and 2. Annu. Rev. Pharmocol. Toxicol. 38:97-120.

Wada S, Okabe E (1997). Susceptibility of caffeine and INS (1,4,5)P3 induced contractions to oxidants in permeabilized vascular smooth muscle. Eur J Pharmacol 320:51-59.

Webb G R. Westacott C I. Elson C J (1998). Osteoarthritic synovial fluid and synovium supernatants up-regulate tumor necrosis factor receptors on human articular chondrocytes. Osteoarthr & Cartil 6167-76.

Wilhelmi G, Faust R (1976). Suitability of the C57 black mouse as an experimental animal for the study of skeletal changes due to ageing, with special reference to osteoarthrosis and its response to tribenoside. Pharmacol 14:289-96.

Wingren A G, Bjorkdahl O, Labuda T, Bjork L, Andersson U, Gullberg U, Hedlund G, Sjogren H O, Kalland T, Widegren B, Dohlsten M (1996). Fusion of a signal sequence to the interleukin-1 beta gene directs the protein from cytoplasmic accumulation to extracellular release. Cell Immunol 169:226-37.

Woodruff T, Blake D R, Freeman J, Andrews F J, Salt P, Lunec J (1986). Is chronic synovitis an example of reperfusion injury? Ann Rheum Dis 45:608-11.

Yaksh T L, Dirig D M, Conway C M, Svensson C, Luo Z D, Isakson P C (2001). The acute antihyperalgesic action of nonsteroidal, anti-inflammatory drugs and release of spinal prostaglandin E2 is mediated by the inhibition of constitutive spinal cyclooxygenase-2 (COX-2) but not COX-1. J Neurosci 21:5847-53.

Yamamoto Y, Yin M J, Lin I and Gaynor R B (1999). Sulindac inhibits activation of the NF-□B pathway. J Biol Chem 274:27307-314.

Yang, D., F. Buchholz, Z. Huang, A. Goga, C.-Y. Chen, F. M. Brodskyand J. M. Bishop. Short RNA duplexes produced by hydrolysis with *Escherichia coli* RNase III mediate effective RNA interference in mammalian cells. Proceedings of the National Academy of Sciences (2002) 99:9942-994.

Yin M J, Yamamoto Y and Gaynor R B (1998). The anti-inflammatory agents aspirin and salicylate inhibit the activity of IkB kinase-β. Nature 396:77-80.

Yoshida H, Fukumura Y, Fujita S, Nishida M, Iizuka T (2002). The expression of cyclooxygenase-2 in human temporomandibular joint samples: an immunohistochemical study. J Oral Rehab 29:1146-52.

Zhang J, S Goorha, R Raghowand, L R Ballou (2002). The tissue-specific, compensatory expression of cyclooxygenase-1 and -2 in transgenic mice. Prostagland Other Lipid Mediat 67:121-35.

Zhu J, Musco M L, Grace M J (1999). Three-color flow cytometry analysis of tricistronic expression of eBFP, eGFP, and eYFP using EMCV-IRES linkages. Cytometry 37: 51-9.

Zhu X, Conklin D, Eisenach J C (2003). Cyclooxygenase-1 in the spinal cord plays an important role in postoperative pain. Pain 104:15-23.

H. Sequences

```
human IL-1alpha mRNA (Accession No. NM_000575)
                                                               SEQ ID NO: 1
    1 accaggcaac accattgaag gctcatatgt aaaaatccat gccttccttt ctcccaatct
   61 ccattcccaa acttagccac tggcttctgg ctgaggcctt acgcatacct cccgggcttc
  121 gcacacacct tcttctacag aagacacacc ttgggcatat cctacagaag accaggcttc
  181 tctctggtcc ttggtagagg gctactttac tgtaacaggg ccagggtgga gagttctctc
  241 ctgaagctcc atcccctcta taggaaatgt gttgacaata ttcagaagag taagaggatc
  301 aagacttctt tgtgctcaaa taccactgtt ctcttctcta ccctgcccta accaggagct
  361 tgtcacccca aactctgagg tgatttatgc cttaatcaag caaacttccc tcttcagaaa
  421 agatggctca ttttccctca aaagttgcca ggagctgcca agtattctgc caattcaccc
  481 tggagcacaa tcaacaaatt cagccagaac acaactacag ctactattag aactattatt
  541 attaataaat tcctctccaa atctagcccc ttgacttcgg atttcacgat ttctcccttc
  601 ctcctagaaa cttgataagt ttcccgcgct tcccttttc taagactaca tgtttgtcat
  661 cttataaagc aaaggggtga ataaatgaac caaatcaata acttctggaa tatctgcaaa
  721 caacaataat atcagctatg ccatctttca ctattttagc cagtatcgag ttgaatgaac
  781 atagaaaaat acaaaactga attcttccct gtaaattccc cgttttgacg acgcacttgt
  841 agccacgtag ccacgcctac ttaagacaat tacaaaaggc gaagaagact gactcaggct
  901 taagctgcca gccagagagg gagtcatttc attggcgttt gagtcagcaa agaagtcaag
  961 atggccaaag ttccagacat gtttgaagac ctgaagaact gttacagtga aaatgaagaa
 1021 gacagttcct ccattgatca tctgtctctg aatcagaaat ccttctatca tgtaagctat
 1081 ggcccactcc atgaaggctg catggatcaa tctgtgtctc tgagtatctc tgaaacctct
 1141 aaaacatcca agcttacctt caaggagagc atggtggtag tagcaaccaa cgggaaggtt
 1201 ctgaagaaga gacggttgag tttaagccaa tccatcactg atgatgacct ggaggccatc
 1261 gccaatgact cagaggaaga aatcatcaag cctaggtcag cacctttag cttcctgagc
 1321 aatgtgaaat acaactttat gaggatcatc aaatacgaat tcatcctgaa tgacgccctc
 1381 aatcaaagta taattcgagc caatgatcag tacctcacgg ctgctgcatt acataatctg
 1441 gatgaagcag tgaaatttga catgggtgct tataagtcat caaaggatga tgctaaaatt
 1501 accgtgattc taagaatctc aaaaactcaa ttgtatgtga ctgcccaaga tgaagaccaa
 1561 ccagtgctgc tgaaggagat gcctgagata cccaaaacca tcacaggtag tgagaccaac
 1621 ctcctcttct tctgggaaac tcacggcact aagaactatt tcacatcagt tgcccatcca
 1681 aacttgttta ttgccacaaa gcaagactac tgggtgtgct tggcaggggg gccaccctct
 1741 atcactgact ttcagatact ggaaaaccag gcgtaggtct ggagtctcac ttgtctcact
 1801 tgtgcagtgt tgacagttca tatgtaccat gtacatgaag aagctaaatc ctttactgtt
 1861 agtcatttgc tgagcatgta ctgagccttg taattctaaa tgaatgttta cactctttgt
 1921 aagagtggaa ccaacactaa catataatgt tgttatttaa agaacacccct atattttgca
 1981 tagtaccaat cattttaatt attattcttc ataacaattt taggaggacc agagctactg
 2041 actatggcta ccaaaaagac tctacccata ttacagatgg gcaaattaag gcataagaaa
 2101 actaagaaat atgcacaata gcagttgaaa caagaagcca cagacctagg atttcatgat
 2161 ttcatttcaa ctgtttgcct tctactttta agttgctgat gaactcttaa tcaaatagca
 2221 taagtttctg ggacctcagt tttatcattt tcaaaatgga gggaataata cctaagcctt
```

-continued

```
2281 cctgccgcaa cagttttta tgctaatcag ggaggtcatt ttggtaaaat acttcttgaa 2341 gccgagcctc aagatgaagg caaagcacga aatgttattt tttaattatt atttatatat 2401 gtatttataa atatatttaa gataattata atatactata tttatgggaa cccccttcatc 2461 ctctgagtgt gaccaggcat cctccacaat agcagacagt gttttctggg ataagtaagt 2521 ttgatttcat taatacaggg cattttggtc caagttgtgc ttatcccata gccaggaaac 2581 tctgcattct agtacttggg agacctgtaa tcatataata aatgtacatt aattaccttg 2641 agccagtaat tggtccgatc tttgactctt ttgccattaa acttacctgg gcattcttgt 2701 ttcaattcca cctgcaatca agtcctacaa gctaaaatta gatgaactca actttgacaa 2761 ccatgagacc actgttatca aaactttctt ttctggaatg taatcaatgt ttcttctagg 2821 ttctaaaaat tgtgatcaga ccataatgtt acattattat caacaatagt gattgataga 2881 gtgttatcag tcataactaa ataaagcttg caacaaaatt ctctgacaaa aaaaaaaaaa 2941 aaa
```

Human IL-1beta mRNA (Accession No. NM_000576)
SEQ ID NO: 2

```
   1 accaaacctc ttcgaggcac aaggcacaac aggctgctct gggattctct tcagccaatc 61 ttcattgctc aagtgtctga agcagccatg gcagaagtac ctgagctcgc cagtgaaatg 121 atggcttatt acagtggcaa tgaggatgac ttgttctttg aagctgatgg ccctaaacag 181 atgaagtgct ccttccagga cctggacctc tgccctctgg atggcggcat ccagctacga 241 atctccgacc accactacag caagggcttc aggcaggccg cgtcagttgt tgtggccatg 301 gacaagctga ggaagatgct ggttccctgc ccacagacct ccaggagaa tgacctgagc 361 accttctttc ccttcatctt tgaagaagaa cctatcttct tcgacacatg gataacgag 421 gcttatgtgc acgatgcacc tgtacgatca ctgaactgca cgctccggga ctcacagcaa 481 aaaagcttgg tgatgtctgg tccatatgaa ctgaaagctc tccacctcca gggacaggat 541 atggagcaac aagtggtgtt ctccatgtcc tttgtacaag gagaagaaag taatgacaaa 601 atacctgtgg ccttgggcct caaggaaaag aatctgtacc tgtcctgcgt gttgaaagat 661 gataagccca ctctacagct ggagagtgta gatcccaaaa attacccaaa gaagaagatg 721 gaaaagcgat ttgtcttcaa caagatagaa atcaataaca gctggaatt tgagtctgcc 781 cagttcccca ctggtacat cagcaccctct caagcagaaa acatgccgt cttcctggga 841 gggaccaaag gcggccagga tataactgac ttcaccatgc aatttgtgtc ttcctaaaga 901 gagctgtacc cagagagtcc tgtgctgaat gtggactcaa tccctagggc tggcagaaag 961 ggaacagaaa ggttttgag tacggctata gcctggactt tcctgttgtc tacaccaatg 1021 cccaactgcc tgccttaggg tagtgctaag aggatctcct gtccatcagc caggacagtc 1081 agctctctcc tttcagggcc aatccccagc ccttttgttg agccaggcct ctctcacctc 1141 tcctactcac ttaaagcccg cctgacagaa accacggcca catttggttc taagaaaccc 1201 tctgtcattc gctcccacat tctgatgagc aaccgcttcc ctatttattt atttatttgt 1261 ttgtttgttt tattcattgg tctaatttat tcaagggggg caagaagtag cagtgtctgt 1321 aaaagagcct agttttaat agctatgaa tcaattcaat ttggactggt gtgctctctt 1381 taaatcaagt cctttaatta agactgaaaa tatataagct cagattattt aaatgggaat 1441 atttataaat gagcaaatat catactgttc aatggttctg aaataaactt cactgaag
```

Human IL-1beta open reading frame-mature form
SEQ ID NO: 3

Gcacctgtacgatcactgaactgcacgctccgggactcacagcaaaaaagcttggtgatgtctggtcca tatgaactgaaagctctccacctccagggacaggatatggagcaacaagtggtgttctccatgtcctttg -continued gtacaaggagaagaaagtaatgacaaaatacctgtggccttgggcctcaaggaaaagaatctgtacctg tcctgcgtgttgaaagatgataagcccactctacagctggagagtgtagatcccaaaaattacccaaag aagaagatggaaaagcgatttgtcttcaacaagatagaaatcaataacaagctggaatttgagtctgcc cagttccccaactggtacatcagcacctctcaagcagaaaacatgcccgtcttcctgggagggaccaaa ggcggccaggatataactgacttcaccatgcaatttgtgtcttcctaaag IL-1β, Sequence of ssIL-1β (539 BP)

SEQ ID NO: 4 atggaaatctgcagaggcctccgcagtcacctaatcactctcctcctcttcctgttccattcagagacg atctgcgcacctgtacgatcactgaactgcacgctccgggactcacagcaaaaaagcttggtgatgtct ggtccatatgaactgaaagctctccacctccagggacaggatatggagcaacaagtggtgttctccatg tcctttgtacaaggagaagaaagtaatgacaaaatacctgtggccttgggcctcaaggaaaagaatctg tacctgtcctgcgtgttgaaagatgataagcccacccacagccggagagtgtagaccccaaaaattac ccaaagaagaagatggaaaagcgatttgtcttcaacaagatagaaatcaataacaagctggaatttgag tctgcccagttccccaactggtacatcagcacctctcaagcagaaaacatgcccgtcttcctgggaggg accaaaggcggccaggatataactgacttcaccatgcaatttgtgtcttcctaaag Human IL1-RA mRNA (Accession No. NM_173842)

SEQ ID NO: 5

```
   1 atttctttat aaaccacaac tctgggcccg caatggcagt ccactgcctt gctgcagtca
  61 cagaatggaa atctgcagag gcctccgcag tcacctaatc actctcctcc tcttcctgtt
 121 ccattcagag acgatctgcc gaccctctgg gagaaaatcc agcaagatgc aagccttcag
 181 aatctgggat gttaaccaga agaccttcta tctgaggaac aaccaactag ttgctggata
 241 cttgcaagga ccaaatgtca atttagaaga aagatagat gtggtaccca ttgagcctca
 301 tgctctgttc ttgggaatcc atggagggaa gatgtgcctg ccctgtgtca agtctggtga
 361 tgagaccaga ctccagctgg aggcagttaa catcactgac ctgagcgaga acagaaagca
 421 ggacaagcgc ttcgccttca tccgctcaga cagcggcccc accaccagtt ttgagtCtgc
 481 cgcctgcccc ggttggttcc tctgcacagc gatggaagct gaccagcccg tcagcctcac
 541 caatatgcct gacgaaggcg tcatggtcac caaattctac ttccaggagg acgagtagta
 601 ctgcccaggc ctgcctgttc ccattcttgc atggcaagga ctgcagggac tgccagtccc
 661 cctgccccag ggctcccggc tatggggggca ctgaggacca gccattgagg ggtggaccct
 721 cagaaggcgt cacaagaacc tggtcacagg actctgcctc ctcttcaact gaccagcctc
 781 catgctgcct ccagaatggt ctttctaatg tgtgaatcag agcacagcag ccctgcaca
 841 aagcccttcc atgtcgcctc tgcattcagg atcaaacccc gaccacctgc caacctgct
 901 ctcctcttgc cactgcctct tcctccctca ttccaccttc ccatgccctg gatccatcag
 961 gccacttgat gaccccaac caagtggctc ccacaccctg ttttacaaaa agaaaagac
1021 cagtccatga gggaggtttt taagggtttg tggaaaatga aaattaggat ttcatgattt
1081 ttttttttca gtccccgtga aggagagccc ttcatttgga gattatgttc tttcggggag
1141 aggctgagga cttaaaatat tcctgcattt gtgaaatgat ggtgaaagta agtggtagct
1201 tttcccttct ttttcttctt ttttttgtgat gtcccaactt gtaaaaatta aaagttatgg
1261 tactatgtta gccccataat ttttttttttc cttttaaaac acttccataa tctggactcc
1321 tctgtccagg cactgctgcc cagcctccaa gctccatctc cactccagat tttttacagc
1381 tgcctgcagt actttacctc ctatcagaag tttctcagct cccaaggctc tgagcaaatg
1441 tggctcctgg gggttctttc ttcctctgct gaaggaataa attgctcctt gacattgtag
```

```
1501 agcttctggc acttggagac ttgtatgaaa gatggctgtg cctctgcctg tctcccccac 1561 cgggctggga gctctgcaga gcaggaaaca tgactcgtat atgtctcagg tccctgcagg 1621 gccaagcacc tagcctcgct cttggcaggt actcagcgaa tgaatgctgt atatgttggg 1682 tgcaaagttc cctacttcct gtgacttcag ctctgtttta caataaaatc ttgaaaatgc 1741 ctaaaaaaaa aaaaaaaaa
```

Human IL1-RA open reading frame
SEQ ID NO: 6
```
atggaaatctgcagaggcctccgcagtcacctaatcactctcctcctcttcctgttccattcagagacg
atctgccgaccctctgggagaaaatccagcaagatgcaagccttcagaatctgggatgttaaccagaag
accttctatctgaggaacaaccaactagttgctggatacttgcaaggaccaaatgtcaatttagaagaa
aagatagatgtggtacccattgagcctcatgctctgttcttgggaatccatggagggaagatgtgcctg
tcctgtgtcaagtctggtgatgagaccagactccagctggaggcagttaacatcactgacctgagcgag
aacagaaagcaggacaagcgcttcgccttcatccgctcagacagcggccccaccaccagttttgagtct
gccgcctgccccggttggttcctctgcacagcgatggaagctgaccagcccgtcagcctcaccaatatg
cctgacgaaggcgtcatggtcaccaaattctacttccaggaggacgagtag
```

IL-1RA, Sequence of hIL-1RA (534 BP, note silent T→C mutation at position 390)
SEQ ID NO: 7
```
atggaaatctgcagaggcctccgcagtcacctaatcactctcctcctcttcctgttccattcagagacg
atctgccgaccctctgggagaaaatccagcaagatgcaagccttcagaatctgggatgttaaccagaag
accttctatctgaggaacaaccaactagttgctggatacttgcaaggaccaaatgtcaatttagaagaa
aagatagatgtggtacccattgagcctcatgctctgttcttgggaatccatggagggaagatgtgcctg
tcctgtgtcaagtctggtgatgagaccagactccagctggaggcagttaacatcactgacctgagcgag
aacagaaagcaggacaagcgcttcgccttcatccgctcagacagcggccccaccaccagtfttgagtct
gccgcctgccccggttggttcctctgcacagcgatggaagctgaccagcccgtcagcctcaccaatatg
cctgacgaaggcgtcatggtcaccaaattctacttccaggaggacgagtag
``` human IL-1R1 mRNA (Accession No. NM_000877)
SEQ ID NO: 8
```
  1 tagacgcacc ctctgaagat ggtgactccc tcctgagaag ctggacccct tggtaaaaga
 61 caaggccttc tccaagaaga atatgaaagt gttactcaga cttatttgtt tcatagctct
121 actgatttct tctctggagg ctgataaatg caaggaacgt gaagaaaaaa taatttagt
181 gtcatctgca aatgaaattg atgttcgtcc ct9tcctctt aacccaaatg aacacaaagg
241 cactataact tggtataaag atgacagcaa gacacctgta tctacagaac aagcctccag
301 gattcatcaa cacaaagaga acttggtt tgttcctgct aaggtggagg attcaggaca
361 ttactattgc gtggtaagaa attcatctta ctgcctcaga attaaaataa gtgcaaaatt
421 tgtggagaat gagcctaact tatgttataa tgcacaagcc atatttaagc agaaactacc
481 cgttgcagga gacggaggac ttgtgtgccc ttatatggag ttttttaaaa atgaaaataa
541 tgagttacct aaattacagt ggtataaagga ttgcaaacct ctacttcttg acaatataca
601 ctttagtgga gtcaaagata ggctcatcgt gatgaatgtg gctgaaaagc atagagggaa
661 ctatacttgt catgcatcct acacatactt gggcaagcaa tatcctatta cccgggtaat
721 agaatttatt actctagagg aaaacaaacc cacaaggcct gtgattgtga gcccagctaa
781 tgagacaatg gaagtagact ggggatccca gatacaattg atctgtaatg tcaccggcca
841 gttgagtgac attgcttact ggaagtggaa tgggtcagta attgatgaag atgacccagt
901 gctaggggaa gactattaca gtgtggaaaa tcctgcaaac aaaagaagga gtaccctcat
```

-continued

```
 961 cacagtgctt aatatatcgg aaattgaaag tagattttat aaacatccat ttacctgttt
1021 tgccaagaat acacatggta tagatgcagc atatatccag ttaatatatc cagtcactaa
1081 tttccagaag cacatgattg gtatatgtgt cacgttgaca gtcataattg tgtgttctgt
1201 ttttctccca ataaaagctt cagatggaaa gacctatgac gcatatatac tgtatccaaa
1261 gactgttggg gaagggtcta cctctgactg tgatatttt gtgtttaaag tcttgcctga
1321 ggtcttggaa aaacagtgtg gatataagct gttcattat ggaagggatg actacgttgg
1381 ggaagacatt gttgaggtca ttaatgaaaa cgtaaagaaa agcagaagac tgattatcat
1441 tttagtcaga gaaacatcag gcttcagctg gctgggtggt tcatctgaag agcaaatagc
1501 catgtataat gctcttgttc aggatggaat taaagttgtc ctgcttgagc tggagaaaat
1561 ccaagactat gagaaaatgc cagaatcgat taaattcatt aagcagaaac atggggctat
1621 ccgctggtca ggggactta cacagggacc acagtctgca aagacaaggt tctggaagaa
1681 tgtcaggtac cacatgccag tccagcgacg gtcaccttca tctaaacacc agttactgtc
1741 accagccact aaggagaaac tgcaaagaga ggctcacgtg cctctcgggt agcatggaga
1801 agttgccaag agttctttag gtgcctcctg tcttatggcg ttgcaggcca ggttatgcct
1861 catgctgact tgcagagttc atggaatgta acatatcat cctttatccc tgaggtcacc
1921 tggaatcaga ttattaaggg aataagccat gacgtcaata gcagcccagg cacttcaga
1981 gtagagggct tgggaagatc ttttaaaaag gcagtaggcc cggtgtggtg gctcacgcct
2041 ataatcccag cactttggga ggctgaagtg ggtggatcac cagaggtcag gagttcgaga
2101 ccagcccagc caacatggca aaccccatc tctactaaaa atacaaaaat gagctaggca
2161 tggtggcaca cgcctgtaat cccagctaca cctgaggctg aggcaggaga attgcttgaa
2221 ccggggagac ggaggttgca gtgagccgag tttgggccac tgcactctag cctggcaaca
2281 gagcaagact ccgtctcaaa aaagggcaa taaatgccct ctctgaatgt tgaactgcc
2341 aagaaaggc atggagacag cgaactagaa gaaagggcaa gaaggaaata gccaccgtct
2401 acagatggct tagttaagtc atccacagcc caagggcggg gctatgcctt gtctggggac
2461 cctgtagagt cactgaccct ggagcggctc tcctgagagg tgctgcaggc aaagtgagac
2521 tgacacctca ctgaggaagg gagacatatt cttggagaac tttccatctg cttgtatttt
2581 ccatacacat ccccagccag aagttagtgt ccgaagaccg aattttattt tacagagctt
2641 gaaaactcac ttcaatgaac aaagggattc tccaggattc caaagttttg aagtcatctt
2701 agctttccac aggaggggaga gaacttaaaa aagcaacagt agcagggaat tgatccactt
2761 cttaatgctt tcctccctgg catgaccatc ctgtcctttg ttattatcct gcattttacg
2821 tctttggagg aacagctccc tagtggcttc ctccgtctgc aatgtcccctt gcacagccca
2881 cacatgaacc atccttccca tgatgccgct cttctgtcat cccgctcctg ctgaaacacc
2941 tcccaggggc tccacctgtt caggagctga agcccatgct ttcccaccag catgtcactc
3001 ccagaccacc tccctgccct gtcctccagc ttccctcgc tgtcctgctg tgtgaattcc
3061 caggttggcc tggtggccat gtcgcctgcc cccagcactc ctctgtctct gctcttgcct
3121 cgacccttcc tcctccttg cctaggaggc cttctcgcat tttctctagc tgatcagaat
3181 tttaccaaaa ttcagaacat cctccaattc cacagtctct gggagacttt ccctaagagg
3241 cgacttcctc tccagcctc tctctctggt caggcccact gcagagatgg tggtgagcac
3301 atctgggagg ctggtctccc tccagctgga attgctgctc tctgagggag aggctgtggt
3361 ggctgtctct gtccctcact gccttccagg agcaatttgc acatgtaaca tagatttatg
3421 taatgcttta tgtttaaaaa cattccccaa ttatcttatt taattttgc aattattcta
```

```
3481 attttatata tagagaaagt gacctatttt ttaaaaaaat cacactctaa gttctattga
3541 acctaggact tgagcctcca tttctggctt ctagtctggt gttctgagta cttgatttca
3601 ggtcaataac ggtcccccct cactccacac tggcacgttt gtgagaagaa atgacatttt
3661 gctaggaagt gaccgagtct aggaatgctt ttattcaaga caccaaattc caaacttcta
3721 aatgttggaa ttttcaaaaa ttgtgtttag attttatgaa aaactcttct actttcatct
3781 attctttccc tagaggcaaa catttcttaa aatgtttcat tttcattaaa aatgaaagcc
3841 aaatttatat gccaccgatt gcaggacaca agcacagttt taagagttgt atgaacatgg
3901 agaggacttt tggttttat atttctcgta tttaatatgg gtgaacacca acttttattt
3961 ggaataataa ttttcctcct aaacaaaaac acattgagtt taagtctctg actcttgcct
4021 ttccacctgc tttctcctgg gcccgctttg cctgcttgaa ggaacagtgc tgttctggag
4081 ctgctgttcc aacagacagg gcctagcttt catttgacac acagactaca gccagaagcc
4141 catggagcag ggatgtcacg tcttgaaaag cctattagat gttttacaaa tttaattttg
4201 cagattattt tagtctgtca tccagaaaat gtgtcagcat gcatagtgct aagaaagcaa
4261 gccaatttgg aaacttaggt tagtgacaaa attggccaga gagtgggggt gatgatgacc
4321 aagaattaca agtagaatgg cagctggaat ttaaggaggg acaagaatca atggataagc
4381 gtgggtggag gaagatccaa acagaaaagt gcaaagttat tccccatctt ccaagggttg
4441 aattctggag gaagaagaca cattcctagt tccccgtgaa cttcctttga cttattgtcc
4501 ccactaaaac aaaacaaaaa acttttaatg ccttccacat taattagatt ttcttgcagt
4561 ttttttatgg cattttttta aagatgccct aagtgttgaa gaagagtttg caaatgcaac
4621 aaaatattta attaccggtt gttaaaactg gtttagcaca atttatattt tccctctctt
4681 gcctttctta tttgcaataa aaggtattga gccattttt aaatgacatt tttgataaat
4741 tatgttgta ctagttgatg aaggagtttt ttttaacctg tttatataat tttgcagcag
4801 aagccaaatt ttttgtatat taaagcacca aattcatgta cagcatgcat cacggatcaa
4861 tagactgtac ttattttcca ataaaatttt caaactttgt actgttaaa
``` human IL-1R2 mRNA (Accession No. NM_173343)

SEQ ID NO: 9

```
  1 gggatgggag atactgttgt ggtcacctct ggaaaataca ttctgctact cttaaaaact
 61 agtgacgctc atacaaatca acagaaagag cttctgaagg aagactttaa agctgcttct
121 gccacgtgct gctgggtctc agtcctccac ttcccgtgtc ctctggaagt tgtcaggagc
181 aatgttgcgc ttgtacgtgt tggtaatggg agtttctgcc ttcacccttc agcctgcggc
241 acacacaggg gctgccagaa gctgccggtt tcgtgggagg cattacaagc gggagttcag
301 gctggaaggg gagcctgtag ccctgaggtg cccccaggtg ccctactggt gtgggcctc
361 tgtcagcccc cgcatcaacc tgacatggca taaaaatgac tctgctagga cggtcccagg
421 agaagaagac acacggatgt gggcccagga cggtgctctg tggcttctgc agccttgca
481 ggaggactct ggcacctacg tctgcactac tagaaatgct tcttactgtg acaaaatgtc
541 cattgagctc agagtttttg agaatacaga tgctttcctg ccgttcatct catacccgca
601 aattttaacc ttgtcaacct ctggggtatt agtatgccct gacctgagtg aattcacccg
661 tgacaaaact gacgtgaaga ttcaatggta caaggattct cttctttgg ataaagacaa
721 tgagaaattt ctaagtgtga gggggaccac tcacttactc gtacacgatg tggccctgga
781 agatgctggc tattaccgct gtgtcctgac atttgcccat gaaggccagc aatacaacat
841 cactaggagt attgagctac gcatcaagaa aaaaaaagaa gagaccattc ctgtgatcat
```

```
 901 ttccccctc  aagaccatat  cagcttctct  ggggtcaaga  ctgacaatcc  cgtgtaaggt 961 gtttctggga  accggcacac  ccttaaccac  catgctgtgg  tggacggcca  atgacaccca 1021 catagagagc  gcctacccgg  gaggccgcgt  gaccgagggg  ccacgccagg  aatattcaga 1081 aaataatgag  aactacattg  aagtgccatt  gatttttgat  cctgtcacaa  gagaggattt 1141 gcacatggat  tttaaatgtg  ttgtccataa  taccctgagt  tttcagacac  tacgcaccac 1201 agtcaaggaa  gcctcctcca  cgttctcctg  gggcattgtg  ctggcccac   tttcactggc 1261 cttcttggtt  ttgggggaa   tatggatgca  cagacggtgc  aaacacagaa  ctggaaaagc 1321 agatggtctg  actgtgctat  ggcctcatca  tcaagacttt  caatcctatc  ccaagtgaaa 1381 taaatggaat  gaaataattc  aaacacaaaa  aaaaaaaaa   aaaaaaaaa   aaaaaa
``` human cOX1 mRNA (Accession No. M59979)

SEQ ID NO: 10
```
   1 gcgccatgag  ccggagtctc  ttgctccggt  tcttgctgtt  cctgctcctg  ctcccgccgc 61 tccccgtcct  gctcgcggac  ccaggggcgc  ccacgccagt  gaatccctgt  tgttactatc 121 catgccagca  ccagggcatc  tgtgtccgct  tcggccttga  ccgctaccag  tgtgactgca 181 cccgcacggg  ctattccggc  cccaactgca  ccatccctgg  cctgtggacc  tg9ttccgga 241 attcactgcg  gcccagcccc  tctttcaccc  acttcctgct  cactcacggg  cgctggttct 301 gggagtttgt  caatgccacc  ttcatccgag  agatgctcat  gcgcctggta  ctcacagtgc 361 gctccaacct  tatccccagt  ccccccacct  acaactcagc  acatgactac  atcagctggg 421 agtctttctc  caacgtgagc  tattacactc  gtattctgcc  ctctgtgcct  aaagattgcc 481 ccacacccat  gggaaccaaa  gggaagaagc  agttgccaga  tgcccagctc  ctggcccgcc 541 gcttcctgct  caggaggaag  ttcatacctg  accccaagg   caccaacctc  atgtttgcct 601 tctttgcaca  acacttcacc  caccagttct  tcaaaactc   tggcaagatg  gtcctggct 661 tcaccaaggc  cttgggccat  ggggtagacc  tcggccacat  ttatggagac  aatctggagc 721 gtcagtatca  actgcggctc  tttaaggatg  gaaactcaa   gtaccaggtg  ctggatggag 781 aaatgtaccc  gcctcggta   gaagaggcgc  ctgtgttgat  gcactacccc  cgaggcatcc 841 cgccccagag  ccagatggct  gtgggccagg  aggtgtttgg  gctgcttcct  gggctcatgc 901 tgtatgccac  gctctggcta  cgtgagcaca  accgtgtgtg  tgacctgctg  aaggctgagc 961 accccacctg  gggcgatgag  cagctttttcc  agacgacccg  cctcatcctc  ataggggaga 1021 ccatcaagat  tgtcatcgag  gagtacgtgc  agcagctgag  tggctatttc  ctgcagctga 1081 aatttgaccc  agagctgctg  ttcggtgtcc  agttccaata  ccgcaaccgc  attgccatgg 1141 agttcaacca  tctctaccac  tggcaccccc  tcatgcctga  ctccttcaag  gtgggctccc 1201 aggagtacag  ctacgagcag  ttcttgttca  acacctccat  gttggtggac  tatgggttg 1261 aggccctggt  ggatgccttc  tctcgccaga  ttgctggccg  gatcggtggg  ggcaggaaca 1321 tggaccacca  catcctgcat  gtggctgtgg  atgtcatcag  ggagtctcgg  agatgcggc 1381 tgcagcccct  caatgagtac  cgcaagaggt  ttggcatgaa  accctacacc  tccttccagg 1441 agctcgtagg  agagaaggag  atggcagcag  agttggagga  attgtatgga  gacattgatg 1501 cgttggagtt  ctaccctgga  ctgcttcttg  aaaagtgcca  tccaaactct  atctttgggg 1561 agagtatgat  agagattggg  gctccctttt  ccctcaaggg  tctcctaggg  aatcccatct 1621 gttctccgga  gtactggaag  ccgagcacat  ttggcggcga  ggtgggcttt  aacattgtca 1681 agacggccac  actgaagaag  ctggtctgcc  tcaacaccaa  gacctgtccc  tacgtttcct 1741 tccgtgtgcc  ggatgccagt  caggatgatg  ggcctgctgt  ggagcgacca  tccacagagc 1801 tctgaggggc  aggaaagcag  cattctggag  gggagagctt  tgtgcttgtc  attccagagt
```

```
1861 gctgaggcca gggctgatgg tcttaaatgc tcattttctg gtttggcatg gtgagtgttg
1921 gggttgacat ttagaacttt aagtctcacc cattatctgg aatattgtga ttctgtttat
1981 tcttccagaa tgctgaactc cttgttagcc cttcagattg ttaggagtgg ttctcatttg
2041 gtctgccaga atactgggtt cttagttgac aacctagaat gtcagatttc tggttgattt
2101 gtaacacagt cattatagga tgtggagcta ctgatgaaat ctgctagaaa gttaggggt
2161 tcttattttg cattccagaa tcttgacttt ctgattggtg attcaaagtg ttgtgttccc
2221 tggctgatga tccagaacag tggctcgtat cccaaatctg tcagcatctg ctgtctaga
2281 atgtggattt gattcatttt cctgttcagt gagatatcat agagacgag atcctaaggt
2341 ccaacaagaa tgcattccct gaatctgtgc ctgcactgag agggcaagga agtggggtgt
2401 tcttcttggg accaccacta agaccctggt ctgaggatgt agagagaaca ggtgggctgt
2461 attcacgcca ttggttggaa gctaccagag ctctatcccc atccaggtct tgactcatgg
2521 cagctgtttc tcatgaagct aataaaattc gccc
``` human cOX2 mRNA (Accession No. NM_000963)

SEQ ID NO: 11

```
   1 caattgtcat acgacttgca gtgagcgtca ggagcacgtc caggaactcc tcagcagcgc
  61 ctccttcagc tccacagcca gacgccctca gacagcaaag cctaccccg cgccgcgccc
 121 tgcccgccgc tcggatgctc gcccgcgccc tgctgctgtg cgcggtcctg cgctcagcc
 181 atacagcaaa tccttgctgt tcccacccat gtcaaaaccg aggtgtatgt atgagtgtgg
 241 gatttgacca gtataagtgc gattgtaccc ggacaggatt ctatggagaa aactgctcaa
 301 caccggaatt tttgacaaga ataaaattat ttctgaaacc cactccaaac acagtgcact
 361 acatacttac ccacttcaag ggattttgga acgttgtgaa taacattccc ttccttcgaa
 421 atgcaattat gagttatgtc ttgacatcca gatcacattt gattgacagt ccaccaactt
 481 acaatgctga ctatggctac aaaagctggg aagccttctc taacctctcc tattatacta
 541 gagcccttcc tcctgtgcct gatgattgcc cgactccctt gggtgtcaaa ggtaaaaagc
 601 agcttcctga ttcaaatgag attgtggaaa aattgcttct aagaagaaag ttcatccctg
 661 atccccaggg ctcaaacatg atgtttgcat tctttgccca gcacttcacg catcagtttt
 721 tcaagacaga tcataagcga gggccagctt tcaccaacgg ctgggccat ggggtggact
 781 taaatcatat ttacggtgaa actctggcta gacagcgtaa actgcgcctt tcaaggatg
 841 gaaaaatgaa atatcagata attgatggag agatgtatcc tcccacagtc aaagatactc
 901 aggcagagat gatctaccct cctcaagtcc ctgagcatct acggtttgct gtggggcagg
 961 aggtctttgg tctggtgcct ggtctgatga tgtatgccac aatctggctg cgggaacaca
1021 acagagtatg cgatgtgctt aaacaggagc atcctgaatg gggtgatgag cagttgttcc
1081 agacaagcag gctaatactg ataggagaga ctattaagat tgtgattgaa gattatgtgc
1141 aacacttgag tggctatcac ttcaaactga aatttgaccc agaactactt ttcaacaaac
1201 aattccagta ccaaaatcgt attgctgctg aatttaacac cctctatcac tggcatccc
1261 ttctgcctga cacctttcaa attcatgacc agaaatacaa ctatcaacag ttatctaca
1321 acaactctat attgctggaa catggaatta cccagtttgt tgaatcattc accaggcaaa
1381 ttgctggcag ggttgctggt ggtaggaatg ttccacccgc agtacagaaa gtatcacagg
1441 cttccattga ccagagcagg cagatgaaat accagtcttt taatgagtac cgcaaacgct
1501 ttatgctgaa gccctatgaa tcatttgaag aacttacagg agaaaaggaa atgtctgcag
1561 agttggaagc actctatggt gacatcgatg ctgtggagct gtatcctgcc cttctggtag
```

-continued

```
1621 aaaagcctcg gccagatgcc atctttggtg aaaccatggt agaagttgga gcaccattct
1681 ccttgaaagg acttatgggt aatgttatat gttctcctgc ctactggaag ccaagcactt
1741 ttggtggaga agtgggtttt caaatcatca acactgcctc aattcagtct ctcatctgca
1801 ataacgtgaa gggctgtccc tttacttcat tcagtgttcc agatccagag ctcattaaaa
1861 cagtcaccat caatgcaagt tcttcccgct ccggactaga tgatatcaat cccacagtac
1921 tactaaaaga acgttcgact gaactgtaga agtctaatga tcatatttat ttatttatat
1981 gaaccatgtc tattaattta attatttaat aatatttata ttaaactcct tatgttactt
2041 aacatcttct gtaacagaag tcagtactcc tgttgcggag aaaggagtca tacttgtgaa
2101 gactttatg tcactactct aaagattttg ctgttgctgt taagtttgga aaacagtttt
2161 tattctgttt tataaaccag agagaaatga gttttgacgt ctttttactt gaatttcaac
2221 ttatattata agaacgaaag taaagatgtt tgaatactta aacactatca caagatggca
2281 aaatgctgaa agttttaca ctgtcgatgt ttccaatgca tcttccatga tgcattagaa
2341 gtaactaatg tttgaaattt taaagtactt ttggttattt ttctgtcatc aaacaaaaac
2401 aggtatcagt gcattattaa atgaatattt aaattagaca ttaccagtaa tttcatgtct
2461 acttttaaa atcagcaatg aaacaataat ttgaaatttc taaattcata gggtagaatc
2521 acctgtaaaa gcttgtttga tttcttaaag ttattaaact tgtacatata ccaaaaagaa
2581 gctgtcttgg atttaaatct gtaaaatcag atgaaatttt actacaattg cttgttaaaa
2641 tattttataa gtgatgttcc ttttcacca agagtataaa ccttttagt gtgactgtta
2701 aaacttcctt ttaaatcaaa atgccaaatt tattaaggtg gtggagccac tgcagtgtta
2761 tctcaaaata agaatatttt gttgagatat tccagaattt gtttatatgg ctggtaacat
2821 gtaaaatcta tatcagcaaa agggtctacc tttaaaataa gcaataacaa agaagaaaac
2881 caaattattg ttcaaattta ggtttaaact tttgaagcaa acttttttt atccttgtgc
2941 actgcaggcc tggtactcag attttgctat gaggttaatg aagtaccaag ctgtgcttga
3001 ataacgatat gttttctcag attttctgtt gtacagttta atttagcagt ccatatcaca
3061 ttgcaaaagt agcaatgacc tcataaaata cctcttcaaa atgcttaaat tcatttcaca
3121 cattaatttt atctcagcct cgaagccaat tcagtaggtg cattggaatc aagcctggct
3181 acctgcatgc tgttccttt cttttcttct tttagccatt ttgctaagag acacagtctt
3241 ctcatcactt cgtttctcct atttttgttt actagtttta agatcagagt tcactttctt
3301 tggactctgc ctatattttc ttacctgaac ttttgcaagt tttcaggtaa acctcagctc
3361 aggactgcta tttagctcct cttaagaaga ttaaaagaga aaaaaaagg ccctttaaa
3421 aatagtatac acttatttta agtgaaaagc agagaatttt atttatagct aattttagct
3481 atctgtaacc aagatggatg caaagaggct agtgcctcag agagaactgt acggggtttg
3541 tgactggaaa aagttacgtt cccattctaa ttaatgccct ttcttattta aaaacaaaac
3601 caaatgatat ctaagtagtt ctcagcaata ataatgaa cgataatact tcttttccac
3661 atcteattgt cactgacatt taatggtact gtatattact taatttattg aagattatta
3721 tttatgtctt attaggacac tatggttata aactgtgttt aagcctacaa tcattgattt
3781 ttttttgtta tgtcacaatc agtatatttt ctttggggtt acctctctga atattatgta
3841 aacaatccaa agaaatgatt gtattaagat ttgtgaataa attttagaa atctgattgg
3901 catattgaga tatttaaggt tgaatgtttg tccttaggat aggcctatgt gctagcccac
3961 aaagaatatt gtctcattag cctgaatgtg ccataagact gaccttttaa aatgttttga
4021 gggatctgtg gatgcttcgt taatttgttc agccacaatt tattgagaaa atattctgtg
```

-continued

```
4081 tcaagcactg tgggttttaa tattttaaa tcaaacgctg attacagata atagtattta
4141 tataaataat tgaaaaaaat tttcttttgg gaagagggag aaaatgaaat aaatatcatt
4201 aaagataact caggagaatc ttctttacaa ttttacgttt agaatgttta aggttaagaa
4261 agaaatagtc aatatgcttg tataaaacac tgttcactgt tttttttaaa aaaaaaactt
4321 gatttgttat taacattgat ctgctgacaa aacctgggaa tttgggttgt gtatgcgaat
4381 gtttcagtgc ctcagacaaa tgtgtattta acttatgtaa aagataagtc tggaaataaa
4441 tgtctgttta tttttgtact attta
``` human mPGES mRNA (Accession No. NM_004878)

SEQ ID NO: 12

```
   1 gctgctcctc tgtcgagctg atcacaccca cagttgagct gcgctggcca gagatgcctg
  61 cccacagcct ggtgatgagc agcccggccc tcccggcctt cctgctctgc agcacgctgc
 121 tggtcatcaa gatgtacgtg gtggccatca tcacgggcca agtgaggctg cggaagaagg
 181 cctttgccaa ccccgaggat gccctgagac acggaggccc ccagtattgc aggagcgacc
 241 ccgacgtgga acgctgcctc agggcccacc ggaacgacat ggagaccatc tacccccttcc
 301 ttttcctggg cttcgtctac tcctttctgg gtcctaaccc ttttgtcgcc tggatgcact
 361 tcctggtctt cctcgtgggc cgtgtggcac acaccgtggc ctacctgggg aagctgcggg
 421 cacccatccg ctccgtgacc tacacccctgg cccagctccc ctgcgcctcc atggctctgc
 481 agatcctctg ggaagcggcc cgccacctgt gaccagcagc tgatgcctcc ttggccacca
 541 gaccatgggc caagagccgc cgtggctata cctggggact tgatgttcct tccagattgt
 601 ggtgggccct gagtcctggt ttcctggcag cctgctgcgc gtgtgggtct ctgggcacag
 661 tgggcctgtg tgtgtgcccg tgtgtgtgta tgtgtgtgtg tatgttctt agccccttgg
 721 attcctgcac gaagtggctg atgggaacca tttcaagaca gattgtgaag attgatagaa
 781 aatccttcag ctaaagtaac agagcatcaa aaacatcact ccctctccct ccctaacagt
 841 gaaaagagag aagggagact ctatttaaga ttcccaaacc taatgatcat ctgaatcccg
 901 ggctaagaat gcagactttt cagactgacc ccagaaaattc tggcccagcc aatctagagg
 961 caagcctggc catctgtatt ttttttttc caagacagag tcttgctctg ttgcccaagc
1021 tggagtgaag tggtacaatc tggctcactg cagcctccgc ctcccgggtt caagcgattc
1081 tcccgcctca gcctcctgag tagctgggat tacaggcgcg tatcaccata cccagctaat
1141 ttttgtattt ttagtagaga cgggttcacc atgttgccca ggagggtctc gaactcctgg
1201 cctcaagtga tccaccggcc tcggcctccc aaagtgctgg gatgacaggc atgaatcact
1261 gtgctcagcc accatctgga gttttaaaag gctcccatgt gagtccctgt gatggccagg
1321 ccaggggacc cctgccagtt ctctgtggaa gcaaggctgg ggtcttgggt tcctgtatgg
1381 tggaagctgg gtgagccaag gacagggctg gctcctctgc ccccgctgac gcttcccttg
1441 ccgttggctt tggatgtctt tgctgcagtc ttctctctgg ctcaggtgtg ggtgggaggg
1501 gcccacagga agctcagcct tctcctccca aggtttgagt ccctccaaag ggcagtgggt
1561 ggaggaccgg gagctttggg tgaccagcca ctcaaaggaa ctttctggtc ccttcagtat
1621 cttcaaggtt tggaaactgc aaatgtcccc ttgatgggga atccgtgtgt gtgtgtgtgt
1681 gtgtgtgtgt gtgtgtgtgt gtgtgtgttt tctcctagac ccgtgacctg agatgtgtga
1741 ttttagtca ttaaatggaa gtgtctgcca gctgggccca gcacctaaaa aaaaaaaaaa
1801 aaaaa
``` human cPGES/p23 mRNA (Accession No. L24804)

SEQ ID NO: 13

-continued

```
  1 ggattcgggc tacactttcc tcttctcccc gaccggagag ccgctctttc cgcgcggtgc
 61 attctgggc ccgaggtcga gcccgccgct gccgccgtcg cctgagggaa gcagaagag
121 gccgcgaccg agagaaaaag cggagtcgca ccggagagaa gtcgactccc tagcagcagc
181 cgccgccaga gagcccgccc accagttcgc ccgtccccct gccccgttca caatgcagcc
241 tgcttctgca aagtggtacg atcgaaggga ctatgtcttc attgaatttt gtgttgaaga
301 cagtaaggat gttaatgtaa attttgaaaa atccaaactt acattcagtt gtctcggagg
361 aagtgataat tttaagcatt taaatgaaat tgatcttttt cactgtattg atccaaatga
421 ttccaagcat aaaagaacgg acagatcaat tttatgttgt ttacgaaaag gagaatctgg
481 ccagtcatgg ccaaggttaa caaaagaaag ggcaaagctt aattggctta gtgtcgactt
541 caataattgg aaagactggg aagatgattc agatgaagac atgtctaatt ttgatcgttt
601 ctctgagatg atgaacaaca tgggtggtga tgaggatgta gatttaccag aagtagatgg
661 agcagatgat gattcacaag acagtgatga tgaaaaaatg ccagatctgg agtaaggaat
721 attgtcatca cctggatttt gagaaagaaa ataacttct ctgcaagatt tcataattga
781 ga
```

Secretion Signal sequence of human IL-1ra: (75 bp)
SEQ ID NO: 14
atggaaatctgcagaggcctccgcagtcacctaatcactctcctcctcttcctgttccattcagagacg
atctgc CMV sequence
SEQ ID NO: 15
Cgatgtacgggccagatatacgcgttgacattgattattgactagttattaatagtaatcaattacggg
gtattagttcatagcccatatatggagttccgcgttacataacttacggtaaatggcccgcctggctga
ccgcccaacgacccccgcccattgacgtcaataatgacgtatgttcccatagtaacgccaatagggact
ttccattgacgtcaatgggtggactatttacggtaaactgcccacttggcagtacatcaagtgtatcat
atgccaagtacgccccctattgacgtcaatgacggtaaatggcccgcctggcattatgcccagtacatg
accttatgggactttcctacttggcagtacatctacgtattagtcatcgctattaccatggtgatgcgg
ttttggcagtacatcaatgggcgtggatagcggtttgactcacggggatttccaagtctccaccccatt
gacgtcaatgggagtttgttttggcaccaaaatcaacgggactttccaaaatgtcgtaacaactccgcc
ccattgacgcaaatgggcggtaggcgtgtacggtgggaggtctatataagcagagctctctggctaact
agagaacccactgcttactggcttatcgaaatt Chicken Beta Actin promoter
SEQ ID NO: 16
tcgaggtgag ccccacgttc tgcttcactc tccccatctc ccccccctcc ccaccccaa      60
ttttgtattt atttattttt taattatttt gtgcagcgat ggggcgggg ggggggggg     120
cgcgcgccag gcggggcggg gcggggcgag gggcggggcg gggcgaggcg gagaggtgcg    180
gcggcagcca atcagagcgg cgcgctccga aagtttcctL ttatggcgag gcggcggcgg    240
cggcggccct ataaaaagcg aagcgcgcgg cgggcggag tcgctgcgtt gccttcgccc    300
cgtgccccgc tccgcgccgc ctcgcgccgc ccgccccggc tctgactgac cgcgttactc    360
ccacaggtga gcgggcggga cggcccttct cctccgggct gtaattagcg cttggtttaa    420
tgacggctcg tttcttttct gtggctgcgt gaaagcctta aagggctccg ggagggccct    480
ttgtgcgggg gggagcggct cggggggtgc gtgcgtgtgt gtgtgcgtgg ggagcgccgc    540
gtgcggcccg cgctgcccgg cggctgtgag cgctgcgggc gcggcgcggg gctttgtgcg    600
ctccgcgtgt gcgcgagggg agcgcggccg ggggcggtgc cccgcggtgc gggggggctg    660
cgaggggaac aaaggctgcg tgcggggtgt gtgcgtgggg gggtgagcag ggggtgtggg    720
```

-continued

```
cgcggcggtc gggctgtaac ccccccctgc acccccctcc ccgagttgct gcgcacggcc      780
cggcttcggg tgcggggctc cgtgcggggc gtggcgcggg gctcgccgtg ccgggcgggg      840
ggtggcggca ggtgggggtg ccggcgggg cggggccgcc tcgggccggg gagggctcgg       900
gggaggggcg cggcggcccc ggagcgccgg cggctgtcga ggcgcggcga gccgcagcca      960 ttgccttta tggtaatcgt gc-
gagagggc gcagggactt cctttgtccc aaatctggcg                              1020
gagccgaaat ctgggaggcg ccgccg-
cacc ccctctagcg ggcgcgggcg aagcggtgcg                                  1080
gcgccggcag gaaggaaatg ggcggg-
gagg gccttcgtgc gtcgccgcgc cgccgtcccc                                  1140
ttctccatct ccagcctcgg ggctgccg-
ca ggggacggc tgccttcggg ggggacgggg                                     1200
cagggcgggg ttcggcttct ggcgttgtac cggcggggtt tatatcttcc cttctctgtt      1260
cctccgcagc cagccatg                                                    1278
```

E06566 Accession # Promoter gene of human beta-actin gene
SEQ ID NO: 17

```
cccgggccca gcaccccaag gcggccaacg ccaaaactct ccctcctcct cttcctcaat      60
ctcgctctcg ctcttttttt ttttcgcaaa aggaggggag aggggtaaa aaaatgctgc       120 actgtgcggc gaagccggtg agtgagcggc gcggggccaa tcagcgtgcg ccgttccgaa      180
agttgccttt tatggctcga gcggccgcgg cggcgcccta taaacccag cggcgcgacg       240 cgccaccacc gccgagaccg cgtccgcccc gcgagcacag agcctcgcct ttgccgatcc      300
gccgcccgtc cacacccgcc gccaggtaag cccggccagc cgaccggggc atgcggccgc      360
ggccccttcg cccgtgcaga gccgccgtct gggccgcagc ggggggcgca tgggggggga     420
accggaccgc cgtggggggc gcgggagaag cccctgggcc tccggagatg ggggacaccc      480
cacgccagtt cggaggcgcg aggccgcgct cgggaggcgc gctccggggg tgccgctctc      540
ggggcggggg caaccggcgg ggtctttgtc tgagccgggc tcttgccaat ggggatcgca      600
gggtgggcgc ggcgtagccc ccgccaggcc cggtgggggc tggggcgcca ttgccggtgc      660
gcgctggtcc tttgggcgct aactgcgtgc gcgctgggaa ttggcgctaa ttgcgcgtgc      720
gcgctgggac tcaaggcgct aattgcgcgt gcgttctggg gccgggggtg ccgcggcctg     780
ggctggggcg aaggcgggct cggccggaag gggtggggtc gccgcggctc ccgggcgctt      840
gcgcgcactt cctgcccgag ccgctggccg cccgagggtg tggccgctgc gtgcgcgcgc      900
gccgacccgg cgctgtttga accgggcgga ggcggggctg gcgcccggtt ggggaggggt      960
tggggcctgg cttcctgccg cgcgccgcgg ggacgcctcc gaccagtgtt tgccttttat     1020
ggtaataacg cggccggccc ggcttccttt gtccccaatc tgggcgcgcg ccggcgcccc     1080
ctggcggcct aaggactcgg cgcgccggaa gtggccaggg cggggcgac ttcggctcac      1140 agcgcgcccg gctattctcg cagctcacca tggatg                               1176
```

CMV-Beta actin promoter
SEQ ID NO: 18

```
gaattcggta ccctagttat taatagtaat caattacggg gtcattagtt catagcccat      60
atatggagtt ccgcgttaca taacttacgg taaatggccc gcctggctga ccgcccaacg      120 accccgccc attgacgtca ataatgacgt atgttcccat agtaacgcca atagggactt       180
tccattgacg tcaatgggtg gactatttac ggtaaactgc ccacttggca gtacatcaag      240
tgtatcatat gccaagtacg ccccctattg acgtcaatga cggtaaatgg cccgcctggc      300
attatgccca gtacatgacc ttatgggact ttcctacttg gcagtacatc tacgtattag      360
```

```
tcatcgctat taccatggtc gaggtgagcc ccacgttctg cttcactctc cccatctccc      420
cccctcccc accccaatt ttgtatttat ttattttta attattttgt gcagcgatgg         480
gggcgggggg gggggggggg cgcgcgccag gcggggcggg gcggggcgag gggcggggcg      540
gggcgaggcg gagaggtgcg gcggcagcca atcagagcgg cgcgctccga aagtttcctt      600
ttatggcgag gcggcggcgg cggcggccct ataaaaagcg aagcgcgcgg cgggcgggag     660
tcgctgcgac gctgccttcg ccccgtgccc cgctccgccg ccgcctcgcg ccgcccgccc     720
cggctctgac tgaccgcgtt actcccacag gtgagcgggc gggacggccc ttctcctccg      780
ggctgtaatt agcgcttggt ttaatgacgg cttgtttctt ttctgtggct gcgtgaaagc      840
cttgaggggc tccgggaggg cccttgtgc gggggggagc ggctcggggg gtgcgtgcgt       900
gtgtgtgtgc gtggggagcg ccgcgtgcgg cccgcgctgc ccggcggctg tgagcgctgc      960
gggcgcggcg cggggctttg tgcgctccgc agtgtgcgcg aggggagcgc ggccgggggc     1020
ggtgccccgc ggtgcggggg gggctgcgag gggaacaaag gctgcgtgcg gggtgtgtgc     1080
gtgggggggt gagcaggggg tgtgggcgcg gcggtcgggc tgtaacccc ccctgcaccc      1140
ccctccccga gttgctgagc acggcccggc ttcgggtgcg gggctccgta cggggcgtgg     1200
cgcgggggctc gccgtgccgg gcgggggggtg cggcaggtg ggggtgccgg gcggggcggg     1260
gccgcctcgg gccggggagg gctcggggga ggggcgcggc ggccccccgga gcgccggcgg    1320
ctgtcgaggc gcggcgagcc gcagccattg cctttatgg taatcgtgcg agagggcgca      1380
gggacttcct ttgtcccaaa tctgtgcgga gccgaaatct gggaggcgcc gccgcacccc     1440
ctctagcggg cgcggggcga agcggtgcgg cgccggcagg aaggaaatgg gcggggaggg     1500
ccttcgtgcg tcgccgcgcc gccgtcccct tctccctctc cagcctcggg gctgtccgcg     1560
gggggacggc tgccttcggg ggggacgggg cagggcgggg ttcggcttct ggcgtgtgac     1620
cggcggctct agagcctctg ctaaccatgt tcatgccttc ttcttttttcc tacagctcct    1680
gggcaacgtg ctggttattg tgctgtctca tcattttggc aaagaattc                 1729
Chicken beta-actin with CMV enhancer elements promoter sequence
                                                       SEQ ID NO: 19
cgatgtacgggccagatatacgcgttgacattgattattgactagttattaatagtaatcaattacggg
gtcattagttcatagcccatatatggagttccgcgttacataacttacggtaaatggcccgcctggctg
accgcccaacgacccccgcccattgacgtcaataatgacgtatgttcccatagtaacgccaataggggac
tttccattgacgtcaatgggtggactatttacggtaaactgcccacttggcagtacatcaagtgtatca
tatgccaagtacgccccctattgacgtcaatgacggtaaatggcccgcctggcattatgcccagtacat
gaccttatgggactttcctacttggcagtacatctacgtattagtcatcgctattaccatggtgatgcg
gttttggcagtacatcaatgggcgtggatagcggtttgactcacggggatttccaagtctccaccccat
tgacgtcaatgggagtttgttttggcaccaaaatcaacgggactttccaaaatgtcgtaacaactccgc
cccattgacgcaaatgggcggtaggcgtgtacggtgggaggtctatataagcagagctctctggctaac
tagagaacccactgcttactggcttatcgaaatt
Fusion promoter-CMV portion
                                                       SEQ ID NO: 20
tagttattaa tagtaatcaa ttacgggtc attagttcat agcccatata tggagttccg       60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggac tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
```

```
catggt                                                              366

Fusion promoter - beta actin portion
                                                          SEQ ID NO: 21
ccaattttgt atttatttat tttttaatta ttttgtgcag cgatgggggc gggggggggg     60 gggggcgcg cgccaggcgg ggcggggcgg ggcgaggggc ggggcggggc gaggcggaga    120
ggtgcggcgg cagccaatca gagcggcgcg ctccgaaagt ttcctttat ggcgaggcgg    180 cggcggcggc ggccctataa aaagcgaagc gcgcggcggg cgggagtcgc tgcgacgctg   240
ccttcgcccc gtgccccgct ccgccgccgc ctcgcgccgc ccgccccggc tctgactgac   300
cgcgttactc ccacaggtga gcgggcggga cggcccttct cctccgggct gtaattagcg   360
cttggtttaa tgacggcttg tttctttct gtggctgcgt gaaagccttg aggggctccg    420
ggagggccct ttgtgcgggg gggagcggct cgggggtgc gtgcgtgtgt gtgtgcgtgg    480
ggagcgccgc gtgcggcccg cgctgcccgg cggctgtgag cgctgcgggc gcggcgcggg   540
gctttgtgcg ctccgcagtg tgcgcgaggg gagcgcggcc ggggcggtg ccccgcggtg    600 cgggggggc tgcgagggga acaaaggctg cgtgcgggt gtgtgcgtgg ggggtgagc     660 aggggtgtg ggcgcggcgg tcgggctgta accccccct gcacccccct ccccgagttg    720
ctgagcacgg cccggcttcg ggtgcgggc tccgtacggg gcgtggcgcg gggctcgccg    780
tgccgggcgg ggggtggcgg caggtggggg tgccgggcgg ggcggggccg cctcgggccg    840
gggagggctc gggggagggg cgcggcggcc cccggagcgc cggcggctgt cgaggcgcgg    900
cgagccgcag ccattgcctt ttatggtaat cgtgcgagag ggcgcaggga cttcctttgt    960
cccaaatctg tgcggagccg aaatctggga ggcgccgccg caccccctct agcgggcgcg   1020
gggcgaagcg gtgcggcgcc ggcaggaagg aaatgggcgg ggagggcctt cgtgcgtcgc   1080
cgcgccgccg tccccttctc cctctccagc ctcgggctg tccgcggggg gacggctgcc   1140
ttcggggggg acgggcagg gcggggttcg gcttctggcg tgtgaccggc ggctctagag   1200
cctctgctaa ccatgttcat gccttcttct ttttcctaca gctcctgggc aacgtgctgg   1260
ttattgtgct gtctcatcat tttggcaaag aattc                            1295

Accession # BD136067. promoter element for sustained gene expression
from CMV promoter
                                                          SEQ ID NO: 22
gtattagtca tcgctattac catggtgatg cggttttggc agtacatcaa tgggcgtgga    60
tagcggtttg actcacgggg atttccaagt ctccaccca ttgacgtcaa tgggagtttg    120
ttttggcacc aaaatcaacg ggactttcca aatgtcgta acaactccgc cccattgacg   180
caaatgggcg gtaggcgtgt acggtgggag gtctatataa gcagagctc              229

BD136066 Accession # promoter element for sustained gene expression
from CMV promoter
                                                          SEQ ID NO: 23
tggcattatg cccagtacat gaccttatgg gactttccta cttggcagta catctacgta    60
ttagtcatcg ctattaccat ggtgatgcgg ttttggcagt acatcaatgg gcgtggatag   120
cggtttgact cacggggatt tccaagtctc cacccattg acgtcaatgg gagtttgttt    180
tggcaccaaa atcaacggga ctttccaaaa tgtcgtaaca actccgcccc attgacgcaa   240
atgggcggta ggcgtgtacg gtgggaggtc tatataagca g                     281

BD136065 Accession # promoter element for sustained gene expression
from CMV promoter
                                                          SEQ ID NO: 24
attatgccca gtacatgacc ttatgggact tcctacttg gcagtacatc tacgtattag     60
tcatcgctat taccatggtg atgcggtttt ggcagtacat caatgggcgt ggatagcggt   120
ttgactcacg gggatttcca gtctccacc ccattgacgt caatgggagt tgttttggc    180
```

```
accaaaatca acgggacttt ccaaaatgtc gtaacaactc cgccccattg acgcaaatgg    240
gcggtaggcg tgtacggtgg gaggtctata taagcagagc tc                      282
```

BD136064 Accession # promoter element for sustained gene expression
from CMV promoter
SEQ ID NO: 25

```
ttgcgttaca taacttacgg taaatggccc gcctggctga ccgcccaacg accccgccc     60 attgacgtca ataatgacgt atgttcccat agtaacgcca atagggactt tccattgacg   120
tcaatgggtg gactatttac ggtaaactgc ccacttggca gtacatcaag tgtatcatat   180
gccaagtacg ccccctattg acgtcaatga cggtaaatgg cccgcctggc attatgccca   240
gtacatgacc ttatgggact ttcctacttg gcagtacatc tacgtattag tcatcgctat   300
taccatggtg atgcggtttt ggcagtacat caatgggcgt ggatagcggt ttgactcacg   360
gggatttcca agtctccacc ccattgacgt caatgggagt ttgttttggc accaaaatca   420
acgggacttt ccaaaatgtc gtaacaactc cgccccattg acgcaaatgg gcggtaggcg   480
tgtacggtgg gaggtctata taagcagagc tc                                 512
```

L77202 Accession # Murine Cytomegalovirus early (E1) gene, promoter
region
SEQ ID NO: 26

```
tcggcgaagc ctcgcgcggc cggccaggac gaggagcgcc actaggttga acatccgcac    60
gagccgccgg gccaggtctc ggacgggctc tcgagactcg atctcgtgca gtcggcggt    120 ccgcggtgag gttatagacc atctgctagg cgggtccggg gagacaggca cattactggc   180
ctcggcgccc agcctaggcg tgtctagagc tcgaccgcgc gtccggagcg ccattcgacc   240
ggcgggtagc gagaagaacg ccggagaccg caggttataa caacgtcatg cataaattaa   300
gaatgggc                                                            308
```

X03922 Accession # Human cytomegalovirus (HCMV) IE1 gene promoter
SEQ ID NO: 27

```
ctgcagtgaa taataaaatg tgtgtttgtc cgaaatacgc gtttgagatt tctgtcccga    60
ctaaattcat gtcgcgcgat agtggtgttt atcgccgata gagatggcga tattggaaaa   120
atcgatattt gaaaatatgg catattgaaa atgtcgccga tgtgagtttc tgtgtaactg   180
atatcgccat ttttccaaaa gttgattttt ggcatacgc gatatctggc gatacgctta   240
tatcgtttac gggggatggc gatagacgcc tttggtgact tgggcgattc tgtgtgtcgc   300
aaatatcgca gtttcgatat aggtgacaga cgatatgagg ctatatcgcc gatagaggcg   360
acatcaagct ggcacatggc caatgcatat cgatctatac attgaatcaa tattggccat   420
tagccatatt attcattggt tatatagcat aaatcaatat tggctattgg ccattgcata   480
cgttgtatcc atatcataat atgtacattt atattggctc atgtccaaca ttaccgccat   540
gttgacattg attattgact agttattaat agtaatcaat tacggggtca ttagttcata   600
gcccatatat ggagttccgc gttacataac ttacggtaaa tggcccgcct ggctgaccgc   660
ccaacgaccc ccgcccattg acgtcaataa tgacgtatgt tcccatagta acgccaatag   720
ggactttcca ttgacgtcaa tgggtggagt atttacggta aactgcccac ttggcagtac   780
atcaagtgta tcatatgcca agtacgcccc ctattgacgt caatgacggt aaatggcccg   840
cctggcatta tgcccagtac atgaccttat gggactttcc tacttggcag tacatctacg   900
tattagtcat cgctattacc atggtgatgc ggttttggca gtacatcaat gggcgtggat   960
agcggtttga ctcacgggga tttccaagtc tccaccccat tgacgtcaat gggagtttgt  1020
tttggcacca aaatcaacgg gactttccaa aatgtcgtaa caactccgcc ccattgacgc  1080
aaatgggcgg taggcgtgta cggtgggagg tctatataag cagagctcgt ttagtgaacc  1140
```

-continued

```
gtcagatcgc ctggagacgc catccacgct gttttgacct ccatagaaga caccgggacc      1200
gatccagcct ccgcggccgg gaacggtgca ttggaacgcg gattcccgt gccaagagtg       1260 acgtaagtac cgcctataga gtctataggc ccaccccctt ggcttcttat gcatgctata     1320
ctgtttttgg cttggggtct atacacccc gcttcctcat gttataggtg atggtatagc     1380
ttagcctata ggtgtgggtt attgaccatt attgaccact cccctattgg tgacgatact    1440
ttccattact aatccataac atggctcttt gcacaactct cttattggc tatatgccaa     1500 tacactgtcc ttcagagact gacacggact ctgtattttt acaggatggg gtctcattta   1560
ttatttacaa attcacatat acaacaccac cgtccccagt gcccgcagtt tttattaaac    1620
ataacgtggg atctccagcg aatctcgggt acgtgttccg gacatggggc tcttctccgg   1680
tagcggcgga gcttctacat ccagccctgc tcccatcctc ccactcatgg tcctcggcag    1740
ctccttgctc ctaacagtgg aggccagact taggcacagc acgatgccca ccaccaccag   1800
tgtgcccaca aggccgtggc ggtagggtat gtgtctgaaa atgagctc                  1848
```

E02198 Accession # Dna encoding 3'end region of beta-actin gene
promoter
                                                      SEQ ID NO: 28
```
cttctggcgt gtgaccggcg gggtttatat cttcccttcc caagcttgg                  49
```

E02197 Accession # DNA encoding 3'end region of beta-actin gene
ptomoter
                                                      SEQ ID NO: 29
```
cttctggcgt gtgaccggcg gggtttatat cttcccttct ctgttcctcc gcagccccaa     60
gcttgg                                                                 66
```

E02196 Accession # DNA encoding 3'end region of beta-actin gene
                                                      SEQ ID NO: 30
```
cttctggcgt gtgaccggcg gggtttatat cttcccttct ctgttcctcc gcagccagcc     60
aagcttgg                                                               68
```

E02195 Accession # DNA encoding 3'end region of beta-actin gene
promoter
                                                      SEQ ID NO: 31
```
cttctggcgt gtgaccggcg gggtttatat cttcccttct ctgttcctcc gcagccagcc     60
atggatgat                                                              69
```

E03011 Accession # DNA encoding hybrid promoter that is composed of
chicken beta-actin gene promoter and rabbit beta-globin gene promoter
                                                      SEQ ID NO: 32
```
tcgaggtgag ccccacgttc tgcttcactc tccccatctc ccccccctcc ccaccccaa      60 ttttgtattt atttattttt taattatttt gtgcagcgat ggggggcggg gggggggggg    120
cgcgcgccag gcggggcggg gcggggcgag gggcggggcg gggcgaggcg gagaggtgcg    180
gcggcagcca atcagagcgg cgcgctccga aagtttcctt ttatggcgag gcggcggcgg    240
cggcggccct ataaaaagcg aagcgcgcgg cgggcgggag tcgctgcgtt gccttcgccc    300
cgtgccccgc tccgcgccgc ctcgcgccgc ccgcccggc tctgactgac cgcgttactc     360
ccacaggtga gcgggcggga cggcccttct cctccgggct gtaattagcg cttggtttaa    420
tgacggctcg tttcttttct gtggctgcgt gaaagcctta aagggctccg ggagggccct   480
ttgtgcgggg gggagcggct cgggggggtgc gtgcgtgtgt gtgtgcgtgg ggagcgccgc   540
gtgcggcccg cgctgcccgg cggctgtgag cgctgcgggc gcggcgcggg gctttgtgcg   600
ctccgcgtgt gcgcgagggg agcgcggccg ggggcggtgc cccgcggtgc gggggggctg   660
cgaggggaac aaaggctgcg tgcgggtgt gtgcgtgggg gggtgagcag ggggtgtggg    720
cgcggcggtc gggctgtaac ccccccctgc accccctcc ccgagttgct gagcacggcc    780
cggcttcggg tgcggggctc cgtgcgggc gtgcgcggg gctcgccgtg ccggcggggg    840
ggtggcggca ggtggggtg ccgggcgggg cggggccgcc tcgggccggg gagggctcgg    900
```

-continued

```
gggaggggcg cggcggcccc ggagcgccgg cggctgtcga ggcgcggcga gccgcagcca      960
ttgccttta tggtaatcgt gcgagagggc gcagggactt cctttgtccc aaatctggcg      1020
gagccgaaat ctgggaggcg ccgccgcacc ccctctagcg ggcgcgggcg aagcggtgcg     1080
gcgccggcag gaaggaaatg ggcggggagg gccttcgtgc gtcgccgcgc cgccgtcccc    1140
ttctccatct ccagcctcgg ggctgccgca gggggacggc tgccttcggg ggggacgggg    1200
cagggcgggg ttcggcttct ggcgtgtgac cggcggctct agagcctctg ctaaccatgt    1260
tcatgccttc ttcttttcc tacagctcct gggcaacgtg ctggttgttg tgctgtctca    1320
tcattttggc aaagaattca agctt                                         1345
```

BD015377 Accession # Baculovirus containing minimum CMV promoter
SEQ ID NO: 33

```
tcaatattgg ccattagcca tattattcat tggttatata gcataaatca atattggcta     60
ttggccattg catacgttgt atctatatca taatatgtac atttatattg gctcatgtcc    120
aatatgaccg ccatgttggc attgattatt gactagttat taatagtaat caattacggg    180
gtcattagtt catagcccat atatggagtt ccgcgttaca aacttacgg taaatggccc    240
gcctggctga ccgcccaacg acccccgccc attgacgtca ataatgacgt atgttcccat    300
agtaacgcca atagggactt tccattgacg tcaatgggtg gagtatttac ggtaaactgc    360
ccacttggca gtacatcaag tgtatcatat gccaagtccg cccctattg acgtcaatga    420
cggtaaatgg cccgcctggc attatgccca gtacatgacc ttacgggact tcctacttg    480
gcagtacatc tacgtattag tcatcgctat taccatggtg atgcggtttt ggcagtacac    540
caatgggcgt ggatagcggt ttgactcacg gggatttcca agtctccacc ccattgacgt    600
caatgggagt ttgttttggc accaaaatca acgggacttt ccaaaatgtc gtaataaccc    660
cgcccccgttg acgcaaatgg gcgg                                         684
```

Mouse GFAP promoter sequence
SEQ ID NO: 34

```
aattccatacctgcttgatccacatatgaactacaggggacatgatgaggtccagtctaaaggtcactg
gcaacctctctcaagatctccctcactatgccattattcaggattggggaagatgtggctggagcctaag
gggctcttcccttccctatggtgggactcattaggagaacctcagcaagcagtccactgtaagctcaaac
aaataccatgtcgctggtatggagtaaggctgttgctatgacaggaactcaggggtcttaactggcttga
gcgctgggaggggcagcagccaggccttgtctgtaagctgaagacctggcagtgctgagctggtcaccc
cccaggacctccttttgtgcccaacgagtgactcaccttgggcatagacataatggtcaggggtgggcac
gcagcctgcttcccgctgtgctccaggcctccttcgatgctttccgagaagtctattgagctgggagctt
tgtactgcacccggggctgacatcctggcatcctgggataaaagcagcccacggggctgcccttgccata
tgcctcactggcggcagagaacaaggctctattcagcaagtgccctggagtagacaccagaagcccaagc
atgggcagaggaaggcaggggttgggggagcagagctgtctgtgttccagaagcccaaggacacagatg
gctaaggcgcctgggagggacctgagtggaagagatagatgggcctgaagtctcaagcagcaacagcctc
ctccccgccattggtgagggtggggtttggtttcccggacctacatatccctcagaggcctggtgtgtag
gaatttaaaggaggtaaatctcctgagagaatcagggtacccaggaagacggggtgttacagaaagact
ccagcatgcacagccaactcactcaaaactactctgtcaggggctgccgggggccaggctcggggtgggg
ggtgggggggcaaagagaagctggaccagggagaaatggcccactaggctggatatgaggccacagaggg
gctcaggaaggaagcctgctgtcttaccctattaggatctgcgtgcataccttctgctgtgcactctaaa
cacacagccagaggctcaagttgaccctggagtcacagagagggctccaaccttagccctccactcctga
actccaggaatgagaagatagagttggagcgattcaggggagaggactctgttgagaatgggggtcacag
```

-continued gaaactgtaatataggttgatcccggaggaagggaataggttcttcaagttcctagcatctcacaggccc cagagaaggacagagtggggtggtcctggcttaacaggctctaagaactggaagctgattacccaccaa gctgtcactctctgtctctgtctctgtgtgtgcgcgctcgtgcacacttatcacacaaatgttc atgtgtgtgcacatagatgagttgacaccagaggtcaacctcaggcactgttgccttggttttctgagag agcatttctctctggacctggaactcgccaattagtgagagccaggaagtctgctgattttcactgccca gcactggagtttacaagtatgcactgtcaacccaggccttttgtattcattctgcagctagaacttgggt gggtcttcatgcttgacaggcaagcaatttatggactaagctgtttcctcggccctctcttgacccattt accagaaaggggttccttgatcaatggcgaacgcaggctggtgtcccaagaaagccttgactctgggta cagtgacctcagtggggtgagaggagttctccccttagctgggctggggcccagctccaccccctcaggc tattcaatgggggtgcttccaggaagtcaggggcagatttagtccaacccgttcctccataaaggccctg acatcccaggagccagcagaggcagggcaggatggagcggagacgcatcacctctgcgcgccgctcctat gcctccgagacggtggtcaggggcctcggtcctagtcgac Rat COL1a1 promoter sequence

SEQ ID NO: 35 tctagaatatagaagccaaggatttcaagggtttccttttctctcttcttcttttttttttcttttctttt ttcctgagatggagtttccttttgtagccctgactgtcctggaattcactctatagaccaggctagcctc acacttagtgatctgcctgcctctgcctcttgggtgcctcaggattcaaggcatgaaccaccactacccg accagggatttcttacacacttctgactggactaaccaggaaagcagagagggagacaggaagaaaatgc tcagaaggaaggagtaggattggaggtgagctgggggaacccagactgagccgtgcagaagacaaggaag aagaaagccacccacacacctaggatccacccacagatttttgctctgggtacccctgtctggagactgta gggctttgtgatggagggtggggtagtcttcatgccccgtgccctttactccagacctaaatgcccaccc ccacatacagctgctcgctctctctcccctgcccttctcccaagagaccagttctccatccctggtct gcagccaaggctgggggcagaagaactttctggaggatttgagtgagaaaagcaagagagcctcaagtag ggactggaacctctgggaagggagtgcagaggagacccgggtatgtgccctacctggtacatttatacct gggcagcctctgctcctgttccagacttcagagcccagacgggtcctctccctccctcatgagggaaac atttggggaaatttggagagagacagaactcagagctcagcacttttcctcttctgttttttcttcttgag gaattttttccccaactgctgatgactttaccattcttgggggtgggggggtggagattctggcttttg ctcccccctacactccaagtgccggacaaagccctacattccacaagaagccagggcttcagagtttccta aagatgaggtggcgtggcgagtctcctccctctcccagctccaactcccctcccccagtctccagccct agcctggccagggaggccccgccaggctgggaggagaccccaagcacattcttcctctcgctgtcatgct gcagaaattaaagacacatctctgagctgggtacccgccaatcgtttcaagttgagaagtggcagaggag gtcccgagcttcagctcatgccacgtgtaaaggaagcttggaacccactgcccacaactcctggggcaaa aacctggagtcagacatggggtgaaggctgtcacacggcacagacacgtcaagcaccccccccaattcta gtagtctcctagcctccaccagaaccccagacccttgatgtggcagtcaccagtccacacctgttaggct cttgtctcttcttccagatgagcctgggggcgtgggggtgctagatcaggagcagggaaaagtagcttt ggataagtgcttttcccaatacaaaacccaacaaagagtgggcagatcacactgtgtagtgcttcgtgga accctaccctagacaactgccttgaacacctattccctctgatgtacaccatccccgtccactgttaggg agtgggcatcctttggaactgaccactgtggaaggcaggactttactgagttccggaactaccatctcag cttctcagcccagcctaccctacaggcactggcataggcgggggcagatcctgggccacaagtcactg ccacatggtttgggataattgatgaagtcctgtccttccattgctgtctccagttctgcttctctggaaac tctatattttccctttaattatagcctctgcagtctccctctgccaccccacccgcaccgcttagccta actgcccacggccagcgacgtggctccctcccccttctgctcccttggtctttttatttttttttcttttg

```
ccttcgttgcacaaaactagctcagggagggcgtgaaggggggggagcaatggaatcttggatggtttg gaggaggcgggactccttgcttccacgtttacagctctgaagacggctgtggggaagtgatacaggacg tctatgggccctgagaggagaccccttatgcttccctgccacccacacagtttaacaaaatgaagttccta agtagagtggggtcaggcagagcacctttgcaggttgatgggagcccagggaaagaaaggacactgtc ttttagggacacatttaaatataagccacttttcttggggacgacaaatgaccctttcctgattgcaga ggtggggaacaatggctgagattttcagcaaagaagcgaggacatgaggagtagccttcaaataaagtca ctcagctaccaaaaacaagtttctgccacacaccgagttacctaggtgtccccagaccagatccaagtac agtaaggaaagcaggttctctacagagagaacacggctctatggccaatgccttctacctgctctttctg gattgatactgctacctaagagggcctctaaccaattcctggctgtagccacagctgacacaagacctt ttctaagacatccctggtcacaggcctcctgtagcaaattccagccctgggatggaggtggtcaggaaag agtttatacaagaagacccaggccacagctttaaggactcagaaaccccctgcccacacggctgcccat cataacgcagaaggtttcttctggaaggacaaggatgtcaaacttctccccaagcctaatcctcagagat gtctccctctgttacacctggggctggagaaaggtgggtctttcatggagccacattcatggcagaacag atagccacccactcctttcaaacaaccacatatctgactcttagtatctgtgaagagatgtctaatttg ttcccaaatattcctaccctgcatacctgggcccacaccatgaggtattcctcccctctaacagtcaca tctgcttagctgcctggttcttcggatttggagagatgcttgcctaacttattcttccttaggtcttccc aaggatgccagaaagactatgagacatggccaagaggaccttttcccaattgtgcctgacactgaaccct ttgtaatgttccccaactcagattcccaattctacatccttctgatttgaggtcccagaaggaaagtgca aggggcatccctacccacaatcagtatatcgaggcccagccacactcagtgatagcacctctggcccat gtagatctgggggacaaggtggcagaattgcaaaggggggaggggctgggtggactccttttcccttcc tttccctcctccccctcttcgttccaaattgggggccgggccaggcagttctgattggctgggggccgg gctgctggctcccctctccaagaggcagggttcctcccagccctcctccatcaggatggtataaaaggg gcccaggccagtcgtcggagcagacgggagtttcacctccggacggagcaggaggcacacggagtgaggc cacgcatgagccgaagctaaccccccaccccagccgcaaagagtctacatgtctagggtctag
```

Rat COL2a1 promoter sequence

SEQ ID NO: 36

```
tggtggtggtggacaactaggaaactctggcgctttctcctcccctcacaaaactgagtccagctggagc cgcctccagactctctggccagggcctcagagtggtcaacagtccctggccagcgttgctctctccaggc taagggcacccactcccctggagattcctgaacctgggccaggaagagccgaattagacaagtgtctcca atccggctgcgtgcggattttgttgcggtgtccctcggttgtctgcagttcctttagtcccttccctggc ctgccccttacacctccacacaggtccccctctgtgtaggaatacaccagaccctctcttagccacacac acctccagtcccccgtctacctagatttttttcatagctagttggatgggggatgggttagggaggctgg gtttgcgagcctccaggtgggagttcaccgacaggtactccgcaaaggagctggaaggcaggtctggaaa actgtccccagatttaggattctgggcagcttccatcagcttatactttggctccccgcccctaaact ccccatccccacctcctttctcccgttacttcgtcctccctcgcctttccagcctcgagtctaaagctcc atgcttatgcctctgcaaacaaccccctcccttctaaccccagcagaactccgaggaaaggggccggagg ccctcttctcgcctgtggttagagggggcagtgtggcagtcccaagtggggcgaccggaggccgtctcg gtgccccgcccgatcaggccactgggcacatcggggcgggaagcgggctcaccaaaggggcgactggcc ttggcaggtgtgggctctggtccgacctgggcaggctccggggcgggtctcaggttacaacgccacgg ggggctgggggcggcccgcggtttggttggtttgccagccttggagcgaccgggagcatataaccggag cctctgctgggagaagcgcagggcgccgctgggctgccgggtctcctgcctcctcctcctgctccgagag
```

-continued

```
cctcctgcatgagggcgaggtagagacccggaccgctccggtctctgccgcctcgccgagcttcgcccg ggccaaggctctgcgggcctcgcggtgagccatgattcgcctcggggctccccagtcgctggtgctgctg acgctgctcatcgccacggtcctacaatgtcagggccaggatgcccgtaggtcgcccaccacccctgcct gcttccctgacttgcgaccccttctcttcttccctccgtccgagttaggcgccaagtcctaggcgcgtagt gcacaggagaacactgatcctaatcctaattctgctagtgaggagttctgtcgcagcatcctcagtcaga gtcg
```

FIV(LacZ) construct 12750 bp

SEQ ID NO: 37

```
atgcggtttt ggcagtacat caatgggcgt ggatagcggt ttgactcacg gggatttcca      60
agtctccacc ccattgacgt caatgggagt ttgttttggc accaaaatca acgggacttt     120
ccaaaatgtc gtaacaactc cgccccattg acgcaaatgg gcggtaggcg tgtacggtgg     180
gaggtctata taagcagagc tctgtgaaac ttcgaggagt ctctttgttg aggacttttg     240
agttctccct tgaggctccc acagatacaa taaatatttg agattgaacc ctgtcgagta     300
tctgtgtaat cttttttacc tgtgaggtct cggaatccgg gccgagaact tcgcagttgg     360
cgcccgaaca gggacttgat tgagagtgat tgaggaagtg aagctagagc aatagaaagc     420
tgttaagcag aactcctgct gacctaaata gggaagcagt agcagacgct gctaacagtg     480
agtatctcta gtgaagcgga ctcgagctca taatcaagtc attgtttaaa ggcccagata     540
aattacatct ggtgactctt cgcggacctt caagccagga gattcgccga gggacagtca     600
acaaggtagg agagattcta cagcaacatg gggaatggac aggggcgaga ttggaaaatg     660
gccattaaga gatgtagtaa tgttgctgta ggagtagggg ggaagagtaa aaaatttgga     720
gaagggaatt tcagatgggc cattagaatg gctaatgtat ctacaggacg agaacctggt     780
gatataccag agactttaga tcaactaagg ttggttattt gcgatttaca agaaagaaga     840
gaaaaatttg gatctagcaa agaaattgat atggcaattg tgacattaaa agtctttgcg     900
gtagcaggac ttttaaatat gacgggtgtc tactgctgct gcagctgaaa atatgtattc     960
tcaaatggga ttagacacta ggccatctat gaaagaagca ggtggaaaag aggaaggccc    1020
tccacaggca tatcctattc aaacagtaaa tggagtacca caatatgtag cacttgaccc    1080
aaaaatggtg tccatttta tggaaaaggc aagagaagga ctaggaggtg aggaagttca    1140
actatggttt actgccttct ctgcaaattt aacacctact gacatggcca cattaataat    1200
ggccgcacca gggtgcgctg cagataaaga aatattggat gaaagcttaa agcaactgac    1260
agcagaatat gatcgcacac atccccctga tgctcccaga ccattaccct attttactgc    1320
agcagaaatt atgggtatag gattaactca agaacaacaa gcagaagcaa gatttgcacc    1380
agctaggatg cagtgtagag catggtatct cgaggcatta ggaaaattgg ctgccataaa    1440
agctaagtct cctcgagctg tgcagttaag acaaggagct aaggaagatt attcatcctt    1500
tatagacaga ttgtttgccc aaatagatca agaacaaaat acagctgaag ttaagttata    1560
tttaaaacag tcattgagca tagctaatgc taatgcagac tgtaaaaagg caatgagcca    1620
ccttaagcca gaaagtaccc tagaagaaaa gttgagagct tgtcaagaaa taggctcacc    1680
aggatataaa atgcaactct tggcagaagc tcttacaaaa gttcaagtag tgcaatcaaa    1740
aggatcagga ccagtgtgtt ttaattgtaa aaaaccagga catctagcaa gacaatgtag    1800
agaagtgaaa aatgtaata aatgtggaaa acctggtcat gtagctgcca atgttggca     1860 aggaaataga aagaattgta caagggaaga aagggataca acaattacaa agtgggaag    1920 attgggtagg atggatagga atattccac aatatttaaa gggactattg ggaggtatct    1980
tgggaatagg attaggagtg ttattattga ttttatgttt acctacattg gttgattgta    2040
```

-continued

```
taagaaattg tatccacaag atactaggat acacagtaat tgcaatgcct gaagtagaag    2100
gagaagaaat acaaccacaa atggaattga ggagaaatgg taggcaatgt ggcatgtctg    2160
aaaaagagga ggaatgatga agtatctcag acttatttta aagggagat actgtgctga     2220 gttcttccct ttgaggaagg tatgtcatat gaatccattt cgaatcaaat caaactaata    2280
aagtatgtat tgtaaggtaa aaggaaaaga caaagaagaa gaagaaagaa gaaagccttc    2340
agtacattta tattggctca tgtccaatat daccgccatg ttgacattga ttattgacta    2400
gttattaata gtaatcaatt acggggtcat tagttcatag cccatatatg gagttccgcg    2460
ttacataact tacggtaatt ggcccgcctg ctgaccgccc aacgaccccc gcccattgac    2520
gtcaataatg acgtatgttc ccatagtaac gccaataggg actttccatt gacgtcaatg    2580
ggtggagtat ttacggtaaa ctgcccactt ggcagtacat caagtgtatc atatgccaag    2640
tccgcccccc tattgacgtc aatgacggta aatggcccgc ctggcattat gcccagtaca    2700
tgaccttacg ggactttggt acttggcagt acatctacgt attagtcatc gctattacca    2760
tggtgatgcg gttttggcag tacaccaatg ggcgtggata gcggtttgac tcacggggat    2820
ttccaagtct ccaccccatt gacgtcaatg ggagtttgtt ttggcaccaa aatcaacggg    2880
actttccaaa atgtcgtaat aaccccgccc cgttgacgca aatgggcggt aggcgtgtac    2940
ggtgggaggt ctatataagc agagctcgtt tagtgaaccg tcagatcgcc tggagacgcc    3000
atccacgctg ttttgacctc catagaagac accgggaccg atccagcctc cgcggccggg    3060
aacggtgcat tggaacgcgg attccccgtg ccaagagtga cgtaagtacc gcctatagac    3120
tctataggca cacccctttg gctcttatgc atgctatact gttttttggct tggggcctat    3180 acaccccgc tccttatgct ataggtgatg gtatagctta gcctataggt gtgggttatt    3240
gaccattatt gaccactccc ctattggtga cgatactttc cattactaat ccataacatg    3300
gctctttgcc acaactatct ctattggcta tatgccaata ctctgtcctt cagagactga    3360
cacggactct gtattttac aggatggggt cccattatt atttacaaat tcacatatac    3420
aacaacgccg tcccccgtgc ccgcagtttt tattaaacat agcgtgggat ctccacgcga    3480
atctcgggta cgtgttccgg acatgggctc ttctccggta gcggcggagc ttccacatcc    3540
gagccctggt cccatgcctc cagcggctca tggtcgctcg gcagctcctt gctcctaaca    3600
gtggaggcca gacttaggca cagcacaatg cccaccacca ccagtgtgcc gcacaaggcc    3660
gtggcggtag ggtatgtgtc tgaaaatgag ctcggagatt gggctcgcac cgtgacgcag    3720
atggaagact taaggcagcg gcagaagaag atgcaggcag ctgagttgtt gtattctgat    3780
aagagtcaga ggtaactccc gttgcggttc tgttaacggt ggagggcagt gtagtctgag    3840
cagtactcgt tgctgccgcg cgcgccacca gacataatag ctgacagact aacagactgt    3900
tcctttccat gggtcttttc tgcagtcacc gtcgtcgaag cttatgacca tgattacgga    3960
ttcactggcc gtcgttttac aacgtcgtga ctggaaaaac cctggcgtta cccaacttaa    4020
tcgccttgca gcacatcccc ctttcgccag ctggcgtaat agcgaagagg cccgcaccga    4080
tcgcccttcc caacagttgc gcagcctgaa tggcgaatgg cgctttgcct ggtttccggc    4140
accagaagcg gtgccggaaa gctggctgga gtgcgatctt cctgaggccg atactgtcgt    4200 cgtccctca aactggcaga tgcacggtta cgatgcgccc atctacacca acgtaaccta    4260
tcccattacg gtcaatccgc cgtttgttcc cacggagaat ccgacgggtt gttactcgct    4320
cacatttaat gttgatgaaa gctggctaca ggaaggccag acgcgaatta ttttgatgg     4380 cgttaactcg gcgtttcatc tgtggtgcaa cgggcgctgg gtcggttacg acaggacag     4440
```

```
-continued
tcgtttgccg tctgaatttg acctgagcgc atttttacgc gccggagaaa accgcctcgc    4500
ggtgatggtg ctgcgttgga gtgacggcag ttatctggaa gatcaggata tgtggcggat    4560
gagcggcatt ttccgtgacg tctcgttgct gcataaaccg actacacaaa tcagcgattt    4620
ccatgttgcc actcgcttta atgatgattt cagccgcgct gtactggagg ctgaagttca    4680
gatgtgcggc gagttgcgtg actacctacg ggtaacagtt tctttatggc agggtgaaac    4740
gcaggtcgcc agcggcaccg cgcctttcgg cggtgaaatt atcgatgagc gtggtggtta    4800
tgccgatcgc gtcacactac gtctgaacgt cgaaaacccg aaactgtgga cgccgaaat     4860 cccgaatctc tatcgtgcgg tggttgaact gcacaccgcc gacggcacgc tgattgaagc    4920
agaagcctgc gatgtcggtt ccgcgaggL gcggattgaa aatggtctgc tgctgctgaa     4980
cggcaagccg ttgctgattc gaggcgttaa ccgtcacgag catcatcctc tgcatggtca    5040
ggtcatggat gagcagacga tggtgcagga tatcctgctg atgaagcaga acaactttaa    5100
cgccgtgcgc tgttcgcatt atccgaacca tccgctgtgg tacacgctgt gcgaccgcta    5160
cggcctgtat gtggtggatg aagccaatat tgaaacccac ggcatggtgc caatgaatcg    5220
tctgaccgat gatccgcgct ggctaccggc gatgagcgaa cgcgtaacgc gaatggtgca    5280
gcgcgatcgt aatcacccga gtgtgatcat ctggtcgctg gggaatgaat caggccacgg    5340
cgctaatcac gacgcgctgt atcgctggat caaatctgtc gatccttccc gcccggtgca    5400
gtatgaaggc ggcggagccg acaccacggc caccgatatt atttgcccga gtacgcgcg     5460 cgtggatgaa gaccagccct tcccggctgt gccgaaatgg tccatcaaaa aatggctttc    5520
gctacctgga gagacgcgcc cgctgatcct ttgcgaatac gcccacgcga tgggtaacag    5580
tcttggcggt ttcgctaaat actggcaggc gtttcgtcag tatccccgtt tacagggcgg    5640
cttcgtctgg gactgggtgg atcagtcgct gattaaatat gatgaaaacg gcaacccgtg    5700
gtcggcttac ggcggtgatt ttggcgatac gccgaacgat cgccagttct gtatgaacgg    5760 tctggtctttt gccgaccgca cgccgcatcc agcgctgacg gaagcaaaac accagcagca    5820 gttttttccag ttccgtttat ccgggcaaac catcgaagtg accagcgaat acctgttccg    5880
tcatagcgat aacgagctcc tgcactggat ggtggcgctg gatggtaagc cgctggcaag    5940
cggtgaagtg cctctggatg tcgctccaca aggtaaacag ttgattgaac tgcctgaact    6000
accgcagccg gagagcgcc ggcaactctg gctcacagta cgcgtagtgc aaccgaacgc     6060
gaccgcatgg tcagaagccg ggcacatcag cgcctggcag cagtggcgtc tggcggaaaa    6120
cctcagtgtg acgctccccg ccgcgtccca cgccatcccg catctgacca ccagcgaaat    6180 ggattttttgc atcgagctgg gtaataagcg.ttggcaatttt aaccgccagt caggctttct    6240
ttcacagatg tggattggcg ataaaaaaca actgctgacg ccgctgcgcg atcagttcac    6300
ccgtgcaccg ctggataacg acattggcgt aagLgaagcg acccgcattg accctaacgc    6360
ctgggtcgaa cgctggaagg cggcgggcca ttaccaggcc gaagcagcgt tgttgcagtg    6420
cacggcagat acacttgctg atgcggtgct gattacgacc gctcacgcgt ggcagcatca    6480
ggggaaaacc ttatttatca gccggaaaac ctaccggatt gatggtagtg gtcaaatggc    6540
gattaccgtt gatgttgaag tggcgagcga tacaccgcat ccggcgcgga ttggcctgaa    6600
ctgccagctg gcgcaggtag cagagcgggt aaactggctc ggattagggc gcaagaaaa     6660 ctatcccgac cgccttactg ccgcctgttt tgaccgctgg gatctgccat tgtcagacat    6720
gtataccccg tacgtcttcc cgagcgaaaa cggtctgcgc tgcgggacgc gcgaattgaa    6780
ttatggccca caccagtggc gcggcgactt ccagttcaac atcagccgct acagtcaaca    6840
gcaactgatg gaaaccagcc atcgccatct gctgcacgcg gaagaaggca catggctgaa    6900
```

-continued

```
tatcgacggt ttccatatgg ggattggtgg cgacgactcc tggagcccgt cagtatcggc    6960
ggaattccag ctgagcgccg gtcgctacca ttaccagttg gtctggtgtc aaaaataact    7020
cgatcgacca gagctgagat cctacaggag tccagggctg gagagaaaac ctctgaagag    7080
gatgatgaca gagttagaag atcgcttcag gaagctattt ggcacgactt ctacaacggg    7140
agacagcaca gtagattctg aagatgaacc tcctaaaaaa gaaaaaaggg tggactggga    7200
tgagtattgg aaccctgaag aaatagaaag aatgcttatg gactagggac tgtttacgaa    7260
caaatgataa aaggaaatag ctgagcatga ctcatagtta aagcgctagc agctgcctaa    7320
ccgcaaaacc acatcctatg gaaagcttgc taatgacgta taagttgttc cattgtaaga    7380
gtatataacc agtgctttgt gaaacttcga ggagtctctt tgttgaggac ttttgagttc    7440
tcccttgagg ctcccacaga tacaataaat atttgagatt gaaccctgtc gagtatctgt    7500
gtaatctttt ttacctgtga ggtctcggaa tccgggccga gaacttcgca gcggccgctc    7560
gagcatgcat ctagagggcc ctattctata gtgtcaccta aatgctagag ctcgctgatc    7620
agcctcgact gtgccttcta gttgccagcc atctgttgtt tgcccctccc ccgtgccttc    7680
cttgaccctg gaaggtgcca ctcccactgt ccttttcctaa taaaatgagg aaattgcatc    7740
gcattgtctg agtaggtgtc attctattct ggggggtggg gtggggcagg acagcaaggg    7800
ggaggattgg gaagacaata gcaggcatgc tggggatgcg gtgggctcta tggcttctga    7860
ggcggaaaga accagctggg gctcgagggg ggatccccac gcgccctgta gcggcgcatt    7920
aagcgcggcg ggtgtggtgg ttacgcgcag cgtgaccgct acacttgcca gcgccctagc    7980
gcccgctcct ttcgctttct tcccttcctt tctcgccacg ttcgccggct ttccccgtca    8040
agctctaaat cggggcatcc ctttagggtt ccgatttagt gctttacggc acctcgaccc    8100
caaaaaactt gattagggtg atggttcacg tagtgggcca tcgccctgat agacggtttt    8160
tcgccctttg acgttggagt ccacgttctt taatagtgga ctcttgttcc aaactggaac    8220
aacactcaac cctatctcgg tctattcttt tgatttataa gggattttgg ggatttcggc    8280
ctattggtta aaaaatgagc tgatttaaca aaaatttaac gcgaatttta acaaaatatt    8340
aacgtttaca atttaaatat ttgcttatac aatcttcctg ttttggggc ttttctgatt    8400
atcaaccggg gtgggtaccg agctcgaatt ctgtggaatg tgtgtcagtt agggtgtgga    8460
aagtccccag gctccccagg caggcagaag tatgcaaagc atgcatctca attagtcagc    8520
aaccaggtgt ggaaagtccc caggctcccc agcaggcaga agtatgcaaa gcatgcatct    8580
caattagtca gcaaccatag tcccgcccct aactccgccc atcccgcccc taactccgcc    8640
cagttccgcc cattctccgc cccatggctg actaattttt tttatttatg cagaggccga    8700
ggccgcctcg gcctctgagc tattccagaa gtagtgagga ggcttttttg gaggcctagg    8760
cttttgcaaa aagctcccgg gagcttggat atccattttc ggatctgatc aagagacagg    8820
atgaggatcg tttcgcatga ttgaacaaga tggattgcac gcaggttctc cggccgcttg    8880
ggtggagagg ctattcggct atgactgggc acaacagaca atcggctgct ctgatgccgc    8940
cgtgttccgg ctgtcagcgc aggggcgccc ggttcttttt gtcaagaccg acctgtccgg    9000
tgccctgaat gaactgcagg acgaggcagc gcggctatcg tggctggcca cgacgggcgt    9060
tccttgcgca gctgtgctcg acgttgtcac tgaagcggga agggactggc tgctattggg    9120
cgaagtgccg gggcaggatc tcctgtcatc tcaccttgct cctgccgaga agtatccat    9180
catggctgat gcaatgcggc ggctgcatac gcttgatccg gctacctgcc cattcgacca    9240
ccaagcgaaa catcgcatcg agcgagcacg tactcggatg gaagccggtc ttgtcgatca    9300
```

-continued

```
ggatgatctg gacgaagagc atcagggggct cgcgccagcc gaactgttcg ccaggctcaa   9360
ggcgcgcatg cccgacggcg aggatctcgt cgtgacccat ggcgatgcct gcttgccgaa   9420
tatcatggtg gaaaatggcc gctttttctgg attcatcgac tgtggccggc tgggtgtggc   9480
ggaccgctat caggacatag cgttggctac ccgtgatatt gctgaagagc ttggcggcga   9540
atgggctgac cgcttcctcg tgctttacgg tatcgccgct cccgattcgc agcgcatcgc   9600
cttctatcgc cttcttgacg agttcttctg agcgggactc tggggttcga aatgaccgac   9660
caagcgacgc ccaacctgcc atcacgagat ttcgattcca ccgccgcctt ctatgaaagg   9720
ttgggcttcg gaatcgtttt ccgggacgcc ggctggatga tcctccagcg cggggatctc   9780
atgctggagt tcttcgccca ccccaacttg tttattgcag cttataatgg ttacaaataa   9840
agcaatagca tcacaaattt cacaaataaa gcattttttt cactgcattc tagttgtggt   9900
ttgtccaaac tcatcaatgt atcttatcat gtctggatcc cgtcgacctc gagagcttgg  9960
cgtaatcatg gtcatagctg tttcctgtgt gaaattgtta tccgctcaca attccacaca  10020
acatacgagc cggaagcata aagtgtaaag cctggggtgc ctaatgagtg agctaactca  10080
cattaattgc gttgcgctca ctgcccgctt tccagtcggg aaacctgtcg tgccagctgc  10140
attaatgaat cggccaacgc gcggggagag cggtttgcg tattgggcgc tcttccgctt  10200
cctcgctcac tgactcgctg cgctcggtcg ttcggctgcg gcgagcggta tcagctcact  10260
caaaggcggt aatacggtta ccacagaat caggggataa cgcaggaaag aacatgtgag  10320
caaaaggcca gcaaaaggcc aggaaccgta aaaaggccgc gttgctggcg tttttccata  10380
ggctccgccc ccctgacgag catcacaaaa atcgacgctc aagtcagagg tggcgaaacc  10440
cgacaggact ataaagatac caggcgtttc ccctggaagc tccctcgtg cgctctcctg  10500
ttccgaccct gccgcttacc ggatacctgt ccgcctttct cccttcggga agcgtggcgc  10560
tttctcaatg ctcacgctgt aggtatctca gttcggtgta ggtcgttcgc tccaagctgg  10620
gctgtgtgca cgaaccccc gttcagcccg accgctgcgc cttatccggt aactatcgtc  10680
ttgagtccaa cccggtaaga cacgacttat cgccactggc agcagccact ggtaacagga  10740
ttagcagagc gaggtatgta ggcggtgcta cagagttctt gaagtggtgg cctaactacg  10800
gctacactag aaggacagta tttggtatct gcgctctgct gaagccagtt accttcggaa  10860
aaagagttgg tagctcttga tccggcaaac aaaccaccgc tggtagcggt ggtttttttg  10920
tttgcaagca gcagattacg cgcagaaaaa aaggatctca agaagatcct ttgatctttt  10980
ctacggggtc tgacgctcag tggaacgaaa actcacgtta agggattttg gtcatgagat  11040
tatcaaaaag gatcttcacc tagatccttt taaattaaaa atgaagtttt aaatcaatct  11100
aaagtatata tgagtaaact tggtctgaca gttaccaatg cttaatcagt gaggcaccta  11160
tctcagcgat ctgtctattt cgttcatcca tagttgcctg actccccgtc gtgtagataa  11220
ctacgatacg ggagggctta ccatctggcc ccagtgctgc aatgataccg cgagacccac  11280
gctcaccggc tccagattta tcagcaataa accagccagc cggaagggcc gagcgcagaa  11340
gtggtcctgc aactttatcc gcctccatcc agtctattaa ttgttgccgg gaagctagag  11400
taagtagttc gccagttaat agtttgcgca acgttgttgc cattgctaca ggcatcgtgg  11460
tgtcacgctc gtcgtttggt atggcttcat tcagctccgg ttcccaacga tcaaggcgag  11520
ttacatgatc ccccatgttg tgcaaaaaag cggttagctc cttcggtcct ccgatcgttg  11580
tcagaagtaa gttggccgca gtgttatcac tcatggttat ggcagcactg cataattctc  11640
ttactgtcat gccatccgta agatgctttt ctgtgactgg tgagtactca accaagtcat  11700
tctgagaata gtgtatgcgg cgaccgagtt gctcttgccc ggcgtcaata cgggataata  11760
```

-continued

```
ccgcgccaca tagcagaact ttaaaagtgc tcatcattgg aaaacgttct tcggggcgaa    11820
aactctcaag gatcttaccg ctgttgagat ccagttcgat gtaacccact cgtgcaccca    11880
actgatcttc agcatctttt actttcacca gcgtttctgg gtgagcaaaa acaggaaggc    11940
aaaatgccgc aaaaaaggga ataagggcga cacggaaatg ttgaatactc atactcttcc    12000
tttttcaata ttattgaagc atttatcagg gttattgtct catgagcgga tacatatttg    12060
aatgtattta gaaaaataaa caaatagggg ttccgcgcac atttccccga aaagtgccac    12120
ctgacgtcga cggatcggga gatctcccga tcccctatgg tcgactctca gtacaatctg    12180
ctctgatgcc gcatagttaa gccagtatct gctccctgct tgtgtgttgg aggtcgctga    12240
gtagtgcgcg agcaaaattt aagctacaac aaggcaagga ttgaccgaca attgcatgaa    12300
gaatctgctt agggttaggc gttttgcgct gcttcgcgat gtacgggcca gatatacgcg    12360
ttgacattga ttattgacta gttattaata gtaatcaatt acggggtcat tagttcatag    12420
cccatatatg gagttccgcg ttacataact tacggtaaat ggcccgcctg gctgaccgcc    12480
caacgacccc cgcccattga cgtcaataat gacgtatgtt cccatagtaa cgccaatagg    12540
gactttccat tgacgtcaat gggtggacta tttacggtaa actgcccact tggcagtaca    12600
tcaagtgtat catatgccaa gtacgccccc tattgacgtc aatgacggta aatggcccgc    12660
ctggcattat gcccagtaca tgaccttatg ggactttcct acttggcagt acatctacgt    12720
attagtcatc gctattacca tggtg                                          12745
```

IL-1ra (IL-1RN)
SEQ ID NO: 38

MEICRGLRSHLITLLLFLFHSETICRPSGRKSSKMQAFRIWDVNQKTFYLRLNNQLVAGYLQGPNVNLEE

KIDVVPTEPHALFLGIHGGKMCLSCVKSGDETRLQLEAVMTDLSENRKQDKRFAHRSDSGPTTSFESAAC

PGWFLCTAMEADQPVSLTMAPDEGVMVTKFYFQEDE

IL-1R1
SEQ ID NO: 39

MKVLLRLICFIALLISSLEADKCKIEREEKIILVSSANEIDVRPCPLNPNLHKGTITWYKDDSKTPVSTE

QASRHQHKFVPAKVEDSGHYYCVVRNSSYCLRIKISAKFVENIEPNLCYNAQAIFKQKLPVAGDGGLVCP

YMEFFKNENNELPKLQWYKDCKPLLLDNIHFSGVKDRLIVMNVAEKIHRGNYTCHASYTYLGKQYPITRV

EFITLEENKPTRPVTVSPANETMEVDLGSQIQLICNVTGQLSDIAYWKWNGSVDEDDPVLGEDYYSVENP

AINKRRSTLITVLMSETESRFYKHPFTCFAKNTHGDAAYIQLWPVTNFQKHMIGICVTLTVIIVCSVFIY

KIFKIDIVLWYRDSCYDFLPTKASDGKTYDAYILYPKTVGEGSTSDCDIIFVFKVLPEVLEKQCGYKLFI

YGRDDYVGEDIVEVTNLNVRKSRRLIIILVRETSGFSWLGGSSEEQIAMYNALVQDGIKVVLLELEKIQD

YEKMPESIKHKQKIIGARWSGDFTQGPQSAKTRFWKNVRYHMPVQRRSPSSKIIQLLSPATKEKLQREAI

IVPLG

IL-1R2
SEQ ID NO: 40

MLRLYVLVMGVSAETLQPAAHTGAARSCRFRGRHYKREFRLEGEPVALRCPQVPYWLWASVSPRINLTWH

KNDSARTVPGEEETRMWAQDGALWLLPALQEDSGTYVCTTRNASYCDKMSIELRVFENTDAFLPFISYPQ

ILTLSTSGVLVCPDLSEFTRDKTDVKIQWYKDSLLLDKDNEKFLSVRGTTHLLVHDVALEDAGYYRCVLT

FAHEGQQYNITRSTELRIKKKKEETIPVIISPLKTISASLGSRLTIPCKVFLGTGTPLTTMLWWTADNTH

IESAYPGGRVTEGPRQEYSENNENYIEVPLTFDPVTRIEDLHMDFKCVVHNTLSFQTLRTTVKEASSTFS

WGIVLAPLSLAFLVLGGIWMHRLRCKHRTGKADGLTVLWPHHQDFQSYPK cPGES_1 siRNA
SEQ ID NO: 41

GGAAGCGAUAAUUUUAAGCtt

-continued

| | |
|---|---|
| cPGES_2 siRNA<br>GGAGAAUCCGGCCAGUCAUtt | SEQ ID NO: 42 |
| cPGES_3 siRNA<br>GGGUUGAUUAUGUACCAUUtt | SEQ ID NO: 43 |
| cPGES_4 siRNA<br>GGCUUCACUAAGGGUUGAUtt | SEQ ID NO: 44 |
| cPGES_5 siRNA<br>GGCAGUAUCCUUAUGCAUGtt | SEQ ID NO: 45 |
| cPGES_6 siRNA<br>GCUUUUACAUCUCUUAGCAtt | SEQ ID NO: 46 |
| COX-1_1 siRNA<br>GGGAAGAAACAGUUACCAGtt | SEQ ID NO: 47 |
| COX-1_2 siRNA<br>GGGCACCAACAUCCUGUUUtt | SEQ ID NO: 48 |
| COX-1_3 siRNA<br>GGAUGGGAAACUUAAGUACtt | SEQ ID NO: 49 |
| COX-1_4 siRNA<br>CCUACAACUCAGCGCAUGAtt | SEQ ID NO: 50 |
| COX-1_5 siRNA<br>GCGCAUGACUACAUCAGCUtt | SEQ ID NO: 51 |
| COX-1_6 siRNA<br>GCUACGAGCAGUUUUUAUUtt | SEQ ID NO: 52 |
| COX-2_1 siRNA<br>GGAUUUGACCAGUAUAAGUtt | SEQ ID NO: 53 |
| COX-2_2 siRNA<br>GGGAGUCUGGAACAUUGUGtt | SEQ ID NO: 54 |
| COX-2_3 siRNA<br>GGUUUUUAGUAUCAGAACUtt | SEQ ID NO: 55 |
| COX-2_4 siRNA<br>GCACAGGAUUUGACCAGUAtt | SEQ ID NO: 56 |
| COX-2_5 siRNA<br>GGGAAAUAAGGAGCUUCCUtt | SEQ ID NO: 57 |
| COX-2_6 siRNA<br>CCCUACAGUACUAAUCAAAtt | SEQ ID NO: 58 |
| mPGES-1 siRNA<br>GGCUUUUGCCAACCCCGAGtt | SEQ ID NO: 59 |
| cPGES_3 shRNA sense<br>GATCCGGggttgattatgtaccattTTCAAGAGAaatggtacataatcaacccTTTTTG | SEQ ID NO: 60 |
| cPGES_3 shRNA antisense<br>GCCCcaactaatacatggtaaAAGTTCTCTttaccatgtattagttgggaAAAACTTAA | SEQ ID NO: 61 |
| mPGES-1shRNA sense | |

```
                                                             SEQ ID NO: 62
GATCCGggcttttgccaaccccgagTTCAAGAGActcggggttggcaaaagccTTTTTG mPGES-1 shRNA antisense
                                                             SEQ ID NO: 63
GCccgaaaacggttggggctcAAGTTCTCTgagcccaaccgttttcggAAAAACTTAA COX-1_3 shRNA sense
                                                             SEQ ID NO: 64
GATCCGggatgggaaacttaagtacTTCAAGAGAgtacttaagtttcccatccTTTTTG COX-1_3 shRNA antisense
                                                             SEQ ID NO: 65
GATCCGggatgggaaacttaagtacTTCAAGAGAgtacttaagtttcccatccTTTTTG COX-2_1 shRNA sense
                                                             SEQ ID NO: 66
GATCCGggatttgaccagtataagtTTCAAGAGAacttatactggtcaaatccTTTTTG COX-2_1 shRNA antisense
                                                             SEQ ID NO: 67
GCcctaaactggtcatattcaAAGTTCTCTtgaatatgaccagtttaggAAAAACTTAA Secretion Signal sequence of human IL-1ra
                                                             SEQ ID NO: 68
MEICRGLRSHLITLLLFLFHSETIC Human CD11b (Mac-1) gene, 5'flank (Accession No. M82856)
                                                             SEQ ID NO: 69
   1 ggttcaagtg attctgctgc ctcagcctcc caggcgggat tacaggtgcc tgccaccacg
  61 cctggctaat ttttttgtct ttttagtaaa gatgaggttt caccatgttg ggcaggctgg
 121 tttcaattgc tgacctcaag tgagccaccc cgcctcagcc tccaaaatgc taggattaca
 181 ggcatgagcc accgcaccca gccaagtttg tacatatatt tttgactaca cttcttaact
 241 attcttagga taaattacta gaagtgaaaa ttcttgggtg aagagcttga ggcctttaca
 301 cacacacaca cacacacaca cacacacaca caaataggct ggatcgagtg gctcacacct
 361 gtaatctcag cagtttggga ggctgaggaa ggaggatcac ttgagtccag gaggttgaga
 421 atagcctgaa caacatagca agatcttgtc tctacaaaaa agtttaaaaa aaattagctg
 481 gccatggcag catgtgcctg tagtaccagc tactcggaag gctgaggtag gaggatcgct
 541 tgagcccagg aggtgattga agctgcagtg agctgtgatt acaccactgc actccagcct
 601 gggcaacaga gctagactct gtctctaaaa aaaggcacaa aataatattt aaaaagcacc
 661 aggtatgcct gtacttgagt tgtctttgtt gatggctaca aatgagacag ctctggctga
 721 agggcggctt ccatttccat gggctggagg aggacatttt gcaaagtgtg ttttcaggaa
 781 gacacagagt tttacctcct acacttgttt gatctgtatt aatgtttgct tatttattta
 841 tttaattttt tttttgagac agagtctcac tctgtcacct gggctggagt gcagtggcat
 901 tattgaggct cattgcagtc tcagactcct gagctcaaac aatcctcctg cctcagcctc
 961 tggagtagct aggactacag gcatgtgcca ccatgcctgg ctaattttt aaatgtattt
1021 ttttgtagag tcggggtctc cctatgttgc ccaggctgga gtgcagtggt gtgatcctag
1081 ctcactgcag cctggacctc gggctcaaga aattctcaca cctcagcctg tccagtagca
1141 ggggctacag gcgcgcacca ccatcccagc taattaaaaa tattttttg tagagacagg
1201 gtctctctat gttgcccagg ctggtttcaa actcccaggc tcaagcaatc ctcctgcctt
1261 gcctcccaaa cgacatcgga ttacaggcgt gagccactga gcctggcccg tattaatgtt
1321 tagaacacga attccaggag gcaggctaag tctattcagc ttgttcatat gcttgggcca
1381 acccaagaaa caagtgggtg acaaatggca ccttttggat agtggtattg actttgaaag
1441 tttgggtcag gagctgggga ggaagggtgg gcaggctgtg ggcagtcctg ggcggaagac
1501 caggcagggc tatgtgctca ctgagcctcc gccctcttcc tttgaatctc tgatagactt
```

-continued

```
1561 ctgcctccta cttctccttt tctgcccttc tttgctttgg tggcttcctt gtggttcctc 1621 agtggtgcct gcaaccctgg ttcactcttc caggttctgg ctccttcctt gtggttcctc 1681 cagagtcctt ctgttaacag gtgcatgggg gtggggtggg ggactctggg tggggagggag 1741 ggtaactttt gggtctgtca taaatagagg gccc
```

| | |
|---|---|
| IL-1beta antisense<br>GTTTCCCTTTCTGCCAGCCCT | SEQ ID NO: 70 |
| IL-1alpha antisense<br>GTGCCGTGAGTTTCCCAGA | SEQ ID NO: 71 |
| COX-1 antisense<br>CCCACTTCCTTGCCCTCTCA | SEQ ID NO: 72 |
| COX-2 antisense<br>ACTCTGTTGTGTTCCCGCA | SEQ ID NO: 73 |
| cPGES antisense<br>CCTCTTCTCGCTTCCCTCA | SEQ ID NO: 74 |
| mPGES antisense<br>GTTCCCATCAGCCACTTCGT | SEQ ID NO: 75 |
| IL-1alpha Hammerhead Ribozyme<br>ATCCTTTGATCUGAUGAGUCCGUGAGGACGAAAGTTATAAGCAC | SEQ ID NO: 76 |
| IL-1beta Hammerhead Ribozyme<br>TCTTTAGAACUGAUGAGUCCGUGAGGACGAAAGACAAATTGCA | SEQ ID NO: 77 |
| COX-1 Hammerhead Ribozyme<br>GGCCGAAGCGCUGAUGAGUCCGUGAGGACGAAAGACAGATGCCC | SEQ ID NO: 78 |
| COX-2 Hammerhead Ribozyme<br>TGGATGTCAACUGAUGAGUCCGUGAGGACGAAAGATAACTCATA | SEQ ID NO: 79 |
| mPGES Hammerhead Ribozyme<br>AGGAGTTCGACUGAUGAGUCCGUGAGGACGAAAGCCTCCTGGGC | SEQ ID NO: 80 |
| cPGES Hammerhead Ribozyme<br>TCTCCGGTGCCUGAUGAGUCCGUGAGGACGAAAGTCCGCTTTTT | SEQ ID NO: 81 |
| CUGAUGAGUCCGUGAGGACGAAAG | SEQ ID NO: 82 |

---

SEQUENCE LISTING

<160> NUMBER OF SEQ ID NOS: 82

<210> SEQ ID NO 1
<211> LENGTH: 2943
<212> TYPE: DNA
<213> ORGANISM: Artificial Sequence
<220> FEATURE:
<223> OTHER INFORMATION: Description of Artificial Sequences; note = synthetic construct

<400> SEQUENCE: 1

```
accaggcaac accattgaag gctcatatgt aaaaatccat gccttccttt ctcccaatct      60
ccattcccaa acttagccac tggcttctgg ctgaggcctt acgcatacct cccggggctt     120
```

```
gcacacacct tcttctacag aagacacacc ttgggcatat cctacagaag accaggcttc      180
tctctggtcc ttggtagagg gctactttac tgtaacaggg ccagggtgga gagttctctc      240
ctgaagctcc atcccctcta taggaaatgt gttgacaata ttcagaagag taagaggatc      300
aagacttctt tgtgctcaaa taccactgtt ctcttctcta ccctgcccta accaggagct      360
tgtcacccca aactctgagg tgatttatgc cttaatcaag caaacttccc tcttcagaaa      420
agatggctca ttttccctca aaagttgcca ggagctgcca agtattctgc caattcaccc      480
tggagcacaa tcaacaaatt cagccagaac acaactacag ctactattag aactattatt      540
attaataaat tcctctccaa atctagcccc ttgacttcgg atttcacgat ttctcccttc      600
ctcctagaaa cttgataagt ttcccgcgct tccctttttc taagactaca tgtttgtcat      660
cttataaagc aaagggggtga ataaatgaac caaatcaata acttctggaa tatctgcaaa      720
caacaataat atcagctatg ccatcttttca ctattttagc cagtatcgag ttgaatgaac      780
atagaaaaat acaaaactga attcttccct gtaaattccc cgttttgacg acgcacttgt      840
agccacgtag ccacgcctac ttaagacaat tacaaaaggc gaagaagact gactcaggct      900
taagctgcca gccagagagg gagtcatttc attggcgttt gagtcagcaa agaagtcaag      960
atggccaaag ttccagacat gtttgaagac ctgaagaact gttacagtga aaatgaagaa     1020
gacagttcct ccattgatca tctgtctctg aatcagaaat ccttctatca tgtaagctat     1080
ggcccactcc atgaaggctg catggatcaa tctgtgtctc tgagtatctc tgaaacctct     1140
aaaacatcca agcttacctt caaggagagc atggtggtag tagcaaccaa cgggaaggtt     1200
ctgaagaaga gacggttgag tttaagccaa tccatcactg atgatgacct ggaggccatc     1260
gccaatgact cagaggaaga aatcatcaag cctaggtcag caccttttag cttcctgagc     1320
aatgtgaaat acaactttat gaggatcatc aaatacgaat tcatcctgaa tgacgccctc     1380
aatcaaagta taattcgagc caatgatcag tacctcacgg ctgctgcatt acataatctg     1440
gatgaagcag tgaaatttga catgggtgct tataagtcat caaaggatga tgctaaaatt     1500
accgtgattc taagaatctc aaaaactcaa ttgtatgtga ctgcccaaga tgaagaccaa     1560
ccagtgctgc tgaaggagat gcctgagata cccaaaacca tcacaggtag tgagaccaac     1620
ctcctcttct tctgggaaac tcacggcact aagaactatt tcacatcagt tgcccatcca     1680
aacttgttta ttgccacaaa gcaagactac tgggtgtgct tggcagggggg gccaccctct     1740 atcactgact ttcagatact ggaaaaccag gcgtaggtct ggagtctcac ttgtctcact     1800
tgtgcagtgt tgacagttca tatgtaccat gtacatgaag aagctaaatc ctttactgtt     1860
agtcatttgc tgagcatgta ctgagccttg taattctaaa tgaatgttta cactcttttgt     1920 aagagtggaa ccaacactaa catataatgt tgttatttaa agaacaccct atattttgca     1980
tagtaccaat cattttaatt attattcttc ataacaattt taggaggacc agagctactg     2040
actatggcta ccaaaaagac tctacccata ttacagatgg gcaaattaag gcataagaaa     2100
actaagaaat atgcacaata gcagttgaaa caagaagcca cagacctagg atttcatgat     2160 ttcattcaa ctgtttgcct tctactttta agttgctgat gaactcttaa tcaaatagca     2220
taagtttctg ggacctcagt tttatcattt tcaaaatgga gggaataata cctaagcctt     2280
cctgccgcaa cagttttta tgctaatcag ggaggtcatt ttggtaaaat acttcttgaa     2340
gccgagcctc aagatgaagg caaagcacga aatgttattt tttaattatt atttatatat     2400
gtatttataa atatatttaa gataattata atatactata tttatgggaa cccccttcatc     2460 ctctgagtgt gaccaggcat cctccacaat agcagacagt gttttctggg ataagtaagt     2520
```

```
ttgatttcat taatacaggg cattttggtc caagttgtgc ttatcccata gccaggaaac    2580
tctgcattct agtacttggg agacctgtaa tcatataata aatgtacatt aattaccttg    2640
agccagtaat tggtccgatc tttgactctt ttgccattaa acttacctgg gcattcttgt    2700
ttcaattcca cctgcaatca agtcctacaa gctaaaatta gatgaactca actttgacaa    2760
ccatgagacc actgttatca aaactttctt ttctggaatg taatcaatgt ttcttctagg    2820
ttctaaaaat tgtgatcaga ccataatgtt acattattat caacaatagt gattgataga    2880
gtgttatcag tcataactaa ataaagcttg caacaaaatt ctctgacaaa aaaaaaaaa     2940 aaa                                                                  2943

<210> SEQ ID NO 2
<211> LENGTH: 1498
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 2
accaaacctc ttcgaggcac aaggcacaac aggctgctct gggattctct tcagccaatc      60
ttcattgctc aagtgtctga agcagccatg gcagaagtac ctgagctcgc cagtgaaatg     120
atggcttatt acagtggcaa tgaggatgac ttgttctttg aagctgatgg ccctaaacag     180
atgaagtgct ccttccagga cctggacctc tgccctctgg atgcggcat ccagctacga     240 atctccgacc accactacag caagggcttc aggcaggccg cgtcagttgt tgtggccatg     300
gacaagctga ggaagatgct ggttccctgc ccacagacct tccaggagaa tgacctgagc     360
accttctttc ccttcatctt tgaagaagaa cctatcttct tcgacacatg ggataacgag     420
gcttatgtgc acgatgcacc tgtacgatca ctgaactgca cgctccggga ctcacagcaa     480
aaaagcttgg tgatgtctgg tccatatgaa ctgaaagctc tccacctcca gggacaggat     540
atggagcaac aagtggtgtt ctccatgtcc tttgtacaag gagaagaaag taatgacaaa     600
ataccgtgtg ccttgggcct caaggaaaag aatctgtacc tgtcctgcgt gttgaaagat     660
gataagccca ctctacagct ggagagtgta gatcccaaaa attacccaaa gaagaagatg     720
gaaaagcgat ttgtcttcaa caagatagaa atcaataaca agctggaatt tgagtctgcc     780
cagttcccca actggtacat cagcacctct caagcagaaa acatgcccgt cttcctggga     840
gggaccaaag gcggcagga taaactgac ttcaccatgc aatttgtgtc ttcctaaaga     900
gagctgtacc cagagagtcc tgtgctgaat gtggactcaa tccctagggc tggcagaaag     960
ggaacagaaa ggttttgag tacggctata gcctggactt tcctgttgtc tacaccaatg    1020
cccaactgcc tgccttaggg tagtgctaag aggatctcct gtccatcagc caggacagtc    1080
agctctctcc tttcagggcc aatccccagc ccttttgttg agccaggcct ctctcacctc    1140
tcctactcac ttaaagcccg cctgacagaa accacggcca catttggttc taagaaaccc    1200
tctgtcattc gctcccacat tctgatgagc aaccgcttcc ctatttattt atttatttgt    1260
ttgtttgttt tattcattgg tctaatttat tcaaggggg caagaagtag cagtgtctgt    1320
aaaagagcct agtttttaat agctatggaa tcaattcaat ttggactggt gtgctctctt    1380
taaatcaagt cctttaatta agactgaaaa tatataagct cagattattt aaatgggaat    1440
atttataaat gagcaaatat catactgttc aatggttctg aaataaactt cactgaag      1498

<210> SEQ ID NO 3
```

```
<211> LENGTH: 464
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 3
gcacctgtac gatcactgaa ctgcacgctc cgggactcac agcaaaaaag cttggtgatg      60
tctggtccat atgaactgaa agctctccac ctccagggac aggatatgga gcaacaagtg     120
gtgttctcca tgtcctttgt acaaggagaa gaaagtaatg acaaaatacc tgtggccttg     180
ggcctcaagg aaaagaatct gtacctgtcc tgcgtgttga agatgataa gcccactcta      240 cagctggaga gtgtagatcc caaaaattac ccaaagaaga gatggaaaa gcgatttgtc      300 ttcaacaaga tagaaatcaa taacaagctg gaatttgagt ctgcccagtt ccccaactgg     360
tacatcagca cctctcaagc agaaaacatg cccgtcttcc tgggagggac caaaggcggc     420
caggatataa ctgacttcac catgcaattt gtgtcttcct aaag                      464

<210> SEQ ID NO 4
<211> LENGTH: 539
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 4
atggaaatct gcagaggcct ccgcagtcac ctaatcactc tcctcctctt cctgttccat      60
tcagagacga tctgcgcacc tgtacgatca ctgaactgca cgctccggga ctcacagcaa     120
aaaagcttgg tgatgtctgg tccatatgaa ctgaaagctc tccacctcca gggacaggat     180
atggagcaac aagtggtgtt ctccatgtcc tttgtacaag gagaagaaag taatgacaaa     240
atacctgtgg ccttgggcct caaggaaaag aatctgtacc tgtcctgcgt gttgaaagat     300
gataagccca ctctacagct ggagagtgta gatcccaaaa attacccaaa gaagaagatg     360
gaaaagcgat ttgtcttcaa caagatagaa atcaataaca agctggaatt tgagtctgcc     420
cagttcccca actggtacat cagcacctct caagcagaaa acatgcccgt cttcctggga     480
gggaccaaag gcggcagga tataactgac ttcaccatgc aatttgtgtc ttcctaaag     539

<210> SEQ ID NO 5
<211> LENGTH: 1760
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 5
atttctttat aaaccacaac tctgggcccg caatggcagt ccactgcctt gctgcagtca      60
cagaatggaa atctgcagag gcctccgcag tcacctaatc actctcctcc tcttcctgtt     120
ccattcagag acgatctgcc gaccctctgg gagaaaatcc agcaagatgc aagccttcag     180
aatctgggat gttaaccaga agaccttcta tctgaggaac aaccaactag ttgctggata     240
cttgcaagga ccaaatgtca atttagaaga aagatagat gtggtaccca ttgagcctca      300
tgctctgttc ttgggaatcc atgggggaa gatgtgcctg tcctgtgtca agtctggtga     360
tgagaccaga ctccagctgg aggcagttaa catcactgac ctgagcgaga acagaaagca     420
ggacaagcgc ttcgccttca tccgctcaga cagcggcccc accaccagtt tgagtctgc     480
```

```
cgcctgcccc ggttggttcc tctgcacagc gatggaagct gaccagcccg tcagcctcac      540
caatatgcct gacgaaggcg tcatggtcac caaattctac ttccaggagg acgagtagta      600
ctgcccaggc ctgcctgttc ccattcttgc atggcaagga ctgcagggac tgccagtccc      660
cctgccccag ggctcccggc tatgggggca ctgaggacca gccattgagg ggtggaccct      720
cagaaggcgt cacaagaacc tggtcacagg actctgcctc ctcttcaact gaccagcctc      780
catgctgcct ccagaatggt ctttctaatg tgtgaatcag agcacagcag ccctgcaca      840 aagcccttcc atgtcgcctc tgcattcagg atcaaacccc gaccacctgc caacctgct      900 ctcctcttgc cactgcctct cctccctca ttccaccttc ccatgccctg gatccatcag      960
gccacttgat gaccccaac caagtggctc ccacaccctg ttttacaaaa aagaaaagac     1020
cagtccatga gggaggtttt taagggtttg tggaaaatga aaattaggat ttcatgattt     1080
ttttttttca gtccccgtga aggagagccc ttcatttgga gattatgttc tttcggggag     1140
aggctgagga cttaaaatat tcctgcattt gtgaaatgat ggtgaaagta agtggtagct     1200
tttcccttct ttttcttctt tttttgtgat gtcccaactt gtaaaaatta aaagttatgg     1260
tactatgtta gccccataat ttttttttc cttttaaaac acttccataa tctggactcc     1320
tctgtccagg cactgctgcc cagcctccaa gctccatctc cactccagat tttttacagc     1380
tgcctgcagt actttacctc ctatcagaag tttctcagct cccaaggctc tgagcaaatg     1440
tggctcctgg gggttctttc ttcctctgct gaaggaataa attgctcctt gacattgtag     1500
agcttctggc acttggagac ttgtatgaaa gatggctgtg cctctgcctg tctccccac      1560 cgggctggga gctctgcaga gcaggaaaca tgactcgtat atgtctcagg tccctgcagg     1620
gccaagcacc tagcctcgct cttggcaggt actcagcgaa tgaatgctgt atatgttggg     1680
tgcaaagttc cctacttcct gtgacttcag ctctgtttta caataaaatc ttgaaaatgc     1740
ctaaaaaaaa aaaaaaaaa                                                 1760

<210> SEQ ID NO 6
<211> LENGTH: 534
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 6
atggaaatct gcagaggcct ccgcagtcac ctaatcactc tcctcctctt cctgttccat       60
tcagagacga tctgccgacc ctctgggaga aaatccagca agatgcaagc cttcagaatc      120
tgggatgtta accagaagac cttctatctg aggaacaacc aactagttgc tggatacttg      180
caaggaccaa atgtcaattt agaagaaaag atagatgtgg tacccattga gcctcatgct      240
ctgttcttgg gaatccatgg agggaagatg tgcctgtcct gtgtcaagtc tggtgatgag      300
accagactcc agctggaggc agttaacatc actgacctga gcgagaacag aaagcaggac      360
aagcgcttcg ccttcatccg ctcagacagc ggccccacca ccagtttga gtctgccgcc      420 tgccccggtt ggttcctctg cacagcgatg gaagctgacc agcccgtcag cctcaccaat      480
atgcctgacg aaggcgtcat ggtcaccaaa ttctacttcc aggaggacga gtag           534

<210> SEQ ID NO 7
<211> LENGTH: 534
<212> TYPE: DNA
<213> ORGANISM: Artificial Sequence
<220> FEATURE:
```

<223> OTHER INFORMATION: Description of Artificial Sequences; note = synthetic construct

<400> SEQUENCE: 7

```
atggaaatct gcagaggcct ccgcagtcac ctaatcactc tcctcctctt cctgttccat      60
tcagagacga tctgccgacc ctctgggaga aaatccagca agatgcaagc cttcagaatc     120
tgggatgtta accagaagac cttctatctg aggaacaacc aactagttgc tggatacttg     180
caaggaccaa atgtcaattt agaagaaaag atagatgtgg tacccattga gcctcatgct     240
ctgttcttgg gaatccatgg agggaagatg tgcctgtcct gtgtcaagtc tggtgatgag     300
accagactcc agctggaggc agttaacatc actgacctga gcgagaacag aaagcaggac     360
aagcgcttcg ccttcatccg ctcagacagc ggccccacca ccagttttga gtctgccgcc     420
tgccccggtt ggttcctctg cacagcgatg gaagctgacc agcccgtcag cctcaccaat     480
atgcctgacg aaggcgtcat ggtcaccaaa ttctacttcc aggaggacga gtag           534
```

<210> SEQ ID NO 8
<211> LENGTH: 4849
<212> TYPE: DNA
<213> ORGANISM: Artificial Sequence
<220> FEATURE:
<223> OTHER INFORMATION: Description of Artificial Sequences; note = synthetic construct

<400> SEQUENCE: 8

```
tagacgcacc ctctgaagat ggtgactccc tcctgagaag ctggacccct tggtaaaaga      60
caaggccttc tccaagaaga atatgaaagt gttactcaga cttatttgtt tcatagctct     120
actgatttct tctctggagg ctgataaatg caaggaacgt gaagaaaaaa taattttagt     180
gtcatctgca aatgaaattg atgttcgtcc ctgtcctctt aacccaaatg aacacaaagg     240
cactataact tggtataaag atgacagcaa gacacctgta tctacagaac aagcctccag     300
gattcatcaa cacaaagaga aactttggtt tgttcctgct aaggtggagg attcaggaca     360
ttactattgc gtggtaagaa attcatctta ctgcctcaga attaaaataa gtgcaaaatt     420
tgtggagaat gagcctaact tatgttataa tgcacaagcc atatttaagc agaaactacc     480
cgttgcagga gacggaggac ttgtgtgccc ttatatggag ttttttaaaa atgaaaataa     540
tgagttacct aaaattacagt ggtataagga ttgcaaacct ctacttcttg acaatataca     600
ctttagtgga gtcaaagata ggctcatcgt gatgaatgtg gctgaaaagc atagagggaa     660
ctatacttgt catgcatcct acacatactt gggcaagcaa tatcctatta cccgggtaat     720
agaatttatt actctagagg aaaacaaacc cacaaggcct gtgattgtga cccagctaa     780
tgagacaatg gaagtagact tgggatccca gatacaattg atctgtaatg tcaccggcca     840
gttgagtgac attgcttact ggaagtggaa tgggtcagta attgatgaag atgacccagt     900
gctagggaa gactattaca gtgtggaaaa tcctgcaaac aaaagaagga gtaccctcat     960
cacagtgctt aatatatcgg aaattgaaag tagatttat aaacatccat ttacctgttt    1020
tgccaagaat acacatggta tagatgcagc atatatccag ttaatatatc cagtcactaa    1080
tttccagaag cacatgattg gtatatgtgt cacgttgaca gtcataattg tgtgttctgt    1140
tttttctccca ataaaagctt cagatggaaa gacctatgac gcatatatac tgtatccaaa    1200
gactgttggg gaagggtcta cctctgactg tgatattttt gtgtttaaag tcttgcctga    1260
ggtcttggaa aaacagtgtg gatataagct gttcatttat ggaagggatg actacgttgg    1320
ggaagacatt gttgaggtca ttaatgaaaa cgtaaagaaa agcagaagac tgattatcat    1380
```

```
tttagtcaga gaaacatcag gcttcagctg gctgggtggt tcatctgaag agcaaatagc   1440
catgtataat gctcttgttc aggatggaat taaagttgtc ctgcttgagc tggagaaaat   1500
ccaagactat gagaaaatgc cagaatcgat taaattcatt aagcagaaac atggggctat   1560
ccgctggtca ggggacttta cacagggacc acagtctgca aagacaaggt tctggaagaa   1620
tgtcaggtac cacatgccag tccagcgacg gtcaccttca tctaaacacc agttactgtc   1680
accagccact aaggagaaac tgcaaagaga ggctcacgtg cctctcgggt agcatggaga   1740
agttgccaag agttctttag gtgcctcctg tcttatggcg ttgcaggcca ggttatgcct   1800
catgctgact tgcagagttc atggaatgta actatatcat cctttatccc tgaggtcacc   1860
tggaatcaga ttattaaggg aataagccat gacgtcaata gcagcccagg gcacttcaga   1920
gtagagggct tgggaagatc tttaaaaag gcagtaggcc cggtgtggtg gctcacgcct   1980
ataatcccag cactttggga ggctgaagtg ggtggatcac cagaggtcag gagttcgaga   2040
ccagcccagc caacatggca aaccccatc tctactaaaa atacaaaaat gagctaggca   2100
tggtggcaca cgcctgtaat cccagctaca cctgaggctg aggcaggaga attgcttgaa   2160
ccggggagac ggaggttgca gtgagccgag tttgggccac tgcactctag cctggcaaca   2220
gagcaagact ccgtctcaaa aaagggcaa taaatgccct ctctgaatgt ttgaactgcc   2280 aagaaaggc atggagacag cgaactagaa gaaagggcaa gaaggaaata gccaccgtct   2340
acagatggct tagttaagtc atccacagcc caagggcggg gctatgcctt gtctggggac   2400
cctgtagagt cactgaccct ggagcggctc tcctgagagg tgctgcaggc aaagtgagac   2460
tgacacctca ctgaggaagg gagacatatt cttggagaac tttccatctg cttgtatttt   2520
ccatacacat ccccagccag aagttagtgt ccgaagaccg aattttatt tacagagctt   2580 gaaaactcac ttcaatgaac aaagggattc tccaggattc caaagttttg aagtcatctt   2640
agctttccac aggagggaga gaacttaaaa aagcaacagt agcagggaat tgatccactt   2700
cttaatgctt tcctccctgg catgaccatc ctgtcctttg ttattatcct gcattttacg   2760
tctttggagg aacagctccc tagtggcttc ctccgtctgc aatgtcccct gcacagccca   2820
cacatgaacc atccttccca tgatgccgct cttctgtcat cccgctcctg ctgaaacacc   2880
tcccaggggc tccacctgtt caggagctga agcccatgct ttcccaccag catgtcactc   2940
ccagaccacc tccctgccct gtcctccagc ttccctcgc tgtcctgctg tgtgaattcc   3000
caggttggcc tggtggccat gtcgcctgcc cccagcactc ctctgtctct gctcttgcct   3060
cgacccttcc tcctccttg cctaggaggc cttctcgcat tttctctagc tgatcagaat   3120
tttaccaaaa ttcagaacat cctccaattc cacagtctct gggagacttt ccctaagagg   3180
cgacttcctc tccagccttc tctctctggt caggcccact gcagagatgg tggtgagcac   3240
atctgggagg ctggtctccc tccagctgga attgctgctc tctgagggag aggctgtggt   3300
ggctgtctct gtccctcact gccttccagg agcaatttgc acatgtaaca tagatttatg   3360
taatgcttta tgtttaaaaa cattccccaa ttatcttatt taattttgc aattattcta   3420 atttatata tagagaaagt gacctatttt ttaaaaaaat cacactctaa gttctattga   3480
acctaggact tgagcctcca tttctggctt ctagtctggt gttctgagta cttgatttca   3540
ggtcaataac ggtccccct cactccacac tggcacgttt gtgagaagaa atgacatttt   3600
gctaggaagt gaccgagtct aggaatgctt ttattcaaga caccaaattc caaacttcta   3660
aatgttggaa ttttcaaaaa ttgtgtttag attttatgaa aaactcttct actttcatct   3720
attctttccc tagaggcaaa catttcttaa aatgtttcat tttcattaaa aatgaaagcc   3780
```

-continued

| | |
|---|---|
| aaatttatat gccaccgatt gcaggacaca agcacagttt taagagttgt atgaacatgg | 3840 |
| agaggacttt tggtttttat atttctcgta tttaatatgg gtgaacacca acttttattt | 3900 |
| ggaataataa ttttcctcct aaacaaaaac acattgagtt taagtctctg actcttgcct | 3960 |
| ttccacctgc tttctcctgg gcccgctttg cctgcttgaa ggaacagtgc tgttctggag | 4020 |
| ctgctgttcc aacagacagg gcctagcttt catttgacac acagactaca gccagaagcc | 4080 |
| catggagcag ggatgtcacg tcttgaaaag cctattagat gttttacaaa tttaattttg | 4140 |
| cagattattt tagtctgtca tccagaaaat gtgtcagcat gcatagtgct aagaaagcaa | 4200 |
| gccaatttgg aaacttaggt tagtgacaaa attggccaga gagtgggggt gatgatgacc | 4260 |
| aagaattaca agtagaatgg cagctggaat ttaaggaggg acaagaatca atggataagc | 4320 |
| gtgggtggag gaagatccaa acagaaaagt gcaaagttat tccccatctt ccaagggttg | 4380 |
| aattctggag gaagaagaca cattcctagt tccccgtgaa cttcctttga cttattgtcc | 4440 |
| ccactaaaac aaaacaaaaa acttttaatg ccttccacat taattagatt ttcttgcagt | 4500 |
| tttttttatgg cattttttta aagatgccct aagtgttgaa gaagagtttg caaatgcaac | 4560 |
| aaaatattta attaccggtt gttaaaactg gtttagcaca atttatattt tccctctctt | 4620 |
| gcctttctta tttgcaataa aaggtattga gccatttttt aaatgacatt tttgataaat | 4680 |
| tatgttgta ctagttgatg aaggagtttt ttttaacctg tttatataat tttgcagcag | 4740 |
| aagccaaatt ttttgtatat taaagcacca aattcatgta cagcatgcat cacggatcaa | 4800 |
| tagactgtac ttattttcca ataaaatttt caaactttgt actgttaaa | 4849 |

<210> SEQ ID NO 9
<211> LENGTH: 1436
<212> TYPE: DNA
<213> ORGANISM: Artificial Sequence
<220> FEATURE:
<223> OTHER INFORMATION: Description of Artificial Sequences; note = synthetic construct

<400> SEQUENCE: 9

| | |
|---|---|
| gggatgggag atactgttgt ggtcacctct ggaaaataca ttctgctact cttaaaaact | 60 |
| agtgacgctc atacaaatca acagaaagag cttctgaagg aagactttaa agctgcttct | 120 |
| gccacgtgct gctgggtctc agtcctccac ttcccgtgtc ctctggaagt tgtcaggagc | 180 |
| aatgttgcgc ttgtacgtgt tggtaatggg agtttctgcc ttcacccttc agcctgcggc | 240 |
| acacacaggg gctgccagaa gctgccggtt tcgtgggagg cattacaagc gggagttcag | 300 |
| gctggaaggg gagcctgtag ccctgaggtg cccccaggtg ccctactggt tgtgggcctc | 360 |
| tgtcagcccc cgcatcaacc tgacatggca taaaaatgac tctgctagga cggtcccagg | 420 |
| agaagaagag acacggatgt gggcccagga cggtgctctg tggcttctgc cagccttgca | 480 |
| ggaggactct ggcacctacg tctgcactac tagaaatgct tcttactgtg acaaaatgtc | 540 |
| cattgagctc agagtttttg agaatacaga tgctttcctg ccgttcatct catacccgca | 600 |
| aattttaacc ttgtcaacct ctggggtatt agtatgccct gacctgagtg aattcacccg | 660 |
| tgacaaaact gacgtgaaga ttcaatggta caaggattct cttcttttgg ataaagacaa | 720 |
| tgagaaattt ctaagtgtga gggggaccac tcacttactc gtacacgatg tggccctgga | 780 |
| agatgctggc tattaccgct gtgtcctgac atttgcccat gaaggccagc aatacaacat | 840 |
| cactaggagt attgagctac gcatcaagaa aaaaaaagaa gagaccattc ctgtgatcat | 900 |
| ttccccctc aagaccatat cagcttctct ggggtcaaga ctgacaatcc cgtgtaaggt | 960 |
| gtttctggga accggcacac ccttaaccac catgctgtgg tggacggcca atgacaccca | 1020 |

```
catagagagc gcctacccgg gaggccgcgt gaccgagggg ccacgccagg aatattcaga    1080
aaataatgag aactacattg aagtgccatt gatttttgat cctgtcacaa gagaggattt    1140
gcacatggat tttaaatgtg ttgtccataa taccctgagt tttcagacac tacgcaccac    1200
agtcaaggaa gcctcctcca cgttctcctg gggcattgtg ctggcccac tttcactggc     1260 cttcttggtt ttgggggaa tatggatgca cagacggtgc aaacacagaa ctggaaaagc     1320
agatggtctg actgtgctat ggcctcatca tcaagacttt caatcctatc ccaagtgaaa    1380
taaatggaat gaaataattc aaacacaaaa aaaaaaaaaa aaaaaaaaaa aaaaaa        1436

<210> SEQ ID NO 10
<211> LENGTH: 2554
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 10
gcgccatgag ccggagtctc ttgctccggt tcttgctgtt cctgctcctg ctcccgccgc    60
tccccgtcct gctcgcggac ccaggggcgc ccacgccagt gaatccctgt tgttactatc    120
catgccagca ccagggcatc tgtgtccgct tcggccttga ccgctaccag tgtgactgca    180
cccgcacggg ctattccggc cccaactgca ccatccctgg cctgtggacc tggctccgga    240
attcactgcg gccagcccc tctttcaccc acttcctgct cactcacggg cgctggttct    300
gggagtttgt caatgccacc ttcatccgag agatgctcat gcgcctggta ctcacagtgc    360
gctccaacct tatccccagt ccccccacct acaactcagc acatgactac atcagctggg    420
agtctttctc caacgtgagc tattcactc gtattctgcc ctctgtgcct aaagattgcc    480
ccacacccat gggaaccaaa gggaagaagc agttgccaga tgcccagctc ctggcccgcc    540
gcttcctgct caggaggaag ttcatacctg acccccaagg caccaacctc atgtttgcct    600 tcttgcaca acacttcacc caccagttct tcaaaacttc tggcaagatg ggtcctggct    660
tcaccaaggc cttgggccat ggggtagacc tcggccacat ttatggagac aatctggagc    720
gtcagtatca actgcggctc tttaaggatg ggaaactcaa gtaccaggtg ctggatggag    780
aaatgtaccc gccctcggta gaagaggcgc ctgtgttgat gcactacccc cgaggcatcc    840
cgccccagag ccagatggct gtgggccagg aggtgtttgg gctgcttcct gggctcatgc    900
tgtatgccac gctctggcta cgtgagcaca ccgtgtgtg tgacctgctg aaggctgagc    960
accccacctg gggcgatgag cagcttttc agacgacccg cctcatcctc ataggggaga    1020
ccatcaagat tgtcatcgag gagtacgtgc agcagctgag tggctatttc ctgcagctga    1080
aatttgaccc agagctgctg ttcggtgtcc agttccaata ccgcaaccgc attgccatgg    1140
agttcaacca tctctaccac tggcaccccc tcatgcctga ctccttcaag gtgggctccc    1200
aggagtacag ctacgagcag ttcttgttca cacctccat gttggtggac tatggggttg    1260
aggccctggt ggatgccttc tctcgccaga ttgctggccg gatcgtgggg ggcaggaaca    1320
tggaccacca catcctgcat gtggctgtgg atgtcatcag ggagtctcgg agatgcggc    1380 tgcagccctt caatgagtac cgcaagaggt tggcatgaa accctacacc tccttccagg    1440
agctcgtagg agagaaggag atggcagcag agttggagga attgtatgga gacattgatg    1500
cgttggagtt ctaccctgga ctgcttcttg aaaagtgcca tccaaactct atctttgggg    1560
agagtatgat agagattggg gctcccttt ccctcaaggg tctcctaggg aatcccatct    1620
```

```
gttctccgga gtactggaag ccgagcacat ttggcggcga ggtgggcttt aacattgtca   1680
agacggccac actgaagaag ctggtctgcc tcaacaccaa gacctgtccc tacgtttcct   1740
tccgtgtgcc ggatgccagt caggatgatg ggcctgctgt ggagcgacca tccacagagc   1800
tctgaggggc aggaaagcag cattctggag gggagagctt tgtgcttgtc attccagagt   1860
gctgaggcca gggctgatgg tcttaaatgc tcattttctg gtttggcatg gtgagtgttg   1920
gggttgacat ttagaacttt aagtctcacc cattatctgg aatattgtga ttctgtttat   1980
tcttccagaa tgctgaactc cttgttagcc cttcagattg ttaggagtgg ttctcatttg   2040
gtctgccaga atactgggtt cttagttgac aacctagaat gtcagatttc tggttgattt   2100
gtaacacagt cattctagga tgtggagcta ctgatgaaat ctgctagaaa gttagggggt   2160
tcttattttg cattccagaa tcttgacttt ctgattggtg attcaaagtg ttgtgttccc   2220
tggctgatga tccagaacag tggctcgtat cccaaatctg tcagcatctg gctgtctaga   2280
atgtggattt gattcatttt cctgttcagt gagatatcat agagacggag atcctaaggt   2340
ccaacaagaa tgcattccct gaatctgtgc ctgcactgag agggcaagga agtggggtgt   2400
tcttcttggg accccactaa agaccctggt ctgaggatgt agagagaaca ggtgggctgt   2460
attcacgcca ttggttggaa gctaccagag ctctatcccc atccaggtct tgactcatgg   2520
cagctgtttc tcatgaagct aataaaattc gccc                               2554
```

<210> SEQ ID NO 11
<211> LENGTH: 4465
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 11

```
caattgtcat acgacttgca gtgagcgtca ggagcacgtc caggaactcc tcagcagcgc    60
ctccttcagc tccacagcca gacgccctca gacagcaaag cctaccccg cgccgcgccc    120 tgcccgccgc tcggatgctc gcccgcgccc tgctgctgtg cgcggtcctg gcgctcagcc    180
atacagcaaa tccttgctgt tcccacccat gtcaaaaccg aggtgtatgt atgagtgtgg    240
gatttgacca gtataagtgc gattgtaccc ggacaggatt ctatggagaa aactgctcaa    300
caccggaatt tttgacaaga ataaaattat ttctgaaacc cactccaaac acagtgcact    360
acatacttac ccacttcaag ggattttgga acgttgtgaa taacattccc ttccttcgaa    420
atgcaattat gagttatgtc ttgacatcca gatcacattt gattgacagt ccaccaactt    480
acaatgctga ctatggctac aaaagctggg aagccttctc taacctctcc tattatacta    540
gagcccttcc tcctgtgcct gatgattgcc cgactccctt gggtgtcaaa ggtaaaaagc    600
agcttcctga ttcaaatgag attgtggaaa aattgcttct aagaagaaag ttcatccctg    660
atccccaggg ctcaaacatg atgtttgcat tctttgccca gcacttcacg catcagtttt    720
tcaagacaga tcataagcga gggccagctt tcaccaacgg gctgggccat ggggtggact    780
taaatcatat ttacggtgaa actctggcta gacagcgtaa actgcgcctt ttcaaggatg    840
gaaaaatgaa atatcagata attgatggag agatgtatcc tcccacagtc aaagatactc    900
aggcagagat gatctaccct cctcaagtcc ctgagcatct acgttttgct gtggggcagg    960
aggtctttgg tctggtgcct ggtctgatga tgtatgccac aatctggctg cgggaacaca   1020
acagagtatg cgatgtgctt aaacaggagc atcctgaatg gggtgatgag cagttgttcc   1080
agacaagcag gctaatactg ataggagaga ctattaagat tgtgattgaa gattatgtgc   1140
```

```
aacacttgag tggctatcac ttcaaactga aatttgaccc agaactactt ttcaacaaac   1200
aattccagta ccaaaatcgt attgctgctg aatttaacac cctctatcac tggcatcccc   1260
ttctgcctga cacctttcaa attcatgacc agaaatacaa ctatcaacag tttatctaca   1320
acaactctat attgctggaa catggaatta cccagtttgt tgaatcattc accaggcaaa   1380
ttgctggcag ggttgctggt ggtaggaatg ttccacccgc agtacagaaa gtatcacagg   1440
cttccattga ccagagcagg cagatgaaat accagtcttt aatgagtac cgcaaacgct    1500 ttatgctgaa gccctatgaa tcatttgaag aacttacagg agaaaaggaa atgtctgcag   1560
agttggaagc actctatggt gacatcgatg ctgtggagct gtatcctgcc cttctggtag   1620
aaaagcctcg gccagatgcc atctttggtg aaaccatggt agaagttgga gcaccattct   1680
ccttgaaagg acttatgggt aatgttatat gttctcctgc ctactggaag ccaagcactt   1740
ttggtggaga gtgggttttt caaatcatca acactgcctc aattcagtct ctcatctgca   1800
ataacgtgaa gggctgtccc tttacttcat tcagtgttcc agatccagag ctcattaaaa   1860
cagtcaccat caatgcaagt tcttcccgct ccggactaga tgatatcaat cccacagtac   1920
tactaaaaga acgttcgact gaactgtaga agtctaatga tcatatttat ttatttatat   1980
gaaccatgtc tattaatttta attatttaat aatatttata ttaaactcct tatgttactt   2040
aacatcttct gtaacagaag tcagtactcc tgttgcggag aaaggagtca tacttgtgaa   2100
gacttttatg tcactactct aaagattttg ctgttgctgt taagtttgga aaacagtttt   2160
tattctgttt tataaaccag agagaaatga gttttgacgt ctttttactt gaatttcaac   2220
ttatattata agaacgaaag taaagatgtt tgaatactta aacactatca caagatggca   2280
aaatgctgaa agttttttaca ctgtcgatgt ttccaatgca tcttccatga tgcattagaa   2340
gtaactaatg tttgaaattt taaagtactt ttggttattt ttctgtcatc aaacaaaaac   2400
aggtatcagt gcattattaa atgaatattt aaattagaca ttaccagtaa tttcatgtct   2460
actttttaaa atcagcaatg aaacaataat ttgaaatttc taaattcata gggtagaatc   2520
acctgtaaaa gcttgtttga tttcttaaag ttattaaact tgtacatata ccaaaaagaa   2580
gctgtcttgg atttaaatct gtaaaatcag atgaaatttt actacaattg cttgttaaaa   2640
tattttataa gtgatgttcc ttttttcacca agagtataaa ccttttttagt gtgactgtta   2700 aaacttcctt ttaaatcaaa atgccaaatt tattaaggtg gtggagccac tgcagtgtta   2760
tctcaaaata agaatatttt gttgagatat tccagaattt gtttatatgg ctggtaacat   2820
gtaaaatcta tatcagcaaa agggtctacc tttaaaataa gcaataacaa agaagaaaac   2880
caaattattg ttcaaattta ggtttaaact tttgaagcaa actttttttt atccttgtgc   2940
actgcaggcc tggtactcag attttgctat gaggttaatg aagtaccaag ctgtgcttga   3000
ataacgatat gttttctcag attttctgtt gtacagttta atttagcagt ccatatcaca   3060
ttgcaaaagt agcaatgacc tcataaaata cctcttcaaa atgcttaaat tcatttcaca   3120
cattaatttt atctcagtct tgaagccaat tcagtaggtg cattggaatc aagcctggct   3180
acctgcatgc tgttcctttt cttttcttct tttagccatt ttgctaagag acacagtctt   3240
ctcatcactt cgtttctcct attttgtttt actagtttta agatcagagt tcactttctt   3300
tggactctgc ctatattttc ttacctgaac ttttgcaagt tttcaggtaa acctcagctc   3360
aggactgcta tttagctcct cttaagaaga ttaaaagaga aaaaaaaggg ccctttttaaa   3420 aatagtatac acttattttta agtgaaaagc agagaatttt atttatagct aattttagct   3480
atctgtaacc aagatggatg caaagaggct agtgcctcag agagaactgt acggggtttg   3540
```

```
tgactggaaa aagttacgtt cccattctaa ttaatgccct ttcttattta aaaacaaaac    3600
caaatgatat ctaagtagtt ctcagcaata ataataatga cgataatact tcttttccac    3660
atctcattgt cactgacatt taatggtact gtatattact taatttattg aagattatta    3720
tttatgtctt attaggacac tatggttata aactgtgttt aagcctacaa tcattgattt    3780 tttttttgtta tgtcacaatc agtatatttt ctttggggtt acctctctga atattatgta    3840
aacaatccaa agaaatgatt gtattaagat ttgtgaataa atttttagaa atctgattgg    3900
catattgaga tatttaaggt tgaatgtttg tccttaggat aggcctatgt gctagcccac    3960
aaagaatatt gtctcattag cctgaatgtg ccataagact gacctttaa aatgttttga    4020 gggatctgtg gatgcttcgt taatttgttc agccacaatt tattgagaaa atattctgtg    4080
tcaagcactg tgggttttaa tatttttaaa tcaaacgctg attacagata atagtattta    4140
tataaataat tgaaaaaaat tttcttttgg gaagagggag aaaatgaaat aaatatcatt    4200
aaagataact caggagaatc ttcttttacaa ttttacgttt agaatgttta aggttaagaa    4260
agaaatagtc aatatgcttg tataaaacac tgttcactgt ttttttttaaa aaaaaaactt    4320 gatttgttat taacattgat ctgctgacaa aacctgggaa tttgggttgt gtatgcgaat    4380
gtttcagtgc ctcagacaaa tgtgtattta acttatgtaa aagataagtc tggaaataaa    4440
tgtctgttta ttttttgtact attta                                          4465

<210> SEQ ID NO 12
<211> LENGTH: 1805
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 12
gctgctcctc tgtcgagctg atcacaccca cagttgagct gcgctggcca gagatgcctg      60
cccacagcct ggtgatgagc agcccggccc tcccggcctt cctgctctgc agcacgctgc     120
tggtcatcaa gatgtacgtg gtggccatca tcacgggcca agtgaggctg cggaagaagg     180
cctttgccaa ccccgaggat gccctgagac acggaggccc ccagtattgc aggagcgacc     240
ccgacgtgga acgctgcctc agggcccacc ggaacgacat ggagaccatc taccccttcc     300 tttttcctggg cttcgtctac tccttttctgg gtcctaaccc tttgtcgcc tggatgcact     360 tcctggtctt cctcgtgggc cgtgtggcac acaccgtggc ctacctgggg aagctgcggg     420
cacccatccg ctccgtgacc tacaccctgg cccagctccc ctgcgcctcc atggctctgc     480
agatcctctg ggaagcggcc cgccaccgtg gaccagcagc tgatgcctcc ttggccacca     540
gaccatgggc caagagccgc cgtggctata cctggggact tgatgttcct tccagattgt     600
ggtgggccct gagtcctggt ttcctggcag cctgctgcgc gtgtgggtct ctgggcacag     660
tgggcctgtg tgtgtgcccg tgtgtgtgta tgtgtgtgtg tatgtttctt agccccttgg     720
attcctgcac gaagtggctg atgggaacca tttcaagaca gattgtgaag attgatagaa     780
aatccttcag ctaaagtaac agagcatcaa aaacatcact ccctctccct ccctaacagt     840
gaaaagagag aagggagact ctatttaaga ttcccaaacc taatgatcat ctgaatcccg     900
ggctaagaat gcagactttt cagactgacc ccagaaattc tggcccagcc aatctagagg     960
caagcctggc catctgtatt tttttttttc caagacagag tcttgctctg ttgcccaagc    1020
tggagtgaag tggtacaatc tggctcactg cagcctccgc ctcccgggtt caagcgattc    1080
```

```
tcccgcctca gcctcctgag tagctgggat tacaggcgcg tatcaccata cccagctaat    1140
ttttgtattt ttagtagaga cgggttcacc atgttgccca ggagggtctc gaactcctgg    1200
cctcaagtga tccaccggcc tcggcctccc aaagtgctgg gatgacaggc atgaatcact    1260
gtgctcagcc accatctgga gttttaaaag gctcccatgt gagtcccgtg atggccagg     1320 ccagggacc cctgccagtt ctctgtggaa gcaaggctgg ggtcttgggt tcctgtatgg    1380
tggaagctgg gtgagccaag gacagggctg gctcctctgc ccccgctgac gcttcccttg    1440
ccgttggctt tggatgtctt tgctgcagtc ttctctctgg ctcaggtgtg ggtgggaggg    1500
gcccacagga agctcagcct tctcctccca aggtttgagt ccctccaaag ggcagtgggt    1560
ggaggaccgg gagctttggg tgaccagcca ctcaaaggaa cttctggtc ccttcagtat     1620 cttcaaggtt tggaaactgc aaatgtcccc ttgatgggga atccgtgtgt gtgtgtgtgt    1680
gtgtgtgtgt gtgtgtgtgt gtgtgtgttt tctcctagac ccgtgacctg agatgtgtga    1740
tttttagtca ttaaatggaa gtgtctgcca gctgggccca gcacctaaaa aaaaaaaaa     1800 aaaaa                                                                1805

<210> SEQ ID NO 13
<211> LENGTH: 782
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 13
ggattcgggc tacactttcc tcttctcccc gaccggagag ccgctctttc cgcgcggtgc      60
attctggggc ccgaggtcga gcccgccgct gccgccgtcg cctgagggaa gcagaagag     120 gccgcgaccg agagaaaaag cggagtcgca ccggagagaa gtcgactccc tagcagcagc    180
cgccgccaga gagcccgccc accagttcgc ccgtccccct gccccgttca caatgcagcc    240
tgcttctgca aagtggtacg atcgaaggga ctatgtcttc attgaatttt gtgttgaaga    300
cagtaaggat gttaatgtaa attttgaaaa atccaaactt acattcagtt gtctcggagg    360
aagtgataat tttaagcatt taaatgaaat tgatcttttt cactgtattg atccaaatga    420
ttccaagcat aaaagaacgg acagatcaat tttatgttgt ttacgaaaag gagaatctgg    480
ccagtcatgg ccaaggttaa caaaagaaag ggcaaagctt aattggctta gtgtcgactt    540
caataattgg aaagactggg aagatgattc agatgaagac atgtctaatt ttgatcgttt    600
ctctgagatg atgaacaaca tgggtggtga tgaggatgta gatttaccag aagtagatgg    660
agcagatgat gattcacaag acagtgatga tgaaaaaatg ccagatctgg agtaaggaat    720
attgtcatca cctggatttt gagaaagaaa ataacttct ctgcaagatt tcataattga    780
ga                                                                   782

<210> SEQ ID NO 14
<211> LENGTH: 75
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 14
atggaaatct gcagaggcct ccgcagtcac ctaatcactc tcctcctctt cctgttccat      60
tcagagacga tctgc                                                      75
```

<210> SEQ ID NO 15
<211> LENGTH: 655
<212> TYPE: DNA
<213> ORGANISM: Artificial Sequence
<220> FEATURE:
<223> OTHER INFORMATION: Description of Artificial Sequences; note = synthetic construct

<400> SEQUENCE: 15

| cgatgtacgg gccagatata cgcgttgaca ttgattattg actagttatt aatagtaatc | 60 |
| aattacgggg tcattagttc atagcccata tatggagttc cgcgttacat aacttacggt | 120 |
| aaatggcccg cctggctgac cgcccaacga cccccgccca ttgacgtcaa taatgacgta | 180 |
| tgttcccata gtaacgccaa tagggacttt ccattgacgt caatgggtgg actatttacg | 240 |
| gtaaactgcc cacttggcag tacatcaagt gtatcatatg ccaagtacgc ccctattga | 300 |
| cgtcaatgac ggtaaatggc ccgcctggca ttatgcccag tacatgacct tatgggactt | 360 |
| tcctacttgg cagtacatct acgtattagt catcgctatt accatggtga tgcggttttg | 420 |
| gcagtacatc aatgggcgtg atagcggtt tgactcacgg ggatttccaa gtctccaccc | 480 |
| cattgacgtc aatgggagtt tgttttggca ccaaaatcaa cgggactttc caaaatgtcg | 540 |
| taacaactcc gccccattga cgcaaatggg cggtaggcgt gtacggtggg aggtctatat | 600 |
| aagcagagct ctctggctaa ctagagaacc cactgcttac tggcttatcg aaatt | 655 |

<210> SEQ ID NO 16
<211> LENGTH: 1278
<212> TYPE: DNA
<213> ORGANISM: Artificial Sequence
<220> FEATURE:
<223> OTHER INFORMATION: Description of Artificial Sequences; note = synthetic construct

<400> SEQUENCE: 16

| tcgaggtgag ccccacgttc tgcttcactc tccccatctc ccccccctcc caccccaa | 60 |
| ttttgtattt atttattttt taattatttt gtgcagcgat ggggcgggg gggggggggg | 120 |
| cgcgcgccag gcggggcggg gcgggcgag gggcggggcg gggcgaggcg gagaggtgcg | 180 |
| gcggcagcca atcagagcgg cgcgctccga aagtttcctt ttatggcgag cggcggcgg | 240 |
| cggcggccct ataaaaagcg aagcgcgcgg cgggcgggag tcgctgcgtt gccttcgccc | 300 |
| cgtgccccgc tccgcgccgc ctcgcgccgc ccgccccggc tctgactgac cgcgttactc | 360 |
| ccacaggtga gcgggcggga cggcccttct cctccgggct gtaattagcg cttggtttaa | 420 |
| tgacggctcg tttcttttct gtggctgcgt gaaagcctta aagggctccg ggagggccct | 480 |
| ttgtgcgggg gggagcggct cgggggtgc gtgcgtgtgt gtgtgcgtgg ggagcgccgc | 540 |
| gtgcggcccg cgctgcccgg cggctgtgag cgctgcgggc gcggcgcggg gctttgtgcg | 600 |
| ctccgcgtgt gcgcgagggg agcgcggccg gggcggtgc cccgcggtgc gggggggctg | 660 |
| cgagggggaac aaaggctgcg tgcggggtgt gtgcgtgggg gggtgagcag ggggtgtggg | 720 |
| cgcggcggtc gggctgtaac ccccccctgc acccccctcc ccgagttgct cgcacggcc | 780 |
| cggcttcggg tgcggggctc cgtgcggggc gtggcgcggg gctcgccgtg ccgggcgggg | 840 |
| ggtggcggca ggtgggggtg ccgggcgggg cggggccgcc tcgggccggg gagggctcgg | 900 |
| gggagggggcg cggcggcccc ggagcgccgg cggctgtcga ggcgcggcga ccgcagcca | 960 |
| ttgccttttta tggtaatcgt gcgagagggc gcagggactt cctttgtccc aaatctggcg | 1020 |
| gagccgaaat ctgggaggcg ccgccgcacc ccctctagcg ggcgcgggcg aagcggtgcg | 1080 |

```
gcgccggcag gaaggaaatg ggcggggagg gccttcgtgc gtcgccgcgc cgccgtcccc   1140
ttctccatct ccagcctcgg ggctgccgca gggggacggc tgccttcggg ggggacgggg   1200
cagggcgggg ttcggcttct ggcgttgtac cggcggggtt tatatcttcc cttctctgtt   1260
cctccgcagc cagccatg                                                 1278

<210> SEQ ID NO 17
<211> LENGTH: 1176
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 17
cccgggccca gcaccccaag gcggccaacg ccaaaactct ccctcctcct cttcctcaat     60
ctcgctctcg ctctttttt tttcgcaaa aggaggggag aggggtaaa aaaatgctgc      120 actgtgcggc gaagccggtg agtgagcggc gcggggccaa tcagcgtgcg ccgttccgaa    180
agttgccttt tatggctcga gcggccgcgg cggcgcccta taaaacccag cggcgcgacg    240
cgccaccacc gccgagaccg cgtccgcccc gcgagcacag agcctcgcct ttgccgatcc    300
gccgcccgtc cacacccgcc gccaggtaag cccggccagc cgaccggggc atgcggccgc    360
ggccccttcg cccgtgcaga gccgccgtct gggccgcagc ggggggcgca tgggggggga    420
accggaccgc cgtgggggggc gcgggagaag ccctgggcc tccggagatg ggggacaccc    480
cacgccagtt cggaggcgcg aggccgcgct cggaggcgc gctccggggg tgccgctctc    540
ggggcggggg caaccggcgg ggtctttgtc tgagccgggc tcttgccaat ggggatcgca    600
gggtgggcgc ggcgtagccc ccgccaggcc cggtgggggc tggggcgcca ttgccggtgc    660
gcgctggtcc tttgggcgct aactgcgtgc gcgctgggaa ttggcgctaa ttgcgcgtgc    720
gcgctgggac tcaaggcgct aattgcgcgt gcgttctggg gccgggggtg ccgcggcctg    780
ggctggggcg aaggcgggct cggccggaag gggtggggtc gccgcggctc ccgggcgctt    840
gcgcgcactt cctgcccgag ccgctggccg cccgagggtg tggccgctgc gtgcgcgcgc    900
gccgacccgg cgctgtttga accgggcgga ggcggggctg gcgcccggtt gggaggggt    960 tggggcctgg cttcctgccg cgcgccgcgg ggacgcctcc gaccagtgtt tgccttttat   1020
ggtaataacg cggccggccc ggcttccttt gtccccaatc tgggcgcgcg ccggcgcccc   1080
ctggcggcct aaggactcgg cgcgccgaa gtgccaggg cggggcgac ttcggctcac    1140 agcgcgcccg gctattctcg cagctcacca tggatg                             1176

<210> SEQ ID NO 18
<211> LENGTH: 1729
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 18
gaattcggta ccctagttat taatagtaat caattacggg gtcattagtt catagcccat     60
atatggagtt ccgcgttaca taacttacgg taaatggccc gcctggctga ccgcccaacg    120 accccgccc attgacgtca ataatgacgt atgttcccat agtaacgcca atagggactt    180
tccattgacg tcaatgggtg gactatttac ggtaaactgc ccacttggca gtacatcaag    240
tgtatcatat gccaagtacg ccccctattg acgtcaatga cggtaaatgg cccgcctggc    300
```

```
attatgccca gtacatgacc ttatgggact tcctacttg gcagtacatc tacgtattag      360
tcatcgctat taccatggtc gaggtgagcc ccacgttctg cttcactctc cccatctccc      420 cccccctcccc acccccaatt ttgtatttat ttatttttta attattttgt gcagcgatgg     480 gggcggggg gggggggggg cgcgcgccag gcggggcggg gcgggggcgag gggcggggcg      540 gggcgaggcg gagaggtgcg gcggcagcca atcagagcgg cgcgctccga aagtttcctt      600
ttatggcgag gcggcggcgg cggcggccct ataaaaagcg aagcgcgcgg cgggcgggag      660
tcgctgcgac gctgccttcg ccccgtgccc cgctccgccg ccgcctcgcg ccgcccgccc      720
cggctctgac tgaccgcgtt actcccacag gtgagcgggc gggacggccc ttctcctccg      780
ggctgtaatt agcgcttggt ttaatgacgg cttgtttctt ttctgtggct gcgtgaaagc      840
cttgaggggc tccgggaggg ccctttgtgc ggggggagc ggctcggggg gtgcgtgcgt       900
gtgtgtgtgc gtggggagcg ccgcgtgcgg cccgcgctgc ccggcggctg tgagcgctgc      960
gggcgcggcg cggggctttg tgcgctccgc agtgtgcgcg aggggagcgc ggccgggggc      1020
ggtgccccgc ggtgcggggg gggctgcgag gggaacaaag gctgcgtgcg gggtgtgtgc      1080
gtgggggggt gagcagggg tgtgggcgcg cggtcgggc tgtaaccccc ccctgcaccc       1140
ccctccccga gttgctgagc acggcccggc ttcgggtgcg gggctccgta cggggcgtgg      1200
cgcggggctc gccgtgccgg gcgggggtg cggcaggtg ggggtgccgg gcggggcggg       1260
gccgcctcgg gccggggagg gctcggggga ggggcgcggc ggccccgga gcgccggcgg       1320 ctgtcgaggc gcggcgagcc gcagccattg ccttttatgg taatcgtgcg agagggcgca     1380
gggacttcct ttgtcccaaa tctgtgcgga gccgaaatct gggaggcgcc gccgcacccc     1440
ctctagcggg cgcggggcga agcggtgcg cgccggcagg aaggaaatgg gcggggaggg     1500
ccttcgtgcg tcgccgcgcc gccgtcccct tctccctctc cagcctcggg gctgtccgcg      1560
gggggacggc tgccttcggg ggggacgggg cagggcgggg ttcggcttct ggcgtgtgac      1620
cggcggctct agagcctctg ctaaccatgt tcatgccttc ttcttttttcc tacagctcct    1680 gggcaacgtg ctggttattg tgctgtctca tcattttggc aaagaattc                 1729
```

<210> SEQ ID NO 19
<211> LENGTH: 655
<212> TYPE: DNA
<213> ORGANISM: Artificial Sequence
<220> FEATURE:
<223> OTHER INFORMATION: Description of Artificial Sequences; note = synthetic construct

<400> SEQUENCE: 19

```
cgatgtacgg gccagatata cgcgttgaca ttgattattg actagttatt aatagtaatc      60
aattacgggg tcattagttc atagcccata tatggagttc cgcgttacat aacttacggt     120
aaatggcccg cctggctgac cgcccaacga ccccccgccca ttgacgtcaa taatgacgta    180
tgttcccata gtaacgccaa tagggacttt ccattgacgt caatgggtgg actatttacg     240
gtaaactgcc cacttggcag tacatcaagt gtatcatatg ccaagtacgc cccctattga     300
cgtcaatgac ggtaaatggc ccgcctggca ttatgcccag tacatgacct tatgggactt     360
tcctacttgg cagtacatct acgtattagt catcgctatt accatggtga tgcggttttg     420
gcagtacatc aatgggcgtg gatagcggtt tgactcacgg ggatttccaa gtctccaccc     480
cattgacgtc aatgggagtt tgttttggca ccaaaatcaa cgggactttc caaaatgtcg     540
taacaactcc gccccattga cgcaaatggg cggtaggcgt gtacggtggg aggtctatat     600
aagcagagct ctctggctaa ctagagaacc cactgcttac tggcttatcg aaatt          655
```

<210> SEQ ID NO 20
<211> LENGTH: 366
<212> TYPE: DNA
<213> ORGANISM: Artificial Sequence
<220> FEATURE:
<223> OTHER INFORMATION: Description of Artificial Sequences; note = synthetic construct

<400> SEQUENCE: 20

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggac tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggt                                                                366
```

<210> SEQ ID NO 21
<211> LENGTH: 1295
<212> TYPE: DNA
<213> ORGANISM: Artificial Sequence
<220> FEATURE:
<223> OTHER INFORMATION: Description of Artificial Sequences; note = synthetic construct

<400> SEQUENCE: 21

```
ccaattttgt atttatttat tttttaatta ttttgtgcag cgatggggc ggggggggg        60
gggggcgcg cgccaggcgg ggcggggcgg ggcgaggggc ggggcgggc gaggcggaga      120
ggtgcggcgg cagccaatca gagcggcgcg ctccgaaagt ttccttttat ggcgaggcgg     180
cggcggcggc ggccctataa aaagcgaagc gcgcggcggg cggagtcgc tgcgacgctg      240
ccttcgcccc gtgccccgct ccgccgccgc ctcgcgccgc ccgccccggc tctgactgac     300
cgcgttactc ccacaggtga gcgggcggga cggcccttct cctccgggct gtaattagcg     360
cttggtttaa tgacggcttg tttcttttct gtggctgcgt gaaagccttg aggggctccg     420
ggagggccct ttgtgcgggg gggagcggct cgggggggtgc gtgcgtgtgt gtgtgcgtgg    480
ggagcgccgc gtgcggcccg cgctgcccgg cggctgtgag cgctgcgggc gcggcgcggg    540
gctttgtgcg ctccgcagtg tgcgcgaggg gagcgcggcc ggggggcggtg ccccgcggtg     600
cggggggggc tgcgagggga acaaaggctg cgtgcgggt gtgtgcgtgg ggggtgagc       660
aggggtgtg ggcgcggcgg tcgggctgta accccccct gcacccccct ccccgagttg       720
ctgagcacgg cccggcttcg ggtgcgggc tccgtacggg gcgtggcgcg gggctcgccg     780
tgccgggcgg ggggtggcgg caggtggggg tgcgggcgg ggcggggccg cctcgggccg     840
gggagggctc gggggagggg cgcggcggcc cccggagcgc cggcggctgt cgaggcgcgg     900
cgagccgcag ccattgcctt ttatggtaat cgtgcgagag ggcgcaggga cttcctttgt     960
cccaaatctg tgcggagccg aaatctggga ggcgccgccg cacccctct agcgggcgcg    1020
gggcgaagcg gtgcggcgcc ggcaggaagg aaatgggcgg ggagggcctt cgtgcgtcgc    1080
cgcgccgccg tcccttctc cctctccagc ctcggggctc tccgcggggg gacggctgcc    1140
ttcggggggg acgggcagg gcggggttcg gcttctggcg tgtgaccggc ggctctagag     1200
cctctgctaa ccatgttcat gccttcttct ttttcctaca gctcctgggc aacgtgctgg    1260
ttattgtgct gtctcatcat tttggcaaag aattc                              1295
```

<210> SEQ ID NO 22
<211> LENGTH: 229
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 22
gtattagtca tcgctattac catggtgatg cggttttggc agtacatcaa tgggcgtgga      60
tagcggtttg actcacgggg atttccaagt ctccacccca ttgacgtcaa tgggagtttg     120
ttttggcacc aaaatcaacg ggactttcca aaatgtcgta caactccgc cccattgacg      180 caaatgggcg gtaggcgtgt acggtgggag gtctatataa gcagagctc                 229

<210> SEQ ID NO 23
<211> LENGTH: 281
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 23
tggcattatg cccagtacat gaccttatgg gactttccta cttggcagta catctacgta      60
ttagtcatcg ctattaccat ggtgatgcgg ttttggcagt acatcaatgg gcgtggatag     120
cggtttgact cacggggatt tccaagtctc accccattg acgtcaatgg gagtttgttt     180
tggcaccaaa atcaacggga ctttccaaaa tgtcgtaaca actccgcccc attgacgcaa     240
atgggcggta ggcgtgtacg gtgggaggtc tatataagca g                         281

<210> SEQ ID NO 24
<211> LENGTH: 282
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 24
attatgccca gtacatgacc ttatgggact ttcctacttg gcagtacatc tacgtattag      60
tcatcgctat taccatggtg atgcggtttt ggcagtacat caatgggcgt ggatagcggt     120
ttgactcacg gggatttcca gtctccacc ccattgacgt caatgggagt tgttttggc      180 accaaaatca acgggacttt ccaaaatgtc gtaacaactc cgccccattg acgcaaatgg     240
gcggtaggcg tgtacggtgg gaggtctata agcagagc tc                          282

<210> SEQ ID NO 25
<211> LENGTH: 512
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 25
ttgcgttaca taacttacgg taaatggccc gcctggctga ccgcccaacg accccgccc      60 attgacgtca ataatgacgt atgttccat agtaacgcca atagggactt ccattgacg      120 tcaatgggtg gactatttac ggtaaactgc ccacttggca gtacatcaag tgtatcatat    180
gccaagtacg cccctattg acgtcaatga cggtaaatgg cccgcctggc attatgccca    240

```
gtacatgacc ttatgggact ttcctacttg gcagtacatc tacgtattag tcatcgctat      300
taccatggtg atgcggtttt ggcagtacat caatgggcgt ggatagcggt ttgactcacg      360
gggatttcca agtctccacc ccattgacgt caatgggagt ttgttttggc accaaaatca      420
acgggacttt ccaaaatgtc gtaacaactc cgccccattg acgcaaatgg gcggtaggcg      480
tgtacggtgg gaggtctata taagcagagc tc                                   512

<210> SEQ ID NO 26
<211> LENGTH: 308
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 26
tcggcgaagc ctcgcgcggc cggccaggac gaggagcgcc actaggttga acatccgcac       60
gagccgccgg gccaggtctc ggacgggctc tcgagactcg atctcgtgca tgtcggcggt      120
ccgcggtgag gttatagacc atctgctagg cgggtccggg gagacaggca cattactggc      180
ctcggcgccc agcctaggcg tgtctagagc tcgaccgcgc gtccggagcg ccattcgacc      240
ggcgggtagc gagaagaacg ccggagaccg caggttataa caacgtcatg cataaattaa      300
gaatgggc                                                              308

<210> SEQ ID NO 27
<211> LENGTH: 1848
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 27
ctgcagtgaa taataaaatg tgtgtttgtc cgaaatacgc gtttgagatt tctgtcccga       60
ctaaattcat gtcgcgcgat agtggtgttt atcgccgata gagatggcga tattggaaaa      120
atcgatattt gaaaatatgg catattgaaa atgtcgccga tgtgagtttc tgtgtaactg      180
atatcgccat ttttccaaaa gttgattttt gggcatacgc gatatctggc gatacgctta      240
tatcgtttac gggggatggc gatagacgcc tttggtgact gggcgattc tgtgtgtcgc      300 aaatatcgca gtttcgatat aggtgacaga cgatatgagg ctatatcgcc gatagaggcg      360
acatcaagct ggcacatggc caatgcatat cgatctatac attgaatcaa tattggccat      420
tagccatatt attcattggt tatatagcat aaatcaatat tggctattgg ccattgcata      480
cgttgtatcc atatcataat atgtacattt atattggctc atgtccaaca ttaccgccat      540
gttgacattg attattgact agttattaat agtaatcaat tacggggtca ttagttcata      600
gcccatatat ggagttccgc gttacataac ttacggtaaa tggcccgcct ggctgaccgc      660
ccaacgaccc ccgcccattg acgtcaataa tgacgtatgt tcccatagta acgccaatag      720
ggactttcca ttgacgtcaa tgggtggagt atttacggta aactgcccac ttggcagtac      780
atcaagtgta tcatatgcca agtacgcccc ctattgacgt caatgacggt aaatggcccg      840
cctggcatta tgcccagtac atgaccttat gggactttcc tacttggcag tacatctacg      900
tattagtcat cgctattacc atggtgatgc ggttttggca gtacatcaat gggcgtggat      960
agcggtttga ctcacgggga tttccaagtc tccaccccat tgacgtcaat gggagtttgt     1020
tttggcacca aaatcaacgg gactttccaa aatgtcgtaa caactccgcc ccattgacgc     1080
```

```
aaatgggcgg taggcgtgta cggtgggagg tctatataag cagagctcgt ttagtgaacc   1140
gtcagatcgc ctggagacgc catccacgct gttttgacct ccatagaaga caccgggacc   1200
gatccagcct ccgcggccgg gaacggtgca ttggaacgcg gattcccgt gccaagagtg    1260 acgtaagtac cgcctataga gtctataggc ccaccccctt ggcttcttat gcatgctata   1320
ctgtttttgg cttggggtct atacaccccc gcttcctcat gttataggtg atggtatagc   1380
ttagcctata ggtgtgggtt attgaccatt attgaccact cccctattgg tgacgatact   1440
ttccattact aatccataac atggctcttt gcacaactct ctttattggc tatatgccaa   1500
tacactgtcc ttcagagact gacacggact ctgtattttt acaggatggg gtctcattta   1560
ttatttacaa attcacatat acaacaccac cgtccccagt gcccgcagtt tttattaaac   1620
ataacgtggg atctccagcg aatctcgggt acgtgttccg gacatggggc tcttctccgg   1680
tagcggcgga gcttctacat ccagccctgc tcccatcctc ccactcatgg tcctcggcag   1740
ctccttgctc ctaacagtgg aggccagact taggcacagc acgatgccca ccaccaccag   1800
tgtgcccaca aggccgtggc ggtagggtat gtgtctgaaa atgagctc                 1848
```

<210> SEQ ID NO 28
<211> LENGTH: 49
<212> TYPE: DNA
<213> ORGANISM: Artificial Sequence
<220> FEATURE:
<223> OTHER INFORMATION: Description of Artificial Sequences; note = synthetic construct

<400> SEQUENCE: 28

```
cttctggcgt gtgaccggcg gggtttatat cttcccttcc caagcttgg             49
```

<210> SEQ ID NO 29
<211> LENGTH: 66
<212> TYPE: DNA
<213> ORGANISM: Artificial Sequence
<220> FEATURE:
<223> OTHER INFORMATION: Description of Artificial Sequences; note = synthetic construct

<400> SEQUENCE: 29

```
cttctggcgt gtgaccggcg gggtttatat cttcccttct ctgttcctcc gcagccccaa   60
gcttgg                                                              66
```

<210> SEQ ID NO 30
<211> LENGTH: 68
<212> TYPE: DNA
<213> ORGANISM: Artificial Sequence
<220> FEATURE:
<223> OTHER INFORMATION: Description of Artificial Sequences; note = synthetic construct

<400> SEQUENCE: 30

```
cttctggcgt gtgaccggcg gggtttatat cttcccttct ctgttcctcc gcagccagcc   60
aagcttgg                                                            68
```

<210> SEQ ID NO 31
<211> LENGTH: 69
<212> TYPE: DNA
<213> ORGANISM: Artificial Sequence
<220> FEATURE:
<223> OTHER INFORMATION: Description of Artificial Sequences; note = synthetic construct

<400> SEQUENCE: 31

```
cttctggcgt gtgaccggcg gggtttatat cttcccttct ctgttcctcc gcagccagcc    60
atggatgat                                                             69

<210> SEQ ID NO 32
<211> LENGTH: 1345
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 32
tcgaggtgag ccccacgttc tgcttcactc tccccatctc ccccccctcc ccaccccaa     60 ttttgtattt atttattttt taattatttt gtgcagcgat gggggcgggg ggggggggg    120 cgcgcgccag gcgggcgggg gcgggcgag gggcggggcg gggcgaggcg gagaggtgcg    180
gcggcagcca atcagagcgg cgcgctccga aagtttcctt ttatggcgag gcggcggcgg    240
cggcggccct ataaaaagcg aagcgcgcgg cgggcgggag tcgctgcgtt gccttcgccc    300
cgtgccccgc tccgcgccgc ctcgcgccgc ccgccccggc tctgactgac cgcgttactc    360
ccacaggtga gcgggcggga cggcccttct cctccgggct gtaattagcg cttggtttaa    420
tgacggctcg tttctttct gtggctgcgt gaaagcctta aagggctccg ggagggccct    480
ttgtgcgggg gggagcggct cggggggtgc gtgcgtgtgt gtgtgcgtgg ggagcgccgc    540
gtgcggcccg cgctgcccgg cggctgtgag cgctgcgggc gcggcgcggg gctttgtgcg    600
ctccgcgtgt gcgcgagggg agcgcggccg ggggcggtgc cccgcggtgc ggggggggctg    660 cgagggggaac aaaggctgcg tgcggggtgt gtgcgtgggg gggtgagcag ggggtgtggg    720
cgcggcggtc gggctgtaac cccccctgc accccctcc ccgagttgct gagcacggcc    780
cggcttcggg tgcggggctc cgtgcgggc gtggcgcggg gctcgccgtg ccggcgggg    840 ggtggcggca ggtgggggtg ccgggcgggg cggggccgcc tcgggccggg gagggctcgg    900
gggaggggcg cggcggcccc ggagcgccgg cggctgtcga ggcgcggcga gccgcagcca    960 ttgccttttα tggtaatcgt gcgagagggc gcagggactt cctttgtccc aaatctggcg   1020
gagccgaaat ctgggaggcg ccgccgcacc ccctctagcg ggcgcgggcg aagcggtgcg   1080
gcgccggcag gaaggaaatg ggcggggagg gccttcgtgc gtcgccgcgc cgccgtcccc   1140
ttctccatct ccagcctcgg ggctgccgca gggggacggc tgccttcggg ggggacgggg   1200
cagggcgggg ttcggcttct ggcgtgtgac cggcggctct agagcctctg ctaaccatgt   1260
tcatgccttc ttcttttcc tacagctcct gggcaacgtg ctggttgttg tgctgtctca   1320
tcattttggc aaagaattca agctt                                         1345

<210> SEQ ID NO 33
<211> LENGTH: 684
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 33
tcaatattgg ccattagcca tattattcat tggttatata gcataaatca atattggcta     60
ttggccattg catacgttgt atctatatca taatatgtac atttatattg gctcatgtcc    120
aatatgaccg ccatgttggc attgattatt gactagttat taatagtaat caattacggg    180
gtcattagtt catagcccat atatggagtt ccgcgttaca taacttacgg taaatggccc    240
```

```
gcctggctga ccgcccaacg accccgccc attgacgtca ataatgacgt atgttcccat      300
agtaacgcca atagggactt tccattgacg tcaatgggtg gagtatttac ggtaaactgc      360
ccacttggca gtacatcaag tgtatcatat gccaagtccg cccctattg acgtcaatga       420 cggtaaatgg cccgcctggc attatgccca gtacatgacc ttacgggact ttcctacttg      480
gcagtacatc tacgtattag tcatcgctat taccatggtg atgcggtttt ggcagtacac      540
caatgggcgt ggatagcggt ttgactcacg gggatttcca gtctccacc ccattgacgt       600 caatgggagt ttgttttggc accaaaatca acgggacttt ccaaaatgtc gtaataaccc      660
cgccccgttg acgcaaatgg gcgg                                             684

<210> SEQ ID NO 34
<211> LENGTH: 2069
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 34
aattccatac ctgcttgatc cacatatgaa ctacaggggg acatgatgag gtccagtcta       60
aaggtcactg gcaacctctc tcaagatctc cctcactatg ccattattca ggattgggga      120
agatgtggct ggagcctaag gggctcttcc cttccctatg gtgggactca ttaggagaac      180
ctcagcaagc agtccactgt aagctcaaac aaataccatg tcgctggtat ggagtaaggc      240
tgttgctatg acaggaactc aggggtctta actggcttga gcgctgggag ggggcagcag      300
ccaggccttg tctgtaagct gaagacctgg cagtgctgag ctggtcaccc ccaggacct       360 cctttgtgc ccaacgagtg actcaccttg gcatagaca taatggtcag gggtgggcac        420
gcagcctgct tcccgctgtg ctccaggcct ccttcgatgc tttccgagaa gtctattgag      480
ctgggagctt gtactgcacc cggggctgac atcctggcat cctgggataa aagcagccca      540
cggggctgcc cttgccatat gcctcactgg cggcagagaa caaggctcta ttcagcaagt      600
gccctggagt agacaccaga agcccaagca tgggcagagg aaggcagggg ttgggggag       660 cagagctgtc tgtgttccag aagcccaagg acacagatgg ctaaggcgcc tgggagggac      720
ctgagtggaa gagatagatg ggcctgaagt ctcaagcagc aacagcctcc tccccgccat      780
tggtgagggt ggggtttggt ttcccggacc tacatatccc tcagaggcct ggtgtgtagg      840
aatttaaagg aggtaaatct cctgagagaa tcagggtac ccaggaagac ggggtgttac       900
agaaagactc cagcatgcac agccaactca ctcaaaacta ctctgtcagg ggctgccggg      960
ggccaggctc ggggtggggg gtgggggggc aaagagaagc tggaccaggg agaaatggcc     1020
cactaggctg gatatgaggc cacagagggg ctcaggaagg aagcctgctg tcttacccta     1080
ttaggatctg cgtgcatacc ttctgctgtg cactctaaac acacagccag aggctcaagt     1140
tgaccctgga gtcacagaga gggctccaac cttagccctc cactcctgaa ctccaggaat     1200
gagaagatag agttggagcg attcagggga gaggactctg ttgagaatgg gggtcacagg     1260
aaactgtaat ataggttgat cccggaggaa gggaataggt tcttcaagtt cctagcatct     1320
cacaggcccc agagaaggac agagtgggt ggtcctggct taacaggctc taagaactgg      1380
aagctgatta ccccaccaag ctgtcactct ctgtctctgt ctctgtctct gtgtgtgcgc     1440
gctcgtgcac acttatcaca caaatgttca tgtgtgtgca catagatgag ttgacaccag     1500
aggtcaacct caggcactgt tgccttggtt ttctgagaga gcatttctct ctggacctgg     1560
```

| | |
|---|---|
| aactcgccaa ttagtgagag ccaggaagtc tgctgatttt cactgcccag cactggagtt | 1620 |
| tacaagtatg cactgtcaac ccaggccttt tgtattcatt ctgcagctag aacttgggtg | 1680 |
| ggtcttcatg cttgacaggc aagcaattta tggactaagc tgtttcctcg gccctctctt | 1740 |
| gacccattta ccagaaaggg ggttccttga tcaatggcga acgcaggctg gtgtcccaag | 1800 |
| aaagccttga ctctgggtac agtgacctca gtggggtgag aggagttctc cccttagctg | 1860 |
| ggctggggcc cagctccacc ccctcaggct attcaatggg ggtgcttcca ggaagtcagg | 1920 |
| ggcagattta gtccaacccg ttcctccata aaggccctga catcccagga gccagcagag | 1980 |
| gcagggcagg atggagcgga gacgcatcac ctctgcgcgc cgctcctatg cctccgagac | 2040 |
| ggtggtcagg ggcctcggtc ctagtcgac | 2069 |

<210> SEQ ID NO 35
<211> LENGTH: 3633
<212> TYPE: DNA
<213> ORGANISM: Artificial Sequence
<220> FEATURE:
<223> OTHER INFORMATION: Description of Artificial Sequences; note = synthetic construct

<400> SEQUENCE: 35

| | |
|---|---|
| tctagaatat agaagccaag gatttcaagg gtttcctttt ctctcttctt ctttttttt | 60 |
| cttttctttt ttcctgagat ggagtttcct tttgtagccc tgactgtcct ggaattcact | 120 |
| ctatagacca ggctagcctc acacttagtg atctgcctgc ctctgcctct gggtgcctc | 180 |
| aggattcaag gcatgaacca ccactacccg accaggatt tcttacacac ttctgactgg | 240 |
| actaaccagg aaagcagaga gggagacagg aagaaaatgc tcagaaggaa ggagtaggat | 300 |
| tggaggtgag ctgggggaac ccagactgag ccgtgcagaa gacaaggaag aagaaagcca | 360 |
| cccacacacc taggatccac ccacagattt tgctctgggt acccctgtct ggagactgta | 420 |
| gggctttgtg atggagggtg gggtagtctt catgccccgt gcccttttact ccagacctaa | 480 |
| atgcccaccc ccacatacag ctgctcgctc tctctctccc ctgcccttct cccaagagac | 540 |
| cagttctcca tccctggtct gcagccaagg ctggggggcag aagaactttc tggaggattt | 600 |
| gagtgagaaa agcaagagag cctcaagtag ggactggaac ctctgggaag ggagtgcaga | 660 |
| ggagacccgg gtatgtgccc tacctggtac atttatacct gggcagcctc tgctcctgtt | 720 |
| ccagacttca gagcccagac gggtcctctc cctccctcat gaggggaaac atttggggaa | 780 |
| atttggagag agacagaact cagagctcag cactttcctc tttctgtttt tcttcttgag | 840 |
| gaatttttc ccccaactgc tgatgacttt accattcttg ggggtggggg ggtggagatt | 900 |
| ctggcttttg ctccccctac actccaagtg ccggacaaag ccctacattc cacaagaagc | 960 |
| cagggcttca gagtttccta aagatgaggt ggcgtggcga gtctcctccc tctcccagct | 1020 |
| ccaactcccc ctcccccagt ctccagccct agcctggcca gggaggcccc gccaggctgg | 1080 |
| gaggagaccc caagcacatt cttcctctcg ctgtcatgct gcagaaatta aagacacatc | 1140 |
| tctgagctgg gtaccgcca atcgtttcaa gttgagaagt ggcagaggag gtcccgagct | 1200 |
| tcagctcatg ccacgtgtaa aggaagcttg gaacccactg cccacaactc ctggggcaaa | 1260 |
| aacctggagt cagacatggg gtgaaggctg tcacacggca cagacacgtc aagcacccc | 1320 |
| cccaattcta gtagtctcct agcctccacc agaaccccag accttgatg tggcagtcac | 1380 |
| cagtccacac ctgttaggct cttgtctctt cttccagatg agcctgggggg gcgtgggggt | 1440 |
| gctagatcag gagcagggaa aagtagcttt ggataagtgc tttcccaat acaaaaccca | 1500 |
| acaaagagtg ggcagatcac actgtgtagt gcttcgtgga accctaccct agacaactgc | 1560 |

```
cttgaacacc tattccctct gatgtacacc atccccgtcc actgttaggg agtgggcatc    1620
ctttggaact gaccactgtg gaaggcagga ctttactgag ttccggaact accatctcag    1680
cttctcagcc ccagccttac cctacaggca ctggcatagg cggggggcaga tcctgggcca   1740 caagtcactg ccacatggtt gggataattg atgaagtcct gtccttccat tgctgtctcc    1800
agttctgctt ctctggaaac tctatatttt tccctttaat tatagcctct gcagtctccc    1860
tctgccaccc caccccgcacc gcttagccta actgccacg gccagcgacg tggctccctc    1920
cccttctgct cccttggtct tttttatttt tttttctttg ccttcgttgc acaaaactag    1980
ctcagggagg gcgtgaaggg gggggagca atggaatctt ggatggtttg gaggaggcgg     2040
gactccttgc ttccacgttt acagctctga agacggctgt ggggggaagtg atacaggacg   2100 tctatgggcc ctgagaggag acccctatgc ttccctgcca cccacacagt ttaacaaaat    2160
gaagttccta agtagagtgg gggtcaggca gagcacctt gcagggttga tgggagccca     2220
gggaaagaaa ggacactgtc ttttagggac acatttaaat ataagccact tttcttgggg    2280
gacgacaaat gacccttttcc tgattgcaga ggtggggaac aatggctgag attttcagca   2340
aagaagcgag gacatgagga gtagccttca aataaagtca ctcagctacc aaaaacaagt    2400
ttctgccaca caccgagtta cctaggtgtc cccagaccag atccaagtac agtaaggaaa    2460
gcaggttctc tacagagaga acacggctct atggccaatg ccttctacct gctctttctg    2520
gattgatact gctacctaag agggcctcta accaattcct ggctgtagcc acagctgaca    2580
caagaccttt ttctaagaca tccctggtca caggcctcct gtagcaaatt ccagccctgg    2640
gatggaggtg gtcaggaaag agtttataca agaagaccca ggccacagct ttaaggactc    2700
agaaaccccc ctgcccacac ggctgcccat cataacgcag aaggtttctt ctggaaggac    2760
aaggatgtca aacttctccc caagcctaat cctcagagat gtctccctct gttacacctg    2820
gggctggaga aagtgggtc tttcatggag ccacattcat ggcagaacag atagccaccc     2880
cactcctttc aaacaaccac atatctgact cttagtatct gtgaagagat gtctaatttg    2940
ttcccaaata ttcctaccct gcatacctgg gcccacacca tgaggtattc tcctccctct    3000
aacagtcaca tctgcttagc tgcctggttc ttcggatttg gagagatgct tgcctaactt    3060
attcttcctt aggtcttccc aaggatgcca gaaagactat gagacatggc caagaggacc    3120
ttttcccaat tgtgcctgac actgaaccct ttgtaatgtt ccccaactca gattcccaat    3180
tctacatcct tctgatttga ggtcccagaa ggaaagtgca agggcatcc cctacccaca     3240 atcagtatat cgaggcccag ccacactcag tgatagcacc tctggcccat gtagatctgg    3300
gggacaaggg tggcagaatt gcaaaggggg gaggggctg gtggactcc tttcccttcc      3360 tttccctcct ccccctcttc cgttccaaat tgggggccgg gccaggcagt tctgattggc    3420
tgggggccgg gctgctggct cccccctctcc aagaggcagg gttcctccca gccctcctcc   3480
atcaggatgg tataaaaggg gcccaggcca gtcgtcggag cagacgggag tttcacctcc    3540
ggacggagca ggaggcacac ggagtgaggc cacgcatgag ccgaagctaa ccccccaccc    3600
cagccgcaaa gagtctacat gtctagggtc tag                                 3633
```

<210> SEQ ID NO 36
<211> LENGTH: 1404
<212> TYPE: DNA
<213> ORGANISM: Artificial Sequence
<220> FEATURE:
<223> OTHER INFORMATION: Description of Artificial Sequences; note = synthetic construct

```
<400> SEQUENCE: 36
tggtggtggt ggacaactag gaaactctgg cgctttctcc tcccctcaca aaactgagtc      60
cagctggagc cgcctccaga ctctctggcc agggcctcag agtggtcaac agtccctggc     120
cagcgttgct ctctccaggc taagggcacc cactcccctg gagattcctg aacctgggcc     180
aggaagagcc gaattagaca gtgtctcca atccggctgc gtgcggattt tgttgcggtg      240
tccctcggtt gtctgcagtt cctttagtcc cttccctggc ctgcccctta cacctccaca     300
caggtccccc tctgtgtagg aatacaccag accctctctt agccacacac acctccagtc     360
ccccgtctac ctagattttt ttcatagcta gttggatggg ggatgggtta gggaggctgg     420
gtttgcgagc ctccaggtgg gagttcaccg acaggtactc cgcaaaggag ctggaaggca     480
ggtctggaaa actgtccccc agatttagga ttctgggcag cttccatcag cttatacttt     540
ggctcccccg ccccctaaact ccccatcccc acctcctttc tcccgttact tcgtcctccc   600
tcgcctttcc agcctcgagt ctaaagctcc atgcttatgc ctctgcaaac aaccccctcc     660
cttctaaccc cagcagaact ccgaggaaag gggccggagg ccctcttctc gcctgtggtt     720
agaggggggca gtgtggcagt cccaagtggg ggcgaccgga ggccgtctcg gtgccccgcc    780
cgatcaggcc actgggcaca tcgggggcgg gaagcgggct caccaaaggg gcgactggcc     840
ttggcaggtg tgggctctgg tccgacctgg gcaggtccg ggggcggggt ctcaggttac      900
aacgccacgg ggggctgggg gcggcccgcg gtttggttgg tttgccagcc tttggagcga     960
ccgggagcat ataaccggag cctctgctgg gagaagcgca gggcgccgct gggctgccgg    1020
gtctcctgcc tcctcctcct gctccgagag cctcctgcat gagggcgagg tagagacccg    1080
gacccgctcc ggtctctgcc gcctcgccga gcttcgcccg ggccaaggct ctgcgggcct    1140
cgcggtgagc catgattcgc ctcggggctc cccagtcgct ggtgctgctg acgctgctca    1200
tcgccacggt cctacaatgt cagggccagg atgcccgtag gtcgcccacc accccctgcct   1260
gcttccctga cttgcgaccc ttctcttctt ccctccgtcc gagttaggcg ccaagtccta    1320
ggcgcgtagt gcacaggaga acactgatcc taatcctaat tctgctagtg aggagttctg    1380
tcgcagcatc ctcagtcaga gtcg                                           1404

<210> SEQ ID NO 37
<211> LENGTH: 12745
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 37
atgcggtttt ggcagtacat caatgggcgt ggatagcggt ttgactcacg gggatttcca     60
agtctccacc ccattgacgt caatgggagt ttgttttggc accaaaatca acgggacttt    120
ccaaaatgtc gtaacaactc cgccccattg acgcaaatgg gcggtaggcg tgtacggtgg    180
gaggtctata taagcagagc tctgtgaaac ttcgaggagt ctctttgttg aggacttttg    240
agttctccct tgaggctccc acagatacaa taaatatttg agattgaacc ctgtcgagta    300
tctgtgtaat ctttttttacc tgtgaggtct cggaatccgg gccgagaact tcgcagttgg    360
cgcccgaaca gggacttgat tgagagtgat tgaggaagtg aagctagagc aatagaaagc    420
tgttaagcag aactcctgct gacctaaata gggaagcagt agcagacgct gctaacagtg    480
agtatctcta gtgaagcgga ctcgagctca taatcaagtc attgtttaaa ggcccagata    540
aattacatct ggtgactctt cgcggacctt caagccagga gattcgccga gggacagtca    600
```

```
acaaggtagg agagattcta cagcaacatg gggaatggac aggggcgaga ttggaaaatg    660
gccattaaga gatgtagtaa tgttgctgta ggagtagggg ggaagagtaa aaaatttgga    720
gaagggaatt tcagatgggc cattagaatg gctaatgtat ctacaggacg agaacctggt    780
gatataccag agactttaga tcaactaagg ttggttattt gcgatttaca agaaagaaga    840
gaaaaatttg gatctagcaa agaaattgat atggcaattg tgacattaaa agtctttgcg    900
gtagcaggac ttttaaatat gacgggtgtc tactgctgct gcagctgaaa atatgtattc    960
tcaaatggga ttagacacta ggccatctat gaaagaagca ggtggaaaag aggaaggccc   1020
tccacaggca tatcctattc aaacagtaaa tggagtacca caatatgtag cacttgaccc   1080
aaaaatggtg tccatttttta tggaaaaggc aagagaagga ctaggaggtg aggaagttca   1140
actatggttt actgccttct ctgcaaattt aacacctact gacatggcca cattaataat   1200
ggccgcacca gggtgcgctg cagataaaga aatattggat gaaagcttaa agcaactgac   1260
agcagaatat gatcgcacac atcccctga tgctcccaga ccattaccct attttactgc   1320
agcagaaatt atgggtatag gattaactca agaacaacaa gcagaagcaa gatttgcacc   1380
agctaggatg cagtgtagag catggtatct cgaggcatta ggaaaattgg ctgccataaa   1440
agctaagtct cctcgagctg tgcagttaag acaaggagct aaggaagatt attcatcctt   1500
tatagacaga ttgtttgccc aaatagatca agaacaaaat acagctgaag ttaagttata   1560
tttaaaacag tcattgagca tagctaatgc taatgcagac tgtaaaaagg caatgagcca   1620
ccttaagcca gaaagtaccc tagaagaaaa gttgagagct tgtcaagaaa taggctcacc   1680
aggatataaa atgcaactct tggcagaagc tcttacaaaa gttcaagtag tgcaatcaaa   1740
aggatcagga ccagtgtgtt ttaattgtaa aaaaccagga catctagcaa gacaatgtag   1800
agaagtgaaa aaatgtaata aatgtggaaa acctggtcat gtagctgcca aatgttggca   1860
aggaaataga aagaattgta caagggaaga aagggataca acaattacaa aagtgggaag   1920
attgggtagg atggatagga atattccac aatatttaaa gggactattg ggaggtatct   1980
tgggaatagg attaggagtg ttattattga ttttatgttt acctacattg gttgattgta   2040
taagaaattg tatccacaag atactaggat acacagtaat tgcaatgcct gaagtagaag   2100
gagaagaaat acaaccacaa atggaattga ggagaaatgg taggcaatgt ggcatgtctg   2160
aaaaagagga ggaatgatga agtatctcag acttatttta aagggagat actgtgctga   2220 gttcttccct ttgaggaagg tatgtcatat gaatccattt cgaatcaaat caaactaata   2280
aagtatgtat tgtaaggtaa aaggaaaaga caaagaagaa gaagaaagaa gaaagccttc   2340
agtacattta tattggctca tgtccaatat gaccgccatg ttgacattga ttattgacta   2400
gttattaata gtaatcaatt acggggtcat tagttcatag cccatatatg gagttccgcg   2460
ttacataact tacggtaatt ggcccgcctg ctgaccgccc aacgaccccc gcccattgac   2520
gtcaataatg acgtatgttc ccatagtaac gccaataggg actttccatt gacgtcaatg   2580
ggtggagtat ttacggtaaa ctgcccactt ggcagtacat caagtgtatc atatgccaag   2640 tccgccccc tattgacgtc aatgacggta aatggcccgc ctggcattat gcccagtaca   2700
tgaccttacg ggactttggt acttggcagt acatctacgt attagtcatc gctattacca   2760
tggtgatgcg gttttggcag tacaccaatg ggcgtggata gcggtttgac tcacgggat   2820 ttccaagtct ccaccccatt gacgtcaatg ggagtttgtt ttggcaccaa aatcaacggg   2880
actttccaaa atgtcgtaat aaccccgccc cgttgacgca aatgggcggt aggcgtgtac   2940
ggtgggaggt ctatataagc agagctcgtt tagtgaaccg tcagatcgcc tggagacgcc   3000
```

```
atccacgctg ttttgacctc catagaagac accgggaccg atccagcctc cgcggccggg    3060
aacggtgcat tggaacgcgg attccccgtg ccaagagtga cgtaagtacc gcctatagac    3120
tctataggca cacccctttg gctcttatgc atgctatact gttttttggct tggggcctat   3180 acaccccgc tccttatgct ataggtgatg gtatagctta gcctataggt gtgggttatt    3240
gaccattatt gaccactccc ctattggtga cgatactttc cattactaat ccataacatg    3300
gctctttgcc acaactatct ctattggcta tatgccaata ctctgtcctt cagagactga    3360
cacggactct gtattttttac aggatggggt cccatttatt atttacaaat tcacatatac   3420
aacaacgccg tcccccgtgc ccgcagtttt tattaaacat agcgtgggat ctccacgcga    3480
atctcgggta cgtgttccgg acatgggctc ttctccggta gcggcggagc ttccacatcc    3540
gagccctggt cccatgcctc cagcggctca tggtcgctcg gcagctcctt gctcctaaca    3600
gtggaggcca gacttaggca cagcacaatg cccaccacca ccagtgtgcc gcacaaggcc    3660
gtggcggtag gtatgtgtc tgaaaatgag ctcggagatt gggctcgcac cgtgacgcag    3720
atggaagact taaggcagcg gcagaagaag atgcaggcag ctgagttgtt gtattctgat    3780
aagagtcaga ggtaactccc gttgcggttc tgttaacggt ggagggcagt gtagtctgag    3840
cagtactcgt tgctgccgcg cgcgccacca gacataatag ctgacagact aacagactgt    3900 tccttttccat gggtcttttc tgcagtcacc gtcgtcgaag cttatgacca tgattacgga    3960
ttcactggcc gtcgttttac aacgtcgtga ctgggaaaac cctggcgtta cccaacttaa    4020
tcgccttgca gcacatcccc ctttcgccag ctggcgtaat agcgaagagg cccgcaccga    4080
tcgcccttcc caacagttgc gcagcctgaa tggcgaatgg cgctttgcct ggtttccggc    4140
accagaagcg gtgccggaaa gctggctgga gtgcgatctt cctgaggccg atactgtcgt    4200
cgtcccctca aactggcaga tgcacggtta cgatgcgccc atctacacca acgtaaccta    4260
tcccattacg gtcaatccgc cgtttgttcc cacggagaat ccgacgggtt gttactcgct    4320
cacatttaat gttgatgaaa gctggctaca ggaaggccag acgcgaatta ttttttgatgg   4380 cgttaactcg gcgtttcatc tgtggtgcaa cgggcgctgg gtcggttacg gccaggacag    4440
tcgtttgccg tctgaatttg acctgagcgc attttttacgc gccggagaaa accgcctcgc    4500
ggtgatggtg ctgcgttgga gtgacggcag ttatctggaa gatcaggata tgtggcggat    4560
gagcggcatt ttccgtgacg tctcgttgct gcataaaccg actacacaaa tcagcgattt    4620
ccatgttgcc actcgcttta tgatgattt cagccgcgct gtactggagg ctgaagttca    4680
gatgtgcggc gagttgcgtg actacctacg ggtaacagtt tctttatggc agggtgaaac    4740
gcaggtcgcc agcggcaccg cgccttcgg cggtgaaatt atcgatgagc gtggtggtta    4800
tgccgatcgc gtcacactac gtctgaacgt cgaaaacccg aaactgtgga gcgccgaaat    4860
cccgaatctc tatcgtgcgg tggttgaact gcacaccgcc gacggcacgc tgattgaagc    4920
agaagcctgc gatgtcggtt ccgcgaggt gcggattgaa aatggtctgc tgctgctgaa    4980
cggcaagccg ttgctgattc gaggcgttaa ccgtcacgag catcatcctc tgcatggtca    5040
ggtcatggat gagcagacga tggtgcagga tatcctgctg atgaagcaga acaactttaa    5100
cgccgtgcgc tgttcgcatt atccgaacca tccgctgtgg tacacgctgt gcgaccgcta    5160
cggcctgtat gtggtggatg aagccaatat tgaaacccac ggcatggtgc caatgaatcg    5220
tctgaccgat gatccgcgct ggctaccggc gatgagcgaa cgcgtaacgc gaatggtgca    5280
gcgcgatcgt aatcacccga gtgtgatcat ctggtcgctg gggaatgaat caggccacgg    5340
cgctaatcac gacgcgctgt atcgctggat caaatctgtc gatcccttccc gcccggtgca    5400
```

```
gtatgaaggc ggcggagccg acaccacggc caccgatatt atttgcccga tgtacgcgcg   5460
cgtggatgaa gaccagccct tcccggctgt gccgaaatgg tccatcaaaa aatggctttc   5520
gctacctgga gagacgcgcc cgctgatcct ttgcgaatac gcccacgcga tgggtaacag   5580
tcttggcggt ttcgctaaat actggcaggc gtttcgtcag tatccccgtt tacagggcgg   5640
cttcgtctgg gactgggtgg atcagtcgct gattaaatat gatgaaaacg gcaacccgtg   5700
gtcggcttac ggcggtgatt ttggcgatac gccgaacgat cgccagttct gtatgaacgg   5760 tctggtctttt gccgaccgca cgccgcatcc agcgctgacg gaagcaaaac caccagcagca   5820 gttttttccag ttccgtttat ccgggcaaac catcgaagtg accagcgaat acctgttccg   5880
tcatagcgat aacgagctcc tgcactggat ggtggcgctg gatggtaagc cgctggcaag   5940
cggtgaagtg cctctggatg tcgctccaca aggtaaacag ttgattgaac tgcctgaact   6000
accgcagccg gagagcgccg ggcaactctg gctcacagta cgcgtagtgc aaccgaacgc   6060
gaccgcatgg tcagaagccg ggcacatcag cgcctggcag cagtggcgtc tggcggaaaa   6120
cctcagtgtg acgctccccg ccgcgtccca cgccatcccg catctgacca ccagcgaaat   6180 ggattttttgc atcgagctgg gtaataagcg ttggcaattt aaccgccagt caggctttct   6240
ttcacagatg tggattggcg ataaaaaaca actgctgacg ccgctgcgcg atcagttcac   6300
ccgtgcaccg ctggataacg acattggcgt aagtgaagcg acccgcattg accctaacgc   6360
ctgggtcgaa cgctggaagg cggcgggcca ttaccaggcc gaagcagcgt tgttgcagtg   6420
cacggcagat acacttgctg atgcggtgct gattacgacc gctcacgcgt ggcagcatca   6480
ggggaaaacc ttatttatca gccggaaaac ctaccggatt gatggtagtg gtcaaatggc   6540
gattaccgtt gatgttgaag tggcgagcga taccgcat ccggcgcgga ttggcctgaa   6600
ctgccagctg gcgcaggtag cagagcgggt aaactggctc ggattagggc gcaagaaaa   6660 ctatcccgac cgccttactg ccgcctgttt tgaccgctgg gatctgccat tgtcagacat   6720
gtataccccg tacgtcttcc cgagcgaaaa cggtctgcgc tgcgggacgc gcgaattgaa   6780
ttatggccca caccagtggc gcggcgactt ccagttcaac atcagccgct acagtcaaca   6840
gcaactgatg gaaaccagcc atcgccatct gctgcacgcg gaagaaggca catggctgaa   6900
tatcgacggt ttccatatgg ggattggtgg cgacgactcc tggagcccgt cagtatcggc   6960
ggaattccag ctgagcgccg gtcgctacca ttaccagttg gtctggtgtc aaaaataact   7020
cgatcgacca gagctgagat cctacaggag tccaggctg gagagaaaac ctctgaagag   7080
gatgatgaca gagttagaag atcgcttcag gaagctattt ggcacgactt ctacaacggg   7140
agacagcaca gtagattctg aagatgaacc tcctaaaaaa gaaaaagggg tggactggga   7200
tgagtattgg aaccctgaag aaatagaaag aatgcttatg gactagggac tgtttacgaa   7260
caaatgataa aaggaaatag ctgagcatga ctcatagtta aagcgctagc agctgcctaa   7320
ccgcaaaacc acatcctatg gaaagcttgc taatgacgta aagttgttc cattgtaaga   7380 gtatataacc agtgctttgt gaacttcga ggagtctctt tgttgaggac ttttgagttc   7440
tcccttgagg ctcccacaga tacaataaat atttgagatt gaaccctgtc gagtatctgt   7500
gtaatctttt ttacctgtga ggtctcggaa tccggccga gaacttcgca gcggccgctc   7560
gagcatgcat ctagagggcc ctattctata gtgtcaccta aatgctagag ctcgctgatc   7620
agcctcgact gtgccttcta gttgccagcc atctgttgtt tgcccctccc ccgtgccttc   7680
cttgaccctg gaaggtgcca ctcccactgt ccttttcctaa taaaatgagg aaattgcatc   7740
gcattgtctg agtaggtgtc attctattct ggggggtggg gtggggcagg acagcaaggg   7800
```

```
ggaggattgg gaagacaata gcaggcatgc tggggatgcg gtgggctcta tggcttctga    7860
ggcggaaaga accagctggg gctcgagggg ggatccccac gcgccctgta gcggcgcatt    7920
aagcgcggcg ggtgtggtgg ttacgcgcag cgtgaccgct acacttgcca gcgccctagc    7980
gcccgctcct ttcgctttct tcccttcctt tctcgccacg ttcgccggct ttccccgtca    8040
agctctaaat cggggcatcc ctttagggtt ccgatttagt gctttacggc acctcgaccc    8100
caaaaaactt gattagggtg atggttcacg tagtgggcca tcgccctgat agacggtttt    8160
tcgccctttg acgttggagt ccacgttctt aatagtgga ctcttgttcc aaactggaac    8220
aacactcaac cctatctcgg tctattcttt tgatttataa gggattttgg ggatttcggc    8280
ctattggtta aaaaatgagc tgatttaaca aaaatttaac gcgaatttta acaaaatatt    8340
aacgtttaca atttaaatat ttgcttatac aatcttcctg tttttggggc ttttctgatt    8400
atcaaccggg gtgggtaccg agctcgaatt ctgtggaatg tgtgtcagtt agggtgtgga    8460
aagtccccag gctccccagg caggcagaag tatgcaaagc atgcatctca attagtcagc    8520
aaccaggtgt ggaaagtccc caggctcccc agcaggcaga agtatgcaaa gcatgcatct    8580
caattagtca gcaaccatag tcccgcccct aactccgccc atcccgcccc taactccgcc    8640
cagttccgcc cattctccgc cccatggctg actaattttt tttatttatg cagaggccga    8700
ggccgcctcg gcctctgagc tattccagaa gtagtgagga ggcttttttg gaggcctagg    8760
cttttgcaaa aagctcccgg gagcttggat atccattttc ggatctgatc aagagacagg    8820
atgaggatcg tttcgcatga ttgaacaaga tggattgcac gcaggttctc cggccgcttg    8880
ggtggagagg ctattcggct atgactgggc acaacagaca atcggctgct ctgatgccgc    8940
cgtgttccgg ctgtcagcgc agggggcgccc ggttcttttt gtcaagaccg acctgtccgg    9000
tgccctgaat gaactgcagg acgaggcagc gcggctatcg tggctggcca cgacgggcgt    9060
tccttgcgca gctgtgctcg acgttgtcac tgaagcggga agggactggc tgctattggg    9120
cgaagtgccg gggcaggatc tcctgtcatc tcaccttgct cctgccgaga agtatccat    9180
catggctgat gcaatgcggc ggctgcatac gcttgatccg gctacctgcc cattcgacca    9240
ccaagcgaaa catcgcatcg agcgagcacg tactcggatg aagccggtc ttgtcgatca    9300
ggatgatctg gacgaagagc atcagggget cgcgccagcc gaactgttcg ccaggctcaa    9360
ggcgcgcatg cccgacggcg aggatctcgt cgtgacccat ggcgatgcct gcttgccgaa    9420
tatcatggtg gaaaatggcc gcttttctgg attcatcgac tgtggccggc tgggtgtggc    9480
ggaccgctat caggacatag cgttggctac ccgtgatatt gctgaagagc ttggcggcga    9540
atgggctgac cgcttcctcg tgctttacgg tatcgccgct cccgattcgc agcgcatcgc    9600
cttctatcgc cttcttgacg agttcttctg agcgggactc tggggttcga atgaccgac    9660
caagcgacgc ccaacctgcc atcacgagat ttcgattcca ccgccgcctt ctatgaaagg    9720
ttgggcttcg gaatcgtttt ccgggacgcc ggctggatga tcctccagcg cggggatctc    9780
atgctgagt tcttcgccca ccccaacttg tttattgcag cttataatgg ttacaaataa    9840
agcaatagca tcacaaattt cacaaataaa gcatttttt cactgcattc tagttgtggt    9900
ttgtccaaac tcatcaatgt atcttatcat gtctggatcc cgtcgacctc gagagcttgg    9960
cgtaatcatg gtcatagctg tttcctgtgt gaaattgtta tccgctcaca attccacaca   10020
acatacgagc cggaagcata aagtgtaaag cctggggtgc ctaatgagtg agctaactca   10080
cattaattgc gttgcgctca ctgcccgctt tccagtcggg aaacctgtcg tgccagctgc   10140
attaatgaat cggccaacgc gcggggagag gcggtttgcg tattgggcgc tcttccgctt   10200
```

```
cctcgctcac tgactcgctg cgctcggtcg ttcggctgcg gcgagcgta tcagctcact   10260 caaaggcggt aatacggtta tccacagaat caggggataa cgcaggaaag aacatgtgag   10320
caaaaggcca gcaaaggcc aggaaccgta aaaggccgc gttgctggcg ttttccata    10380 ggctccgccc ccctgacgag catcacaaaa atcgacgctc aagtcagagg tggcgaaacc   10440
cgacaggact ataaagatac caggcgtttc ccctggaag ctccctcgtg cgctctcctg    10500
ttccgaccct gccgcttacc ggatacctgt ccgcctttct cccttcggga agcgtggcgc   10560
tttctcaatg ctcacgctgt aggtatctca gttcggtgta ggtcgttcgc tccaagctgg   10620
gctgtgtgca cgaacccccc gttcagcccg accgctgcgc cttatccggt aactatcgtc   10680
ttgagtccaa cccggtaaga cacgacttat cgccactggc agcagccact ggtaacagga   10740
ttagcagagc gaggtatgta ggcggtgcta cagagttctt gaagtggtgg cctaactacg   10800
gctacactag aaggacagta tttggtatct gcgctctgct gaagccagtt accttcggaa   10860
aaagagttgg tagctcttga tccggcaaac aaaccaccgc tggtagcggt ggtttttttg   10920
tttgcaagca gcagattacg cgcagaaaaa aaggatctca agaagatcct ttgatctttt   10980
ctacggggtc tgacgctcag tggaacgaaa actcacgtta agggattttg gtcatgagat   11040
tatcaaaaag gatcttcacc tagatccttt taaattaaaa atgaagtttt aaatcaatct   11100
aaagtatata tgagtaaact tggtctgaca gttaccaatg cttaatcagt gaggcaccta   11160
tctcagcgat ctgtctattt cgttcatcca tagttgcctg actccccgtc gtgtagataa   11220
ctacgatacg ggagggctta ccatctggcc ccagtgctgc aatgataccg cgagacccac   11280
gctcaccggc tccagattta tcagcaataa accagccagc cggaagggcc gagcgcagaa   11340
gtggtcctgc aactttatcc gcctccatcc agtctattaa ttgttgccgg gaagctagag   11400
taagtagttc gccagttaat agtttgcgca acgttgttgc cattgctaca ggcatcgtgg   11460
tgtcacgctc gtcgtttggt atggcttcat tcagctccgg ttcccaacga tcaaggcgag   11520
ttacatgatc ccccatgttg tgcaaaaaag cggttagctc cttcggtcct ccgatcgttg   11580
tcagaagtaa gttggccgca gtgttatcac tcatggttat ggcagcactg cataattctc   11640
ttactgtcat gccatccgta agatgctttt ctgtgactgg tgagtactca accaagtcat   11700
tctgagaata gtgtatgcgg cgaccgagtt gctcttgccc ggcgtcaata cgggataata   11760
ccgcgccaca tagcagaact ttaaaagtgc tcatcattgg aaaacgttct tcggggcgaa   11820
aactctcaag gatcttaccg ctgttgagat ccagttcgat gtaacccact cgtgcaccca   11880
actgatcttc agcatctttt actttcacca gcgtttctgg gtgagcaaaa acaggaaggc   11940
aaaatgccgc aaaaaaggga ataagggcga cacggaaatg ttgaatactc atactcttcc   12000
tttttcaata ttattgaagc atttatcagg gttattgtct catgagcgga tacatatttg   12060
aatgtattta gaaaaataaa caaataggggg ttccgcgcac atttccccga aaagtgccac   12120
ctgacgtcga cggatcggga gatctcccga tcccctatgg tcgactctca gtacaatctg   12180
ctctgatgcc gcatagttaa gccagtatct gctccctgct tgtgtgttgg aggtcgctga   12240
gtagtgcgcg agcaaaattt aagctacaac aaggcaaggc ttgaccgaca attgcatgaa   12300
gaatctgctt agggttaggc gttttgcgct gcttcgcgat gtacgggcca gatatacgcg   12360
ttgacattga ttattgacta gttattaata gtaatcaatt acgggtcat tagttcatag   12420 cccatatatg gagttccgcg ttacataact tacggtaaat ggcccgcctg gctgaccgcc   12480
caacgacccc cgcccattga cgtcaataat gacgtatgtt cccatagtaa cgccaatagg   12540
gactttccat tgacgtcaat gggtggacta tttacggtaa actgcccact tggcagtaca   12600
```

```
tcaagtgtat catatgccaa gtacgccccc tattgacgtc aatgacggta aatggcccgc    12660
ctggcattat gcccagtaca tgaccttatg ggactttcct acttggcagt acatctacgt    12720
attagtcatc gctattacca tggtg                                          12745
```

<210> SEQ ID NO 38
<211> LENGTH: 177
<212> TYPE: PRT
<213> ORGANISM: Artificial Sequence
<220> FEATURE:
<223> OTHER INFORMATION: Description of Artificial Sequences; note = synthetic construct

<400> SEQUENCE: 38

```
Met Glu Ile Cys Arg Gly Leu Arg Ser His Leu Ile Thr Leu Leu Leu
 1               5                  10                  15

Phe Leu Phe His Ser Glu Thr Ile Cys Arg Pro Ser Gly Arg Lys Ser
                20                  25                  30

Ser Lys Met Gln Ala Phe Arg Ile Trp Asp Val Asn Gln Lys Thr Phe
            35                  40                  45

Tyr Leu Arg Asn Asn Gln Leu Val Ala Gly Tyr Leu Gln Gly Pro Asn
        50                  55                  60

Val Asn Leu Glu Glu Lys Ile Asp Val Val Pro Ile Glu Pro His Ala
65                  70                  75                  80

Leu Phe Leu Gly Ile His Gly Gly Lys Met Cys Leu Ser Cys Val Lys
                85                  90                  95

Ser Gly Asp Glu Thr Arg Leu Gln Leu Glu Ala Val Asn Ile Thr Asp
               100                 105                 110

Leu Ser Glu Asn Arg Lys Gln Asp Lys Arg Phe Ala Phe Ile Arg Ser
            115                 120                 125

Asp Ser Gly Pro Thr Thr Ser Phe Glu Ser Ala Ala Cys Pro Gly Trp
        130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu
```

<210> SEQ ID NO 39
<211> LENGTH: 569
<212> TYPE: PRT
<213> ORGANISM: Artificial Sequence
<220> FEATURE:
<223> OTHER INFORMATION: Description of Artificial Sequences; note = synthetic construct

<400> SEQUENCE: 39

```
Met Lys Val Leu Leu Arg Leu Ile Cys Phe Ile Ala Leu Leu Ile Ser
 1               5                  10                  15

Ser Leu Glu Ala Asp Lys Cys Lys Glu Arg Glu Glu Lys Ile Ile Leu
                20                  25                  30

Val Ser Ser Ala Asn Glu Ile Asp Val Arg Pro Cys Pro Leu Asn Pro
            35                  40                  45

Asn Glu His Lys Gly Thr Ile Thr Trp Tyr Lys Asp Asp Ser Lys Thr
        50                  55                  60

Pro Val Ser Thr Glu Gln Ala Ser Arg Ile His Gln His Lys Glu Lys
65                  70                  75                  80

Leu Trp Phe Val Pro Ala Lys Val Glu Asp Ser Gly His Tyr Tyr Cys
```

-continued

```
                85                  90                  95
Val Val Arg Asn Ser Ser Tyr Cys Leu Arg Ile Lys Ile Ser Ala Lys
                    100                 105                 110

Phe Val Glu Asn Glu Pro Asn Leu Cys Tyr Asn Ala Gln Ala Ile Phe
                    115                 120                 125

Lys Gln Lys Leu Pro Val Ala Gly Asp Gly Gly Leu Val Cys Pro Tyr
                    130                 135                 140

Met Glu Phe Phe Lys Asn Glu Asn Glu Leu Pro Lys Leu Gln Trp
145                 150                 155                 160

Tyr Lys Asp Cys Lys Pro Leu Leu Leu Asp Asn Ile His Phe Ser Gly
                    165                 170                 175

Val Lys Asp Arg Leu Ile Val Met Asn Val Ala Glu Lys His Arg Gly
                    180                 185                 190

Asn Tyr Thr Cys His Ala Ser Tyr Thr Tyr Leu Gly Lys Gln Tyr Pro
                    195                 200                 205

Ile Thr Arg Val Ile Glu Phe Ile Thr Leu Glu Glu Asn Lys Pro Thr
                    210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                    245                 250                 255

Ile Ala Tyr Trp Lys Trp Asn Gly Ser Val Ile Asp Glu Asp Pro
                    260                 265                 270

Val Leu Gly Glu Asp Tyr Tyr Ser Val Glu Asn Pro Ala Asn Lys Arg
                    275                 280                 285

Arg Ser Thr Leu Ile Thr Val Leu Asn Ile Ser Glu Ile Glu Ser Arg
                    290                 295                 300

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Phe Gln Lys
                    325                 330                 335

His Met Ile Gly Ile Cys Val Thr Leu Thr Val Ile Ile Val Cys Ser
                    340                 345                 350

Val Phe Ile Tyr Lys Ile Phe Lys Ile Asp Ile Val Leu Trp Tyr Arg
                    355                 360                 365

Asp Ser Cys Tyr Asp Phe Leu Pro Ile Lys Ala Ser Asp Gly Lys Thr
                    370                 375                 380

Tyr Asp Ala Tyr Ile Leu Tyr Pro Lys Thr Val Gly Glu Gly Ser Thr
385                 390                 395                 400

Ser Asp Cys Asp Ile Phe Val Phe Lys Val Leu Pro Glu Val Leu Glu
                    405                 410                 415

Lys Gln Cys Gly Tyr Lys Leu Phe Ile Tyr Gly Arg Asp Asp Tyr Val
                    420                 425                 430

Gly Glu Asp Ile Val Glu Val Ile Asn Glu Asn Val Lys Lys Ser Arg
                    435                 440                 445

Arg Leu Ile Ile Ile Leu Val Arg Glu Thr Ser Gly Phe Ser Trp Leu
450                 455                 460

Gly Gly Ser Ser Glu Glu Gln Ile Ala Met Tyr Asn Ala Leu Val Gln
465                 470                 475                 480

Asp Gly Ile Lys Val Val Leu Leu Glu Leu Glu Lys Ile Gln Asp Tyr
                    485                 490                 495

Glu Lys Met Pro Glu Ser Ile Lys Phe Ile Lys Gln Lys His Gly Ala
                    500                 505                 510
```

-continued

```
Ile Arg Trp Ser Gly Asp Phe Thr Gln Gly Pro Gln Ser Ala Lys Thr
    515                 520                 525

Arg Phe Trp Lys Asn Val Arg Tyr His Met Pro Val Gln Arg Arg Ser
    530                 535                 540

Pro Ser Ser Lys His Gln Leu Leu Ser Pro Ala Thr Lys Glu Lys Leu
545                 550                 555                 560

Gln Arg Glu Ala His Val Pro Leu Gly
                565

<210> SEQ ID NO 40
<211> LENGTH: 398
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 40

Met Leu Arg Leu Tyr Val Leu Val Met Gly Val Ser Ala Phe Thr Leu
  1               5                  10                  15

Gln Pro Ala Ala His Thr Gly Ala Ala Arg Ser Cys Arg Phe Arg Gly
             20                  25                  30

Arg His Tyr Lys Arg Glu Phe Arg Leu Glu Gly Glu Pro Val Ala Leu
         35                  40                  45

Arg Cys Pro Gln Val Pro Tyr Trp Leu Trp Ala Ser Val Ser Pro Arg
     50                  55                  60

Ile Asn Leu Thr Trp His Lys Asn Asp Ser Ala Arg Thr Val Pro Gly
 65                  70                  75                  80

Glu Glu Glu Thr Arg Met Trp Ala Gln Asp Gly Ala Leu Trp Leu Leu
                 85                  90                  95

Pro Ala Leu Gln Glu Asp Ser Gly Thr Tyr Val Cys Thr Thr Arg Asn
            100                 105                 110

Ala Ser Tyr Cys Asp Lys Met Ser Ile Glu Leu Arg Val Phe Glu Asn
        115                 120                 125

Thr Asp Ala Phe Leu Pro Phe Ile Ser Tyr Pro Gln Ile Leu Thr Leu
    130                 135                 140

Ser Thr Ser Gly Val Leu Val Cys Pro Asp Leu Ser Glu Phe Thr Arg
145                 150                 155                 160

Asp Lys Thr Asp Val Lys Ile Gln Trp Tyr Lys Asp Ser Leu Leu Leu
                165                 170                 175

Asp Lys Asp Asn Glu Lys Phe Leu Ser Val Arg Gly Thr Thr His Leu
            180                 185                 190

Leu Val His Asp Val Ala Leu Glu Asp Ala Gly Tyr Tyr Arg Cys Val
        195                 200                 205

Leu Thr Phe Ala His Glu Gly Gln Gln Tyr Asn Ile Thr Arg Ser Ile
    210                 215                 220

Glu Leu Arg Ile Lys Lys Lys Glu Glu Thr Ile Pro Val Ile Ile
225                 230                 235                 240

Ser Pro Leu Lys Thr Ile Ser Ala Ser Leu Gly Ser Arg Leu Thr Ile
                245                 250                 255

Pro Cys Lys Val Phe Leu Gly Thr Gly Thr Pro Leu Thr Thr Met Leu
            260                 265                 270

Trp Trp Thr Ala Asn Asp Thr His Ile Glu Ser Ala Tyr Pro Gly Gly
        275                 280                 285

Arg Val Thr Glu Gly Pro Arg Gln Glu Tyr Ser Glu Asn Asn Glu Asn
    290                 295                 300
```

-continued

| Tyr | Ile | Glu | Val | Pro | Leu | Ile | Phe | Asp | Pro | Val | Thr | Arg | Glu | Asp | Leu |
| 305 | | | | | 310 | | | | | 315 | | | | | 320 |

| His | Met | Asp | Phe | Lys | Cys | Val | Val | His | Asn | Thr | Leu | Ser | Phe | Gln | Thr |
| | | | | 325 | | | | | 330 | | | | | 335 | |

| Leu | Arg | Thr | Thr | Val | Lys | Glu | Ala | Ser | Ser | Thr | Phe | Ser | Trp | Gly | Ile |
| | | | 340 | | | | | 345 | | | | | 350 | | |

| Val | Leu | Ala | Pro | Leu | Ser | Leu | Ala | Phe | Leu | Val | Leu | Gly | Gly | Ile | Trp |
| | | | 355 | | | | | 360 | | | | | 365 | | |

| Met | His | Arg | Arg | Cys | Lys | His | Arg | Thr | Gly | Lys | Ala | Asp | Gly | Leu | Thr |
| | | 370 | | | | | 375 | | | | | 380 | | | |

| Val | Leu | Trp | Pro | His | His | Gln | Asp | Phe | Gln | Ser | Tyr | Pro | Lys | | |
| 385 | | | | | 390 | | | | | 395 | | | | | |

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 41
ggaagcgaua auuuuaagct t                                              21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 42
ggagaauccg gccagucaut t                                              21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 43
ggguugauua uguaccauut t                                              21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 44
ggcuucacua aggguugaut t                                              21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 45

```
ggcaguaucc uuaugcaugt t                                                   21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 46
gcuuuuacau cucuuagcat t                                                   21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 47
gggaagaaac aguuaccagt t                                                   21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 48
gggcaccaac auccuguuut t                                                   21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 49
ggaugggaaa cuuaaguact t                                                   21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 50
ccuacaacuc agcgcaugat t                                                   21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 51
gcgcaugacu acaucagcut t                                                   21
```

```
<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 52
gcuacgagca guuuuuauut t                                               21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 53
ggauuugacc aguauaagut t                                               21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 54
gggagucugg aacauugugt t                                               21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 55
gguuuuuagu aucagaacut t                                               21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 56
gcacaggauu ugaccaguat t                                               21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 57
gggaaauaag gagcuuccut t                                               21
```

```
<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 58
cccuacagua cuaaucaaat t                                            21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 59
ggcuuuugcc aaccccgagt t                                            21

<210> SEQ ID NO 60
<211> LENGTH: 59
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 60
gatccggggt tgattatgta ccattttcaa gagaaatggt acataatcaa cccttttg    59

<210> SEQ ID NO 61
<211> LENGTH: 59
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 61
gccccaacta atacatggta aaagttctct ttaccatgta ttagttggga aaaacttaa   59

<210> SEQ ID NO 62
<211> LENGTH: 59
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 62
gatccgggct tttgccaacc ccgagttcaa gagactcggg gttggcaaaa gccttttg    59

<210> SEQ ID NO 63
<211> LENGTH: 59
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 63
gcccgaaaac ggttggggct caagttctct gagccccaac cgttttcgga aaaacttaa   59

<210> SEQ ID NO 64
<211> LENGTH: 59
```

```
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 64
gatccgggat gggaaactta agtacttcaa gagagtactt aagtttccca tcctttttg      59

<210> SEQ ID NO 65
<211> LENGTH: 59
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 65
gatccgggat gggaaactta agtacttcaa gagagtactt aagtttccca tcctttttg      59

<210> SEQ ID NO 66
<211> LENGTH: 59
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 66
gatccgggat ttgaccagta taagtttcaa gagaacttat actggtcaaa tcctttttg      59

<210> SEQ ID NO 67
<211> LENGTH: 59
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 67
gccctaaact ggtcatattc aaagttctct tgaatatgac cagtttagga aaaacttaa      59

<210> SEQ ID NO 68
<211> LENGTH: 25
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 68

Met Glu Ile Cys Arg Gly Leu Arg Ser His Leu Ile Thr Leu Leu Leu
  1               5                  10                  15

Phe Leu Phe His Ser Glu Thr Ile Cys
            20                  25

<210> SEQ ID NO 69
<211> LENGTH: 1774
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 69
ggttcaagtg attctgctgc ctcagcctcc caggcgggat tacaggtgcc tgccaccacg      60
cctggctaat ttttttgtct ttttagtaaa gatgaggttt caccatgttg gcaggctgg     120
```

```
tttcaattgc tgacctcaag tgagccaccc cgcctcagcc tccaaaatgc taggattaca      180
ggcatgagcc accgcaccca gccaagtttg tacatatatt tttgactaca cttcttaact      240
attcttagga taaattacta gaagtgaaaa ttcttgggtg aagagcttga ggcctttaca      300
cacacacaca cacacacaca cacacacaca caaataggct ggatcgagtg gctcacacct      360
gtaatctcag cagtttggga ggctgaggaa ggaggatcac ttgagtccag gaggttgaga      420
atagcctgaa caacatagca agatcttgtc tctacaaaaa agtttaaaaa aaattagctg      480
gccatggcag catgtgcctg tagtaccagc tactcggaag gctgaggtag gaggatcgct      540
tgagcccagg aggtgattga agctgcagtg agctgtgatt acaccactgc actccagcct      600
gggcaacaga gctagactct gtctctaaaa aaaggcacaa aataatattt aaaaagcacc      660
aggtatgcct gtacttgagt tgtctttgtt gatggctaca aatgagacag ctctggctga      720
agggcggctt ccatttccat gggctggagg aggacatttt gcaaagtgtg ttttcaggaa      780
gacacagagt tttacctcct acacttgttt gatctgtatt aatgtttgct tatttattta      840
tttaattttt tttttgagac agagtctcac tctgtcacct gggctggagt gcagtggcat      900
tattgaggct cattgcagtc tcagactcct gagctcaaac aatcctcctg cctcagcctc      960
tggagtagct aggactacag gcatgtgcca ccatgcctgg ctaatttttt aaatgtattt     1020
ttttgtagag tcgggtctc cctatgttgc ccaggctgga gtgcagtggt gtgatcctag     1080
ctcactgcag cctggacctc gggctcaaga aattctcaca cctcagcctg tccagtagca     1140
ggggctacag gcgcgcacca ccatcccagc taattaaaaa tattttttg tagagacagg     1200 gtctctctat gttgcccagg ctggtttcaa actcccaggc tcaagcaatc ctcctgcctt     1260
gcctcccaaa tgcatcgga ttacaggcgt gagccactga gcctggcccg tattaatgtt     1320
tagaacacga attccaggag gcaggctaag tctattcagc ttgttcatat gcttgggcca     1380
acccaagaaa caagtgggtg acaaatggca ccttttggat agtggtattg actttgaaag     1440
tttgggtcag gagctgggga ggaagggtgg gcaggctgtg ggcagtcctg ggcggaagac     1500
caggcagggc tatgtgctca ctgagcctcc gccctcttcc tttgaatctc tgatagactt     1560
ctgcctccta cttctccttt tctgcccttc tttgctttgg tggcttcctt gtggttcctc     1620
agtggtgcct gcaaccctgg ttcactcttc caggttctgg ctccttccag ccatggctct     1680
cagagtcctt ctgttaacag gtgcatgggg gtggggtggg ggactctggg tggggaggag     1740
ggtaactttt gggtctgtca taaatagagg gccc                                 1774

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 70 gttcccttc tgccagccct                                                    20

<210> SEQ ID NO 71
<211> LENGTH: 19
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 71
```
gtgccgtgag tttcccaga                                                      19

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 72
cccacttcct tgccctctca                                                     20

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 73
actctgttgt gttcccgca                                                      19

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 74
cctcttctcg cttccctca                                                      19

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 75
gttcccatca gccacttcgt                                                     20

<210> SEQ ID NO 76
<211> LENGTH: 44
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 76
atcctttgat cugaugaguc cgugaggacg aaagttataa gcac                          44

<210> SEQ ID NO 77
<211> LENGTH: 43
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 77
tctttagaac ugaugagucc gugaggacga aagacaaatt gca                           43

```
<210> SEQ ID NO 78
<211> LENGTH: 44
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 78
ggccgaagcg cugaugaguc cgugaggacg aaagacagat gccc                44

<210> SEQ ID NO 79
<211> LENGTH: 44
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 79
tggatgtcaa cugaugaguc cgugaggacg aaagataact cata                44

<210> SEQ ID NO 80
<211> LENGTH: 44
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 80
aggagttcga cugaugaguc cgugaggacg aaagcctcct gggc                44

<210> SEQ ID NO 81
<211> LENGTH: 44
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 81
tctccggtgc cugaugaguc cgugaggacg aaagtccgct tttt                44

<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 82
cugaugaguc cgugaggacg aaag                                      24
```

What is claimed is:

1. A composition comprising a viral vector, wherein delivery of the vector to a cell inhibits a mediator of inflammation, wherein the vector comprises a lentivirus, wherein the lentivirus is a feline immuno deficiency virus (FIV), wherein the vector comprises a nucleic acid operably linked to an expression control sequence and wherein the nucleic acid inhibits expression of the mediator of inflammation, wherein the nucleic acid is an siRNA, wherein the siRNA inhibits gene expression of COX-2, and wherein the siRNA comprises the nucleic acid sequence SEQ ID NO:53.

2. A composition comprising a cell, wherein the cell comprises the vector of claim 1.

* * * * *